(12) United States Patent
Hirokazu et al.

(10) Patent No.: US 7,375,074 B2
(45) Date of Patent: May 20, 2008

(54) BODY WEIGHT GAIN INHIBITOR

(75) Inventors: Matsumoto Hirokazu, Ibaraki (JP); Noguchi Jiro, Ibaraki (JP); Harada Mioko, Ibaraki (JP); Mori Masaaki, Ibaraki (JP)

(73) Assignee: Takeda Chemical Industries, Ltd., Osaka (JP)

(*) Notice: Subject to any disclaimer, the term of this patent is extended or adjusted under 35 U.S.C. 154(b) by 480 days.

(21) Appl. No.: 10/500,175

(22) PCT Filed: Dec. 27, 2002

(86) PCT No.: PCT/JP02/13781

§ 371 (c)(1),
(2), (4) Date: Jun. 25, 2004

(87) PCT Pub. No.: WO03/057236

PCT Pub. Date: Jul. 17, 2003

(65) Prior Publication Data

US 2005/0124539 A1 Jun. 9, 2005

(30) Foreign Application Priority Data

Dec. 28, 2001 (JP) .............................. 2001-403260
Mar. 28, 2002 (JP) .............................. 2002-093096

(51) Int. Cl.
*A61K 38/00* (2006.01)
(52) U.S. Cl. .......................................... 514/2; 530/300
(58) Field of Classification Search .................... None
See application file for complete search history.

(56) References Cited

U.S. PATENT DOCUMENTS 7,193,033 B2 * 3/2007 Mori et al. .................. 530/300

FOREIGN PATENT DOCUMENTS

| EP | 1 293 567 A1 | 3/2003 |
|---|---|---|
| EP | 1 344 823 | 9/2003 |
| EP | 1 403 281 | 3/2004 |
| JP | 09-121865 | 5/1997 |
| WO | WO 95/12670 | 5/1995 |
| WO | WO-03/082907 | 10/2003 |

OTHER PUBLICATIONS

Rohner-Jearnrenaud et al., The New Eng. J. Med., 334: 324-325, 1996.*
Campfield et al., Science 280: 1383-1387, 1998.*
Grasso et al., Endocrinol. 138: 1413-1418, 1997.*
Mickle et al., Med. Clin. North Am., 2000, vol. 84(3), p. 597-607.*
Adelhorst et al., J. Biol. Chem. 269: 6275-6278, 1994.*
O'Dowd et al., "The Cloning and Chromosomal Mapping of Two Novel Human Opioid-Somatostatin-like Receptor Genes, GPR7 and GPR8, Expressed in Discrete Areas of the Brain," *Genomics* 28:84-91 (1995).

* cited by examiner

*Primary Examiner*—Robert S. Landsman
*Assistant Examiner*—Gyan Chandra
(74) *Attorney, Agent, or Firm*—Edwards, Angell, Palmer and Dodge, LLP; David G. Conlin; Dwight D. Kim

(57) ABSTRACT

The present invention intends to provide a body weight gain inhibitor and the like. The ligand of the present invention is useful as a superior body weight gain inhibitor and the like, or for a screening of the superior body weight gain inhibitor and the like.

4 Claims, 27 Drawing Sheets

Fig. 6

```
                          GGC GGG GCC ACC GAG CGG TTA TAG CTG GGC CTG CAG GGG ACC   42
CAC GGC TCG CCT CCA GCC TCC TGC GCT CCG GTA CCT GGG CGT CCC AAC TCC ACT GCG CGC  102
CCA AAC CCA GCC GAG CCG GTT CGT GGC CCG CCC CGC CGG GCG GCC GTC GAC GCG AGC GCC  162

CTG GCG TGG CGC CCA GGG GAG CGG GGG GCT CCC GCG AGC CGG CCG CGG CTG GCA CTG CTG  222
Leu Ala Trp Arg Pro Gly Glu Arg Gly Ala Pro Ala Ser Arg Pro Arg Leu Ala Leu Leu   20

CTG CTT CTG CTC CTG CTG CCG CTG CCC TCC GGC GCG TGG TAC AAG CAC GTG GCG AGT CCC  282
Leu Leu Leu Leu Leu Leu Pro Leu Pro Ser Gly Ala Trp Tyr Lys His Val Ala Ser Pro   40

CGC TAC CAC ACG GTG GGC CGC GCC GCT GGC CTG CTC ATG GGG CTG CGT CGC TCA CCC TAT  342
Arg Tyr His Thr Val Gly Arg Ala Ala Gly Leu Leu Met Gly Leu Arg Arg Ser Pro Tyr   60

CTG TGG CGC CGC GCG CTG CGC GCG GCC GCC GGG CCC CTG GCC AGG GAC ACC CTC TCC CCC  402
Leu Trp Arg Arg Ala Leu Arg Ala Ala Ala Gly Pro Leu Ala Arg Asp Thr Leu Ser Pro   80

GAA CCC GCA GCC CGC GAG GCT CCT CTC CTG CTG CCC TCG TGG GTT CAG GAG CTG TGG GAG  462
Glu Pro Ala Ala Arg Glu Ala Prp Leu Leu Leu Pro Ser Trp Val Gln Glu Leu Trp Glu  100

ACG CGA CGC AGG AGC TCC CAG GCA GGG ATC CCC GTC CGT GCG CCC CGG AGC CCG CGC GCC  522
Thr Arg Arg Arg Ser Ser Gln Ala Gly Ile Pro Val Arg Ala Pro Arg Ser Pro Arg Ala  120

CCA GAG CCT GCG CTG GAA CCG GAG TCC CTG GAC TTC AGC GGA GCT GGC CAG AGA CTT CGG  582
Pro Glu Pro Ala Leu Glu Pro Glu Ser Leu Asp Phe Ser Gly Ala Gly Gln Arg Leu Arg  140

AGA GAC GTC TCC CGC CCA GCG GTG GAC CCC GCA GCA AAC CGC CTT GGC CTG CCC TGC CTG  642
Arg Asp Val Ser Arg Pro Ala Val Asp Pro Ala Ala Asn Arg Leu Gly Leu Pro Cys Leu  160

GCC CCC GGA CCG TTC TGA CAG CGT CCC CCG CCC GCC CGT GGC GCC TCC GCG CCT GAC CCA  702
Ala Pro Gly Pro Phe ***                                                          165

719
GGA GGA GTG GCC GCG CG
```

Fig. 7

```
                              CC TCC GGA GCC AGT TCC TGG TCC GCC CCG CCG GGA GCC GTC AGC   44

ATG AAC CCC CGG GCA CGC GGC ATG GGA GCG CGG GGC CCG GGA CCG GGG GCC ACT GCG AGG  104
Met Asn Pro Arg Ala Arg Gly Met Gly Ala Arg Gly Pro Gly Pro Gly Ala Thr Ala Arg   20

CGC CGG CTG CTG GCA TTG CTG TTA CTG CTG CTG CTG CCG CTG CCC GCC CGT GCC  TGG     164
Arg Arg Leu Leu Ala Leu Leu Leu Leu Leu Leu Leu Pro Leu Pro Ala Arg Ala  Trp      40

TAC AAG CAC ACG GCG AGT CCC CGC TAC CAC ACG GTG GGC CGC GCC GCG GGC CTG CTC ATG  224
Tyr Lys His Thr Ala Ser Pro Arg Tyr His Thr Val Gly Arg Ala Ala Gly Leu Leu Met   60

GGG CTG  CGC CGC TCG CCC TAC ATG TGG CGC CGC GCG CTG CGC CCG GCG GCC GGG CCC CTG 284
Gly Leu  Arg Arg Ser Pro Tyr Met Trp Arg Arg Ala Leu Arg Pro Ala Ala Gly Pro Leu  80

GCC TGG GAC ACT TTC GGC CAG GAC GTG CCC CCT CGG GGA CCC TCC GCC AGG AAC GCC CTC  344
Ala Trp Asp Thr Phe Gly Gln Asp Val Pro Pro Arg Gly Pro Ser Ala Arg Asn Ala Leu  100

TCT CCG GGG CCC GCC CCT CGC GAC GCT CCG CTG CTT CCC CCC GGG GTT CAG ACA CTG TGG  404
Ser Pro Gly Pro Ala Pro Arg Asp Ala Pro Leu Leu Pro Pro Gly Val Gln Thr Leu Trp  120

CAG GTG CGA CGC GGA AGC TTC CGC TCC GGG ATC CCG GTC AGT GCG CCC CGC AGC CCG CGC  464
Gln Val Arg Arg Gly Ser Phe Arg Ser Gly Ile Pro Val Ser Aal Pro Arg Ser Pro Arg  140

GCC CGG GGG TCC GAG CCG CAA CCG GAA TTG GGC GCC TCT TCC TGG ACC TCG GCG GAG TAG  524
Ala Arg Gly Ser Glu Pro Gln Pro Glu Leu Gly Ala Ser Ser Trp Thr Ser Ala Glu ***  159

ACC AGA GCC TTC GGA GAG TCT TCA GCT CAG CGG TGG TCT GC                           565
```

Fig. 8

```
                                    TGT AGT CGC ACC AAC TGA CTA GTC TCT TCC ATC CTC   36
CGG AGC TCC GAC GTT CTC GGG GAC ATA AAC CCT GTT CTT GTC CTA ACC CGC CAA GGG GCC       96

ATG GAC TTG AGC GCG CTG GCG TCG AGC AGA GAA GTA CGG GGC CCT GGG CCC GGG GCT CCG      156
Met Asp Leu Ser Ala Leu Ala Ser Ser Arg Glu Val Arg Gly Pro Gly Pro Gly Ala Pro       20

GTG AAC CGG CCC CTG CTA CCG CTA CTG CTG CTT CTG CTC TTG CTA CCT CTG CCC GCC AGC      216
Val Asn Arg Pro Leu Leu Pro Leu Leu Leu Leu Leu Leu Leu Pro Leu Pro Ala Ser           40

GCC TGG TAC AAG CAC GTG GCG AGC CCT CGC TAT CAC ACA GTG GGT CGT GCC TCC GGG CTG      276
Ala Trp Tyr Lys His Val Ala Ser Pro Arg Tyr His Thr Val Gly Arg Ala Ser Gly Leu       60

CTC ATG GGG CTG CGC CGC TCG CCC TAC CTG TGG CGC CGT GCC TTG GGT GGG GCC GCT GGA      336
Leu Met Gly Leu Arg Arg Ser Pro Tyr Leu Trp Arg Arg Ala Leu Gly Gly Ala Ala Gly       80

CCG CTC GTG GGG CTC CCG GGA CAG ATG GCC CGC AGC GCT CTC CTG CTT CCT TCC CCC GGG      396
Pro Leu Val Gly Leu Pro Gly Gln Met Ala Arg Ser Ala Leu Leu Leu Pro Ser Pro Gly      100

CAG GAG CTG TGG GAG GTA CGA AGC AGG AGT TCA CCG GCA GGA CTT CCC GTG CAT GCA ACC      456
Gln Glu Leu Trp Glu Val Arg Ser Arg Ser Ser Pro Ala Gly Leu Pro Val His Ala Thr      120

CGG AGT CTG CGG GAC CTG GAG GGA GCC GGC CAA CCT GAG CAG TCG CTA AGC TTT CAG TCC      516
Arg Ser Leu Arg Asp Leu Glu Gly Ala Gle Gln Pro Glu Gln Ser Leu Ser Phe Gln Ser      140

TGG ACT TCA GCA GAG CCC GCT GCT AGA GCC TTC GGT GAG ACG CTT CGT GCC CAG CCA TGG      576
Trp Thr Ser Ala Glu Pro Ala Ala Arg Ala Phe Gly Glu Thr Leu Arg Ala Gln Pro Trp      160

TTC CTG CAG CAA ATC ATC TTT GCC GAT CCT GTC AGG CTC GAC GAC CGT CTC AAG AAC CGA      636
Phe Leu Gln Gln Ile Ile Phe Ala Asp Pro Val Arg Leu Asp Asp Arg Leu Lys Asn Arg      180

TGG CGC CCC CGT GCT TGA CCT AAG CAG GAG CAC AGC TTG TAG CTC CAG                      684
Trp Arg Pro Arg Ala ***                                                               185
```

Fig. 9

```
                                      TGA CTG GTC TCC ATC CTC TGG AGC TCC GAC GTG CTC GTT  39
CTC GGA GAC ATA AAC CCA GTT CTT GTC CTA ACC CTC CAA GGG GCA ATT GAC GTG AGC GCG  99

CTG GCG TCT AAC AGA GAA GTA CGG GGC CCT GGG CCC GGG ACT CCC AGG AAC CGG CCC CTG  159
Leu Ala Ser Asn Arg Glu Val Arg Gly Pro Gly Pro Gly Thr Pro Arg Asn Arg Pro Leu   20

CTG CCC CTG CTG CTG CTT CTG CTC TTG CTA CCG CTG CCC GCC AGC GCC TGG TAT AAG CAC  219
Leu Pro Leu Leu Leu Leu Leu Leu Leu Pro Leu Pro Ala Ser Ala Trp Tyr Lys His   40

GTG GCG AGT CCC CGC TAT CAC ACA GTG GGT CGT GCC TCC GGG CTG CTC ATG GGG CTG CGC  279
Val Ala Ser Pro Arg Tyr His Thr Val Gly Arg Ala Ser Gly Leu Leu Met Gly Leu Arg  60

CGC TCG CCC TAC CAG TGG CGC CGT GCC CTG GGC GGG GCT GCT GGA CCC CTC TCC CGG CTC  339
Arg Ser Pro Tyr Gln Trp Arg Arg Ala Leu Gly Gly Ala Ala Gly Pro Leu Ser Arg Leu  80

CCA GGA CCG GTC GCC CGC GGC GCT CTC CTG CTT CCT TCC TCA GGG CAG GAG CTG TGG GAG  399
Pro Gly Pro Val Ala Arg Gly Ala Leu Leu Leu Pro Ser Ser Gly Gln Glu Leu Trp Glu  100

GTA CGA AGC AGG AGC TCA CCT GCA GGG CTT CCC GTC CAT GCA CCC TGG AGT CCG CGG GAC  459
Val Arg Ser Arg Ser Ser Pro Ala Gly Leu Pro Val His Ala Pro Trp Ser Pro Arg Asp  120

CTG GAG GGA GTC CGC CAA CCG GAG CAG TCG CTA AGC CTT CAC TCC TGG ATC TCA GAG GAG  519
Leu Glu Gly Val Arg Gln Pro Glu Gln Ser Leu Ser Leu His Ser Trp Ile Ser Glu Glu  140

CCC GCT GCT AGA GCC TTC GGA GAG ACG CTT CGT GCC CAG CCA TGG TTC CTG CAG CAA GTC  579
Pro Ala Ala Arg Ala Phe Gly Glu Thr Leu Arg Ala Gln Pro Trp Phe Leu Gln Gln Val  160

ATC TTT GCC GAT CCT GTC AGG CCC AAG AAC CGA TGG CGC CCC CAT GCT TGA CCT AGG CAG  639
Ile Phe Ala Asp Pro Val Arg Pro Lys Asn Arg Trp Arg Pro His Ala ***                176
GAG CAC AGC TTG AAG CTC CA                                                         659
```

Fig. 23
(a) Blood glucose
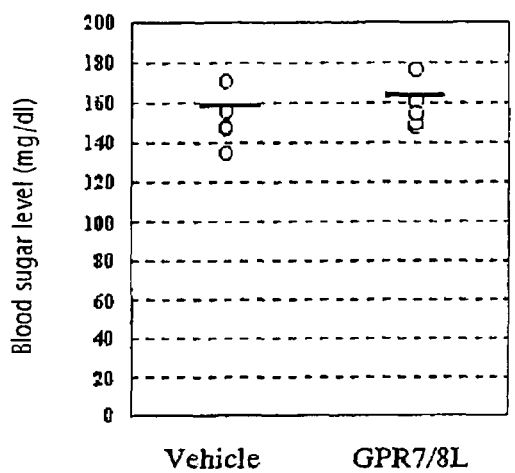
(b) Total blood cholesterol
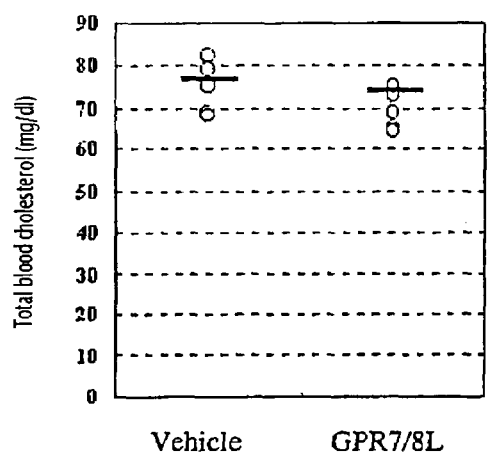
(c) Blood triglyceride level
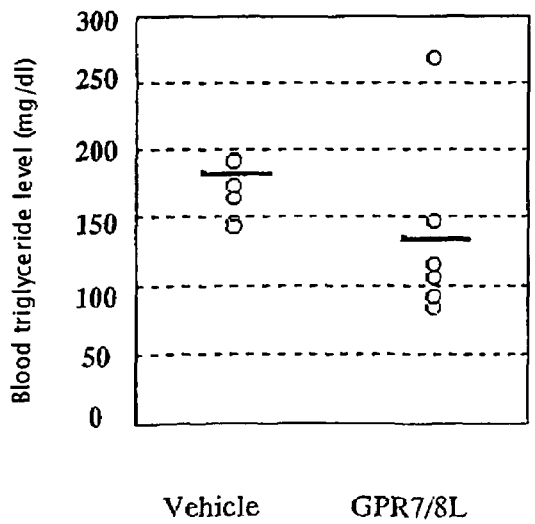

BODY WEIGHT GAIN INHIBITOR

CROSS-REFERENCE TO RELATED APPLICATION(S)

This application is a §371 application of copending international patent application PCT/JP02/13781, filed on Dec. 27, 2002, which application designates the United States.

FIELD OF THE INVENTION

The present invention relates to a body weight gain inhibitor, a body weight loss agent, an adipose gain inhibitor, a feeding inhibitor and the like.

BACKGROUND ART

A main cause for increase of lifestyle related diseases including diabetes, is that vital functions directed to accumulate adipose to prepare for starvation, which are typified by a so-called thrifty gene such as PPARγ, cannot adopt to modern dietary habit with a central focus on high fat diet or living environment such as immunobilization. Since resulting adiposis becomes a risk factor for hypertension as well as a cause for diabetes, development of anti-adiposis drug, which has a little side effect and is safe, is conductive to prevent onset of many lifestyle related diseases. Further, it has medical economically highest demands. As such antiadiposis drug, sibutramine, which is an inhibitor for reincorporation of catecholamine-serotonin, and orlistat, which is an inhibitor for fat absorption, are used at present. In addition to these drugs, β3 agonist, which is a calorigenic accelerator, neuropeptide Y antagonist, which is a central feeding inhibitor, melanocortin receptor subtype 4 agonist, and the like are developed or developing (J. C. Clapham et al., Pharmacol. Ther. 89: 81-121 (2001); M. Chiesi et al., Trends Pharmacol. Sci. 22: 247-254 (2001)).

In addition to these references, (1) Genomics 28: 84-91 (1995), and (2) WO 01/98494 publication are included.

However, it has been desired for development of safe body weight gain inhibitor or body weight loss agent, which has strong action and little side effect based on novel mechanism.

DISCLOSURE OF THE INVENTION

As a result of extensive investigations in order to solve the above problems, the present inventors have found that an endogenous ligand (WO 01/98494 publication) bound to GPR8 (Genomics 28: 84-91 (1995)) has a body weight gain inhibiting activity, and have come to accomplish the present invention.

Thus, the present invention relates to the following features:

(1) A body weight gain inhibitor, which comprises a polypeptide containing the same or substantially the same amino acid sequence as that represented by SEQ ID NO: 16, or its amide or ester, or salts thereof;

(2) A body weight loss agent, which comprises a polypeptide containing the same or substantially the same amino acid sequence as that represented by SEQ ID NO: 16, or its amide or ester, or salts thereof;

(3) An adipose gain inhibitor, which comprises a polypeptide containing the same or substantially the same amino acid sequence as that represented by SEQ ID NO: 16, or its amide or ester, or salts thereof;

(4) A feeding inhibitor, which comprises a polypeptide containing the same or substantially the same amino acid sequence as that represented by SEQ ID NO: 16, or its amide or ester, or salts thereof;

(5) A screening method of weight gain inhibitor, agent for weight loss, adipose gain inhibitor or feeding inhibitor, which is characterized by using a polypeptide containing the same or substantially the same amino acid sequence as that represented by SEQ ID NO: 16, or its amide or ester, or salts thereof;

(6) Further, the screening method according to (5), which uses a protein containing the same or substantially the same amino acid sequence as that represented by SEQ ID NO: 4, SEQ ID NO: 126, SEQ ID NO: 138 or SEQ ID NO: 144, its partial peptide, or salts thereof;

(7) A screening kit for body weight gain inhibitor, body weight loss agent, adipose gain inhibitor or feeding inhibitor, which is characterized by using a polypeptide containing the same or substantially the same amino acid sequence as that represented by SEQ ID NO: 16, or its amide or ester, or salts thereof;

(8) Further, the screening kit according to (7), which contains a protein containing the same or substantially the same amino acid sequence as that represented by SEQ ID NO: 4, SEQ ID NO: 126, SEQ ID NO: 138 or SEQ ID NO: 144, its partial peptide, or salts thereof;

(9) A body weight gain inhibitor, a body weight loss agent, an adipose gain inhibitor or a feeding inhibitor, which is obtained using the screening method according to (5) or the screening kit according to (7);

(10) A body weight gain inhibitor, a body weight loss agent, an adipose gain inhibitor or a feeding inhibitor, which comprises a compound or a salt thereof having an activity of a polypeptide containing the same or substantially the same amino acid ssequence as that represented by SEQ ID NO: 16, its amide or ester, or salts thereof;

(11) A body weight gain inhibitor, a body weight loss agent, an adipose gain inhibitor or a feeding inhibitor, which comprises an agonist to a protein containing the same or substantially the same amino acid sequence as that represented by SEQ ID NO: 4, SEQ ID NO: 126, SEQ ID NO: 138 or SEQ ID NO: 144, its partial peptide or salts thereof;

(12) A body weight gain inhibitor, a body weight loss agent, an adipose gain inhibitor or a feeding inhibitor, which comprises a polynucleotide containing the base sequence encoding a polypeptide containing the same or substantially the same amino acid ssequence as that represented by SEQ ID NO: 16, its amide or ester, or salts thereof;

(13) A screening method of body weight gain inhibitor, body weight loss agent, adipose gain inhibitor or feeding inhibitor, which is characterized by using a polynucleotide containing the base sequence encoding a polypeptide containing the same or substantially the same amino acid ssequence as that represented by SEQ ID NO: 16, its amide or ester, or salts thereof;

(14) A screening kit for body weight gain inhibitor, body weight loss agent, adipose gain inhibitor or feeding inhibitor, which is characterized by comprising a polynucleotide containing the base sequence encoding a polypeptide containing the same or substantially the same amino acid ssequence as that represented by SEQ ID NO: 16, its amide or ester, or salts thereof;

(15) A body weight gain inhibitor, a body weight loss agent, an adipose gain inhibitor or a feeding inhibitor, which is obtained using the screening method according to (13) or the screening kit according to (14);

(16) A polypeptide, which is characterized by comprising the amino acid sequence represented by SEQ ID NO: 149;
(17) The polypeptide according to (16), which is labeled;
(18) The screening method according to (5), in which the polypeptide according to (16) is used;
(19) The screening method according to (6), in which (i) the polypeptide according to (17) and (ii) a protein containing the same or substantially the same amino acid sequence as that represented by SEQ ID NO: 4, SEQ ID NO: 126, SEQ ID NO: 138 or SEQ ID NO: 144, its partial peptide or salts thereof, are used;
(20) The screening method according to (19), in which (i) the polypeptide according to (17) and (ii) a protein containing the same or substantially the same amino acid sequence as that represented by SEQ ID NO: 4 or SEQ ID NO: 144, its partial peptide or salts thereof, are used;
(21) The screening method according to (19), in which the polypeptide according to (17) and a protein containing the amino acid sequence represented by SEQ ID NO: 144, its partial peptide or salts thereof, are used;
(22) A method for body weight gain inhibition, body weight loss agent, adipose gain inhibition or feeding inhibition, which is characterized by administering to mammals an effective amount of (i) a polypeptide containing the same or substantially the same as that represented by SEQ ID NO: 16, its amide or ester, or salts thereof, (ii) a compound or a salt thereof having an activity of the polypeptide, the amide or ester, or salts thereof, or (iii) an agonist to a protein containing the same or substantially the same amino acid sequence as that represented by SEQ ID NO: 4, SEQ ID NO: 126, SEQ ID NO: 138 or SEQ ID NO: 144, its partial peptide or salts thereof;
(23) Use of (i) a polypeptide containing the same or substantially the same as that represented by SEQ ID NO: 16, its amide or ester, or salts thereof, (ii) a compound or a salt thereof having an activity of the polypeptide, the amide or ester, or salts thereof, or (iii) an agonist to a protein containing the same or substantially the same amino acid sequence as that represented by SEQ ID NO: 4, SEQ ID NO: 126, SEQ ID NO: 138 or SEQ ID NO: 144, its partial peptide or salts thereof for manufacturing a body weight gain inhibitor, a body weight loss agent, an adipose gain inhibitor or a feeding inhibitor.

BRIEF DESCRIPTION OF THE DRAWINGS

FIG. 6 shows the entire base sequence of cDNA encoding human derived GPR8 ligand peptide homologue precursor protein (SEQ ID NO: 41) and the entire amino acid sequence of human derived GPR8 ligand peptide homologue precursor receptor protein translated from the above base sequence. The deduced sequence of human derived GPR8 ligand peptide homologue consisting of 23 residues represents squares.

FIG. 7 shows the entire base sequence of cDNA encoding swine derived GPR8 ligand peptide homologue precursor protein (SEQ ID NO: 55) and the entire amino acid sequence of swine derived GPR8 ligand peptide homologue precursor receptor protein translated from the above base sequence. The deduced sequence of swine derived GPR8 ligand peptide homologue consisting of 23 residues represents squares.

FIG. 8 shows the entire base sequence of cDNA encoding rat derived GPR8 ligand peptide homologue precursor protein (SEQ ID NO: 72) and the entire amino acid sequence of rat derived GPR8 ligand peptide homologue precursor receptor protein translated from the above base sequence. The deduced sequence of rat derived GPR8 ligand peptide homologue consisting of 23 residues represents squares.

FIG. 9 shows the entire base sequence of cDNA encoding mouse derived GPR8 ligand peptide homologue precursor protein (SEQ ID NO: 90) and the entire amino acid sequence of mouse derived GPR8 ligand peptide homologue precursor receptor protein translated from the above base sequence. The deduced sequence of mouse derived GPR8 ligand peptide homologue consisting of 23 residues represents squares.

FIGS. 23A-C show an action of the hGPR8L(1-23), which was continuously administered under the skin, on (a) a blood glucose level, (b) total blood cholesterol level and (c) concentration of blood triglyceride for rat. In the figure, open circle and – (minus) represent numeral values for indivisuals and means, respectively.

BEST MODE FOR CARRYING OUT THE INVENTION

Figure 1:
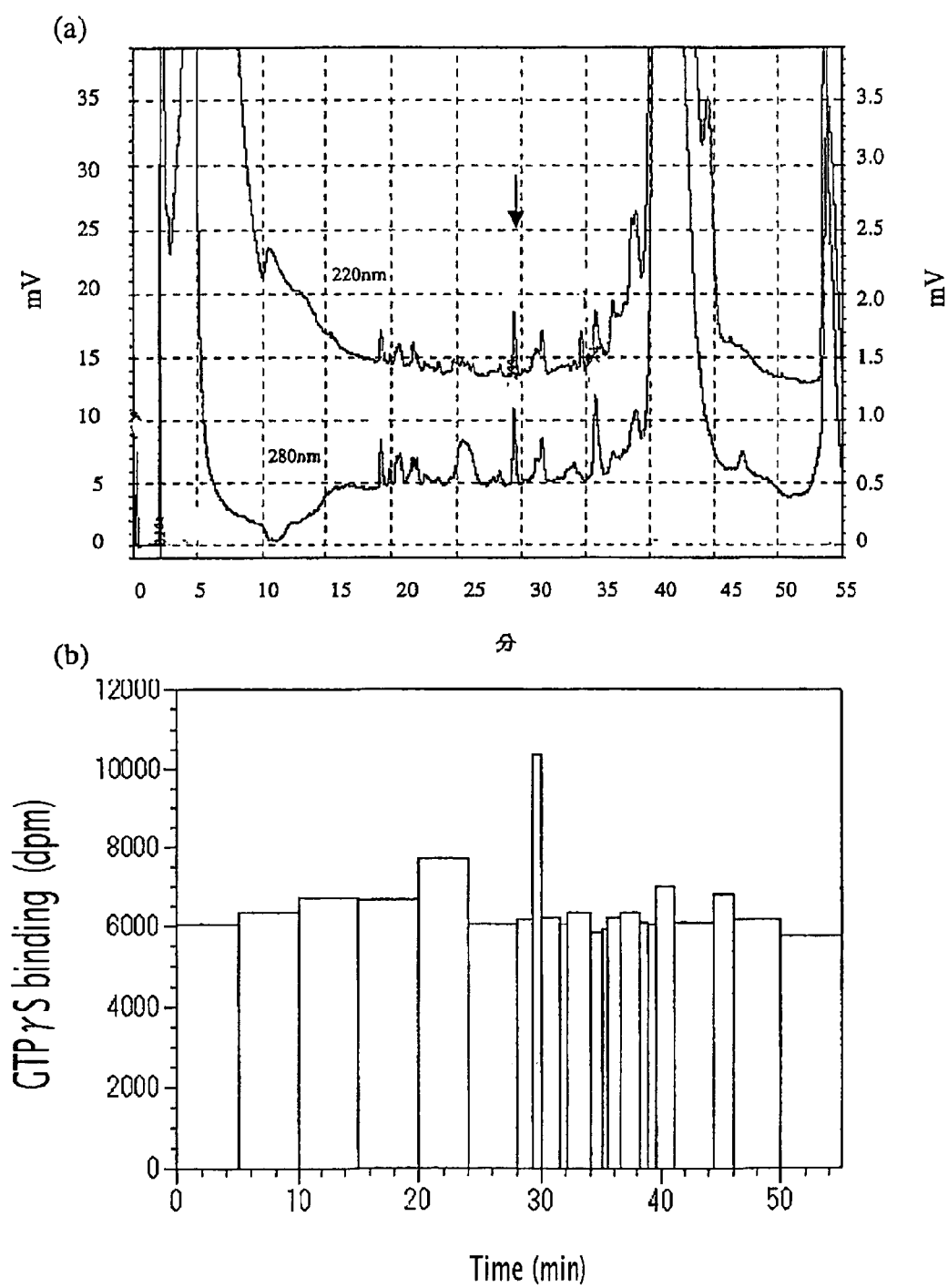
FIGS. 1A-1B show a UV absorbance obtained by HPLC (a) and a GTPγS activity of each peak (b) in the final step of purification for GPR8 using Wakosil-II 3C18HG column. The activity was recovered in the peak indicated by arrowhead.

The polypeptide having the same or substantially the same amino acid sequence as that represented by SEQ ID NO: 16, which is used in the present invention (hereinafter, sometimes referred to as the polypeptide of the present invention), may be any polypeptide derived from any cells (e.g., retina cells, liver cells, splenocytes, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophage, T cells, B cells, natural killer cells, mast cells, neutrophil, basophil, eosinophil, monocyte), megakaryocyte, synovial cells, chondrocytes, bone cells, osteoblasts, osteoclasts, mammary gland cells, hepatocytes or interstitial cells, the corresponding precursor cells, stem cells, cancer cells, etc.), or any tissues where such cells are present, e.g., brain or any region of the brain (e.g., retina, olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc. or hematocytes or its cultured cells (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01 and the like) from human and warm-blooded animals (e.g., guinea pigs, rats, mice, fowls, rabbits, swine, sheep, bovine, monkeys, etc.). The polypeptide may also be a synthetic polypeptide.

The amino acid sequence which has substantially the same amino acid sequence as that represented by SEQ ID NO: 16 includes an amino acid sequence having at least about 70% homology, preferably at least about 80% homology, more preferably at least about 90% homology, further preferably at least about 95% homology, or furthermore preferably at least about 98% to the amino acid sequence represented by SEQ ID NO: 16.

In particular, the amino acid sequence which has substantially the same amino acid sequence as that represented by SEQ ID NO: 16 includes, in addition to the above, (i) an amino acid sequence wherein 1 to 5 (preferably 1 to 3, more preferably 1 to 2, further preferably 1 (one)) amino acids are deleted from the amino acid sequence represented by SEQ ID NO: 16, (ii) an amino acid sequence wherein 1 to 5 (preferably 1 to 3, more preferably 1 to 2, further preferably 1 (one)) amino acids are added to the amino acid sequence represented by SEQ ID NO: 16, (iii) an amino acid sequence wherein 1 to 5 (preferably 1 to 3, more preferably 1 to 2, further preferably 1 (one)) amino acids are inserted into the amino acid sequence represented by SEQ ID NO: 16, (iv) an amino acid sequence wherein 1 to 5 (preferably 1 to 3, more preferably 1 to 2, further preferably 1 (one)) amino acids in the amino acid sequence represented by SEQ ID NO: 16 are substituted with other amino acids, or (v) an amino acid sequence in combination thereof.

Examples of the polypeptide having substantially the same amino acid sequence as that shown by SEQ ID NO: 16 preferably include a polypeptide having substantially the same amino acid sequence as that shown by SEQ ID NO: 16 and having the activity substantially equivalent to the amino acid sequence represented by SEQ ID NO: 16, etc.

Examples of the substantially equivalent activity include an activity, which the polypeptide of the present invention has, such as body weight gain inhibiting action, adipose gain inhibiting action, feeding inhibiting action, etc.

The term "substantially equivalent" is used to mean that the nature of the activity is the same.

Specific examples of substantially the same amino acid sequence as that represented by SEQ ID NO: 16 include the amino acid sequence represented by SEQ ID NO: 6, SEQ ID NO: 17, SEQ ID NO: 20, SEQ ID NO: 21, SEQ ID NO: 22, SEQ ID NO: 23, SEQ ID NO: 24, SEQ ID NO: 25, SEQ ID NO: 56, SEQ ID NO: 57, SEQ ID NO: 73, SEQ ID NO: 74, SEQ ID NO: 91, SEQ ID NO: 92, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113 or SEQ ID NO: 149.

Specific examples of the polypeptide of the present invention include the polypeptide having an ability of specific binding to GPR8 such as the polypeptide having the amino acid sequence represented by SEQ ID NO: 16, the polypeptide having the amino acid sequence represented by SEQ ID NO: 6, the polypeptide having the amino acid sequence represented by SEQ ID NO: 17, the polypeptide having the amino acid sequence represented by SEQ ID NO: 20, the polypeptide having the amino acid sequence represented by SEQ ID NO: 21, the polypeptide having the amino acid sequence represented by SEQ ID NO: 22, the polypeptide having the amino acid sequence represented by SEQ ID NO: 23, the polypeptide having the amino acid sequence represented by SEQ ID NO: 24, the polypeptide having the amino acid sequence represented by SEQ ID NO: 25, the polypeptide having the amino acid sequence represented by SEQ ID NO: 56, the polypeptide having the amino acid sequence represented by SEQ ID NO: 57, the polypeptide having the amino acid sequence represented by SEQ ID NO: 73, the polypeptide having the amino acid sequence represented by SEQ ID NO: 74, the polypeptide having the amino acid sequence represented by SEQ ID NO: 91, the polypeptide having the amino acid sequence represented by SEQ ID NO: 92, the polypeptide having the amino acid sequence represented by SEQ ID NO: 95, the polypeptide having the amino acid sequence represented by SEQ ID NO: 96, the polypeptide having the amino acid sequence represented by SEQ ID NO: 97, the polypeptide having the amino acid sequence represented by SEQ ID NO: 98, the polypeptide having the amino acid sequence represented by SEQ ID NO: 99, the polypeptide having the amino acid sequence represented by SEQ ID NO: 100, the polypeptide having the amino acid sequence represented by SEQ ID NO: 101, the polypeptide having the amino acid sequence represented by SEQ ID NO: 102, the polypeptide having the amino acid sequence represented by SEQ ID NO: 103, the polypeptide having the amino acid sequence represented by SEQ ID NO: 104, the polypeptide having the amino acid sequence represented by SEQ ID NO: 105, the polypeptide having the amino acid sequence represented by SEQ ID NO: 106, the polypeptide having the amino acid sequence represented by SEQ ID NO: 107, the polypeptide having the amino acid sequence represented by SEQ ID NO: 108, the polypeptide having the amino acid sequence represented by SEQ ID NO: 109, the polypeptide having the amino acid sequence represented by SEQ ID NO: 110, the polypeptide having the amino acid sequence represented by SEQ ID NO: 111, the polypeptide having the amino acid sequence represented by SEQ ID NO: 112, the polypeptide having the amino acid sequence represented by SEQ ID NO: 113, the polypeptide having the amino acid sequence represented by SEQ ID NO: 149 and the like.

The polypeptide of the present invention also includes a precursor polypeptide of the polypeptide of the present invention.

Specific examples of the precursor polypeptide include the polypeptide characterized by containing the same or substantially the same amino acid sequence as that represented by SEQ iD NO: 15.

More specifically, substantially the same amino acid sequence as that represented by SEQ ID NO: 15 includes the amino acid sequence having at least about 80%, preferably at least about 90%, more preferably at least about 95% homology to the amino acid sequence represented by SEQ ID NO: 15.

In particular, the amino acid sequence which has substantially the same amino acid sequence as that represented by SEQ ID NO: 15 includes, in addition to the above, (i) an amino acid sequence wherein 1 to 15 (preferably 1 to 10, more preferably 1 to 5, further preferably 1 to 3) amino acids are deleted from the amino acid sequence represented by SEQ ID NO: 15, (ii) an amino acid sequence wherein 1 to 100 (preferably 1 to 50, more preferably 1 to 5, further preferably 1 to 3) amino acids are added to the amino acid sequence represented by SEQ ID NO: 15, (iii) an amino acid sequence wherein 1 to 15 (preferably 1 to 10, more preferably 1 to 5, further preferably 1 to 3) amino acids are inserted into the amino acid sequence represented by SEQ ID NO: 15, (iv) an amino acid sequence wherein 1 to 15 (preferably 1 to 10, more preferably 1 to 5, further preferably 1 to 3) amino acids in the amino acid sequence represented by SEQ ID NO: 15 are substituted with other amino acids, or (v) an amino acid sequence in combination of (i) to (iv).

Specific examples of substantially the same amino acid sequence as that represented by SEQ ID NO: 15 include the amino acid sequence represented by SEQ ID NO: 42, SEQ ID NO: 55, SEQ ID NO: 72 or SEQ ID NO: 90, and the like.

Specific examples of the above-mentioned precursor polypeptide include the polypeptide having the amino acid sequence represented by SEQ ID NO: 15, the polypeptide having the amino acid sequence represented by SEQ ID NO: 42, the polypeptide having the amino acid sequence represented by SEQ ID NO: 55, the polypeptide having the amino acid sequence represented by SEQ ID NO: 72, the polypeptide having the amino acid sequence represented by SEQ ID NO: 90 and the like.

Receptors for the polypeptide of the present invention include, among various receptors, receptors having a binding activity to the polypeptide of the present invention and detecting cell stimulating activities (e.g., the activities that accelerate arachidonic acid release, acetylcholine release, intracellular $Ca^{2+}$ release, intracellular cAMP production/suppression, intracellular cGMP production, inositol phosphate production, change in cell membrane potential, phosphorylation of intracellular proteins, activation of c-fos, pH reduction, GTPγS binding activity, etc.) in the receptor-expressing cells by the polypeptide of the present invention.

Specifically, (1) GPR8 (SEQ ID NO: 4: Genomics, 28, 84-91, 1995) or substantially the same amino acid sequence as GPR8 (the protein containing substantially the same amino acid sequence as that represented by SEQ ID NO: 4), (2) the receptor containing the same or substantially the same amino acid sequence as that represented by SEQ ID NO: 126, (3) the receptor containing the same or substantially the same amino acid sequence as that represented by SEQ ID NO: 138, (4) GPR7 (SEQ ID NO: 144: Genomics, 28, 84-91, 1995) and others are included.

The protein having the same or substantially the same amino acid sequence as that represented by SEQ ID NO: 4, the protein having the same or substantially the same amino acid sequence as that represented by SEQ ID NO: 126, the protein having the same or substantially the same amino acid sequence as that represented by SEQ ID NO: 138, the protein having the same or substantially the same amino acid sequence as that represented by SEQ ID NO: 144 (hereinafter, sometimes referred to as the polypeptide of the present invention), may be any polypeptide derived from any cells (e.g., retina cells, liver cells, splenocytes, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophage, T cells, B cells, natural killer cells, mast cells, neutrophil, basophil, eosinophil, monocyte), megakaryocyte, synovial cells, chondrocytes, bone cells, osteoblasts, osteoclasts, mammary gland cells, hepatocytes or interstitial cells, the corresponding precursor cells, stem cells, cancer cells, etc.), or any tissues where such cells are present, e.g., brain or any region of the brain (e.g., retina, olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc. or hematocytes or its cultured cells (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01 and the like) from human and warm-blooded animals (e.g., guinea pigs, rats, mice, fowls, rabbits, swine, sheep, bovine, monkeys, etc.). The polypeptide may also be a synthetic polypeptide.

The amino acid sequence which has substantially the same amino acid sequence as that represented by SEQ ID NO: 4 includes an amino acid sequence having at least about 70% homology, preferably at least about 80% homology, more preferably at least about 90% homology to the amino acid sequence represented by SEQ ID NO: 4.

The amino acid sequence which has substantially the same amino acid sequence as that represented by SEQ ID NO: 126 includes an amino acid sequence having at least about 85% homology, preferably at least about 90% homology, more preferably at least about 95% homology to the amino acid sequence represented by SEQ ID NO: 126.

The amino acid sequence which has substantially the same amino acid sequence as that represented by SEQ ID NO: 138 includes an amino acid sequence having at least about 86% homology, preferably at least about 90% homology, more preferably at least about 95% homology to the amino acid sequence represented by SEQ ID NO: 138.

The amino acid sequence which has substantially the same amino acid sequence as that represented by SEQ ID NO: 144 includes an amino acid sequence having at least about 70% homology, preferably at least about 80% homology, more preferably at least about 90% homology to the amino acid sequence represented by SEQ ID NO: 144.

Examples of the protein having substantially the same amino acid sequence as that shown by SEQ ID NO: 4, SEQ ID NO: 126, SEQ ID NO: 138 or SEQ ID NO: 144 preferably include a polypeptide having substantially the same amino acid sequence as that shown by SEQ ID NO: 4, SEQ ID NO: 126, SEQ ID NO: 138 or SEQ ID NO: 144, and having the activity substantially equivalent to the protein having the amino acid sequence represented by SEQ ID NO: 4, SEQ ID NO: 126, SEQ ID NO: 138 or SEQ ID NO: 144, etc.

Substantially the same amino acid sequence as that represented by SEQ ID NO: 4, SEQ ID NO: 126, SEQ ID NO: 138 or SEQ ID NO: 144 includes (i) an amino acid sequence wherein 1 to 15 (preferably 1 to 10, more preferably 1 to 5, further preferably 1 to 3) amino acids are deleted from the amino acid sequence represented by SEQ ID NO: 4, SEQ ID NO: 126, SEQ ID NO: 138 or SEQ ID NO: 144, (ii) an amino acid sequence wherein 1 to 15 (preferably 1 to 10, more preferably 1 to 5, further preferably 1 to 3) amino acids are added to the amino acid sequence represented by SEQ ID NO: 4, SEQ ID NO: 126, SEQ ID NO: 138 or SEQ ID NO: 144, (iii) an amino acid sequence wherein 1 to 15 (preferably 1 to 10, more preferably 1 to 5, further preferably 1 to 3) amino acids are inserted into the amino acid sequence represented by SEQ ID NO: 4, SEQ ID NO: 126, SEQ ID NO: 138 or SEQ ID NO: 144, (iv) an amino acid sequence wherein 1 to 15 (preferably 1 to 10, more preferably 1 to 5, further preferably 1 to 3) amino acids in the amino acid sequence represented by SEQ ID NO: 4, SEQ ID NO: 126, SEQ ID NO: 138 or SEQ ID NO: 144 are substituted with other amino acids, or (v) an amino acid sequence in combination of (i) to (iv).

As specific examples of the receptor of the present invention, the protein containing the amino acid sequence represented by SEQ ID NO: 4, the protein containing the amino acid sequence represented by SEQ ID NO: 126, the protein containing the amino acid sequence represented by SEQ ID NO: 138, the protein containing the amino acid sequence represented by SEQ ID NO: 144 and the like are used.

A partial peptide of the receptor of the present invention (hereinafter, sometimes referred to as a partial peptide of the present invention) may be any peptide as long as it is a partial peptide that can be utilized for a method of screening medicines described below. Preferably, a partial peptide having an ability to bind to the polypeptide of the present invention, a partial peptide containing the amino acid sequence corresponding to the region out of cell membrane, and the like are used. Preferred partial peptides are those having at least 20, preferably at least 50, and more preferably at least 100 amino acids, in the amino acid sequence which constitutes the receptor of the present invention. It may be (i) an amino acid sequence wherein 1 or at least 2 (preferably 1 to 10, more preferably several (1 to 5)) amino acids are deleted, (ii) an amino acid sequence wherein 1 or at least 2 (preferably 1 to 20, more preferably 1 to 10, further preferably several (1 to 5)) amino acids are added, (iii) an amino acid sequence wherein 1 or at least 2 (preferably 1 to 10, more preferably several, further preferably 1 to 5) amino acids are substituted with other amino acids.

Specific examples include (a) a partial peptide containing 1 or at least 2 partial amino acid sequences selected from a partial amino acid sequence or a portion thereof consisting of amino acid residues 1 (Met)-123 (Phe), a partial amino acid sequence or a portion thereof consisting of amino acid residues 301 (Asn)-358 (Lys), a partial amino acid sequence or a portion thereof consisting of amino acid residues 548 (Tyr)-593 (Arg) and a partial amino acid sequence or a portion thereof consisting of amino acid residues 843 (Ala)-895 (Ile) in the amino acid sequence represented by SEQ ID NO: 4, (b) a partial amino acid sequence or a portion thereof consisting of amino acid residues 1 (Met)-85 (Asp) and a partial amino acid sequence or a portion thereof consisting of amino acid residues 222 (Cys)-329 (Ala) in the amino acid sequence represented by SEQ ID NO: 126, and the like.

The polypeptide, the receptor or its partial peptide of the present invention are represented in accordance with the conventional way of describing peptides, that is, the N-terminus (amino terminus) at the left hand and the C-terminus (carboxyl terminus) at the right hand. In the polypeptide, the receptor or its partial peptide of the present invention, the C-terminus may be in the form of a carboxyl group (—COOH), a carboxylate (—COO), an amide (—CONH$_2$) or an ester (—COOR).

Examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl group such as a phenyl-$C_{1-2}$-alkyl group, e.g., benzyl, phenethyl, etc., or an α-naphthyl-$C_{1-2}$-alkyl group such as α-naphthylmethyl, etc.; and the like. In addition, pivaloyloxymethyl or the like, which is used widely as an ester for oral administration, may also be used.

Where the polypeptide, the receptor or its partial peptide of the present invention contains a carboxyl group (or a carboxylate) at a position other than the C-terminus, its amide or ester form is also included. The ester group may be the same group as that described with respect to the C-terminus described above.

Furthermore, examples of the polypeptide, the receptor or its partial peptide of the present invention include variants of the above receptor proteins, wherein the amino group at the N-terminal methionine residue is protected with a protecting group (for example, a $C_{1-6}$ acyl group such as a $C_{2-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated proteins such as glycoproteins bound to sugar chains.

For salts of the polypeptide, the receptor or the partial peptide of the present invention, salts with physiologically acceptable acids (e.g., inorganic acids, organic acids) or bases (e.g., alkali metal salts) are used. In particular, preferred are salts with physiologically acceptable acid addition salts. Examples of the salts include salts with, for example, inorganic acids (e.g., hydrochloric acid, phosphoric acid, hydrobromic acid, sulfuric acid); salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The polypeptide, the receptor or its partial peptide of the present invention may be manufactured by a publicly known method used to purify a polypeptide from human and warm blooded animal cells or tissues described above, or by culturing a transformant that contains the DNA encoding the polypeptide, as will be later described. Furthermore, the polypeptide, the receptor or its partial peptide of the present invention may also be manufactured by the methods for synthesizing proteins or by modifications thereof, which will also be described hereinafter.

Where the polypeptide, the receptor or its partial peptide of the present invention are manufactured from human or other mammalian tissues or cells, human or other mammalian tissues or cells are homogenized, then extracted with an acid or the like, and the extract obtained can be isolated and purified by a combination of chromatography techniques such as reverse phase chromatography, ion exchange chromatography, and the like.

To synthesize the polypeptide, the receptor, its partial peptide, or salts or amides thereof according to the present invention, commercially available resins that are used for polypeptide synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmehtylphenyl acetamidomethyl resin, polyacrylamide resin, 4-(2',4'-dimethoxyphenyl-hydroxymethyl)phenoxy resin, 4-(2',4'-dimethoxyphenyl-Fmoc aminoethyl) phenoxy resin, etc. Using these resins, amino acids in which α-amino groups and functional groups on the side chains are appropriately protected are condensed on the resin in the order of the sequence of the objective polypeptide according to various condensation methods publicly known in the art. At the end of the reaction, the receptor protein is excised from the resin and at the same time, the protecting groups are removed. Then, intramolecular disulfide bond-forming reaction is performed in a highly diluted solution to obtain the objective polypeptide, receptor, partial peptide, or amides thereof.

For condensation of the protected amino acids described above, a variety of activation reagents for polypeptide synthesis may be used, and carbodiimides are particularly preferable. Examples of such carbodiimides include DCC, N,N'-diisopropylcarbodiimide, N-ethyl-N'-(3-dimethylaminoprolyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents known to be usable for polypeptide condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to polypeptide binding reactions and is usually selected in the range of approximately −20° C. to 50° C. The activated amino acid derivatives are used generally in an excess of 1.5 to 4 times. The condensation is examined by a test using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to exert no influence on the following reactions.

Examples of the protecting groups used to protect the amino groups of the starting materials include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups suitable for the esterification include a lower ($C_{1-6}$) alkanoyl group, such as acetyl group, an aroyl group such as benzoyl group, and a group derived from carbonic acid such as benzyloxycarbonyl group, ethoxycarbonyl group, etc. Examples of a group suitable for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting materials include the corresponding acid anhydrides, azides, activated esters (esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)). As the activated amino acids, in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethane-sulfonic acid or trifluoroacetic acid, or a mixture solution of these acids; a treatment with a base such as diisopropylethylamine, triethylamine, piperidine or piperazine; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol or 1,4-butanedithiol, as well as by a treatment with an alkali such as a dilute sodium hydroxide solution and dilute ammonia.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the amides of the polypeptide, receptor or its partial peptide of the present invention, for example, the α-carboxyl group of the carboxy terminal amino acid is first protected by amidation; the peptide (polypeptide) chain is then extended from the amino group side to a desired length. Thereafter, a polypeptide in which only the protecting group of the N-terminal α-amino group in the peptide chain has been eliminated and a polypeptide in which only the protecting group of the C-terminal carboxyl group has been eliminated are prepared. Both polypeptides are condensed in a mixture of the solvents described above. The details of the condensation reaction are the same as described above. After the protected polypeptide obtained by the condensation is purified, all the protecting groups are eliminated by the method described above to give the desired crude polypeptide. This crude polypeptide is purified by various known purification means. Lyophilization of the major fraction gives the amide of the desired polypeptide, the receptor or a partial peptide of the present invention.

To prepare the esterified form of the polypeptide, the receptor or its partial peptide of the present invention, for example, the α-carboxyl group of the carboxy terminal amino acid is condensed with a desired alcohol to prepare the amino acid ester, which is followed by procedure similar to the preparation of the amidated form of the polypeptide, the receptor or its partial peptide of the present invention to give the ester form of the desired polypeptide, the receptor or its partial peptide of the present invention.

The polypeptide, the receptor, or its partial peptide of the present invention can be manufactured by publicly known methods for peptide synthesis, or the partial peptide of the receptor can be manufactured by cleaving the receptor with an appropriate peptidase. For the methods for peptide synthesis, for example, either solid phase synthesis or liquid phase synthesis may be used. That is, the partial peptide or amino acids that can constitute the polypeptide, the receptor or its partial peptide of the present invention are condensed with the remaining part. Where the product contains protecting groups, these protecting groups are removed to give the desired peptide. Publicly known methods for condensation and elimination of the protecting groups are described in (a)-(e) below.

(a) M. Bodanszky & M. A. Ondetti: Peptide Synthesis, Interscience Publishers, New York (1966)

(b) Schroeder & Luebke: The Peptide, Academic Press, New York (1965)

(c) Nobuo Izumiya, et al.: *Peptide Gosei-no-Kiso to Jikken* (Basics and experiments of peptide synthesis), published by Maruzen Co. (1975)

(d) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)

(e) Haruaki Yajima, ed.: *Zoku Iyakuhin no Kaihatsu* (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the polypeptide, the receptor or its partial peptide of the present invention. When the polypeptide, the receptor or its partial peptide obtained by the above methods are in a free form, they can be converted into an appropriate salt by a publicly known method; when the polypeptide, the receptor or its partial peptide is obtained in a salt form, they can be converted into a free form by a publicly known method.

The DNA encoding the polypeptide, the receptor or its partial peptide of the present invention may be any DNA so long as it contains the base sequence encoding the polypeptide, the receptor or its partial peptide of the present invention described above. In addition, the DNA may be any of genomic DNA, genomic DNA library, cDNA derived from the cells and tissues described above, cDNA library derived from the cells and tissues described above and synthetic DNA.

The vector to be used for the library may be any of bacteriophage, plasmid, cosmid and phagemid. The DNA may also be directly amplified by reverse transcriptase polymerase chain reaction (hereinafter abbreviated as RT-PCR) using the total RNA or mRNA fraction prepared from the cells and tissues described above.

The DNA encoding the polypeptide of the present invention includes, for example, (a) DNA containing the base sequence represented by SEQ ID NO: 18, SEQ ID NO: 19, SEQ ID NO: 26, SEQ ID NO: 27, SEQ ID NO: 28, SEQ ID NO: 29, SEQ ID NO: 30, SEQ ID NO: 31, SEQ ID NO: 58, SEQ ID NO: 59, SEQ ID NO: 75, SEQ ID NO: 76, SEQ ID NO: 93, SEQ ID NO: 94, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125 or SEQ ID NO: 150, (b) DNA having the base sequence hybridizable to the base sequence represented by SEQ ID NO: 18, SEQ ID NO: 19, SEQ ID NO: 26, SEQ ID NO: 27, SEQ ID NO: 28, SEQ ID NO: 29, SEQ ID NO: 30, SEQ ID NO: 31, SEQ ID NO: 58, SEQ ID NO: 59, SEQ ID NO: 75, SEQ ID NO: 76, SEQ ID NO: 93, SEQ ID NO: 94, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125 or SEQ ID NO: 150 under highly stringent conditions and encoding a polypeptide having the activities substantially equivalent to those of the polypeptide of the present invention, (c) DNA having the base sequence represented by SEQ ID NO: 14, SEQ ID NO: 41, SEQ ID NO: 54, SEQ ID NO: 71 or SEQ ID NO: 89, or (d) DNA having the base sequence hybridizable to the base sequence represented by SEQ ID NO: 14, SEQ ID NO: 41, SEQ ID NO: 54, SEQ ID NO: 71 or SEQ ID NO: 89 under highly stringent conditions.

Specific examples of the DNA hybridizable to the base sequence represented by (i) SEQ ID NO: 18, SEQ ID NO: 19, SEQ ID NO: 26, SEQ ID NO: 27, SEQ ID NO: 28, SEQ ID NO: 29, SEQ ID NO: 30, SEQ ID NO: 31, SEQ ID NO: 58, SEQ ID NO: 59, SEQ ID NO: 75, SEQ ID NO: 76, SEQ ID NO: 93, SEQ ID NO: 94, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125 or SEQ ID NO: 150 or (ii) SEQ ID NO: 14, SEQ ID NO: 41, SEQ ID NO: 54, SEQ ID NO: 71 or SEQ ID NO: 89 under highly stringent conditions include DNA containing a base sequence having at least about 70% homology, preferably at least about 80% homology, more preferably at least about 90% homology, and further preferably at least about 95% homology to the base sequence represented by (i) SEQ ID NO: 18, SEQ ID NO: 19, SEQ ID NO: 26, SEQ ID NO: 27, SEQ ID NO: 28, SEQ ID NO: 29, SEQ ID NO: 30, SEQ ID NO: 31, SEQ ID NO: 58, SEQ ID NO: 59, SEQ ID NO: 75, SEQ ID NO: 76, SEQ ID NO: 93, SEQ ID NO: 94, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125 or SEQ ID NO: 150 or (ii) SEQ ID NO: 14, SEQ ID NO: 41, SEQ ID NO: 54, SEQ ID NO: 71 or SEQ ID NO: 89.

The hybridization can be carried out by publicly known methods or by modifications of these methods, for example, according to the method described in Molecular Cloning, 2nd (J. Sambrook et al., Cold Spring Harbor Lab. Press, 1989). A commercially available library may also be used according to the instructions of the attached manufacturer's protocol. More preferably, the hybridization can be carried out under highly stringent conditions.

The highly stringent conditions used herein are, for example, those in a sodium concentration at about 19 mM to about 40 mM, preferably about 19 mM to about 20 mM at a temperature of about 50° C. to about 70° C., preferably about 60° C. to about 65° C. In particular, hybridization conditions in a sodium concentration of about 19 mM at a temperature of about 65° C. are most preferred.

More specifically,
(i) for the DNA encoding the polypeptide containing the amino acid sequence represented by SEQ ID NO: 16, there may be employed DNA containing the base sequence represented by SEQ ID NO: 18;
(ii) for the DNA encoding the polypeptide containing the amino acid sequence represented by SEQ ID NO: 17, there may be employed DNA containing the base sequence represented by SEQ ID NO: 19;
(iii) for the DNA encoding the polypeptide containing the amino acid sequence represented by SEQ ID NO: 20, there may be employed DNA containing the base sequence represented by SEQ ID NO: 26;
(iv) for the DNA encoding the polypeptide containing the amino acid sequence represented by SEQ ID NO: 21, there may be employed DNA containing the base sequence represented by SEQ ID NO: 27;
(v) for the DNA encoding the polypeptide containing the amino acid sequence represented by SEQ ID NO: 22, there may be employed DNA containing the base sequence represented by SEQ ID NO: 28;
(vi) for the DNA encoding the polypeptide containing the amino acid sequence represented by SEQ ID NO: 23, there may be employed DNA containing the base sequence represented by SEQ ID NO: 29;
(vii) for the DNA encoding the polypeptide containing the amino acid sequence represented by SEQ ID NO: 24, there may be employed DNA containing the base sequence represented by SEQ ID NO: 30;
(viii) for the DNA encoding the polypeptide containing the amino acid sequence represented by SEQ ID NO: 25, there may be employed DNA containing the base sequence represented by SEQ ID NO: 31;
(ix) for the DNA encoding the polypeptide containing the amino acid sequence represented by SEQ ID NO: 56, there may be employed DNA containing the base sequence represented by SEQ ID NO: 58;
(x) for the DNA encoding the polypeptide containing the amino acid sequence represented by SEQ ID NO: 57, there may be employed DNA containing the base sequence represented by SEQ ID NO: 59;
(xi) for the DNA encoding the polypeptide containing the amino acid sequence represented by SEQ ID NO: 73, there may be employed DNA containing the base sequence represented by SEQ ID NO: 75;

(xii) for the DNA encoding the polypeptide containing the amino acid sequence represented by SEQ ID NO: 74, there may be employed DNA containing the base sequence represented by SEQ ID NO: 76;

(xiii) for the DNA encoding the polypeptide containing the amino acid sequence represented by SEQ ID NO: 91, there may be employed DNA containing the base sequence represented by SEQ ID NO: 93;

(xiv) for the DNA encoding the polypeptide containing the amino acid sequence represented by SEQ ID NO: 92, there may be employed DNA containing the base sequence represented by SEQ ID NO: 94;

(xv) for the DNA encoding the polypeptide containing the amino acid sequence represented by SEQ ID NO: 95, there may be employed DNA containing the base sequence represented by SEQ ID NO: 18;

(xvi) for the DNA encoding the polypeptide containing the amino acid sequence represented by SEQ ID NO: 96, there may be employed DNA containing the base sequence represented by SEQ ID NO: 114;

(xvii) for the DNA encoding the polypeptide containing the amino acid sequence represented by SEQ ID NO: 97, there may be employed DNA containing the base sequence represented by SEQ ID NO: 115;

(xviii) for the DNA encoding the polypeptide containing the amino acid sequence represented by SEQ ID NO: 98, there may be employed DNA containing the base sequence represented by SEQ ID NO: 116;

(xix) for the DNA encoding the polypeptide containing the amino acid sequence represented by SEQ ID NO: 99, there may be employed DNA containing the base sequence represented by SEQ ID NO: 117;

(xx) for the DNA encoding the polypeptide containing the amino acid sequence represented by SEQ ID NO: 100, there may be employed DNA containing the base sequence represented by SEQ ID NO: 118;

(xxi) for the DNA encoding the polypeptide containing the amino acid sequence represented by SEQ ID NO: 101, there may be employed DNA containing the base sequence represented by SEQ ID NO: 119;

(xxii) for the DNA encoding the polypeptide containing the amino acid sequence represented by SEQ ID NO: 102, there may be employed DNA containing the base sequence represented by SEQ ID NO: 120;

(xxiii) for the DNA encoding the polypeptide containing the amino acid sequence represented by SEQ ID NO: 103, there may be employed DNA containing the base sequence represented by SEQ ID NO: 58;

(xxiv) for the DNA encoding the polypeptide containing the amino acid sequence represented by SEQ ID NO: 104, there may be employed DNA containing the base sequence represented by SEQ ID NO: 75;

(xxv) for the DNA encoding the polypeptide containing the amino acid sequence represented by SEQ ID NO: 105, there may be employed DNA containing the base sequence represented by SEQ ID NO: 18;

(xxvi) for the DNA encoding the polypeptide containing the amino acid sequence represented by SEQ ID NO: 106, there may be employed DNA containing the base sequence represented by SEQ ID NO: 18;

(xxvii) for the DNA encoding the polypeptide containing the amino acid sequence represented by SEQ ID NO: 107, there may be employed DNA containing the base sequence represented by SEQ ID NO: 121;

(xxviii) for the DNA encoding the polypeptide containing the amino acid sequence represented by SEQ ID NO: 108, there may be employed DNA containing the base sequence represented by SEQ ID NO: 122;

(xxix) for the DNA encoding the polypeptide containing the amino acid sequence represented by SEQ ID NO: 109, there may be employed DNA containing the base sequence represented by SEQ ID NO: 123;

(xxx) for the DNA encoding the polypeptide containing the amino acid sequence represented by SEQ ID NO: 110, there may be employed DNA containing the base sequence represented by SEQ ID NO: 124;

(xxxi) for the DNA encoding the polypeptide containing the amino acid sequence represented by SEQ ID NO: 6, there may be employed DNA containing the base sequence represented by SEQ ID NO: 125;

(xxxii) for the DNA encoding the polypeptide containing the amino acid sequence represented by SEQ ID NO: 111, there may be employed DNA containing the base sequence represented by SEQ ID NO: 121;

(xxxiii) for the DNA encoding the polypeptide containing the amino acid sequence represented by SEQ ID NO: 112, there may be employed DNA containing the base sequence represented by SEQ ID NO: 18;

(xxxiv) for the DNA encoding the polypeptide containing the amino acid sequence represented by SEQ ID NO: 113, there may be employed DNA containing the base sequence represented by SEQ ID NO: 121;

(xxxv) for the DNA encoding the polypeptide containing the amino acid sequence represented by SEQ ID NO: 149, there may be employed DNA containing the base sequence represented by SEQ ID NO: 150.

For the DNA encoding the receptor of the present invention, it may be any of DNA, which includes, for example, (1) DNA containing the base sequence represented by SEQ ID NO: 32, or DNA having the base sequence hybridizable to that represented by SEQ ID NO: 32 under high stringent conditions and encoding the protein having a substantially equivalent activity to that of the protein containing the amino acid ssequence represented by SEQ ID NO: 4, (2) DNA containing the base sequence represented by SEQ ID NO: 127, or DNA having the base sequence hybridizable to that represented by SEQ ID NO: 32 under high stringent conditions and encoding the protein having a substantially equivalent activity to that of the protein containing the amino acid ssequence represented by SEQ ID NO: 126, (3) DNA containing the base sequence represented by SEQ ID NO: 139, or DNA having the base sequence hybridizable to that represented by SEQ ID NO: 139 under high stringent conditions and encoding the protein having a substantially equivalent activity to that of the protein containing the amino acid ssequence represented by SEQ ID NO: 138, (4) DNA containing the base sequence represented by SEQ ID NO: 143, or DNA having the base sequence hybridizable to that represented by SEQ ID NO: 143 under high stringent conditions and encoding the protein having a substantially equivalent activity to that of the protein containing the amino acid ssequence represented by SEQ ID NO: 143.

For the DNA hybridizable to the base sequence represented by SEQ ID NO: 32, SEQ ID NO: 127, SEQ ID NO: 139 or SEQ ID NO: 143 under high stringent conditions, there may be utilized, for example, DNA containg the base sequence having at least about 70% homology, preferably at least about 80% homology, more preferably at least about 90% homology, further preferably at least about 95% homology to that represented by SEQ ID NO: 32, SEQ ID NO: 127, SEQ ID NO: 139 or SEQ ID NO: 143.

The hybridization can be carried out by publicly known methods or by a modification thereof, for example, in accordance with the method described in Molecular Cloning, 2nd ed., J. Sambrook et al., Cold Spring Harbor Lab. Press, (1989). A commercially available library may also be used according to the instructions of the attached manufacturer's protocol. Preferably, the hybridization can be carried out under high stringent conditions.

The high stringent conditions used herein are, for example, those in a sodium concentration at about 19 to about 40 mM, preferably about 19 to about 20 mM at a temperature of about 50 to about 70° C., preferably about 60 to about 65° C. In particular, hybridization conditions in a sodium concentration at about 19 mM at a temperature of about 65° C. are most preferred.

More specifically, for the DNA encoding the protein containing the amino acid sequence represented by SEQ ID NO: 4, there may be employed DNA containing the base sequence represented by SEQ ID NO: 32; for the DNA encoding the protein containing the amino acid sequence represented by SEQ ID NO: 126, there may be employed DNA containing the base sequence represented by SEQ ID NO: 127; for the DNA encoding the protein containing the amino acid sequence represented by SEQ ID NO: 138, there may be employed DNA containing the base sequence represented by SEQ ID NO: 139; for the DNA encoding the protein containing the amino acid sequence represented by SEQ ID NO: 144, there may be employed DNA containing the base sequence represented by SEQ ID NO: 143.

For the DNA encoding a partial peptide of the receptor of the present invention, it may be any of DNA containing the base sequence encoding the partial peptide of the receptor of the present invention described above. Alternatively, it may be any one of genomic DNA, genomic DNA library, cDNA derived from the cells/tissues described above, cDNA library derived from the cells/tissues described above and synthetic DNA.

For the DNA encoding the partial peptide of the receptor of the present invention, there may be utilized, for example, (1) DNA having the partial bese sequence of the DNA containing the base sequence represented by SEQ ID NO: 32, or DNA having the base sequence hybridizable to that represented by SEQ ID NO: 32 under high stringent conditions and having the partial base sequence of the DNA encoding the protein having a substantially equivalent activity to that of the protein containing the amino acid ssequence represented by SEQ ID NO: 4, (2) DNA having the partial bese sequence of the DNA containing the base sequence represented by SEQ ID NO: 127, or DNA having the base sequence hybridizable to that represented by SEQ ID NO: 127 under high stringent conditions and having the partial base sequence of the DNA encoding the protein having a substantially equivalent activity to that of the protein containing the amino acid ssequence represented by SEQ ID NO: 126, (3) DNA having the partial bese sequence of the DNA containing the base sequence represented by SEQ ID NO: 139, or DNA having the base sequence hybridizable to that represented by SEQ ID NO: 139 under high stringent conditions and having the partial base sequence of the DNA encoding the protein having a substantially equivalent activity to that of the protein containing the amino acid ssequence represented by SEQ ID NO: 138, (4) DNA having the partial bese sequence of the DNA containing the base sequence represented by SEQ ID NO: 143, or DNA having the base sequence hybridizable to that represented by SEQ ID NO: 143 under high stringent conditions and having the partial base sequence of the DNA encoding the protein having a substantially equivalent activity to that of the protein containing the amino acid ssequence represented by SEQ ID NO: 143.

The DNA hybridizable to the base sequence represented by SEQ ID NO: 32, SEQ ID NO: 127, SEQ ID NO: 139 or SEQ ID NO: 143 means equivalence to the DNA described above.

The method for hybridization and the high stringent conditions utilized are the same as that described above.

More specifically, DNA encoding the partial peptide of the receptor of the present invention includes DNA containing the DNA having the base sequence encoding the partial peptide, which contains one or at least two partial amino acid sequence selected from the partial amino acid sequences represented by 1 (Met) through 43 (Phe), 101 (Asn) through 118 (Lys), 188 (Tyr) through 213 (Arg) and 283 (Ala) through 295 (Ile) in the amino acid sequence represented by SEQ ID NO: 4, or DNA containing the DNA having the base sequence hybridizable to the above under high stringent conditions.

The DNA encoding the polypeptide, the receptor or its partial peptide of the present invention may be labeled by a publicly known method, and specifically includes isotope-labeled DNA, fluorescence-labeled DNA (e.g., fluorescence labeling with fluorescein), biotinylated DNA or enzyme-labeled DNA.

For cloning of the DNA that completely encodes the polypeptide, the receptor of the present invention or its partial peptide (hereinafter sometimes merely referred to as the polypeptide of the present invention in the description for cloning and expression of the DNA encoding the polypeptide and the like), the DNA may be either amplified by publicly known PCR method using synthetic DNA primers having a part of the base sequence of DNA encoding the polypeptide of the present invention, or the DNA inserted into an appropriate vector can be selected by hybridization with a labeled DNA fragment or synthetic DNA that encodes a part or entire region of the polypeptide of the present invention. The hybridization can be carried out, for example, according to the method described in Molecular Cloning, 2nd, J. Sambrook et al., Cold Spring Harbor Lab. Press, 1989. The hybridization may also be performed using commercially available library in accordance with the protocol described in the attached instructions.

Conversion of the base sequence of the DNA can be effected by publicly known methods such as the ODA-LA PCR method, the Gapped duplex method or the Kunkel method or its modification by using a publicly known kit available as Mutan™-super Express Km or Mutan™-K (both manufactured by Takara Shuzo Co., Ltd.).

The cloned DNA encoding the polypeptide can be used as it is, depending upon purpose or, if desired, after digestion with a restriction enzyme or after addition of a linker thereto. The DNA may contain ATG as a translation initiation codon at the 5' end thereof and may further contain TAA, TGA or TAG as a translation termination codon at the 3' end thereof. These translation initiation and termination codons may also be added by using an appropriate synthetic DNA adapter.

The expression vector for the polypeptide of the present invention can be manufactured, for example, by (a) excising the desired DNA fragment from the DNA encoding the polypeptide of the present invention, and then (b) ligating the DNA fragment with an appropriate expression vector downstream a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter if it matches well with a host to be used for gene expression. In the case of using animal cells as the host, examples of the promoter include SRα promoter, SV40 promoter, LTR promoter, CMV promoter, HSV-TK promoter, etc.

Among them, CMV (cytomegalovirus) promoter or SRα promoter is preferably used. Where the host is bacteria of the genus *Escherichia*, preferred examples of the promoter include trp promoter, lac promoter, recA promoter, $\lambda P_L$ promoter, 1 pp promoter, T7 promoter, etc. In the case of using bacteria of the genus *Bacillus* as the host, preferred example of the promoter are SPO1 promoter, SPO2 promoter and penP promoter. When yeast is used as the host, preferred examples of the promoter are PHO5 promoter, PGK promoter, GAP promoter and ADH promoter. When insect cells are used as the host, preferred examples of the promoter include polyhedrin prompter and P10 promoter.

In addition to the foregoing examples, the expression vector may further optionally contain an enhancer, a splicing signal, a polyA addition signal, a selection marker, SV40 replication origin (hereinafter sometimes abbreviated as SV40ori) etc. Examples of the selection marker include dihydrofolate reductase (hereinafter sometimes abbreviated as dhfr) gene [methotrexate (MTX) resistance], ampicillin resistant gene (hereinafter sometimes abbreviated as Amp$^r$), neomycin resistant gene (hereinafter sometimes abbreviated as Neo$^r$, G418 resistance), etc. In particular, when dhfr gene is used as the selection marker in Chinese hamster cells, selection can also be made on thymidine free media.

If necessary and desired, a signal sequence that matches with a host is added to the N-terminus of the polypeptide of the present invention. Examples of the signal sequence that can be used are PhoA signal sequence, OmpA signal sequence, etc. in the case of using bacteria of the genus *Escherichia* as the host; α-amylase signal sequence, subtilisin signal sequence, etc. in the case of using bacteria of the genus *Bacillus* as the host; MFα signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector containing the DNA encoding the polypeptide of the present invention thus constructed, transformants can be manufactured.

Examples of the host, which may be employed, are bacteria belonging to the genus *Escherichia*, bacteria belonging to the genus *Bacillus*, yeast, insect cells, insects and animal cells, etc.

Specific examples of the bacteria belonging to the genus *Escherichia* include *Escherichia coli* K12 DH1 (Proc. Natl. Acad. Sci. U.S.A., 60, 160 (1968)), JM103 (Nucleic Acids Research, 9, 309 (1981)), JA221 (Journal of Molecular Biology, 120, 517 (1978)), HB101 (Journal of Molecular Biology, 41, 459 (1969)), C600 (Genetics, 39, 440 (1954)), etc.

Examples of the bacteria belonging to the genus *Bacillus* include *Bacillus subtilis* MI114 (Gene, 24, 255 (1983)), 207-21 (Journal of Biochemistry, 95, 87 (1984)), etc.

Examples of yeast include *Saccharomyces cereviseae* AH22, AH22R$^-$, NA87-11A, DKD-5D, 20B-12, *Schizosaccharomyces pombe* NCYC1913, NCYC2036, *Pichia pastoris* KM71, etc.

Examples of insect cells include, for the virus AcNPV, *Spodoptera frugiperda* cells (Sf cells), MG1 cells derived from mid-intestine of *Trichoplusia ni*, cells derived from egg of *Trichoplusia ni*, cells derived from *Mamestra brassicae*, cells derived from Estigmena acrea, etc.; and for the virus BmNPV, *Bombyx mori* N cells (BmN cells), etc. are used. Examples of the Sf cell which can be used are Sf9 cells (ATCC CRL1711) and Sf21 cells (both cells are described in Vaughn, J. L. et al., In Vivo, 13, 213-217 (1977).

As the insect, for example, a larva of *Bombyx mori* can be used (Maeda, et al., Nature, 315, 592 (1985)).

Examples of animal cells include monkey cells COS-7, Vero, Chinese hamster cells CHO (hereinafter referred to as CHO cells), dhfr gene deficient Chinese hamster cells CHO (hereinafter simply referred to as CHO(dhfr$^-$) cell), mouse L cells, mouse AtT-20, mouse myeloma cells, rat GH3, human FL cells, etc.

Bacteria belonging to the genus *Escherichia* can be transformed, for example, by the method described in Proc. Natl. Acad. Sci. U.S.A., 69, 2110 (1972) or Gene, 17, 107 (1982).

Bacteria belonging to the genus *Bacillus* can be transformed, for example, by the method described in Molecular & General Genetics, 168, 111 (1979).

Yeast can be transformed, for example, by the method described in Methods in Enzymology, 194, 182-187 (1991), Proc. Natl. Acad. Sci. U.S.A., 75, 1929 (1978), etc.

Insect cells or insects can be transformed, for example, according to the method described in Bio/Technology, 6, 47-55(1988), etc.

Animal cells can be transformed, for example, according to the method described in *Saibo Kogaku* (Cell Engineering), extra issue 8, *Shin Saibo Kogaku Jikken Protocol* (New Cell Engineering Experimental Protocol), 263-267 (1995), published by Shujunsha, or Virology, 52, 456 (1973).

Thus, the transformant transformed with the expression vector containing the DNA encoding the polypeptide can be obtained.

Where the host is bacteria belonging to the genus *Escherichia* or the genus *Bacillus*, the transformant can be appropriately incubated in a liquid medium which contains materials required for growth of the transformant such as carbon sources, nitrogen sources, inorganic materials, and so on. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast extract, vitamins, growth promoting factors etc. may also be added to the medium. Preferably, pH of the medium is adjusted to about 5 to about 8.

A preferred example of the medium for incubation of the bacteria belonging to the genus *Escherichia* is M9 medium supplemented with glucose and Casamino acids (Miller, Journal of Experiments in Molecular Genetics, 431-433, Cold Spring Harbor Laboratory, New York, 1972). If necessary and desired, a chemical such as 3β-indolylacrylic acid can be added to the medium thereby to activate the promoter efficiently.

Where the bacteria belonging to the genus *Escherichia* are used as the host, the transformant is usually cultivated at about 15° C. to about 43° C. for about 3 hours to about 24 hours. If necessary and desired, the culture may be aerated or agitated.

Where the bacteria belonging to the genus *Bacillus* are used as the host, the transformant is cultivated generally at about 30° C. to about 40° C. for about 6 hours to about 24 hours. If necessary and desired, the culture can be aerated or agitated.

Where yeast is used as the host, the transformant is cultivated, for example, in Burkholder's minimal medium (Bostian, K. L. et al., Proc. Natl. Acad. Sci. U.S.A., 77, 4505 (1980)) or in SD medium supplemented with 0.5% Casamino acids (Bitter, G A. et al., Proc. Natl. Acad. Sci. U.S.A., 81, 5330 (1984)). Preferably, pH of the medium is adjusted to about 5 to about 8. In general, the transformant is cultivated at about 20° C. to about 35° C. for about 24 hours to about 72 hours. If necessary and desired, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary and desired, the culture can be aerated or agitated.

Where animal cells are employed as the host, the transformant is cultivated in, for example, MEM medium containing about 5% to about 20% fetal bovine serum (Science, 122, 501 (1952)), DMEM medium (Virology, 8, 396 (1959)), RPMI 1640 medium (The Journal of the American Medical Association, 199, 519 (1967)), 199 medium (Proceeding of the Society for the Biological Medicine, 73, 1 (0.1950)), etc. Preferably, pH of the medium is adjusted to about 6 to about 8. The transformant is usually cultivated at about 30° C. to about 40° C. for about 15 hours to about 60 hours and, if necessary and desired, the culture can be aerated or agitated.

As described above, the polypeptide of the present invention can be produced into the cell, in the cell membrane or out of the cell of the transformant.

The polypeptide of the present invention can be separated and purified from the culture described above by the following procedures.

When the polypeptide of the present invention is extracted from the cultured bacteria or cells, after cultivation the bacteria or cells are collected by a publicly known method and suspended in an appropriate buffer. The bacteria or cells are then disrupted by publicly known methods such as ultrasonication, a treatment with lysozyme and/or freeze-thaw cycling, followed by centrifugation, filtration, etc. Thus, the crude extract of the polypeptide of the present invention can be obtained. The buffer used for the procedures may contain a protein modifier such as urea or guanidine hydrochloride, or a surfactant such as Triton X-100™, etc. When the receptor protein is secreted in the culture, after completion of the cultivation the supernatant can be separated from the bacteria or cells to collect the supernatant by a publicly known method.

The polypeptide contained in the supernatant or the extract thus obtained can be purified by appropriately combining the publicly known methods for separation and purification. Such publicly known methods for separation and purification include a method utilizing difference in solubility such as salting out, solvent precipitation, etc.; a method utilizing mainly difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the polypeptide thus obtained is in a free form, it can be converted into the salt by publicly known methods or modifications thereof. On the other hand, when the polypeptide is obtained in the form of a salt, it can be converted into the free form or in the form of a different salt by publicly known methods or modifications thereof.

The polypeptide produced by the recombinant can be treated, prior to or after the purification, with an appropriate protein-modifying enzyme so that the polypeptide can be appropriately modified to partially remove a polypeptide. Examples of the protein-modifying enzyme include trypsin, chymotrypsin, arginyl endopeptidase, protein kinase, glycosidase or the like.

Antibodies to the polypeptide of the present invention (hereinafter sometimes merely referred to as the antibody of the present invention) may be any of polyclonal antibodies and monoclonal antibodies, as long as they are capable of recognizing the polypeptide of the present invention, its amide or ester, or salts thereof.

The antibodies to the polypeptide of the present invention may be manufactured by publicly known methods for manufacturing antibodies or antisera, using as antigens the polypeptide of the present invention.

Preparation of Monoclonal Antibody (a) Preparation of Monoclonal Antibody-Producing Cells The polypeptide of the present invention is administered to warm-blooded animals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once in every two to six weeks and 2 to 10 times in total. Examples of the applicable warm-blooded animals are monkeys, rabbits, dogs, guinea pigs, mice, rats, sheep, goats and fowls, with mice and rats being preferred.

In the preparation of monoclonal antibody-producing cells, warm-blooded animals, e.g., mice, immunized with an antigen wherein the antibody titer is noted is selected, then the spleen or lymph node is collected after 2 to 5 days from the final immunization and antibody-producing cells contained therein are fused with myeloma cells to give monoclonal antibody-producing hybridomas. Measurement of the antibody titer in antisera may be made, for example, by reacting a labeled form of the polypeptide, which will be described later, with the antiserum followed by assaying the binding activity of the labeling agent bound to the antibody. The fusion may be operated, for example, by the known Koehler and Milstein method (Nature, 256, 495, 1975). Examples of the fusion accelerator are polyethylene glycol (PEG), Sendai virus, etc., of which PEG is preferably employed.

Examples of the myeloma cells are NS-1, P3U1, SP2/0, AP1, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubating at about 20 to about 40, preferably at about 30° C. to about 37° C. for about 1 to about 10 minutes, an efficient cell fusion can be carried out.

Various methods can be used for screening of a monoclonal antibody-producing hybridoma. Examples of such methods include a method which comprises adding the supernatant of hybridoma to a solid phase (e.g., microplate) adsorbed with the polypeptide (protein) as an antigen directly or together with a carrier, adding an anti-immunoglobulin antibody (when mouse cells are used for the cell fusion, anti-mouse immunoglobulin antibody is used) labeled with a radioactive substance or an enzyme, or Protein A and detecting the monoclonal antibody bound to the solid phase, and a method which comprises adding the supernatant of hybridoma to a solid phase adsorbed with an anti-immunoglobulin antibody or Protein A, adding the polypeptide labeled with a radioactive substance or an enzyme and detecting the monoclonal antibody bound to the solid phase.

The monoclonal antibody can be selected by publicly known methods or by modifications of these methods. In general, the selection can be effected in a medium for animal cells supplemented with HAT (hypoxanthine, aminopterin and thymidine). Any selection and growth medium can be employed as far as the hybridoma can grow therein. For example, RPMI 1640 medium containing 1% to 20%, preferably 10% to 20% fetal bovine serum, GIT medium (Wako Pure Chemical Industries, Ltd.) containing 1% to 10% fetal bovine serum, a serum free medium for cultivation of a hybridoma (SFM-101, Nissui Seiyaku Co., Ltd.) and the like can be used for the selection and growth medium. The temperature for cultivation is generally at 20° C. to 40° C., preferably at about 37° C. The cultivation time is for 5 days to 3 weeks, preferably 1 to 2 weeks. The cultivation can be conducted normally in 5% $CO_2$. The antibody titer of the culture supernatant of hybridomas can be determined as in the assay for the antibody titer in antisera described above.

(b) Purification of Monoclonal Antibody

Separation and purification of a monoclonal antibody can be carried out by publicly known methods such as methods for separation and purification of immunoglobulins [e.g., salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A, Protein G, etc. and dissociating the binding to obtain the antibody].

Preparation of Polyclonal Antibody

The polyclonal antibody of the present invention can be manufactured by publicly known methods or modifications thereof. For example, a complex of immunogen (antigen such as the polypeptide of the present invention) and a carrier protein is prepared, and a warm-blooded animal is immunized with the complex in a manner similar to the method described above for the manufacture of monoclonal antibodies. The product containing the antibody to the polypeptide of the present invention is collected from the immunized animal followed by separation and purification of the antibody.

In the complex of an immunogen and a carrier protein used to immunize a warm-blooded animal, the type of carrier protein and the mixing ratio of a carrier to hapten may be any type and in any ratio, as long as the antibody is efficiently produced to the hapten immunized by crosslinking to the carrier. For example, bovine serum albumin, bovine thyroglobulins, keyhole limpet hemocyanin, etc. are coupled to hapten in a carrier-to-hapten weight ratio of approximately 0.1 to 20, preferably about 1 to about 5.

A variety of condensing agents can be used for the coupling of a carrier to hapten. Glutaraldehyde, carbodiimide, maleimide activated ester, activated ester reagents containing thiol group or dithiopyridyl group, etc. are used for the coupling.

The condensation product is administered to warm-blooded animals either solely or together with carriers or diluents to the site in which the antibody can be produced by the administration. In order to potentiate the antibody productivity upon the administration, complete Freund's adjuvant or incomplete Freund's adjuvant may be administered. The administration is usually made once approximately in every 2 to 6 weeks and about 3 to about 10 times in total.

The polyclonal antibody can be collected from the blood, ascites, etc., preferably from the blood of warm-blooded animals immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as applied to the separation and purification of monoclonal antibodies described hereinabove.

The antisense polynucleotide containing a complementary or substantially conplementary base sequence to the DNA encoding the polypeptide, the receptor or its partil peptide of the present invention (herein after these DNAs are sometimes abbreviated as the DNA of the present invention) or a portion thereof (hereinafter these DNAs are sometimes abbreviated as the antisense DNA) may be any antisense polynucleotide (preferably the antisense DNA) so long as it contains the base sequence complementary or substantially complementary to the DNA of the present invention or a portion thereof, and has an action that can inhibit the expression of the DNA.

Examples of the substantially complementary base sequence to the DNA of the present invention include, for example, the base sequence having at least about 70% homology, preferably at least about 80% homology, more preferably at least about 90% homology, most preferably at least about 95% homology to the entire or partial base sequence of the complementary base sequence of the DNA of the present invention (i.e., the complementary strand of the DNA of the present invention). In particular, among the entire base sequence of the complementary strand of the DNA of the present invention, (a) in the antisense nucleotide directed to the inhibition of translation, the antisense nucleotide having at least about 70% homology, preferably at least about 80% homology, more preferably at least about 90% homology, most preferably at least about 95% homology to the complementary strand of the partial base sequence encoding the N-terminal region of the protein of the present invention (e.g., the base sequence around the initiation codon), or (b) in the antisense nucleotide directed to RNA degradation by RNaseH, the antisense nucleotide having at least about 70% homology, preferably at least about 80% homology, more preferably at least about 90% homology, most preferably at least about 95% homology to the complementary strand of the entire base sequence of the DNA of the present invention containing intron is preferred. For example, it includes the antisense nucleotide (DNA) having the base sequence complementary or substantially complementary to the base sequence of the DNA containing the base sequence encoding the polypeptide or the receptor of the present invention, or a portion thereof.

The antisense nucleotide is generally comprised of about 10 to 40, preferably about 15 to 30 bases.

The antissense nucleotide of the present invention can be manufactured using the publicly known DNA synthesizer, etc.

Hereinafter, it is described about use of (a) the polypeptide of the present invention, (b) the DNA of the present invention, (c) the antibody of the present invention, and (d) the antisense DNA of the present invention.

(1) A Therapeutic and/or Prophylactic Agent for Various Diseases Associated with the Polypeptide of the Present Invention The polypeptide of the present invention is an endogenous ligand of the receptor of the present invention having a cell stimulating activity in the cells, in which the receptor of the present invention (e.g., GPR8, GPR7, rat TGR26, mouse TGR26 and the like) is expressed.

Therefore, where the polypeptide or the DNA of the present invention is abnormal or deficient, or where the receptor of the present invention or the DNA encoding the receptor is abnormal or deficient, there is highly possibility to gain the body weight. Thus the polypeptide or the DNA of the present invention can be used as, for example, a body weight gain inhibitor, a body weight loss agent, an adipose gain inhibitor, a feeding inhibitor. In addition, they can be used as, for example, a prophylactic and/or therapeutic agent for obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogodanal obesity, systemic mastocytosis, simple obesity, central obesity, and the like).

For example, when the polypeptide of the present invention is decreased or deficient in a patient, the function of the polypeptide of the present invention can sufficiently or normally be demonstrated by (i) administering the DNA of the present invention to the patient thereby to express the polypeptide of the present invention in vivo, (ii) inserting the DNA of the present invention into the cell thereby to express the polypeptide of the present invention and transplanting the cells to the patient, or (iii) administering the polypeptide of the present invention to the patient.

Where the DNA of the present invention is used as the therapeutic and/or prophylactic agents described above, the DNA itself is administered; alternatively, the DNA is inserted into an appropriate vector such as retrovirus vector, adenovirus vector, adenovirus-associated virus vector, etc. and then administered to human or warm-blooded animals in a conventional manner. The DNA of the present invention may also be administered as naked DNA, or can be formulated with physiologically acceptable carriers such as adjuvants to assist its uptake to administer by gene gun or through a catheter such as a catheter with a hydrogel.

Where the polypeptide of the present invention is used as the therapeutic and/or prophylactic agent described above, the product purified to at least 90% purity, preferably at least 95% purity, more preferably at least 98% purity, further preferably at least 99% purity is preferably used.

For example, the polypeptide of the present invention can be used orally, for example, in the form of tablets which may be sugar coated if necessary and desired, capsules, elixirs, microcapsules etc., or parenterally (preferably subcutaneous administration) in the form of injectable preparations such as a sterile solution and a suspension in water or with other pharmaceutically acceptable liquid. For example, these preparations can be manufactured by mixing the polypeptide of the present invention with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The effective component in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, akamono oil and cherry. When the unit dosage is in the form of capsules, liquid carriers such as oils and fats may further be used together with the additives described above. A sterile composition for injection may be formulated by conventional procedures used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol and polyethylene glycol), a nonionic surfactant (e.g., POLYSORBATE 80™ and HCO-50), etc. Examples of the oily medium include sesame oil and soybean oil, which may also be used in combination with a dissolution aid such as benzyl benzoate and benzyl alcohol. The prophylactic and/or therapeutic agent described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule.

The vector, in which the DNA of the present invention is inserted, is also formulated as described above, and in general can be used parenterally.

Since the thus obtained pharmaceutical preparation is safe and low toxic, the preparation can be administered to human or warm-blooded animals (e.g., rats, mice, guinea pigs, rabbits, fowls, sheep, swine, bovine, horse, cats, dogs, monkeys, etc.).

The dose of the polypeptide of the present invention varies depending on diseases to be subjected, subject to be administered, routes for administration, etc.; in subcutaneou administration to adult, e.g., for the purpose of inhibition of body weight gain, the dose is normally about 0.1 mg to about 100 mg, preferably about 1.0 to about 50 mg, and more preferably about 1.0 to about 20 mg per day (as 60 kg body weight). Other animals can be administered at the dose converted to 60 kg body weight.

(2) A Screening of Candidate Compound for Medicine to Diseases

Since the polypeptide of the present invention has a function as a ligand to the receptor of the present invention, a compound that enhances activities and functions of the polypeptide of the present invention, or a salt thereof has, for example, actions of body weight gain inhibition, body weight loss, adipose gain inhibition, feeding inhibition and the like, and can be used as a body weight gain inhibitor, a body weight loss agent, an adipose gain inhibitor, a feeding inhibitor and the like, which is low toxic and safe.

On the other hand, a compound that inhibits activities and functions of the polypeptide of the present invention, or a salt thereof has, for example, an action of body weight gain, and can be used as a low toxic and safe body weight gain agent.

For screening of compounds or salts thereof that enhance or inhibit activities or functions of the polypeptide of the present invention, the polypeptide of the present invention or the receptor binding assay system using the expression system constructed by the recombinant polypeptide can be used. By this screening, compounds or salts thereof that alter the binding property between the polypeptide of the present invention and its receptor (compounds that enhance or inhibit activities of the polypeptide of the present invention) such as peptides, proteins, non-peptide compounds, synthetic compounds, fermentation products and the like can be screened. Such compounds include compounds that have the receptor-mediated cell-stimulating activities (e.g., activities that promote arachidonic acid release, acetylcholine release, intracellular $Ca^{2+}$ release, enhancement and inhibition of intracellular cAMP production, intracellular cGMP production, inositol phosphate production, changes in cell membrane potential, phosphorylation of intracellular proteins, activation of c-fos, pH reduction, GTPγS binding activity, etc.) (so-called agonists to the receptor of the present invention), compounds that do not have the cell-stimulating activity (so-called antagonists to the receptor of the present invention) and the like. The phrase "alter the binding property to the polypeptide of the present invention", means both the case where the binding with the polypeptide of the present invention is inhibited and the case where the binding with the polypeptide of the present invention is enhanced.

Specific examples of the screening method of the compounds or salts thereof that enhance or inhibit activities of the polypeptide of the present invention, which is characterized by using the polypeptide of the present invention, include a screening method of compounds that alter the binding property between the polypeptide and the receptor of the present invention (compounds that enhance or inhibit activities of the polypeptide of the present invention) or salts thereof, which comprises comparing (i) the case where the polypeptide of the present invention is brought into contact with the receptor of the present invention or its partial peptide (hereinafter, sometimes merely referred to as the receptor of the present invention) and (ii) the case where the polypeptide of the present invention and a test compound is brought into contact with the receptor of the present invention.

In the above-described screening method, for example, an amount of ligand binding to the receptor of the present invention or cell stimulating activity in (i) the case where the polypeptide of the present invention is brought into contact with the receptor of the present invention and (ii) the case where the polypeptide of the present invention and a test compound is brought into contact with the receptor of the present invention is measured, and both results are compared.

More specifically, the above-described screening method includes:

(a) A method for screening a compound that alters the binding property between the polypeptide of the present invention and the receptor of the present invention (a compound that enhances or inhibits activities of the polypeptide of the present invention) or its salt, which comprises measuring the amount of the labeled polypeptide of the present invention bound to the receptor of the present invention in the case where the polypeptide of the present invention is brought into contact with the receptor of the present invention and the case where the polypeptide of the present invention and a test compound is brought into contact with the receptor of the present invention and comparing both results;

(b) A method for screening a compound that alters the binding property between the polypeptide of the present invention and the receptor of the present invention (a compound that enhances or inhibits activities of the polypeptide of the present invention) or its salt, which comprises measuring the amount of the labeled polypeptide of the present invention bound to the receptor of the present invention in the case where the polypeptide of the present invention is brought into contact with cells containing the receptor of the present invention or membrane fraction of the cells and the case where the polypeptide of the present invention and a test compound is brought into contact with cells containing the receptor of the present invention or membrane fraction of the cells and comparing both results;

(c) A method for screening a compound that alters the binding property between the polypeptide of the present invention and the receptor of the present invention (a compound that enhances or inhibits activities of the polypeptide of the present invention) or its salt, which comprises measuring the amount of the labeled polypeptide of the present invention bound to the receptor of the present invention in the case where the labeled polypeptide of the present invention is brought into contact with the receptor of the present invention that is expressed on the cell membrane by culturing the transformant containing the DNA encoding the receptor of the present invention and the case where the labeled polypeptide of the present invention and a test compond are brought into contact with the receptor of the present invention that is expressed on the cell membrane by culturing the transformant containing the DNA encoding the receptor of the present invention;

(d) A method for screening a compound that alters the binding property between the polypeptide of the present invention and the receptor of the present invention (a compound that enhances or inhibits activities of the polypeptide of the present invention) or its salt, which comprises measuring the receptor-mediated cell stimulating activities (e.g., the activities that promote or suppress arachidonic acid release, acetylcholine release, intracellular $Ca^{2+}$ release, enhancement and inhibition of intracellular cAMP production, intracellular cGMP production, inositol phosphate production, change in cell membrane potential, phosphorylation of intracellular proteins, activation of c-fos, pH reduction, GTPγS binding activity, etc.) in the case where a compound that activates the receptor of the present invention (e.g., the polypeptide of the present invention) is brought into contact with the cells containing the receptor of the present invention and the case where a compound that activates the receptor of the present invention and a test compound are brought into contact with the cells containing the receptor of the present invention, and comparing both results; and, (e) A method for screening a compound that alters the binding property between the polypeptide of the present invention and the receptor of the present invention (a compound that enhances or inhibits activities of the polypeptide of the present invention) or its salt, which comprises measuring the receptor-mediated cell stimulating activities (e.g., the activities that promote or suppress arachidonic acid release, acetylcholine release, intracellular $Ca^{2+}$ release, enhancement and inhibition of intracellular cAMP production, intracellular cGMP production, inositol phosphate production, change in cell membrane potential, phosphorylation of intracellular proteins, activation of c-fos, pH reduction, GTPγS binding activity, etc.) in the case where a compound that activates the receptor of the present invention (e.g., the polypeptide of the present invention) is brought into contact with the receptor of the present invention that is expressed on the cell membrane by culturing the transformant containing the DNA encoding the receptor of the present invention and the case where a compound that activates the receptor of the present invention and a test compound are brought into contact with the receptor of the present invention that is expressed on the cell membrane by culturing the transformant containing the DNA encoding the receptor of the present invention, and comparing both results.

Preferred specific examples of the labeled polypeptide of the present invention include a polypeptide having the amino acid sequence represented by SEQ ID NO: 149, SEQ ID NO: 16, SEQ ID NO: 6, SEQ ID NO: 17, SEQ ID NO: 56, SEQ ID NO: 57, SEQ ID NO: 73, SEQ ID NO: 74, SEQ ID NO: 91 or SEQ ID NO: 92, which is labeled with radioisotopes (e.g., $[^{125}I]$, $[^{131}I]$, $[^3H]$, $[^{14}C]$), fluorescent substances (e.g., cyanine fluorescent substances (e.g., Cy2, Cy3, Cy5, Cy5.5, Cy7 (Amersham Biosciences)), fluorescamine, fluorescein isothiocyanate), enzymes (e.g., β-galactosidase, β-glucosidase, alkalinephosphatase, peroxidase, malate dehydrogenase), luminescent substances (e.g., luminol, luminal derivatives, luciferin, lucigenin) or lanthanide. Preferably, it includes a polypeptide having the amino acid sequence represented by SEQ ID NO: 149, which is labled with $[^{125}I]$.

Hereinafter, the above screening methods are described more specifically.

First, for the receptor of the present invention used for the screening methods of the present invention, any substance may be used so long as it recogniszes the polypeptide of the present invention as a ligand. The cell membrane fraction from human or warm-blooded animals' organs is preferred. However, it is very difficult to obtain human organs. It is thus preferable to use the receptor of the present invention, produced by large-scale expression using recombinants.

For manufacturing the receptor of the present invention, the method for manufacturing the polypeptide of the present invention, which is described above, and the like are utilized.

In the screening methods of the present invention, when cells containing the receptor of the present invention or the cell membrane fraction derived from the cells are used, it may be according to the preparation method described below.

Where cells containing the receptor of the present invention are used, the cells may be fixed using glutaraldehyde, formalin, etc. The fixation can be made by a publicly known method.

The cells containing the receptor of the present invention are host cells that have expressed the receptor of the present invention, which host cells include *Escherichia coli, Bacillus subtilis*, yeast, insect cells, animal cells, and the like. In addition, the host cells, in which the receptor of the present invention has been expressed, can be manufactured using the same method as that of manufacturing the transformant transformed by the expression vector containing the polypeptide of the present invention.

The cell membrane fraction refers to a fraction abundant in cell membrane obtained by cell disruption and subsequent fractionation by a publicly known method. Useful cell disruption methods include cell squashing using a Potter-Elvehjem homogenizer, disruption using a Waring blender or Polytron (manufactured by Kinematica Inc.), disruption by ultrasonication, and disruption by cell spraying through thin nozzles under an increased pressure using a French press or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in the receptor protein expressed and membrane components such as cell-derived phospholipids and membrane proteins.

The amount of the receptor in the cells containing the receptor and in the membrane fraction is preferably $10^3$ to $10^8$ molecules per cell, more preferably $10^5$ to $10^7$ molecules per cell. As the amount of expression increases, the ligand binding activity per unit of membrane fraction (specific activity) increases so that not only the highly sensitive screening system can be constructed but also large quantities of samples can be assayed with the same lot.

To perform the methods (a) through (c) supra for screening of a compound that alters the binding property between the polypweptide of the present invention and the receptor of the present invention (a compound that enhances or inhibits activities of the polypeptide of the present invention), an appropriate receptor fraction of the present invention and the labeled polypeptide of the present invention are used. The receptor fraction of the present invention is preferably a fraction of naturally occurring receptor or a recombinant receptor fraction having an activity equivalent to that of the natural protein. Herein, the term "equivalent activity" is intended to mean a ligand binding activity or the like that is equivalent to that possessed by naturally occurring receptor proteins. Examples of the labeled polypeptide include a polypeptide, which is labeled with, for example, radioisotopes (e.g., $[^{125}I]$, $[^{131}I]$, $[^3H]$, $[^{14}C]$), fluorescent substances (e.g., cyanine fluorescent substances (e.g., Cy2, Cy3, Cy5, Cy5.5, Cy7 (Amersham Biosciences)), fluorescamine, fluorescein isothiocyanate), enzymes (e.g., β-galactosidase, β-glucosidase, alkalinephosphatase, peroxidase, malate dehydrogenase), luminescent substances (e.g., luminol, luminal derivatives, luciferin, lucigenin) or lanthanide. Preferably, it includes a polypeptide, which is labled with $[^{125}I]$.

Specifically, to screen the compound that alters the binding property between the polypeptide of the present invention and the receptor of the present invention, firstly, a standard receptor preparation is prepared by suspending cells containing the receptor of the present invention or the membrane fraction thereof in a buffer appropriate for screening. Any buffer can be used so long as it does not inhibit the ligand-receptor binding, such buffers including a phosphate buffer or a Tris-HCl buffer having pH of 4 to 10 (preferably pH of 6 to 8). For the purpose of minimizing non-specific binding, a surfactant such as CHAPS, TWEEN-80™ (manufactured by Kao-Atlas Inc.), digitonin or deoxycholate, may optionally be added to the buffer. Further for the purpose of suppressing the degradation of the receptor of the present invention or the polypeptide of the present invention by proteases, a protease inhibitor such as PMSF, leupeptin, E-64 (manufactured by Peptide Institute, Inc.) and pepstatin may also be added. A given amount (5,000 to 500,000 cpm) of the labeled polypeptide of the present invention is added to 0.01 ml to 10 ml of the receptor solution. At the same time, $10^{-10}$ to $10^{-7}$ M of the test compound is also co-existed. To determine the amount of non-specific binding (NSB), a reaction tube containing the unlabeled polypeptide of the present invention in large excess is also prepared. The reaction is carried out at approximately 0 to 50° C., preferably about 4 to 37° C. for about 20 minutes to about 24 hours, preferably about 30 minutes to about 3 hours. After completion of the reaction, the reaction mixture is filtered through glass fiber filter paper, etc. and washed with an appropriate volume of the same buffer. The residual radioactivity on the glass fiber filter paper is then measured by means of a liquid scintillation counter or γ-counter. When counts obtained by subtracting nonspecific binding (NSB) from the count of no competitor ($B_0$) ($B_0$ minus NSB) are represented by 100%, a test compound having 50% or less of the specific binding (B minus NSB) may be selected as a candidate substance having the ability of competitive inhibition.

In order to carry out the method (d) or (e) supra for screening the compound that alters the binding property between the polypeptide of the present invention and the receptor of the present invention (the compound that promotes or inhibits the activity of the polypeptide of the present invention), the receptor-mediated cell-stimulating activities (e.g., the activities that promote or suppress arachidonic acid release, acetylcholine release, intracellular $Ca^{2+}$ release, enhancement and inhibition of intracellular cAMP production, intracellular cGMP production, inositol phosphate production, change in cell membrane potential, phosphorylation of intracellular proteins, activation of c-fos, pH reduction, GTPγS binding activity, etc.) can be measured by a publicly known method, or using an assay kit commercially available. Specifically, cells containing the receptor are first cultured on a multi-well plate, etc. Prior to the screening, the medium is replaced with fresh medium or with an appropriate non-cytotoxic buffer, followed by incubation for a given period of time in the presence of a test compound, etc. Subsequently, the cells are extracted or the supernatant is recovered and the resulting product is quantified by appropriate procedures. Where it is difficult to detect the production of the index substance (e.g., arachidonic acid) for the cell-stimulating activity due to a degrading enzyme contained in the cells, an inhibitor against such a degrading enzyme may be added prior to the assay. For detecting activities such as the cAMP production suppression activity, the baseline production in the cells is increased by forskolin or the like and the suppressing effect on the increased baseline production may then be detected.

For the screening by measuring the cell-stimulating activities, an appropriate cell, in which the receptor of the present invention is expressed, is required. As the cell, in which the receptor of the present invention is expressed, preferred is the aforementioned receptor-expressing cell line.

Examples of the test compound include peptide, protein, non-peptide compound, synthetic compound, fermentation product, cell extract, plant extract, extract from animal tissue, and the like.

The kit for screening the compound that alters the binding property between the polypeptide of the present invention and the receptor of the present invention (the compound that promotes or inhibits activities of the polypeptide of the present invention) or salts thereof comprises the receptor of the present invention or its salt, the partial peptide of the receptor of the present invention or its salt, cells containing the receptor of the present invention or the membrane fraction of the cells containing the receptor of the present invention, and the polypeptide of the present invention.

Examples of the screening kit of the present invention are given below.

1. Reagents for Screening
   (a) Buffers for Assay and Washing
   Hanks' Balanced Salt Solution (manufactured by Gibco Co.) supplemented with 0.05% bovine serum albumin (Sigma Co.).
   The solution is sterilized by filtration through a 0.45 μm filter and stored at 4° C. Alternatively, the solution may be prepared at use.
   (b) Standard Receptor of the Present Invention
   CHO cells on which the receptor of the present invention has been expressed are passaged in a 12-well plate in a density of $5\times10^5$ cells/well followed by culturing at 37° C. under 5% $CO_2$ and 95% air for 2 days.
   (c) Labeled Polypeptide of the Present Invention
   The polypeptide of the present invention, which is labeled with [$^3$H], [$^{125}$I], [$^{14}$C], [$^{35}$S], etc., is dissolved with an appropriate solvent or buffer and stored at 4° C. or −20° C. This solution is diluted to 1 μM with the buffer for assay at use.
   (d) Standard Solution of the Polypeptide of the Present Invention
   The polypeptide of the present invention is dissolved at the concentration of 1 mM with PBS containing 0.1% bovine serum albumin (Sigma), and is stored at −20° C.

2. Method for Assay
   (a) The cells, in which the receptor of the present invention has been expressed, are cultured in a 12-well culture plate. After washing twice with 1 ml of an assay buffer, 490 μl of the assay buffer is added to each well.
   (b) After 51 μl of $10^{-3}$ to $10^{-10}$ M test compound is added, to the mixture 5 μl of the labeled polypeptide of the present invention is added. The resulting mixture is incubated at room temperature for an hour. To determine the non-specific binding, 5 μl of $10^{-3}$ M of the polypeptide of the present invention is added instead of the test compound.
   (c) The reaction mixture is removed and the wells are washed 3 times with 1 ml of washing buffer. The labeled polypeptide of the present invention bound to the cells is dissolved in 0.2N NaOH-1% SDS and then mixed with 4 ml of liquid scintillator A (manufactured by Wako Pure Chemical Industries, Ltd.).
   (d) The radioactivity is measured using a liquid scintillation counter (manufactured by Beckman Co.). The Percent Maximum Binding (PMB) is calculated by the following equation.

$$PMB=[(B-NSB)/(B_0-NSB)]\times 100 \qquad \text{[Equation 1]}$$

PMB: Percent maximum binding
   B: Value obtained in the presence of a sample
   NSB: Non-specific binding
   $B_0$: Maximum binding The compound or salts thereof, which is obtained by using the above screening method or the above screening kit, is a compound that alters the binding property between the polypeptide of the present invention and the receptor of the present invention (inhibits or promotes the binding), i.e., a compound that promotes or inhibits activities of the polypeptide of the present invention. Specifically, it is a compound or salts thereof having the receptor-mediated cell stimulating activities (i.e., the agonist for the receptor of the present invention), or a compound or salts thereof having no stimulating activity (i.e., the antagonist for the receptor of the present invention). The compound includes peptide, protein, non-peptide compound, synthetic compound, fermentation product, or the like. These compounds may be novel compounds or publicly known compounds.

Specific valuation method for determining whether the compound is an agonist or an antagonist may be the following (i) or (ii).

(i) By carrying out the binding assay shown as the screening methods described in (a) through (c) above, a compound that alters the binding property between the polypeptide of the present invention and the receptor of the present invention (especially, inhibits the binding) is obtained. Then whether or not the compound has the receptor-mediated cell stimulating activity is assayed. The compounds having the cell stimulating activity or salts thereof are an agonist to the receptor of the present invention, whereas the compounds having no activity or salts thereof are an antagonist to the receptor of the present invention.

(ii) (a) By contacting a test compound with the cell containing the receptor of the present invention, the receptor-mediated cell stimulating activities are measured. The compounds having the cell stimulating activity or salts thereof are an agonist to the receptor of the present invention.

(b) In the case where the compound that activates the receptor of the present invention (e.g., the polypeptide of the present invention or the agonist to the receptor of the present invention) is brought into contact with the cell containing the receptor of the present invention and the case where the compound that activates the receptor of the present invention and a test compound are brought into contact with the cell containing the receptor of the present invention, the cell stimulating activities, which are mediated by the receptor of the present invention, are assayed and compared. A compound, which can decrease the cell stimulating activity mediated by the compound that activates the receptor of the present invention, or salts thereof is an antagonist to the receptor of the present invention.

Since the agonist to the receptor of the present invention has a similar action to the physiological activity that the polypeptide of the present invention has, it has actions such as suppression of body weight gain, body weight loss, suppression of adipose gain, feeding suppression as well as the polypeptide of the present invention and can be used as a safe and low toxic agent such as a body weight gain inhibitor, a body weight loss agent, an adipose gain inhibitor, a feeding inhibitor.

Since the antagonist to the receptor of the present invention can suppress the physiological activity that the polypeptide for the receptor of the present invention has, it can be used as a safe and low toxic body weight gain agent.

The compounds or salts thereof obtained using the screening method or the screening kit of the present invention are compounds selected from, for example, peptide, protein, non-peptide compound, synthetic compound, fermentation product, cell extract, plant extract, extract from animal tissue, and plasma, which promotes or inhibits functions of the polypeptide of the present invention.

As salt form of the compound, the same as the salt of the polypeptide of the present invention can be used.

When the compounds, which are obtained by the screening methods or the screening kit of the present invention, are used as the therapeutic and/or prophylactic agent described above, the compounds can be formulated by the conventional methods. For example, as described for the pharmaceuticals containing the polypeptide of the present invention, the compounds can be prepared into tablets, capsules, elixir, microcapsules, aseptic solution, or suspension.

Since the preparations obtained as described above are safe and low toxic, it can be administered to human and warm-blooded animals (e.g., mice, rats, rabbits, sheep, swine, bovine, horse, fowls, cats, dogs, monkeys, chimpanzee, etc.).

The dose of the compounds or their salt forms varies depending on its action, target diseases, subject to be administered, routes for administration, etc.; in subcutaneous administration of the compound that promotes activities and/or functions of the polypeptide of the present invention, e.g., for adult (per 60 kg of body weight), the dose for the purpose of suppression of body weight gain is normally about 0.1 mg to about 100 mg, preferably about 1.0 to about 50 mg, and more preferably about 1.0 to about 20 mg per day (as 60 kg body weight). In other animals, the amounts converted to that per 60 kg of body weight can be administered.

For the purpose of body weight gain, in subcutaneous administration of the compound that inhibits activities and/or functions of the polypeptide of the present invention, e.g., for adult (per 60 kg of body weight), the dose is normally about 0.1 mg to about 100 mg, preferably about 1.0 to about 50 mg, and more preferably about 1.0 to about 20 mg per day (as 60 kg body weight). In other animals, the amounts converted to that per 60 kg of body weight can be administered.

(3) Quantification of the Polypeptide of the Present Invention

Since the antibody against the polypeptide of the present invention (hereinafter, sometimes referred to as the antibody of the present invention) can specifically recognize the polypeptide of the present invention, it can be used for quantification of the polypeptide of the present invention in a test fluid, especially quantification by sandwitch immunoassay.

In other words, the present invention provides:

(i) A method of quantifying the polypeptide of the present invention in a test fluid, which comprises competitively reacting the antibody of the present invention with the test fluid and a labeled form of the polypeptide of the present invention, and measuring the ratio of the labeled polypeptide of the present invention bound to the antibody; and, (ii) A method of quantifying the polypeptide of the present invention in a test fluid, which comprises reacting the test fluid with the antibody of the present invention immobilized on a carrier and a labeled form of another antibody of the present invention simultaneously or sequentially, and measuring the activity of the label on the immobilized carrier.

In (ii) described above, it is preferred that one antibody recognizes the N-terminal region of the polypeptide of the present invention, and another antibody reacts with the C-terminal region of the polypeptide of the present invention.

Using monoclonal antibodies against the polypeptide of the present invention, the polypeptide of the present invention can be quantified and also detected by tissue staining or the like. For this purpose, an antibody molecule itself may be used, or $F(ab')_2$, Fab' or Fab fractions of the antibody molecule may also be used.

The methods for quantifying the polypeptide of the present invention using antibodies of the present invention are not particularly limited. Any assay method can be used, so long as the amount of antibody, antigen, or antibody-antigen complex corresponding to the amount of antigen (e.g., the amount of the polypeptide) in the test fluid can be detected by chemical or physical means and the amount of the antigen can be calculated from a standard curve prepared from standard solutions containing known amounts of the antigen. For example, nephrometry, competitive methods, immunometric method, and sandwich method are appropriately used, with the sandwich method described below being most preferable in terms of sensitivity and specificity.

As the labeling agent for the assay methods using labeled substances, there are employed, for example, radioisotopes, enzymes, fluorescent substances, luminescent substances, lanthanoid, etc. For the radioisotope, for example, $[^{125}I]$, $[^{131}I]$, $[^{3}H]$ and $[^{14}C]$ are used. As the enzyme described above, stable enzymes with high specific activity are preferred; for example, β-galactosidase, β-glucosidase, alkaline phosphatase, peroxidase, malate dehydrogenase and the like are used. Example of the fluorescent substance used is fluorescamine and fluorescein isothiocyanate are used. For the luminescent substance, for example, luminol, luminol derivatives, luciferin, and lucigenin can be used. Furthermore, the biotin-avidin system may be used for binding antibody or antigen to the label.

For immobilization of antigen or antibody, physical adsorption may be used. Chemical binding methods conventionally used for insolubilization or immobilization of polypeptide or enzymes may also be used. For the carrier, insoluble polysaccharides such as agarose, dextran, cellulose, synthetic resin such as polystyrene, polyacrylamide, silicon, and glass and the like are included.

In the sandwich method, the immobilized monoclonal antibody of the present invention is reacted with a test fluid (primary reaction), then with the other labeled monoclonal antibody of the present invention (secondary reaction), and the activity of the label on the immobilizing carrier is measured, whereby the amount of the polypeptide of the present invention in the test fluid can be quantified. The order of the primary and secondary reactions may be reversed, and the reactions may be performed simultaneously or with an interval. The methods of labeling and immobilization can be performed by the methods described above. In addition, in immunoassay by sandwitch method, antibodies used for solid phase or labeling are not necessary for one species. For potentiating the sensitivity, a mixture of at least two species of antibodies may be used.

In the methods of assaying the polypeptide of the present invention by the sandwich method of the present invention, antibodies that bind to different sites of the polypeptide are preferably used as the monoclonal antibodies of the present invention for the primary and secondary reactions. That is, in the antibodies used for the primary and secondary reactions are, for example, when the antibody used in the secondary reaction recognizes the C-terminal region of the polypeptide of the present invention, it is preferable to use the antibody recognizing the region other than the C-terminal region for the primary reaction, e.g., the antibody recognizing the N-terminal region.

The monoclonal antibodies of the present invention can be used for the assay systems other than the sandwich method, for example, competitive method, immunometric method, nephrometry, etc.

In the competitive method, antigen in a test fluid and the labeled antigen are competitively reacted with antibody, and the unreacted labeled antigen (F) and the labeled antigen bound to the antibody (B) are separated (B/F separation). The amount of the label in B or F is measured, and the amount of the antigen in the test fluid is quantified. This reaction method includes a liquid phase method using a soluble antibody as an antibody, polyethylene glycol for B/F separation and a secondary antibody to the soluble antibody, and an immobilized method either using an immobilized antibody as the primary antibody, or using a soluble antibody as the primary antibody and immobilized antibody as the secondary antibody.

In the immunometric method, antigen in a test fluid and immobilized antigen are competitively reacted with a given amount of labeled antibody, the immobilized phase is separated from the liquid phase, or antigen in a test fluid and an excess amount of labeled antibody are reacted, immobilized antigen is then added to bind the unreacted labeled antibody to the immobilized phase, and the immobilized phase is separated from the liquid phase. Then, the amount of the label in either phase is measured to quantify the antigen in the test fluid.

In the nephrometry, insoluble precipitate produced after the antigen-antibody reaction in gel or solution is quantified. When the amount of antigen in the test fluid is small and only a small amount of precipitate is obtained, laser nephrometry using scattering of laser is advantageously employed.

For applying these immunological methods to the quantification methods of the present invention, any particular conditions or procedures are not required. Systems for quantifying the polypeptide of the present invention or its salts are constructed by adding the usual technical consideration in the art to the conventional conditions and procedures. For the details of these general technical means, reference can be made to the following reviews and texts.

For example, the followings are referred: Hiroshi Irie, ed. "Radioimmunoassay" (Kodansha, published in 1974), Hiroshi Irie, ed. "Sequel to the Radioimmunoassay" (Kodansha, published in 1979), Eiji Ishikawa, et al. ed. "Enzyme immuonoassay" (Igakushoin, published in 1978), Eiji Ishikawa, et al. ed. "Immunoenzyme assay" (2nd ed.) (Igakushoin, published in 1982), Eiji Ishikawa, et al. ed. "Immunoenzyme assay" (3rd ed.) (Igakushoin, published in 1987), Methods in ENZYMOLOGY, Vol. 70 (Immunochemical Techniques (Part A)), ibid., Vol. 73 (Immunochemical Techniques (Part B)), ibid., Vol. 74 (Immunochemical Techniques (Part C)), ibid., Vol. 84 (Immunochemical Techniques (Part D: Selected Immunoassays)), ibid., Vol. 92 (Immunochemical Techniques (Part E: Monoclonal Antibodies and General Immunoassay Methods)), ibid., Vol. 121 (Immunochemical Techniques (Part I: Hybridoma Technology and Monoclonal Antibodies))(all published by Academic Press Publishing).

As described above, the polypeptide of the present invention can be quantified with high sensitivity, using the antibodies of the present invention.

Further, by quantifying the polypeptide of the present invention using the antibodies of the present invention, when decrease in the polypeptide of the present invention is detected, it can be diagnosed that there is body weight gain or adipose gain, or that there is high possibility to be body weight gain or adipose gain in the future.

Furthermore, when increase in the polypeptide of the present invention is detected, it can be diagnosed that there have diseases associated with body weight loss, or there is high possibility to have susceptibility to the disease.

The antibodies of the present invention can also be used for specifically detecting the polypeptide of the present invention present in test samples such as body fluids or tissues. The antibodies may also be used for preparation of antibody columns for purification of the polypeptide of the present invention, for detection of the polypeptide of the present invention in each fraction upon purification, and for analysis of the behavior of the polypeptide of the present invention in the test cells.

(4) Gene Diagnosis Product

By using the DNA of the present invention as a probe, an abnormality (gene abnormality) of the DNA or mRNA encoding the polypeptide of the present invention or its partial peptide in human and warm-blooded animals (e.g., rats, mice, guinea pig, rabbits, fowls, sheep, swine, bovine, horse, cats, dogs, monkeys, etc.) can be detected. Therefore, the DNA of the present invention is useful as a gene diagnostic product for the damage against the DNA or mRNA, its mutation, or its decreased expression, or increased expression or overexpression of the DNA or mRNA.

The gene diagnosis described above using the DNA of the present invention can be performed by, for example, the publicly known Northern hybridization assay or the PCR-SSCP assay (Genomics, 5, 874-879 (1989); Proceedings of the National Academy of Sciences of the United States of America, 86, 2766-2770 (1989)).

For example, when decreased expression is detected by Northern hybridization, diagnosis can be made that it is highly possible that the body weight or adipose increases, or will increase in the future.

In addition, when increased expression is detected by Northern hybridization, diagnosis can be made that it is highly possible that the body weight decreases, or will decrease in the future.

(5) Medicines Comprising the Antisense DNA of the Present Invention

Since the antisense DNA of the present invention can suppress expression of the polypeptide or the receptor of the present invention, for example, it can be used as a body weight gain agent.

Where the antisense DNA is used, the antisense DNA itself is administered; alternatively, the antisense DNA is inserted into an appropriate vector such as retrovirus vector, adenovirus vector, adenovirus-associated virus vector, etc. and then administered in a conventional manner. The antisense DNA can also be administered as naked DNA, or formulated with physiologically acceptable carriers such as adjuvants to assist its uptake and administered by gene gun or through a catheter such as a catheter with a hydrogel.

Further, the antisense DNA can be used as a oligonucleotide probe for diagnosis to study the existence of the DNA of the present invention in tissues or cells, or the state of expression.

(6) Medicines Comprising the Antibody of the Present Invention

The antibody of the present invention having a neutralizing action to the polypeptide of the present invention can be used, for example, as a body weight gain agent.

The above-described agent for diseases comprising the antibody of the present invention can be administered orally or parenterally as a liquid formulation or a pharmaceutical composition having appropriate formulations to human or mammals (e.g., rats, rabbits, sheep, swine, bovine, cats, dogs, monkeys). The dose varies depending on subjects to be administered, target diseases, conditions, route for administration. For example, when it is used for suppression of the body weight gain of adults, it is advantageous to administer intraveneously for a dose, normally 0.01 to 20 mg/kg of body weight, preferably 0.1 to 10 mg/kg of body weight, further preferably 0.1 to 5 mg/kg of body weight of the antibody of the present invention one to five times a day, preferably one to three a day. In the case of other parenteral or oral administration, the dose according to the above can be administered. Where the symptom is particularly severe, the dose may be increased depending on the symptom.

The antibody of the present invention can be administered per se, or as an appropriate pharmaceutical composition. The pharmaceutical compositions used for the above administration includes the aforementioned substance, its salts, and pharmacologically acceptable carriers, diluents or excipients. Such compositions are provided as formulations suitable for oral or pareteral administration.

In other words, compositions for oral administration include, for example, solid or liquid formulation, specifically tablets (including sugar coated tablets and film coating tablets), pils, granules, powders, capsules (including soft capsules), syrups, emulsions and suspensions, Such compositions may be manufactured by publicly known methods and contain carriers, diluents or excipients, which are ordinary used in the field of formulation. For example, as carriers or excipients for tablets, lactose, starch, sucrose, magnesium stearate and the like are used.

For compositions for parenteral administration, for example, injections or suppositories are used. The injections encompass formulations such as intraveneous solution, hypodermic solution, endermic solution, intramuscular medication, drops and the like. Such injections are prepared by publicly known methods, for example, by dissolving, suspending or emulsifying the above antibody or salts thereof in aseptic aqueous or oily solution ordinary used as injections. Examples of an aqueous medium for injection include physiological saline and an isotonic solution containing glucose and other auxiliary agents and may be used in combination with an appropriate dissolution aid such as an alcohol (e.g., ethanol), a polyalcohol (e.g., propylene glycol and polyethylene glycol), a nonionic surfactant (e.g., POLYSORBATE 80™ and HCO-50 (polyoxyethylene (50 mol) adduct of hydrogenated castor oil)), etc. Examples of the oily medium include sesame oil and soybean oil, which may also be used in combination with a dissolution aid such as benzyl benzoate and benzyl alcohol. The thus-prepared injections are normally filled in an appropriate ampoule. Suppository for administration to rectum is prepared by mixing the above antibody or salts thereof with normal substrate for suppository.

The pharmaceutical compositions for oral or pareteral administration described above are advantageously prepared in a dose unit formulation adapted to a dose amount of the active ingredient. For such dose unit formulation, exemplified are tablets, pils, capsules, injections (ampoules), suppository and the like. Ordinary 5 through 500 mg of the above antibody per each dose unit formulation, in particular, 5 to 100 mg of the above antibody in injections and 10 to 250 mg of the above antibody in other formulations are preferably comprised.

In addition, the aforementioned compositions may include other active gradient so long as undesirable interactions occur by blending with the above antibody.

(7) DNA Transferred Animals

Non-human mammals having an exogenous DNA encoding the polypeptide of the present invention (hereafter referred to as the exogenous DNA of the present invention) or its mutant DNA (sometimes referred to as the exogenous mutant DNA of the present invention) may also be used for screening a body weight gain inhibitor, a body weight loss agent, an adipose gain inhibitor, a feeding inhibitor and the like.

The non-human mammals having the exogenous DNA of the present invention or its mutant DNA (hereafter referred to as a DNA transferred animals of the present invention) can be prepared by transferring an objective DNA preferably to an unfertilized egg, fertilized egg, sperm, and a germinative cell including its initial cell in a stage of ontogenesis (more preferably, the unicellular amphicytula stage generally before an 8-cell stage) in ontogenesis of the non-human mammals by calcium phosphate method, electric pulse method, lipofection method, microinjection method, particle gun method, DEAE dextran method, etc. In addition, the DNA transfer method enables a use of the objective exogenous DNA of the present invention for a cell culture and tissue culture by transferring it to a somatic cell, an organ of a living body, a tissue cell. Further, the DNA transferred animals of the present invention can be prepared by fusing these cells with each other applying the aforementioned germinative cell and a publicly known cell fusion method.

Non-human mammals used are exemplified by bovine, swine, sheep, goats, rabbits, dogs, cats, guinea pigs, hamsters, mice, rats or the like. Particularly, in consideration of preparation of a disease animal model system, rodents, which are relatively short in ontogenesis and a biological cycle and easy to breed, particularly mice (e.g., pure lies of C57, BL/6 line, DBA2 line, etc.; hybrid lines such as B6C3F$_1$ line, BDF$_1$ line, B6D2F$_1$ line BALB/c line, ICR line, etc.) or rats (e.g., Wistar, SD, etc.) are preferable.

"Mammals" in a recombinant vector that can be expressed in the mammals include the aforesaid non-human mammals and human.

The exogenous DNA of the invention refers to the DNA of the invention that is once isolated and extracted from mammals, not the DNA of the invention inherently possessed by the non-human mammals.

The mutant DNA of the invention includes mutants resulting from variation (e.g., mutation, etc.) in the base sequence of the original DNA of the invention, specifically DNAs resulting from base addition, deletion, substitution with other bases, etc. and further including abnormal DNA.

The abnormal DNA is intended to mean DNA that expresses the abnormal polypeptide of the invention and exemplified by the DNA that expresses a polypeptide for suppressing the function of the normal polypeptide of the invention.

The exogenous DNA of the invention may be any one of those derived from a mammal of the same species as, or a different species from, the mammal as the target animal. To transfer the DNA of the present invention to a target animal, it is generally advantageous to use the DNA in a DNA construct ligated downstream a promoter capable of expressing the DNA in an animal cell. For example, when human DNA of the present invention is transferred, the DNA construct (e.g., vector etc.,) in which the DNA of the present invention is ligated downstream various promoters that can expresses the mammal (rabbits, dogs, cats, guinea pigs, hamsters, rats, mice, or the like) derived DNA having the DNA of the present invention highly homologous thereto, is microinjected to the fertilized egg of the target mammal, e.g., a fertilized fertilized egg of a mouse. Thus, the DNA transfer mammal capable of producing a high level of the DNA of the present invention can be prepared.

Examples of the expression vector for the polypeptide of the present invention include plasmids derived form *E. coli*, plasmids derived from *Bacillus subtilis*, plasmids derived from yeast, bacteriophages such as λ phage, etc., animal viruses such as retrovirus exemplified by Moloney leukemia virus, vaccinia virus, baculovirus, etc. Among these vectors, plasmids derived form *E. coli*, plasmids derived from *Bacillus subtilis*, plasmids derived from yeast and the like are preferably used.

Examples of these promoters for regulating the DNA expression include (a) promoters for DNA derived from viruses (e.g., simian virus, cytomegalovirus, Moloney leukemia virus, JC virus, breast cancer virus, poliovirus, etc.), and (b) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na,K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), polypeptide chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle a actin, preproencephalin A, vasopressin, etc. Among them, cytomegalovirus promoters, human polypeptide chain elongation factor 1α (EF-1α) promoters, human and chicken β actin promoters, etc., which are capable of high expression in the whole body are preferred.

Preferably, the vectors described above have a sequence that terminates the transcription of the desired messenger RNA in the DNA transgenic animal (generally termed terminator); for example, a sequence of each DNA derived from viruses and various mammals, and SV40 terminator of the simian virus and the like are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region for the normal polypeptide of the invention can be obtained using as a starting material the entire genomic DNA or its portion of liver, kidney, thyroid cell or fibroblast origin from human or various mammals (e.g., rabbits, dogs, cats, guinea pigs, hamsters, rats, mice, etc.) or of various commercially available genomic DNA libraries, or using cDNA prepared by a publicly known method from RNA of liver, kidney, thyroid cell or fibroblast origin as a starting material. Also, an exogenous abnormal DNA can produce the translational region through variation of the translational region of normal protein obtained from the cells or tissues described above by point mutagenesis.

The translational region can be prepared by a conventional genetic engineering technique in which the DNA is ligated downstream the aforesaid promoter and if desired, upstream the translation termination site, as a DNA construct capable of being expressed in the transgenic animal.

The exogenous DNA of the present invention is transfected at the amphicytula stage in a manner such that the DNA is certainly present in all the germinal cells and somatic cells of the target mammals. The fact that the exogenous DNA of the present invention is present in the germinal cells of the animal prepared by DNA transfection means that all offspring of the prepared animal will maintain the exogenous DNA of the present invention in all of the germinal cells and somatic cells thereof. The offspring of the animal that inherits the exogenous DNA of the present invention also have the exogenous DNA in all of the germinal cells and somatic cells thereof.

The non-human mammal in which the normal exogenous DNA of the present invention has been transfected can be passaged as the DNA-bearing animal under ordinary rearing environment, by confirming that the exogenous DNA is stably retained by mating.

By the transfection of the exogenous DNA of the present invention at the amphicytula stage, the DNA is retained to be excess in all the germinal and somatic cells. The fact that the exogenous DNA of the present invention is excessively present in the germinal cells of the prepared animal after transfection means that the DNA of the present invention is excessively present in all of the germinal cells and somatic cells thereof. The offspring of the animal that inherits the exogenous DNA of the present invention have excessively the DNA of the present invention in all of the germinal cells and somatic cells thereof.

By obtaining a homozygous animal having the transfected DNA in both of homologous chromosomes and mating a male and female of the animal, all offspring can be passaged to retain the DNA.

In a non-human mammal bearing the normal DNA of the present invention, the normal DNA of the present invention has expressed to a high level, and may eventually develop the hyperfunction of the polypeptide of the present invention by promoting the functions of endogenous normal DNA. Therefore, the animal can be utilized as a pathologic model animal for such a disease. Specifically, using the normal DNA transgenic animal of the present invention, it is possible to elucidate the mechanism of the hyperfunction of the polypeptide of the present invention and the pathological mechanism of the disease associated with the polypeptide of the present invention and to determine how to treat the disease.

Furthermore, since a mammal transfected with the exogenous normal DNA of the present invention exhibits an increasing symptom of the polypeptide of the present invention librated, the animal is usable for screening of therapeutic agents for the disease associated with the polypeptide of the present invention.

On the other hand, non-human mammal having the exogenous abnormal DNA of the present invention can be passaged under normal breeding conditions as the exogenous abnormal DNA-bearing animal by confirming the stable retention of the exogenous DNA via crossing. Moreover, the objective exogenous DNA can be utilized as a starting material by inserting the DNA into the plasmid described above. The DNA construct with a promoter can be prepared by conventional DNA engineering techniques. The transfection of the abnormal DNA of the present invention at the amphicytula stage is preserved to be present in all the germinal and somatic cells of the target mammal. The fact that the abnormal DNA of the present invention is present in the germinal cells of the animal after DNA transfection means that all of the offspring of the animal prepared have the abnormal DNA of the present invention in all of the germinal and somatic cells. Such an offspring which passaged the exogenous DNA of the present invention retains the abnormal DNA of the present invention in all of the germinal and somatic cells. By obtaining a homozygous animal having the transfected DNA in both of homologous chromosomes and mating a male and female of the animal, all offspring can be passaged to retain the DNA.

Since non-human mammal having the abnormal DNA of the present invention may express the abnormal DNA of the present invention at a high level, the animal may sometimes be the function inactivation type inadaptability to the polypeptide of the present invention by inhibiting the function of the endogenous normal DNA and can be utilized as its disease model animal. For example, using the abnormal DNA transgenic animal of the present invention, it is possible to elucidate the mechanism of inadaptability to the polypeptide of the present invention and to perform to study a method for treatment of this disease.

More specifically, the animal of the present invention expressing the abnormal DNA of the present invention to a high level is also expected to serve as an experimental model to elucidate the mechanism of the functional inhibition (dominant negative effect) of normal polypeptide by the abnormal polypeptide of the present invention in the function inactive type inadaptability to the polypeptide of the present invention.

A mammal received the abnormal exogenous DNA of the present invention is also expected to serve for screening a candidate drug for the treatment of the function inactive type inadaptability to the polypeptide of the present invention, since the polypeptide of the present invention increases in such an animal in its free form.

Other potential applications for two kinds of the transgenic animals described above include:
(a) Use as a cell source for tissue culture;
(b) Elucidation of the relation to a polypeptide that is specifically expressed or activated by the polypeptide of the present invention, by direct analysis of DNA or RNA in tissues of the DNA transgenic animal of the present invention or by analysis of the tissues, in which the polypeptide has been expressed by the DNA;
(c) Research in the function of cells derived from tissues that are usually cultured only with difficulty, using cells in tissues bearing the DNA cultured by a standard tissue culture technique;
(d) Screening a drug that enhances the functions of cells using the cells described in (c) above; and,
(e) Isolation and purification of the variant polypeptide of the present invention and preparation of an antibody thereto.

Furthermore, clinical conditions of a disease associated with the polypeptide of the present invention, including the function inactive type inadaptability to the polypeptide of the present invention can be determined by using the DNA transgenic animal of the present invention. Also, pathological findings on each organ in a disease model associated with the polypeptide of the present invention can be obtained in more detail, leading to the development of a new method for treatment as well as the research and therapy of any secondary diseases associated with the disease.

It is also possible to obtain a free cell, in which the DNA is transfected, by withdrawing each organ from the DNA transgenic animal of the present invention, mincing the organ and degrading with a proteinase such as trypsin, etc., followed by establishing the line of culturing or cultured cells. Furthermore, the DNA transgenic animal of the present invention can serve to identify cells capable of producing the polypeptide of the present invention, and to study in association with apoptosis, differentiation or propagation or on the mechanism of signal transduction in these properties to inspect any abnormality therein. Thus, the DNA transgenic animal of the present invention can provide an effective research material for the polypeptide of the present invention and for elucidation of the function and effect thereof.

To develop a drug for the treatment of diseases associated with the polypeptide of the present invention, including the function inactive type inadaptability to the polypeptide of the present invention, using the DNA transgenic animal of the present invention, an effective and rapid method for screening can be provided by using the method for inspection and the method for quantification, etc. described above. It is also possible to investigate and develop a method for DNA therapy for the treatment of diseases associated with the polypeptide of the present invention, using the DNA transgenic animal of the present invention or a vector capable of expressing the exogenous DNA of the present invention.

(8) Knockout Animals

Non-human mammalian embryonic stem cell, wherein the DNA of the present invention is inactivated, and non-human mammals, in which the DNA of the present invention is barely expressed, may also be used for screening a body weight gain inhibitor, a body weight loss agent, an adipose gain inhibitor, a feeding inhibitor and the like.

The non-human mammal embryonic stem cell in which the DNA of the present invention is inactivated refers to a non-human mammal embryonic stem cell that suppresses the ability of the non-human mammal to express the DNA by artificially mutating the DNA of the present invention, or the DNA has no substantial ability to express the polypeptide of the present invention (hereinafter sometimes referred to as the knockout DNA of the present invention) by substantially inactivating the activities of the polypeptide of the present invention encoded by the DNA (hereinafter merely referred to as ES cell).

As the non-human mammal, the same examples as described above apply.

Methods for artificially mutating the DNA of the present invention include, for example, deletion of a part or all of the DNA sequence and insertion of or substitution with other DNA, by genetic engineering. By these mutations, the knockout DNA of the present invention may be prepared, for example, by shifting the reading frame of a codon or by disrupting the function of a promoter or exon.

Specifically, the non-human mammal embryonic stem cell in which the DNA of the present invention is inactivated (hereinafter merely referred to as the ES cell with the DNA of the present invention inactivated or the knockout ES cell of the present invention) can be obtained by, for example, isolating the DNA of the present invention that the desired non-human mammal possesses, inserting a DNA fragment having a DNA sequence constructed by inserting a drug resistant gene such as a neomycin resistant gene or a hygromycin resistant gene, or a reporter gene such as lacZ (β-galactosidase gene) or cat (chloramphenicol acetyltransferase gene), etc. into its exon site thereby to disable the functions of exon, or integrating to a chromosome of the subject animal by, e.g., homologous recombination, a DNA sequence which terminates gene transcription (e.g., polyA additional signal, etc.) in the intron between exons to, thus inhibit the synthesis of intact messenger RNA and eventually destroy the gene (hereinafter simply referred to as targeting vector). The thus-obtained ES cells to the Southern hybridization analysis with a DNA sequence on or near the DNA of the present invention as a probe, or to PCR analysis with a DNA sequence on the targeting vector and another DNA sequence near the DNA of the present invention which is not included in the targeting vector as primers, to select the knockout ES cell of the present invention.

The parent ES cells to inactivate the DNA of the present invention by homologous recombination, etc. may be of a strain already established as described above, or may be originally established in accordance with a modification of the publicly known method by Evans and Kaufman. For example, in the case of mouse ES cells, currently it is common practice to use ES cells of the 129 strain. However, since their immunological background is obscure, the C57BL/6 mouse or the $BDF_1$ mouse ($F_1$ hybrid between C57BL/6 and DBA/2), wherein the low ovum availability per C57BL/6 in the C57BL/6 mouse has been improved by crossing with DBA/2, may be preferably used, instead of obtaining a pure line of ES cells with the clear immunological genetic background and for other purposes. The $BDF_1$ mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes at 3.5 days after fertilization are commonly used. In the present invention, embryos are preferably collected at the 8-cell stage, after culturing until the blastocyte stage, the embryos are used to efficiently obtain a large number of early stage embryos.

Although the ES cells used may be of either sex, male ES cells are generally more convenient for generation of a germ cell line chimera and are therefore preferred. It is desirable to identify sexes as soon as possible also in order to save painstaking culture time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, which karyotype analysis, for example G-banding method, requires about $10^6$ cells; therefore, the first selection of ES cells at the early stage of culture can be based on sex identification, and male cells can be selected early, which saves a significant amount of time at the early stage of culture.

Second selection can be achieved by, for example, number of chromosome confirmation by the G-banding method. It is usually desirable that the chromosome number of the obtained ES cells be 100% of the normal number. However, when it is difficult to obtain the cells having the normal number of chromosomes due to physical operation etc. in cell establishment, it is desirable that the ES cell be again cloned to a normal cell (e.g., in mouse cells having the number of chromosomes being 2n=40) after the gene of the ES cells is rendered knockout.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably about 5% carbon dioxide and about 95% air, or about 5% oxygen, about 5% carbon dioxide and 90% air) in the presence of LIF (1-10000 U/ml) on appropriate feeder cells such as STO fibroblasts, treated with a trypsin/EDTA solution (normally about 0.001 to about 0.5% trypsin/about 0.1 to about 5 mM EDTA, preferably about 0.1% trypsin/1 mM EDTA) at the time of passage to obtain separate single cells, which are then seeded on freshly prepared feeder cells. This passage is normally conducted every 1 to 3 days; it is desirable that cells be observed at passage and cells found to be morphologically abnormal in culture, if any, be abandoned.

By allowing ES cells to reach a high density in monolayers or to form cell aggregates in suspension under appropriate conditions, it is possible to spontaneously differentiate them to various cell types, for example, parental muscle, visceral muscles, cardiac muscle or the like (M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985). The cells deficient in expression of the DNA of the present invention, which are obtainable from the differentiated ES cells of the present invention, are useful for studying the functions of the polypeptide of the present invention cytologically or molecular biologically.

The non-human mammal deficient in expression of the DNA of the present invention can be identified from a normal animal by measuring the amount of mRNA in the subject animal by a publicly known method, and indirectly comparing the degrees of expression.

As the non-human mammal, the same examples supra can be applied.

With respect to the non-human mammal deficient in expression of the DNA of the present invention, the DNA of the present invention can be made knockout by transfecting a targeting vector, prepared as described above, to mouse embryonic stem cells or mouse oocytes, and conducting homologous recombination in which a targeting vector DNA sequence, wherein the DNA of the present invention is inactivated by the transfection, is replaced with the DNA of the present invention on a chromosome of a mouse embryonic stem cell or mouse oocyte.

The knockout cells with the DNA of the present invention disrupted can be identified by Southern hybridization analysis with a DNA sequence on or near the DNA of the present invention as a probe, or by PCR analysis using a DNA sequence on the targeting vector and another DNA sequence derived from mouse, which is not included in the targeting vector, as primers. When non-human mammalian embryonic stem cells are used, a cell line wherein the DNA of the present invention is inactivated by homologous recombination is cloned; the resulting cloned cell line is injected to, e.g., a non-human mammalian embryo or blastocyte, at an appropriate stage such as the 8-cell stage. The resulting chimeric embryos are transplanted to the uterus of the pseudopregnant non-human mammal. The prepared animal is a chimeric animal composed of both cells having the normal locus of the DNA of the present invention and those having an artificially mutated locus of the DNA of the present invention.

When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the polypeptide of the present invention. The individuals deficient in homozygous expression of the polypeptide of the present invention can be obtained from offspring of the intercross between the heterozygotes.

When an oocyte is used, a DNA solution may be injected, e.g., to the nucleus of the oocyte by microinjection thereby to obtain a transgenic non-human mammal having a targeting vector introduced in a chromosome thereof. From such transgenic non-human mammals, those having a mutation at the locus of the DNA of the present invention can be obtained by selection based on homologous recombination.

As described above, individuals in which the DNA of the present invention is rendered knockout permit passage rearing under ordinary rearing conditions, after the individuals obtained by their crossing have proven to have been knockout.

Furthermore, the genital system may be obtained and maintained by conventional methods. That is, by crossing male and female animals each having the inactivated DNA, homozygoous animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammal embryonic stem cell in which the DNA of the present invention is inactivated is very useful for preparing a non-human mammal deficient in expression of the DNA of the present invention.

Since the non-human mammal in which the DNA of the present invention is inactivated lacks various biological activities derived from the polypeptide or the receptor of the present invention, such an animal can be a disease model suspected of inactivated biological activities of the polypeptide or the receptor of the present invention and thus, offers an effective study to investigate causes for and therapy for these diseases.

(8a) Methods for Screening of Compounds having Therapeutic and/or Prophylactic Effects for Diseases Caused by Deficiency, Damages, etc. of the DNA of the Present Invention The non-human mammal deficient in expression of the DNA of the present invention can be employed for the screening of compounds having therapeutic and/or prophylactic effects for diseases caused by deficiency, damages, etc. of the DNA of the present invention.

That is, the present invention provides a method for screening of a compound having therapeutic and/or prophylactic effects for diseases caused by deficiency, damages, etc. of the DNA of the present invention, which comprises administering a test compound to the non-human mammal deficient in expression of the DNA of the present invention and observing and measuring a change occurred in the animal.

As the non-human mammal deficient in expression of the DNA of the present invention, which can be employed for the screening method, the same examples as given hereinabove apply.

Examples of the test compounds include peptides, proteins, non-peptide compounds, synthetic compounds, fermentation products, cell extracts, plant extracts, animal tissue extracts, blood plasma and the like. These compounds may be novel compounds or publicly known compounds.

Specifically, the non-human mammal deficient in the expression of the DNA of the present invention is treated with a test compound, and by comparison with an intact animal for control, a change in each organ, tissue, disease conditions, etc. of the animal is used as an index to assess the therapeutic and/or prophylactic effects of the test compound.

For treating an animal to be tested with a test compound, for example, oral administration, intravenous injection, etc. are applied and the treatment is appropriately selected depending upon conditions of the test animal, properties of the test compound, etc. Furthermore, an amount of a test compound administered can be selected depending on administration route, nature of the test compound, and the like.

For example, in the case of screening a body weight gain inhibitor, the non-human mammal deficient in expression of the DNA of the present invention is subjected to a sugar loading treatment, and a test compound is administered to the animal before or after the sugar loading treatment. Then, blood sugar level, body weight change, etc. of the animal is measured with passage of time.

In the screening method, when a test compound is administered to an animal to be tested and found to reduce the blood sugar level of the animal to at least about 10%, preferably at least about 30% and more preferably at least about 50%, the test compound can be selected as a compound having the therapeutic and/or prophylactic effect for the above-mentioned diseases.

The compound obtained using the above screening method is a compound selected from the test compounds described above and exhibits a therapeutic and/or prophylactic effect for the diseases caused by deficiencies, damages, etc. of the polypeptide of the present invention. Therefore, the compound can be employed as a medicine such as a safe and low toxic agent for the treatment and prevention of these diseases. Furthermore, compounds derived from such a compound obtained by the above screening can be likewise employed.

The compound obtained by the screening method may be used in the form of salts with physiologically acceptable acids (e.g., inorganic acids or organic acids) or bases (e.g., alkali metal), preferably in the form of physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

A medicine containing the compound obtained by the screening method or salts thereof can be manufactured in a manner similar to the method for preparing the medicine comprising the rpolypeptide of the present invention described hereinabove.

Since the formulation thus obtained is safe and low toxic, it can be administered to human or mammals (e.g., rat, mouse, guinea pig, rabbit, sheep, swine, bovine, horse, cat, dog, monkey, etc.).

Although the dose of the compound or its salt varies depending upon target disease, subject to be administered, route of administration, etc., but when the compound is subcutaneously administered, the compound is generally administered to an adult patient (as 60 kg body weight) in a dose of about 0.1 mg/day to about 100 mg/day, preferably about 1.0 mg/day to about 50 mg/day, more preferably about 1.0 mg to about 20 mg. For parenteral administration, a single dose of the compound varies depending upon subject to be administered, target disease, etc., but when the compound that enhances promoter activity for the DNA of the present invention is administered to an adult patient with anorexia (as 60 kg body weight) in the form of an injectable preparation, it is generally advantageous to administer the compound intravenously in a dose of about 0.01 mg/day to about 30 mg/day, preferably about 0.1 mg/day to about 20 mg/day, more preferably about 0.1 mg/day to about 10 mg/day. As for other animals, the compound can be administered in the above amount with converting it into that for the body weight of 60 kg.

(8b) Method for Screening a Compound that Enhances or Inhibits the Activities of a Promoter to the DNA of the Present Invention The present invention provides a method for screening a compound or its salt that enhances or inhibits the activities of a promoter to the DNA of the present invention, which comprises administering a test compound to a non-human mammal deficient in expression of the DNA of the present invention and detecting expression of the reporter gene.

In the screening method described above, as the non-human mammal deficient in expression of the DNA of the present invention, an animal in which the DNA of the present invention is inactivated by introducing a reporter gene and the reporter gene can be expressed under control of a promoter to the DNA of the present invention is used from the aforementioned non-human mammal deficient in expression of the DNA of the present invention.

The same examples of the test compound apply to specific compounds used for the screening.

As the reporter gene, the same specific examples described above apply, and β-galactosidase (lacZ), soluble alkaline phosphatase gene, luciferase gene and the like are preferably employed.

Since a reporter gene is present under control of a promoter to the DNA of the present invention in the non-human mammal deficient in expression of the DNA of the present invention wherein the DNA of the present invention is substituted with the reporter gene, the activity of the promoter can be detected by tracing the expression of a substance encoded by the reporter gene.

When a part of the DNA region encoding the polypeptide of the present invention is substituted with, e.g., β-galactosidase gene (lacZ) derived from *Escherichia coli*, β-galactosidase is expressed in a tissue where the polypeptide of the present invention should originally be expressed, instead of the polypeptide of the present invention. Thus, the state of expression of the polypeptide of the present invention can be readily observed in vivo of an animal by staining with a reagent, e.g., 5-bromo-4-chloro-3-indolyl-β-galactopyranoside (X-gal), which is substrate for β-galactosidase. Specifically, a mouse deficient in the polypeptide of the present invention, or its tissue section is fixed with glutaraldehyde, etc. After washing with phosphate buffered saline (PBS), the system is reacted with a staining solution containing X-gal at room temperature or about 37° C. for approximately 30 minutes to an hour. After that, by washing the tissue preparation with 1 mM EDTA/PBS solution, the β-galactosidase reaction is terminated, and the color formed is observed. Alternatively, mRNA encoding lacZ may be detected in a conventional manner.

The compound or salts thereof obtained using the above screening method, are compounds that are selected from the test compounds described above and that promote or inhibit the promoter activity to the DNA of the present invention.

The compound obtained by the screening method above may be used in the form of salts with physiologically acceptable acids (e.g., inorganic acids) or bases (e.g., organic acids), preferably in the form of physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

Since the compounds or salts thereof that enhance the promoter activity to the DNA of the present invention can promote the expression of the polypeptide of the present invention, or can promote the functions of the polypeptide, they can be used as a body weight gain inhibitor, a body weight loss agent, an adipose gain inhibitor, a feeding inhibitor and the like.

Further, the compounds or salts thereof that inhibit the promoter activity to the DNA of the present invention can inhibit the expression of the polypeptide of the present invention, or can inhibit the functions of the polypeptide, they can be used as a body weight gain agent.

Further, compound derived from the compounds obtained by the screening above may be likewise employed.

A medicine containing the compounds or salts thereof obtained by the screening method can be manufactured in a manner similar to the method for preparing the medicine containing the polypeptide of the present invention described above.

Since the formulation thus obtained is safe and low toxic, it can be administered to human or mammals (e.g., rat, mouse, guinea pig, rabbit, sheep, swine, bovine, horse, cat, dog, monkey, etc.).

The dose of the compound or salts thereof varies depending on target disease, subject to be administered, route for administration, etc.; for example, when the compound that enhances the promoter activity to the DNA of the present invention is orally administered, the dose is normally about 0.1 to about 100 mg, preferably about 1.0 to about 50 mg, more preferably about 1.0 to about 20 mg per day for adult patient (as 60 kg body weight). In parenteral administration, a single dose of the compound varies depending on subject to be administered, target disease, etc. but when the compound that enhances the promoter activity to the DNA of the present invention is administered in the form of injectable preparation, it is advantageous to administer the compound intravenously at a single dose of about 0.01 to about 30 mg/day, preferably about 0.1 to about 20 mg/day, more preferably about 0.1 to about 10 mg/day for adult patient with anorexia (as 60 kg body weight). For other animal species, the corresponding dose as converted per 60 kg weight can be administered.

On the other hand, when the compound that inhibits the promoter activity to the DNA of the present invention is orally administered, the dose is normally about 0.1 to about 100 mg, preferably about 1.0 to about 50 mg, more preferably about 1.0 to about 20 mg per day for adult patient (as 60 kg body weight). In parenteral administration, a single dose of the compound varies depending on subject to be administered, target disease, etc. but when the compound that inhibits the promoter activity to the DNA of the present invention is administered in the form of injectable preparation, it is advantageous to administer the compound intravenously at a single dose of about 0.01 to about 30 mg/day, preferably about 0.1 to about 20 mg/day, more preferably about 0.1 to about 10 mg/day for adult patient with adiposis (as 60 kg body weight). For other animal species, the corresponding dose as converted per 60 kg weight can be administered.

As stated above, the non-human mammal deficient in expression of the DNA of the present invention is extremely useful for screening the compound or its salt that promotes or inhibits the activity of a promoter to the DNA of the present invention and can greatly contribute to the elucidation of causes for various diseases suspected of deficiency in expression of the DNA of the present invention and for the development of medicine for prevention and/or treatment of these diseases.

Furthermore, a so-called transgenic animal (gene introduced animal) can be prepared by using DNA containing a promoter region of the polypeptide of the present invention, ligating genes encoding various proteins downstream and injecting the same into oocyte of an animal. It is then possible to synthesize the protein therein specifically and study its activity in vivo. When an appropriate reporter gene is ligated to the promoter site above and a cell line that express the gene is established, the resulting system can be utilized as the survey system for a low molecular compound having the action of specifically promoting or inhibiting the in vivo productivity of the polypeptide per se of the present invention.

In the specification and drawings, the codes of bases and amino acids are denoted in accordance with the IUPAC-IUB Commission on Biochemical Nomenclature or by the common codes in the art, examples of which are shown below. For amino acids that may have the optical isomer, L form is presented unless otherwise indicated.

| | |
|---|---|
| DNA: | deoxyribonucleic acid |
| cDNA: | complementary deoxyribonucleic acid |
| A: | adenine |
| T: | thymine |
| G: | guanine |
| C: | cytosine |
| I: | inosine |
| R: | adenine (A) or guanine (G) |
| Y: | thymine (T) or cytosine (C) |
| M: | adenine (A) or cytosine (C) |
| K: | guanine (G) or thymine (T) |
| S: | guanine (G) or cytosine (C) |
| W: | adenine (A) or thymine (T) |
| B: | guanine (G), guanine (G) or thymine (T) |
| D: | adenine (A), guanine (G) or thymine (T) |
| V: | adenine (A), guanine (G) or cytosine (C) |
| N: | adenine (A), guanine (G), cytosine (C) or thymine (T), or unknown or other bases |
| RNA: | ribonucleic acid |
| mRNA: | messenger ribonucleic acid |
| dATP: | deoxyadenosine triphosphate |
| dTTP: | deoxythymidine triphosphate |
| dGTP: | deoxyguanosine triphosphate |
| dCTP: | deoxycytidine triphosphate |
| ATP: | adenosine triphosphate |
| EDTA: | ethylenediaminetetraacetic acid |
| SDS: | sodium dodecyl sulfate |
| BHA: | benzhydrilamine |
| pMBHA: | p-methylbenzhydrilamine |
| Tos: | p-toluenesulfonyl |
| Bzl: | benzyl |
| Bom: | benzyloxymethyl |
| Boc: | t-butoxycarbonyl |
| DCM: | dichloromethane |
| HOBt: | 1-hydroxybenztriazole |
| DCC: | N,N'-dicyclohexylcarbodiimide |
| TFA: | trifluoroacetic acid |
| DIEA: | diisopropylethylamine |
| BSA: | bovine serum albumin |
| CHAPS: | 3-[(3-cholamidopropyl)dimethylammonio]-1-propanesulfonate |
| Gly or G: | glycine |
| Ala or A: | alanine |
| Val or V: | valine |

-continued

| | |
|---|---|
| Leu or L: | leucine |
| Ile or I: | isoleucine |
| Ser or S: | serine |
| Thr or T: | threonine |
| Cys or C: | cysteine |
| Met or M: | methionine |
| Glu or E: | glutamic acid |
| Asp or D: | aspartic acid |
| Lys or K: | lysine |
| Arg or R: | arginine |
| His or H: | histidine |
| Phe or F: | phenylalanine |
| Tyr or Y: | tyrosine |
| Trp or W: | tryptophan |
| Pro or P: | proline |
| Asn or N: | asparagine |
| Gln or Q: | glutamine |
| pGlu: | pyroglutamic acid |
| Tyr(I): | 3-iode tyrosine |
| DMF: | N,N-dimethyl formamide |
| Fmoc: | N-9-fluorenylmethoxycarbonyl |
| Trt: | trityl |
| Pbf: | 2,2,4,6,7-pentamethyldihydrobenzofuran-5-sulfonyl |
| Clf: | 2-chlorotrityl |
| $Bu^t$: | t-buthyl |
| Met(O): | methionine sulfoxide |

The sequence identification numbers in the sequence listing of the specification indicates the following sequence, respectively.

[SEQ ID NO: 1]
This shows the base sequence of synthetic DNA used in the screening of cDNA encoding human GPR8 protein.

[SEQ ID NO: 2]
This shows the base sequence of synthetic DNA used in the screening of cDNA encoding human GPR8 protein.

[SEQ ID NO: 3]
This shows the entire base sequence of cDNA encoding human GPR8 protein, wherein the restriction enzyme ClaI recognition base sequence has been added to the 5' terminus and the restriction enzyme SpeI recognition base sequence has been added to 3' terminus.

[SEQ ID NO: 4]
This shows the entire amino acid sequence of human GPR8 protein.

[SEQ ID NO: 5]
This shows the sequence of riboprobe used for determining an expression level of mRNA encoding GPR8 protein in each clone of the GPR8-expressing CHO cells.

[SEQ ID NO: 6]
This shows the amino acid sequence obtained from the amino acid sequence analysis for the amino terminus of ligand peptide to GPR8, which has been purified from porcine hypothalamus.

[SEQ ID NO: 7]
This shows the EST sequence (Accession No.: AW007531), wherein the complementary strand is deduced to encode a portion of human homologue precursor protein for GPR8 ligand peptide.

[SEQ ID NO: 8]
This shows the EST sequence (Accession No.: AI500303), wherein the complementary strand is deduced to encode a portion of human homologue precursor protein for GPR8 ligand peptide.

[SEQ ID NO: 9]
This shows the EST sequence (Accession No.: AI990964), wherein the complementary strand is deduced to encode a portion of human homologue precursor protein for GPR8 ligand peptide.

[SEQ ID NO: 10]
This shows the EST sequence (Accession No.: AA744804), wherein the complementary strand is deduced to encode a portion of human homologue precursor protein for GPR8 ligand peptide.

[SEQ ID NO: 11]
This shows the EST sequence (Accession No.: H31598), which is deduced to encode a portion of rat homologue precursor protein for GPR8 ligand peptide.

[SEQ ID NO: 12]
This shows the base sequence of synthetic DNA used in the screening of cDNA encoding a portion of human homologue precursor protein for ligand peptide to GPR8.

[SEQ ID NO: 13]
This shows the base sequence of synthetic DNA used in the screening of cDNA encoding a portion of human homologue precursor protein for ligand peptide to GPR8.

[SEQ ID NO: 14]
This shows the DNA sequence encoding a portion of the precursor protein of human homologue of ligand peptide to GPR8, which was amplified from cDNA derived from human brain.

[SEQ ID NO: 15]
This shows the amino acid sequence of a portion of the precursor protein of human homologue of ligand peptide to GPR8.

[SEQ ID NO: 16]
This shows the amino acid sequence of human homologue of ligand peptide to GPR8, which is deduced from SEQ ID NO: 15.

[SEQ ID NO: 17]
This shows the amino acid sequence of human homologue of ligand peptide to GPR8, which is deduced from SEQ ID NO: 15.

[SEQ ID NO: 18]
This shows the base sequence encoding the amino acid sequence represented by SEQ ID NO: 16.

[SEQ ID NO: 19]
This shows the base sequence encoding the amino acid sequence represented by SEQ ID NO: 17.

[SEQ ID NO: 20]
This shows the amino acid sequence of human GPR ligand (1-29) synthesized in Reference Example 14 described below.

[SEQ ID NO: 21]
This shows the amino acid sequence of human GPR ligand (1-28) synthesized in Reference Example 15 described below.

[SEQ ID NO: 22]
This shows the amino acid sequence of human GPR ligand (1-27) synthesized in Reference Example 16 described below.

[SEQ ID NO: 23]

This shows the amino acid sequence of human GPR ligand (1-26) synthesized in Reference Example 17 described below.

[SEQ ID NO: 24]

This shows the amino acid sequence of human GPR ligand (1-25) synthesized in Reference Example 18 described below.

[SEQ ID NO: 25]

This shows the amino acid sequence of human GPR ligand (1-24) synthesized in Reference Example 19 described below.

[SEQ ID NO: 26]

This shows the base sequence encoding the amino acid sequence represented by SEQ ID NO: 20.

[SEQ ID NO: 27]

This shows the base sequence encoding the amino acid sequence represented by SEQ ID NO: 21.

[SEQ ID NO: 28]

This shows the base sequence encoding the amino acid sequence represented by SEQ ID NO: 22.

[SEQ ID NO: 29]

This shows the base sequence encoding the amino acid sequence represented by SEQ ID NO: 23.

[SEQ ID NO: 30]

This shows the base sequence encoding the amino acid sequence represented by SEQ ID NO: 24.

[SEQ ID NO: 31]

This shows the base sequence encoding the amino acid sequence represented by SEQ ID NO: 25.

[SEQ ID NO: 32]

This shows the base sequence encoding the amino acid sequence represented by SEQ ID NO: 4.

[SEQ ID NO: 33]

This shows the base sequence of synthetic DNA used for obtaining 5' upstream sequence of cDNA encoding the precursor protein of human homologue of ligand peptide to GPR8.

[SEQ ID NO: 34]

This shows the base sequence of synthetic DNA used for obtaining 5' upstream sequence of cDNA encoding the precursor protein of human homologue of ligand peptide to GPR8.

[SEQ ID NO: 35]

This shows the base sequence of 5' upstream DNA of cDNA encoding the precursor protein of human homologue of ligand peptide to GPR8.

[SEQ ID NO: 36]

This shows the base sequence of synthetic DNA used for obtaining 3' downstream sequence of cDNA encoding the precursor protein of human homologue of ligand peptide to GPR8.

[SEQ ID NO: 37]

This shows the base sequence of synthetic DNA used for obtaining 3' downstream sequence of cDNA encoding the precursor protein of human homologue of ligand peptide to GPR8.

[SEQ ID NO: 38]

This shows the base sequence of 3' downstream DNA of cDNA encoding the precursor protein of human homologue of ligand peptide to GPR8.

[SEQ ID NO: 39]

This shows the base sequence of synthetic DNA used for obtaining cDNA encoding the precursor protein of human homologue of ligand peptide to GPR8.

[SEQ ID NO: 40]

This shows the base sequence of synthetic DNA used for obtaining cDNA encoding the precursor protein of human homologue of ligand peptide to GPR8.

[SEQ ID NO: 41]

This shows the base sequence of cDNA encoding the precursor protein of human homologue of ligand peptide to GPR8.

[SEQ ID NO: 42]

This shows the amino acid sequence of the precursor protein of human homologue of ligand peptide to GPR8.

[SEQ ID NO: 43]

This shows the base sequence of synthetic DNA used for obtaining 5' upstream sequence of cDNA encoding the precursor protein of porcine homologue of ligand peptide to GPR8.

[SEQ ID NO: 44]

This shows the base sequence of synthetic DNA used for obtaining 5' upstream sequence of cDNA encoding the precursor protein of porcine homologue of ligand peptide to GPR8.

[SEQ ID NO: 45]

This shows the base sequence of 5' upstream DNA of cDNA encoding the precursor protein of porcine homologue of ligand peptide to GPR8.

[SEQ ID NO: 46]

This shows the base sequence of synthetic DNA used for obtaining 5' upstream sequence of cDNA encoding the precursor protein of porcine homologue of ligand peptide to GPR8.

[SEQ ID NO: 47]

This shows the base sequence of synthetic DNA used for obtaining 5' upstream sequence of cDNA encoding the precursor protein of porcine homologue of ligand peptide to GPR8

[SEQ ID NO: 48]

This shows the base sequence of 5' upstream DNA of cDNA encoding the precursor protein of porcine homologue of ligand peptide to GPR8.

[SEQ ID NO: 49]

This shows the base sequence of synthetic DNA used for obtaining 3' downstream sequence of cDNA encoding the precursor protein of porcine homologue of ligand peptide to GPR8.

[SEQ ID NO: 50]

This shows the base sequence of synthetic DNA used for obtaining 3' downstream sequence of cDNA encoding the precursor protein of porcine homologue of ligand peptide to GPR8.

[SEQ ID NO: 51]
This shows the base sequence of 3' downstream DNA of cDNA encoding the precursor protein of porcine homologue of ligand peptide to GPR8.

[SEQ ID NO: 52]
This shows the base sequence of synthetic DNA used for obtaining cDNA encoding the precursor protein of porcine homologue of ligand peptide to GPR8.

[SEQ ID NO: 53]
This shows the base sequence of synthetic DNA used for obtaining cDNA encoding the precursor protein of porcine homologue of ligand peptide to GPR8.

[SEQ ID NO: 54]
This shows the cDNA sequence, which encodes the precursor protein of porcine homologue of ligand peptide to GPR8.

[SEQ ID NO: 55]
This shows the amino acid sequence of the precursor protein of porcine homologue of ligand peptide to GPR8.

[SEQ ID NO: 56]
This shows the amino acid sequence of porcine homologue of ligand peptide to GPR8 deduced from SEQ ID NO: 55.

[SEQ ID NO: 57]
This shows the amino acid sequence of porcine homologue of ligand peptide to GPR8 deduced from SEQ ID NO: 55.

[SEQ ID NO: 58]
This shows the base sequence encoding the amino acid sequence represented by SEQ ID NO: 56.

[SEQ ID NO: 59]
This shows the base sequence encoding the amino acid sequence represented by SEQ ID NO: 57.

[SEQ ID NO: 60]
This shows the base sequence of synthetic DNA used for obtaining the cDNA encoding a portion of the precursor protein of rat homologue of ligand peptide to GPR8.

[SEQ ID NO: 61]
This shows the base sequence of synthetic DNA used for obtaining the cDNA encoding a portion of the precursor protein of rat homologue of ligand peptide to GPR8.

[SEQ ID NO: 62]
This shows the cDNA sequence, which encodes a portion of the precursor protein of rat homologue of ligand peptide to GPR8.

[SEQ ID NO: 63]
This shows the base sequence of synthetic DNA used for obtaining 5' upstream sequence of cDNA encoding the precursor protein of rat homologue of ligand peptide to GPR8.

[SEQ ID NO: 64]
This shows the base sequence of synthetic DNA used for obtaining 5' upstream sequence of cDNA encoding the precursor protein of rat homologue of ligand peptide to GPR8.

[SEQ ID NO: 65]
This shows the base sequence of 5' upstream DNA of cDNA encoding the precursor protein of rat homologue of ligand peptide to GPR8.

[SEQ ID NO: 66]
This shows the base sequence of synthetic DNA used for obtaining 3' downstream sequence of cDNA encoding the precursor protein of rat homologue of ligand peptide to GPR8.

[SEQ ID NO: 67]
This shows the base sequence of synthetic DNA used for obtaining 3' downstream sequence of cDNA encoding the precursor protein of rat homologue of ligand peptide to GPR8.

[SEQ ID NO: 68]
This shows the base sequence of 3' downstream DNA of cDNA encoding the precursor protein of rat homologue of ligand peptide to GPR8.

[SEQ ID NO: 69]
This shows the synthetic DNA used for obtaining the cDNA encoding the precursor protein of rat homologue of ligand peptide to GPR8.

[SEQ ID NO: 70]
This shows the base sequence of synthetic DNA used for obtaining the cDNA encoding the precursor protein of rat homologue of ligand peptide to GPR8.

[SEQ ID NO: 71]
This shows the cDNA sequence, which encodes the precursor protein of rat homologue of ligand peptide to GPR8.

[SEQ ID NO: 72]
This shows the amino acid sequence of the precursor protein of rat homologue of ligand peptide to GPR8.

[SEQ ID NO: 73]
This shows the amino acid sequence of rat homologue of ligand peptide to GPR8 deduced from SEQ ID NO: 72.

[SEQ ID NO: 74]
This shows the amino acid sequence of rat homologue of ligand peptide to GPR8 deduced from SEQ ID NO: 72.

[SEQ ID NO: 75]
This shows the base sequence encoding the amino acid sequence represented by SEQ ID NO: 73.

[SEQ ID NO: 76]
This shows the base sequence encoding the amino acid sequence represented by SEQ ID NO: 74.

[SEQ ID NO: 77]
This shows the sequence of synthetic DNA used as a probe for determining an expression level of GPR7 gene in human GPR7-expressing CHO cells.

[SEQ ID NO: 78]
This shows the base sequence of synthetic DNA used in the screening of the cDNA encoding a portion of the precursor protein of mouse homologue of ligand peptide to GPR8.

[SEQ ID NO: 79]
This shows the base sequence of synthetic DNA used in the screening of the cDNA encoding a portion of the precursor protein of mouse homologue of ligand peptide to GPR8.

[SEQ ID NO: 80]
This shows the base sequence of DNA encoding a portion of the precursor protein of human homologue of ligand peptide to GPR8, which was amplified from cDNA derived from mouse testis.

[SEQ ID NO: 81]

This shows the base sequence of synthetic DNA used for obtaining 5' upstream sequence of cDNA encoding the precursor protein of mouse homologue of ligand peptide to GPR8.

[SEQ ID NO: 82]

This shows the base sequence of synthetic DNA used for obtaining 5' upstream sequence of cDNA encoding the precursor protein of mouse homologue of ligand peptide to GPR8.

[SEQ ID NO: 83]

This shows the base sequence of 5' upstream DNA of cDNA encoding the precursor protein of mouse homologue of ligand peptide to GPR8.

[SEQ ID NO: 84]

This shows the base sequence of synthetic DNA used for obtaining 3' downstream sequence of cDNA encoding the precursor protein of mouse homologue of ligand peptide to GPR8.

[SEQ ID NO: 85]

This shows the base sequence of synthetic DNA used for obtaining 3' downstream sequence of cDNA encoding the precursor protein of mouse homologue of ligand peptide to GPR8.

[SEQ ID NO: 86]

This shows the base sequence of 3' downstream DNA of cDNA encoding the precursor protein of mouse homologue of ligand peptide to GPR8.

[SEQ ID NO: 87]

This shows the base sequence of synthetic DNA used for obtaining the cDNA encoding the precursor protein of mouse homologue of ligand peptide to GPR8.

[SEQ ID NO: 88]

This shows the base sequence of synthetic DNA used for obtaining the cDNA encoding the precursor protein of mouse homologue of ligand peptide to GPR8.

[SEQ ID NO: 89]

This shows the cDNA sequence encoding the precursor protein of mouse homologue of ligand peptide to GPR8.

[SEQ ID NO: 90]

This shows the amino acid sequence of the precursor protein of mouse homologue of ligand peptide to GPR8.

[SEQ ID NO: 91]

This shows the amino acid sequence of mouse homologue of ligand peptide to GPR8 deduced from SEQ ID NO: 90.

[SEQ ID NO: 92]

This shows the amino acid sequence of mouse homologue of ligand peptide to GPR8 deduced from SEQ ID NO: 90.

[SEQ ID NO: 93]

This shows the base sequence encoding the amino acid sequence represented by SEQ ID NO: 91.

[SEQ ID NO: 94]

This shows the base sequence encoding the amino acid sequence represented by SEQ ID NO: 92.

[SEQ ID NO: 95]

This shows the amino acid sequence of human GPR8 ligand (1-23) oxidant, which was synthesized in Reference Example 44 described below.

[SEQ ID NO: 96]

This shows the amino acid sequence of human GPR8 ligand (1-22), which was synthesized in Reference Example 45 described below.

[SEQ ID NO: 97]

This shows the amino acid sequence of human GPR8 ligand (1-21), which was synthesized in Reference Example 46 described below.

[SEQ ID NO: 98]

This shows the amino acid sequence of human GPR8 ligand (1-20), which was synthesized in Reference Example 47 described below.

[SEQ ID NO: 99]

This shows the amino acid sequence of human GPR8 ligand (1-19), which was synthesized in Reference Example 48 described below.

[SEQ ID NO: 100]

This shows the amino acid sequence of human GPR8 ligand (1-18), which was synthesized in Reference Example 49 described below.

[SEQ ID NO: 101]

This shows the amino acid sequence of human GPR8 ligand (1-17), which was synthesized in Reference Example 50 described below.

[SEQ ID NO: 102]

This shows the amino acid sequence of human GPR8 ligand (1-16), which was synthesized in Reference Example 51 described below.

[SEQ ID NO: 103]

This shows the amino acid sequence of porcine GPR8 ligand (1-23) oxidant, which was synthesized in Reference Example 54 described below.

[SEQ ID NO: 104]

This shows the amino acid sequence of rat or mouse GPR8 ligand (1-23) oxidant, which was synthesized in Reference Example 55 described below.

[SEQ ID NO: 105]

This shows the amino acid sequence of human GPR8 ligand (1-23) modified by Fmoc, which was synthesized in Reference Example 12 described below.

[SEQ ID NO: 106]

This shows the amino acid sequence of [$N^{\alpha}$-Acetyl-Trp$^1$]-human GPR8 ligand (1-23) oxidant, which was synthesized in Reference Example 56 described below.

[SEQ ID NO: 107]

This shows the amino acid sequence of human GPR8 ligand (2-23), which was synthesized in Reference Example 57 described below.

[SEQ ID NO: 108]

This shows the amino acid sequence of human GPR8 ligand (4-23), which was synthesized in Reference Example 58 described below.

[SEQ ID NO: 109]

This shows the amino acid sequence of human GPR8 ligand (9-23), which was synthesized in Reference Example 59 described below.

[SEQ ID NO: 110]

This shows the amino acid sequence of human GPR8 ligand (15-23), which was synthesized in Reference Example 60 described below.

[SEQ ID NO: 111]
This shows the amino acid sequence of [N-Acetyl-Tyr$^2$]-human GPR8 ligand (2-23), which was synthesized in Reference Example 61 described below.

[SEQ ID NO: 112]
This shows the amino acid sequence of [D-Trp$^1$]-human GPR8 ligand (1-23), which was synthesized in Reference Example 62 described below.

[SEQ ID NO: 113]
This shows the amino acid sequence of [N-3-Indolepropanoyl-Tyr$^2$]-human GPR8 ligand (2-23), which was synthesized in Reference Example 63 described below.

[SEQ ID NO: 114]
This shows the base sequence encoding the amino acid sequence represented by SEQ ID NO: 96.

[SEQ ID NO: 115]
This shows the base sequence encoding the amino acid sequence represented by SEQ ID NO: 97.

[SEQ ID NO: 116]
This shows the base sequence encoding the amino acid sequence represented by SEQ ID NO: 98.

[SEQ ID NO: 117]
This shows the base sequence encoding the amino acid sequence represented by SEQ ID NO: 99.

[SEQ ID NO: 118]
This shows the base sequence encoding the amino acid sequence represented by SEQ ID NO: 100.

[SEQ ID NO: 119]
This shows the base sequence encoding the amino acid sequence represented by SEQ ID NO: 101.

[SEQ ID NO: 120]
This shows the base sequence encoding the amino acid sequence represented by SEQ ID NO: 102.

[SEQ ID NO: 121]
This shows the base sequence encoding the amino acid sequence represented by SEQ ID NO: 107.

[SEQ ID NO: 122]
This shows the base sequence encoding the amino acid sequence represented by SEQ ID NO: 108.

[SEQ ID NO: 123]
This shows the base sequence encoding the amino acid sequence represented by SEQ ID NO: 109.

[SEQ ID NO: 124]
This shows the base sequence encoding the amino acid sequence represented by SEQ ID NO: 110.

[SEQ ID NO: 125]
This shows the base sequence encoding the amino acid sequence represented by SEQ ID NO: 6.

[SEQ ID NO: 126]
This shows the amino acid sequence of TGR26, the rat-derived novel G protein-coupled receptor protein of the present invention.

[SEQ ID NO: 127]
This shows the base sequence of cDNA encoding TGR26, the rat-derived novel G protein-coupled receptor protein of the present invention.

[SEQ ID NO: 128]
This shows the base sequence of primer 1 used for the PCR reaction in Reference Example 67 described below.

[SEQ ID NO: 129]
This shows the base sequence of primer 2 used for the PCR reaction in Reference Example 67 described below.

[SEQ ID NO: 130]
This shows the base sequence of primer used for determining an expression level of TGR26 receptor gene of TGR26-expressing CHO cells in Reference Example 68 described below.

[SEQ ID NO: 131]
This shows the base sequence of primer used for determining an expression level of TGR26 gene of TGR26-expressing CHO cells in Reference Example 68 described below.

[SEQ ID NO: 132]
This shows the base sequence of primer used for the PCR reaction in Reference Example 75 described below.

[SEQ ID NO: 133]
This shows the base sequence of primer used for the PCR reaction in Reference Example 75 described below.

[SEQ ID NO: 134]
This shows the base sequence of 5' upstream end of the DNA encoding mouse TGR26, which was obtained in Reference Example 75 below.

[SEQ ID NO: 135]
This shows the base sequence of the primer used in the PCR reaction of Reference Example 24 below.

[SEQ ID NO: 136]
This shows the base sequence of the primer used in the PCR reaction of Reference Example 24 below.

[SEQ ID NO: 137]
This shows the base sequence of the cDNA encoding mouse TGR26, which was obtained in Reference Example 24 below.

[SEQ ID NO: 138]
This shows the amino acid sequence of mouse-derived TGR26.

[SEQ ID NO: 139]
This shows the base sequence of the cDNA encoding mouse-derived TGR26.

[SEQ ID NO: 140]
This shows the base sequence of probe used for determining an expression level of TGR26 gene of the TGR26-expressing CHO cells in Reference Example 68 below.

[SEQ ID NO: 141]
This shows the base sequence of synthetic DNA used in the screening of cDNA encoding human GPR7.

[SEQ ID NO: 142]
This shows the base sequence of synthetic DNA used in the screening of cDNA encoding human GPR7.

[SEQ ID NO: 143]
This shows the entire base sequence of cDNA encoding human GPR7 protein, wherein the restriction enzyme ClaI recognition base sequence has been added to the 5' terminus and the restriction enzyme SpeI recognition base sequence has been added to 3' terminus.

[SEQ ID NO: 144]

This shows the entire amino acid sequence of human GPR7.

[SEQ ID NO: 145]

This shows the base sequence of DNA used as a primer for amplifying standard human GPR7 DNA.

[SEQ ID NO: 146]

This shows the base sequence of DNA used as a primer for amplifying standard human GPR7 DNA.

[SEQ ID NO: 147]

This shows the base sequence of synthetic DNA used as a primer for determining an expression level of GPR7 gene in human GPR7-expressing CHO cells.

[SEQ ID NO: 148]

This shows the base sequence of synthetic DNA used as a primer for determining an expression level of GPR7 gene in human GPR7-expressing CHO cells.

[SEQ ID NO: 149]

This shows the amino acid sequence of [$Phe^2$] human GPR8 ligand (1-20).

[SEQ ID NO: 150]

This shows the base sequence encoding the amino acid sequence represented by SEQ ID NO: 149.

The transformant *Escherichia coli* DH5α/pAKKO-GPR8 obtained in Reference Example 3 described below was on deposit with Institute for Fermentation (IFO), located at 2-17-85 Juso-homnachi, Yodogawa-ku, Osaka-shi, Osaka, Japan, as the Accession Number IFO 16564 on Feb. 27, 2001, and with International Patent Organisms Depository, National Institute of Advanced Industrial Science and Technology, located at Central 6, 1-1-1 Higashi, Tsukuba, Ibaraki, 305-8566, Japan, as the Accession Number FERM BP-7540 on Apr. 11, 2001.

The transformant *Escherichia coli* TOP10/pCR2.1-TOPO human GPR8 Ligand Precursor obtained in Reference Example 28 described below was on deposit with Institute for Fermentation (IFO), located at 2-17-85 Juso-honmachi, Yodogawa-ku, Osaka-shi, Osaka, Japan, as the Accession Number IFO 16568 on Feb. 27, 2001, and with International Patent Organisms Depository, National Institute of Advanced Industrial Science and Technology, located at Central 6, 1-1-1 Higashi, Tsukuba, Ibaraki, 305-8566, Japan, as the Accession Number FERM BP-7544 on Apr. 11, 2001.

The transformant *Escherichia coli* TOP10/pCR2.1-TOPO Porcine GPR8 Ligand Precursor obtained in Reference Example 32 described below was on deposit with Institute for Fermentation (IFO), located at 2-17-85 Juso-honmachi, Yodogawa-ku, Osaka-shi, Osaka, Japan, as the Accession Number IFO 16565 on Feb. 27, 2001, and with International Patent Organisms Depository, National Institute of Advanced Industrial Science and Technology, located at Central 6, 1-1-1 Higashi, Tsukuba, Ibaraki, 305-8566, Japan, as the Accession Number FERM BP-7541 on Apr. 11, 2001.

The transformant *Escherichia coli* TOP10/pCR2.1-TOPO Rat GPR8 Ligand Precursor obtained in Reference Example 36 described below was on deposit with Institute for Fermentation (IFO), located at 2-17-85 Juso-honmachi, Yodogawa-ku, Osaka-shi, Osaka, Japan, as the Accession Number IFO 16567 on Feb. 27, 2001, and with International Patent Organisms Depository, National Institute of Advanced Industrial Science and Technology, located at Central 6, 1-1-1 Higashi, Tsukuba, Ibaraki, 305-8566, Japan, as the Accession Number FERM BP-7543 on Apr. 11, 2001.

The transformant *Escherichia coli* TOP10/pCR2.1-TOPO Mouse GPR8 Ligand Precursor obtained in Reference Example 41 described below was on deposit with Institute for Fermentation (IFO), located at 2-17-85 Juso-honmachi, Yodogawa-ku, Osaka-shi, Osaka, Japan, as the Accession Number IFO 16566 on Feb. 27, 2001, and with International Patent Organisms Depository, National Institute of Advanced Industrial Science and Technology, located at Central 6, 1-1-1 Higashi, Tsukuba, Ibaraki, 305-8566, Japan, as the Accession Number FERM BP-7542 on Apr. 11, 2001.

The transformant *Escherichia coli* DH10B/pAK-rGPR7 obtained in Reference Example 67 described below was on deposit with Institute for Fermentation (IFO), located at 2-17-85 Juso-honmachi, Yodogawa-ku, Osaka-shi, Osaka, Japan, as the Accession Number IFO 16496 on Oct. 31, 2000, and with International Patent Organisms Depository, National Institute of Advanced Industrial Science and Technology (formerly, National Institute of Bioscience and Human-Technology (NIBH), Ministry of International Trade and Industry), located at Central 6, 1-1-1 Higashi, Tsukuba, Ibaraki, 305-8566, Japan, as the Accession Number FERM BP-7365 on Nov. 13, 2000.

The transformant *Escherichia coli* TOP10/pCR2.1-TOPO Mouse GPR7 obtained in Reference Example 24 described below was on deposit with Institute for Fermentation (IFO), located at 2-17-85 Juso-honmachi, Yodogawa-ku, Osaka-shi, Osaka, Japan, as the Accession Number IFO 16704 on Sep. 20, 2001, and with International Patent Organisms Depository, National Institute of Advanced Industrial Science and Technology, located at Central 6, 1-1-1 Higashi, Tsukuba, Ibaraki, 305-8566, Japan, as the Accession Number FERM BP-7775 on Oct. 15, 2001.

EXAMPLES

The present invention is described in detail below with reference to EXAMPLES and REFERENCE EXAMPLES, but is not deemed to limit the scope of the present invention thereto.

Reference Example 1

Amplification of human GPR8 cDNA by PCR Method Using Human Brain-Derived cDNA

Using the human brain-derived poly(A)$^+$ RNA (CLONTECH) as a template and random primers, reverse transcription reaction was carried out. For the reverse transcription, reagents for RNA PCR ver 2.1 Kit (Takra Shuzo) were used. Subsequently, using the reverse transcript as a template and the synthetic DNA primers represented by SEQ ID NO: 1 and SEQ ID NO: 2, amplification by PCR method was performed. The synthetic primers were constructed to allow a region of the gene to be translated to the receptor protein to amplify. Therewith, at the 5' end of the gene, the base sequence recognized by restriction enzyme ClaI was added, and at the 3' end, the base sequence recognized by restriction enzyme SpeI was added. The reaction solution in the above reaction comprised of 5 μl of cDNA template, 0.4 μM each of synthetic DNA primers, 0.8 mM dNTPs, 0.5 μl of Pfu Polymerase (STRATAGENE) and a buffer attached to the enzyme to make the total volume 50 μl. The PCR reaction was carried out using a thermal cycler (PE Biosystems) by heating of 94° C. for 60 seconds, then a cycle set to include 94° C. for 60 seconds followed by 65° C. for 60 seconds and 72° C. for 150 seconds, which was repeated 35 times. The amplified product was confirmed by 0.8% agarose gel electrophoresis follwed by ethidium bromide staining.

Reference Example 2

Subcloning of PCR Product into Plasmid Vector and Confirmation of Amplified cDNA Sequence by Decoding a Base Sequence of the Inserted cDNA Region Using the PCR reaction solution in Reference Example 1, DNA was isolated by 0.8% low melting agarose gel electrophoresis. The DNA band was excised from the gel with razor, and was recovered by crashing the pieces of agarose, phenol extraction, phenol-chroloform extraction and ethanol precipitation. In the manner prescribed in PCR-SCRIPT™ Amp SK(+) Cloning Kit (Stratagene), the recovered DNA was subcloned to plasmid vector pCR-Script Amp SK(+). After transformation of *Escherichia coli* DH5α competent cell (TOYOBO) by introducing the above-mentioned vector, clones harboring cDNA insert fragment was selected on LB agar medium containing ampicillin, IPTG and X-gal. All the white-colored clones were isolated with sterilized toothpick, and then the transformant *E. coli* DH5α/GPR8 was obtained. Respective clones were cultured in LB medium containing ampicillin for overnight. Subsequently, the plasmid DNA was prepared using QIAwell 8 Plasmid Kit (Qiagen). A portion of the prepared DNA was cleaved with the restriction enzymes ClaI and SpeI, and a size of the receptor cDNA fragment inserted was confirmed. The reaction for determination of the base sequence was carried out using DyeDeoxy Terminator Cycle Sequence Kit (PE Biosystems PE Biosystems). The sequence was analyzed with the fluorescent automated sequencer (SEQ ID NO: 3). The entire base sequence of cDNA encoding human GPR8 receptor protein is represented by SEQ ID NO: 3, and the entire amino acid sequence of human GPR8 receptor protein translated therefrom is represented by SEQ ID NO: 4.

Reference Example 3

Preparation of GPR8-Expressing CHO Cells

Using Plasmid Midi Kit (Qiagen), plasmid DNA was prepared from clones of *E. coli* transformed by the plasmid encoding the human brain-derived GPR8 full-length amino acid sequence, which sequence was confirmed in Reference Example 2, with the ClaI recognition sequence added at the 5' side and with the SpeI recognition sequence added at the 3' side. The plasmid DNA was digested with restriction enzymes ClaI and SpeI to excise the insert part out. After electrophoresis, the insert DNA was excised from the agarose gel with a razor and then homogenized. The homogenate was extracted with phenol and then with phenol/chloroform, followed by precipitation in ethanol. Thus, the insert DNA was recovered. The insert DNA was added to ClaI- and SpeI-cleaved expression vector plasmid pAKK0-111H for animal cell (the same as the vector plasmid pAKK01.11G described in Hinuma, S. et al., Biochim. Biophys. Acta, Vol. 1219, pp. 251-259 (1994)) followed by ligation using T4 ligase (Takara Shuzo). Thus, plasmid pAKKO-GPR8 for protein expression was constructed. *Escherichia coli* transformed with the plasmid pAKKO-GPR8 was designated DH5α/pAKKO-GPR8 (*Escherichia coli* DH5α/pAKKO-GPR8).

After *E. coli* DH5α (TOYOBO) transformed by pAKKO-GPR8 was cultured, pAKKO-GPR8 plasmid DNA was prepared using Plasmid Midi Kit (Qiagen). Using CellPhect Transfection Kit (Amersham Pharmacia Biotech Co.), the plasmid DNA was introduced into CHO dhfr⁻ cells in accordance with the protocol attached to the kit. The DNA, 4.5 μg, was co-precipitated with calcium phosphate in suspension. The resulting suspension was added to a 6 cm Petri dish in which 5×10⁵ or 1×10⁶ CHO dhfr⁻ cells had been seeded before 24 hours. The cells were cultured in MEMα containing 10% fetal calf serum for one day. After passage, the cells were cultured in nucleic acid-free selection medium MEMα containing 10% dialyzed fetal calf serum and 47 clones of the transformant GPR8 expressing CHO cells, growing in the selection medium, were selected.

Reference Example 4

Selection of CHO/GPR8 Cell Line, in Which an Expression Level of mRNA for Full Length of human GPR8 Protein is High The expression level of mRNA of the full-length GPR8 protein of 47 clones from the CHO/GPR8 cell line established in Reference Example 3 was measured as follows using Cytostar T Plate (Amersham Pharmacia Biotech Co.), in accordance with the protocol attached thereto. Each clone of the CHO/GPR8 cell line was inoculated on Cytostar T Plate in 2.5×10⁴ cells/well. After culturing for 24 hours, the cells were fixed with 10% formalin. After 0.25% Triton X-100 was added to each well to increase cell permeability, ³⁵S-labeled riboprobe represented by SEQ ID NO: 5 was added to the cells for hybridization. By adding 20 μg/ml RNaseA to each well, free riboprobe was digested. After the plate was thoroughly washed, radioactivity of the riboprobe hybridized was measured with Topcounter. The cell line with a high radioactivity provides a high expression amount of mRNA. Three clones (#17, #41 and #46) that showed high expression level of mRNA were used for the following experiment, especially clone #17 as a main clone.

Reference Example 5

Assay for a Level of Intracellular cAMP Production Using GPR8-Expressing CHO Cells The CHO/GPR8 cells prepared in Reference Example 4 and mock CHO cells were inoculated on a 24-well plate in 5×10⁴ cells/well followed by cultivation for 48 hours. The cells were then washed with Hanks' buffer (pH 7.4) containing 0.2 mM 3-isobutyl-methylxanthine, 0.05% BSA and 20 mM HEPES (hereinafter Hanks' buffer (pH 7.4) containing 0.2 mM 3-isobutyl-methylxanthine, 0.05% BSA and 20 mM HEPES is referred to as a reaction buffer). Thereafter, 0.5 ml of the reaction buffer was added to the system, which was kept in the incubator for 30 minutes. The reaction buffer was removed and 0.25 ml of a fresh reaction buffer was added to the cells. Then, 0.25 ml of the reaction buffer containing sample and 2 μM forskolin was added to the cells followed by reacting at 37° C. for 24 minutes. By adding 100 μl of 20% perchloric acid, the reaction was terminated. The reaction mixture was then allowed to stand on ice for an hour to extract intracellular cAMP. The amount of cAMP in the extract was measured using cAMP EIA kit (Amersham Pharmacia Biotech).

Reference Example 6

Assay for a GTPγS Binding Activity Using a Membrane Fraction of GPR8 Expressing CHO Cells The promoting activity of [³⁵S]-guanosine 5'-(γ-thio) triphosphate binding to membrane fraction of the GPR8 expressing CHO cell was assayed by the following method.

First, preparation of the membrane fraction is described. To $1 \times 10^8$ CHO/GPR8 cells was added 10 ml of a homogenate buffer (10 mM $NaHCO_3$, 5 mM EDTA, 0.5 mM PMSF, 1 µg/ml pepstatin, 4 µg/ml E64, 20 µg/ml leupeptin), followed by cell disruption with a polytron (12,000 rpm, 1 minute). The disrupted cells were then centrifuged (1,000 g, 15 minutes) to give the supernatant. Next, the supernatant was subjected to ultracentrifugation (Beckman type 30 rotor, 30,000 rpm, 1 hour). The resulting precipitate was used as a membrane fraction of GPR8 expressing CHO cell.

The GTPγS binding activity was assayed as follows. The membrane fraction of the GPR8 expressing CHO cell was diluted with a buffer for membrane dilution (50 mM Tris-hydrochloride buffer (pH 7.4), 5 mM $MgCl_2$, 150 mM NaCl, 1 µM GDP) to make a cell membrane fraction solution for assay having a protein concentration of 30 mg/ml. To 200 µl of the cell membrane fraction solution for assay were added 2 µl of 51.5 nM [$^{35}$S]-guanosine 5'-(γ-thio) triphosphate (NEN) and sample. The resulting solution mixture was kept at 25° C. for an hour. The mixture was filtrated through a filter. After washing twice with 1.5 ml of a washing buffer (50 mM Tris-hydrochloride buffer (pH 7.4), 5 mM $MgCl_2$, 1 mM EDTA, 0.1% BSA), radioactivity of the filter was measured using a liquid scintillation counter.

Reference Example 7

Detection of an Activity Exhibiting an Inhibition of cAMP Production and a Promotion of GTPγS Binding Specific to CHO/GPR8 Cell Line, Which is Contained in Porcine Hypothalamus Extract Fractions of the porcine hypothalamus extract by high performance liquid chromatography (HPLC) were prepared by the method described below. Porcine hypothalamus, 500 g (corresponding to 30 pigs), which had been purchased from Tokyo Shibaura Zoki Co. and kept under ice cooling after the hypothalamus was withdrawn from porcine on the day of their sacrifice, was homogenized, immediately put into 2.0 liters of boiling distilled water and boiled for 10 minutes. Immediately after the boiling, the homogenate was ice-cooled and 120 ml of acetic acid was added to the homogenate to make the final concentration 1.0 M. Using a polytron (20,000 rpm, 6 minutes), the mixture was homogenized. The homogenate was centrifuged (8,000 rpm, 30 minutes) and the supernatant was taken out. After 2.0 liters of 1.0 M acetic acid was added to the precipitate, the mixture was again homogenized by a polytron. The homogenate was stirred for overnight and then centrifuged (8,000 rpm, 30 minutes) to obtain the supernatant. After 2-fold volume of chilled acetone was slowly added dropwise to the supernatant at 4° C., the supernatant obtained by the first centrifugation was stirred for overnight and, the supernatant obtained by the second centrifugation was stirred for 4 hours. The acetone-added extract was centrifuged (8,000 rpm, 30 minutes) to remove the precipitate and acetone was evaporated off in vacuum from the supernatant, using an evaporator. An equal volume of diethyl ether was added to the acetone-removed extract, the ethereal layer containing lipids was separated using a separating funnel to recover the aqueous layer. After the lipids were removed with ether, the extract was concentrated in vacuum using an evaporator to completely remove the ether. The concentrate was filtrated through a glass fiber filter paper (Advantech, DP70 (90 mmΦ)) and the filtrate was charged in a glass-made column (30Φ×240 mm) packed with C18 column (YMC, YMCgel ODS-AM 120-S50). After washing with 400 ml of 1.0 M acetic acid, the column was eluted with 500 ml of 60% acetonitrile containing 0.1% trifluoroacetic acid. The eluate was concentrated in vacuum, the solvent was distilled off and then the concentrate was lyophilized. About 0.5 g of the lyophilized product was dissolved in 30 ml of 10% acetonitrile containing 0.1% trifluoroacetic acid. An aliquot of 10 ml each was subjected to HPLC on 10% to 60% acetonitrile containing 0.1% trifluoroacetic acid by concentration gradient elution using C18 column (Toso, TSKgel ODS-80TS (21.5Φ×300 mm)). HPLC was performed three times. The eluate was fractionated into 60 fractions and the eluates in three runs were collected. Each fraction was concentrated and evaporated to dryness in vacuum. The residue was dissolved in 0.5 ml of dimethylsulfoxide (DMSO).

The DMSO solution of HPLC fraction obtained as described above was administered to the CHO/GPR8 cells by the method shown in Reference Example 5, and a level of intracellular cAMP production was measured. As a result, it was perceived that fraction number 30 has a significant inhibiting activity of cAMP production. In addition, using GPR8 expressing CHO cells, for the same sample, promoting activity of GTPγS binding was investigated. The fraction around the number 30 was confirmed to have a significant activity. Since these activities were not found in other receptor expressing cells, it was shown that a substance having ligand activity specific to GPR8 exists in porcine hypothalamus extract.

Reference Example 8

Inactivation of an Active Substance Exhibiting an Inhibiting Activity of Intracellular cAMP Production Specific to GPR8 Expressing CHO Cells in Porcinr Hypothalamus Extract by Pronase The HPLC fraction #30 which showed the inhibiting activity of intracellular cAMP production to the GPR8 expressing CHO cells in Reference Example 7 was treated with proteolytic enzyme, Pronase (Sigma, protease Type XIV (P5147)) to examine if the active substance is proteinaceous.

The HPLC fraction (#30), 2 µl, from the hypothalamus extract described above was added to 200 µl of 0.2 M ammonium acetate and 3 µg of Pronase was further added thereto. After incubation at 37° C. for 2 hours, the culture was boiled in boiling water for 10 minutes to inactivate the Pronase. To the reaction solution was added 2 ml of distilled water containing 0.05 mg of BSA and 0.05 mg of CHAPS, followed by lyophilization. In order to examine if Pronase itself, or heating and lyophilization have an affect, Pronase alone, the HPLC fraction alone, and a mixture of the HPLC fraction with Pronase alone after its heating were treated in a similar manner and then lyophilized. Each sample fluid lyophilized was administered to the GPR8 expressing CHO cells in accordance with the method described in Reference Example 5, and the inhibiting activity of intracellular cAMP production was assayed. Since the active substance showing the inhibiting activity of intracellular cAMP production on the GPR8 expressing CHO cells in the porcine hypothalamus extract was completely inactivated by Pronase, the substance was shown to be proteins or peptides.

Reference Example 9

Purification of the Active Substances Showing the Promoting Activity of GTPγS Binding Specific to the Membrane Fraction of GPR8 Expressing CHO Cells, from Porcine Hypothalamus Extract A representative example of purifying from porcine hypothalamus the active substance exhibiting a ligand activity specific to GPR8, using the promoting activity of GTPγS binding to the membrane fraction of GPR8 expressing CHO cells as an index, is specifically described below. In the same manner as described in Reference Example 7, the extract was extracted with 1.0 M acetic acid from 500 g of porcine hypothalamus (corresponding to 30 pigs). After acetone precipitation and defatting by ether, the extract was adsorbed to C18 column (YMC, YMCgel ODS-AM 120-S50), and was eluted with 60% acetonitrile containing 0.1% trifluoroacetic acid. The eluate was concentrated and lyophilized. Then, an active fraction was obtained by HPLC using C18 column (Toso, TSKgel ODS-80TS (21.5Φ×300 mm)). The activity was recovered in the fraction number 30. This fraction was further purified by the following method.

This fraction was dissolved in 10 ml of 10 mM ammonium formate containing 10% acetonitrile. The solution was loaded on a cation exchange column (Toso, TSKgel SP-5PW (20 mmΦ×150 mm)). Then the column was eluted with 10 mM to 2.0 M ammonium formate containing 10% acetonitrile by means of concentration gradient. The activity was recovered around 0.8 M ammonium formate. The active fraction was lyophilized followed by dissolving in 1.0 ml of 10% acetonitrile containing 0.1% trifluoroacetic acid. After passing the resulting solution through a CN column (Nomura Kagaku, Develosil CN-UG-5), elution was performed by concentration gradient with 21% to 26% acetonitrile containing 0.1% trifluoroacetic acid. The activity appeared around 22.1% acetonitrile. The active fraction was lyophilized and dissolved in 0.1 ml of DMSO. Further, 0.4 ml of 10% acetonitrile containing 0.1% trifluoroacetic acid was added to the above solution. After passing the solution through an ODS column (Wako Junyaku, Wakosil-II 3C18HG (2.0 mmΦ×150 mm)), elution was performed by concentration gradient with 22.5% to 32.5% acetonitrile containing 0.1% trifluoroacetic acid. The activity appeared around 26.5% acetonitrile as a single peak (FIG. 1).

Reference Example 10

Analysis of an Amino Acid Sequence of Amino-Terminus of the Active Substance Exhibiting a Promoting Activity of GTPγS Binding Specific to the Membrane Fraction of GPR8 Expressing CHO Cells, Which was Purified from Porcine Hypothalamus, and EST Sequence Presumed to be Coded for a Portion of Precursor Protein of Human and Rat Homologue Peptide of GPR8 Ligand Amino acid sequencing of the active substances showing the promoting activity of GTPγS binding specific to the membrane fraction of GPR8 expressing CHO cells, which was purified in Reference Example 9 was performed. Since it was presumed that the active substances would be proteins or peptides as shown in Reference Example 8, amino-terminal amino acid sequencing was conducted by use of Precise 494 Protein Sequencer available from Perkin-Elmer, using the eluates containing the active peaks. As a result, the sequence shown by SEQ ID NO: 6, which is from the amino terminus to the 17th residue, was obtained.

When gene database was screened based on the above sequence, some EST (Expressed Sequence Tag) sequences were found, wherein the sequences or complement strands thereof were presumed to be encoding a portion of precursor protein of the peptide. Their accession numbers, origins, length of the sequences, and SEQ ID NOs are as follows: AW007531 (anaplastic oligodendroglioma, 438 bases, SEQ ID NO: 7); AI500303 (anaplastic oligodendroglioma, 264 basses, SEQ ID NO: 8); AI990964 (colonic mucosa from patient of Crohn's disease, 424 bases, SEQ ID NO: 9); AA744804 (germinal center B cell, 375 bases, SEQ ID NO: 10); and H31598 (PC12 cells, 260 bases, SEQ ID NO: 11). The first four sequences are derived from human, and the last is derived from rat. The DNA sequences of these ESTs is highly identical to that of the region encoding an amino acid sequence, which corresponds to the sequence of active peptide isolated from porcine hypothalamus. Further, an amino acid sequence translated was nearly identical to that of the peptide, which was isolated from porcine hypothalamus and elucidated, excluding that Thr at the 5th residue is replaced to Val. From the fact described above, it was presumed that these EST is coded for a portion of the precursor protein of human and rat homologues of GPR8 ligand peptide.

Reference Example 11

Amplification of Human cDNA Encoding a Portion of the GPR8 Ligand Peptide Precursor and Decoding of the Amplified cDNA Ssequence Based on EST sequences presumed to be encoding a portion of the GPR8 ligand peptide precursor described in Reference Example 10, primers were designed, and from human brain-derived cDNA, cDNA encoding a portion of the GPR8 ligand peptide precursor was amplified by PCR.

Using human brain-derived polyA(+) RNA (CLONTECH) as a template, and random primers, a reverse transcription reaction was carried out. For the reverse transcription reaction, ReverTra Ace (TOYOBO), the reverse transcriptase derived from MMLV, which is deficient for RNase H activity, was used. Subsequently, using synthetic primers represented by SEQ ID NO: 12 and SEQ ID NO: 13, which were designed based on the EST sequences described in Reference Example 10, amplification was performed by PCR method. The reaction solution comprised of 2 µl of cDNA template, 0.5 µM each of synthetic DNA primers, 1.6 mM dNTPs, 0.2 µl of LATaq (Takara Shuzo) and a buffer attached to the enzyme to make the total volume 20 µl. The PCR reaction was carried out using a thermal cycler (PE Biosystems) by heating of 96° C. for 120 seconds, then a cycle set to include 96° C. for 30 seconds followed by 72° C. for 45 seconds, which was repeated 4 times, 96° C. for 30 seconds followed by 70° C. for 45 seconds, which was repeated 4 times, 96° C. for 30 seconds followed by 68° C. for 45 seconds, which was repeated 4 times, 96° C. for 30 seconds followed by 64° C. for 30 seconds and 72° C. for 45 seconds, which was repeated 5 times, 96° C. for 30 seconds followed by 60° C. for 30 seconds and 72° C. for 45 seconds, which was repeated 20 times, and finally, incubation at 72° C. for 10 minutes. The amplified product was confirmed by 3% agarose gel electrophoresis and staining with ethidium bromide.

The PCR reaction solution was subjected to a 3% low melting agarose gel electrophoresis for isolation of the product band. After excision of the band by a razor, the DNA was recovered with QIAquick Gel Extraction Kit (Qiagen). According to the protocol of the TOPO TA Cloning Kit (Invitrogen), the recovered DNA was subcloned into a plasmid vector pCR2.1-TOPO. After transformation of *Escherichia coli* TOP10 competent cell (Invitrogen) by introducing the above-mentioned vector, clones harboring cDNA insert fragment was selected on LB agar medium containing ampicillin and X-gal. All the white-colored clones were isolated with sterilized toothpick, and then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using DyeDeoxyTerminator Cycle Sequence Kit (PE Biosystems). As a result, after decoding with the fluorescent automated sequencer, the DNA sequence represented by SEQ ID NO: 14, was obtained. In a portion of GPR8 ligand peptide precursor protein translated from this sequence (SEQ ID NO: 15), a peptide sequence exists predictably, wherein the peptide corresponds to an active peptide isolated from porcine hypothalamus, which sequence was elucidated. In addition, at the C-terminus, 2 sites of Arg-Arg sequence (Seidah, N. G, et al., Ann. N.Y. Acad. Sci., 839, 9-24, 1998), which is predicted to be a site where, in general, physiologically active peptide is excised, were present. From this result, it was presumed that the amino acid sequence of human homologue of GPR8 ligand peptide is either SEQ ID NO: 16 or SEQ ID NO: 17, or both.

Reference Example 12

Production of Fmoc-Added Human GPR8L (1-23): Fmoc-Trp-Tyr-Lys-His-Val-Ala-Ser-Pro-Arg-Tyr-His-Thr-Val-Gly-Arg-Ala-Ala-Gly-Leu-Leu-Met-Gly-Leu (SEQ ID NO: 105) and human GPR8L (1-23): Trp-Tyr-Lys-His-Val-Ala-Ser-Pro-Arg-Tyr-His-Thr-Val-Gly-Arg-Ala-Ala-Gly-Leu-Leu-Met-Gly-Leu (SEQ ID NO: 16)

Using 0.25 mmol of Fmoc-Leu-O-Clt resin (0.76 mmol/g) that Fmoc-Leu was introduced to a commercially available 2-chlorotrityl resin (Clt resin, 1.33 mmol/g) as a starting material, with Peptide Synthesizer ABI 433A, by Fmoc/DCC/HOBt method, Fmoc-Gly, Fmoc-Met, Fmoc-Leu, Fmoc-Leu, Fmoc-Gly, Fmoc-Ala, Fmoc-Ala, Fmoc-Arg (Pbf), Fmoc-Gly, Fmoc-Val, Fmoc-Thr (Bu$^t$), Fmoc-His (Trt), Fmoc-Tyr (Bu$^t$), Fmoc-Arg (Pbf), Fmoc-Pro, Fmoc-Ser (Bu$^t$), Fmoc-Ala, Fmoc-Val, Fmoc-His (Trt), Fmoc-Lys (Boc), Fmoc-Tyr (Bu$^t$), and Fmoc-Trp (Boc) was condensed in sequences to give a 830 mg of Fmoc-Trp-Tyr-Lys-His-Val-Ala-Ser-Pro-Arg-Tyr-His-Thr-Val-Gly-Arg-Ala-Ala-Gly-Leu-Leu-Met-Gly-Leu-O-Clt resin. To 150 mg of the resin, 5 ml of TFA/thioanisole/m-cresol/triisopropylsilane/etlianedithiol (85/5/5/2.5/2.5) were added. After shaking at room temperature for 2 hours, the resin was removed by filtration, and a solvent was concentrated. Then ether was added for obtaining a crude Fmoc-Trp-Tyr-Lys-His-Val-Ala-Ser-Pro-Arg-Tyr-His-Thr-Val-Gly-Arg-Ala-Ala-Gly-Leu-Leu-Met-Gly-Leu as a precipitate. With a fractionated HPLC using YMC D-ODS-5-ST S-5 120A column (20×150 mm), an elution by linear concentration gradient (60 minutes) from A/B: 72/28 to 52/48 was performed, wherein eluent A and eluent B were 0.1% TFA-water and acetonitrile containing 0.1% TFA, respectively. Fractions containing a target were recovered and were lyophilized to give a 9.7 mg of white-colored powder.

(M+H)$^+$ by mass spectrometry: 2805.7 (calculated value 2805.4) Elution time on HPLC: 25.1 minutes Conditions for elution Column: Wakosil-II 5C18HG (4.6×100 mm) Eluant: using Solution A: 0.1% TFA-water and Solution B: acetonitrile containing 0.1% TFA, elution by linear concentration gradient from A/B: 100/0 to 30/70 (35 minutes) Flow rate: 1.0 ml/minute To 5 mg of Fmoc-Trp-Tyr-Lys-His-Val-Ala-Ser-Pro-Arg-Tyr-His-Thr-Val-Gly-Arg-Ala-Ala-Gly-Leu-Leu-Met-Gly-Leu, 1 ml of 20% diethylamine/DMF was added, and the mixture was stirred at room temperature for 2 hours. After removal of solvent by distillation, with a fractionated HPLC using YMC D-ODS-5-ST S-5 120A column (20×150 mm), an elution by linear concentration gradient (60 minutes) from A/B: 74/26 to 64/36 was performed, wherein eluent A and eluent B were 0.1% TFA-water and acetonitrile containing 0.1% TFA, respectively. Fractions containing a target were recovered and were lyophilized to give a 1.2 mg of white-colored powder.

(M+H)$^+$ by mass spectrometry: 2583.6 (calculated value 2583.4) Elution time on HPLC: 20.4 minutes Conditions for elution Column: Wakosil-II 5C18HG (4.6×100 mm) Eluant: using Solution A: 0.1% TFA-water and Solution B: acetonitrile containing 0.1% TFA, elution by linear concentration gradient from A/B: 100/0 to 30/70 (35 minutes) Flow rate: 1.0 ml/minute Reference Example 13

Production of Human GPR8L (1-30): Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser-Pro-Tyr-Leu-Trp (SEQ ID NO: 17)

Using 0.25 mmol of Fmoc-Trp-O-Clt resin (0.64 mmol/g) that Fmoc-Trp (Boc) was introduced to a commercially available 2-chlorotrityl resin (Clt resin, 1.33 mmol/g) as a starting material, amino acids were condensed in sequences in the same manner as reference example 12. Fmoc group was removed from the resin prior to excision from the resin immediately after introduction of the last Trp. Then, excision from the resin and removal of protecting group of side chain were simultaneously performed by treatment of TFA/thioanisole/m-cresol/triisopropylsilane/ethanedithiol (85/5/5/2.5/2.5). Crude peptide was purified in a similar manner to Reference Example 12 to give Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser-Pro-Tyr-Leu-Trp.

(M+H)$^+$ by mass spectrometry: 3543.4 (calculated value 3544.2) Elution time on HPLC: 21.5 minutes Conditions for elution Column: Wakosil-II 5C18HG (4.6×100 mm) Eluant: using Solution A: 0.1% TFA-water and Solution B: acetonitrile containing 0.1% TFA, elution by linear concentration gradient from A/B: 100/0 to 30/70 (35 minutes) Flow rate: 1.0 ml/minute Reference Example 14

Production of Human GPR8 ligand (1-29): Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser-Pro-Tyr-Leu (SEQ ID NO: 20)

Using the resin in Reference Example 12, just like Reference Example 13, condensation of amino acids and excision from the resin in the sequence order, and purification were carried out to give Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser-Pro-Tyr-Leu.

Reference Example 15

Production of Human GPR8 ligand (1-28): Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser-Pro-Tyr (SEQ ID NO: 21)

Fmoc-Tyr(Bu$^t$) was introduced to commercially available 2-chlorotrityl resin (Clt resin, 1.33 mmol/g). Then, just like Reference Example 13, condensation of amino acids and excision from the resin in the sequence order, and purification were carried out to give Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser-Pro-Tyr.

Reference Example 16

Production of Human GPR8 Ligand (1-27): Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser-Pro (SEQ ID NO: 22)

Fmoc-Pro was introduced to commercially available 2-chlorotrityl resin (Clt resin, 1.33 mmol/g). Then, just like Reference Example 13, condensation of amino acids and excision from the resin in the sequence order, and purification were carried out to give Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser-Pro.

Reference Example 17

Production of Human GPR8 Ligand (1-26): Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser (SEQ ID NO: 23)

Fmoc-Ser (Bu$^t$) was introduced to commercially available 2-chlorotrityl resin (Clt resin, 1.33 mmol/g). Then, just like Reference Example 13, condensation of amino acids and excision from the resin in the sequence order, and purification were carried out to give Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser.

Reference Example 18

Production of Human GPR8 Ligand (1-25): Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg (SEQ ID NO: 24)

Fmoc-Arg (Pbf) was introduced to commercially available 2-chlorotrityl resin (Clt resin, 1.33 mmol/g). Then, just like Reference Example 13, condensation of amino acids and excision from the resin in the sequence order, and purification were carried out to give Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg.

Reference Example 19

Production of Human GPR8 Ligand (1-24): Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg (SEQ ID NO: 25)

Fmoc-Arg (Pbf) was introduced to commercially available 2-chlorotrityl resin (Clt resin, 1.33 mmol/g). Then, just like Reference Example 13, condensation of amino acids and excision from the resin in the sequence order, and purification were carried out to give Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg.

Reference Example 20

Figure 2:
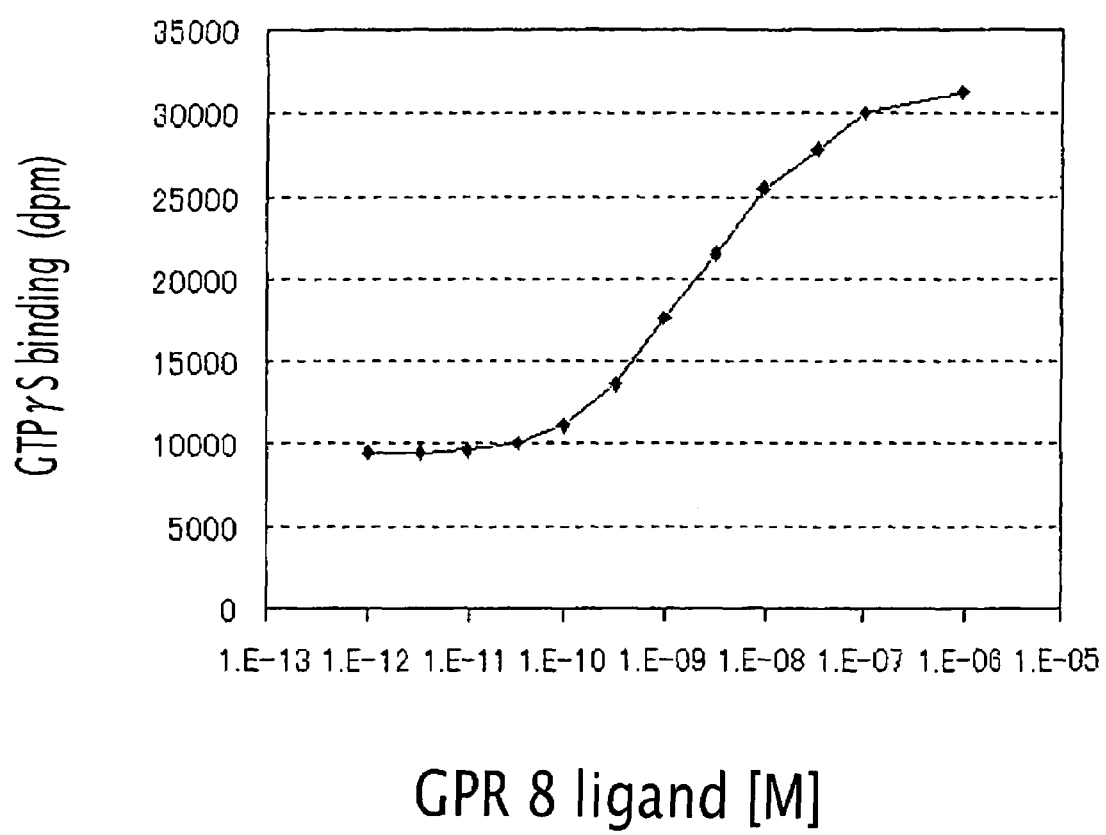
FIG. 2 shows a GTPγS binding promoting activity for various concentrations of human derived GPR8 ligand peptide homologue consisting of 23 residues against cell membrane fraction of CHO/GPR8.

Promoting Activity to GTPγS Binding of Human Homologue of GPR8 Ligand Peptide Consisting of 23 Residues, which is Measured Using the Membrane Fraction of GPR8 Expressing CHO Cells The human homologue of GPR8 ligand peptide consisting of 23 residues, which was synthesized in Reference Example 12 (hereafter, sometimes referred to as hGPR8L (1-23)), was administered at various concentrations to membrane fraction of the GPR8 expressing CHO cells by the method described in Reference Example 6, and a promoting activity to GTPγS binding was measured. The result was shown in FIG. 2. The hGPR8L(1-23) apparently promoted to GTPγS binding by the membrane fraction of GPR8 expressing CHO cells depending on the concentration. From this result, it was found that the peptide having a structure of SEQ ID NO: 16, is a ligand to GPR8.

Reference Example 21

Figure 3:
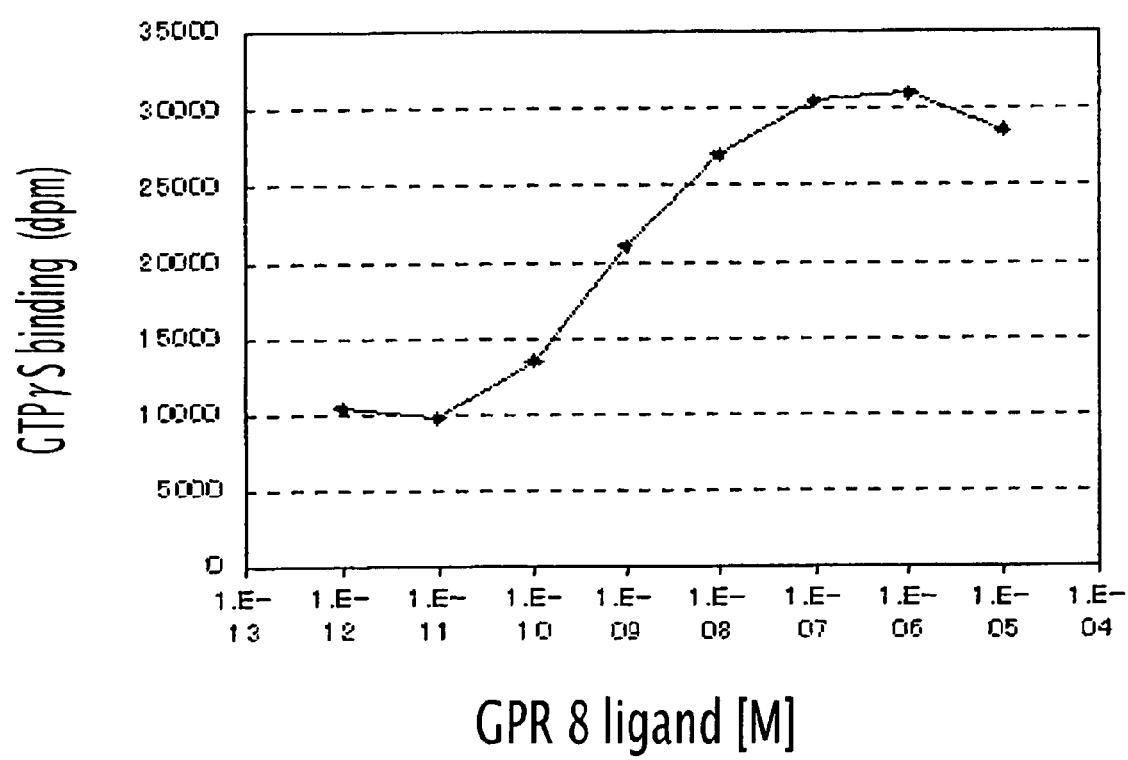
FIG. 3 shows a GTPγS binding promoting activity for various concentrations of human derived GPR8 ligand peptide homologue consisting of 30 residues against cell membrane fraction of CHO/GPR8.

Promoting Activity to GTPγS Binding of Human Homologue of GPR8 Ligand Peptide Consisting of 30 Residues, which is Measured Using the Membrane Fraction of GPR8 Expressing CHO Cells The human homologue of GPR8 ligand peptide consisting of 30 residues, which was synthesized in Reference Example 13 (hereafter, sometimes referred to as hGPR8L (1-30)), was administered at various concentrations to membrane fraction of the GPR8 expressing CHO cells by the method described in Reference Example 6, and a promoting activity to GTPγS binding was measured. The result was shown in FIG. 3. The hGPR8L(1-30) apparently promoted to GTPγS binding by the membrane fraction of GPR8 expressing CHO cells depending on the concentration. From this result, it was found that the peptide having a structure of SEQ ID NO: 17, is a ligand to GPR8.

Reference Example 22

Figure 4:
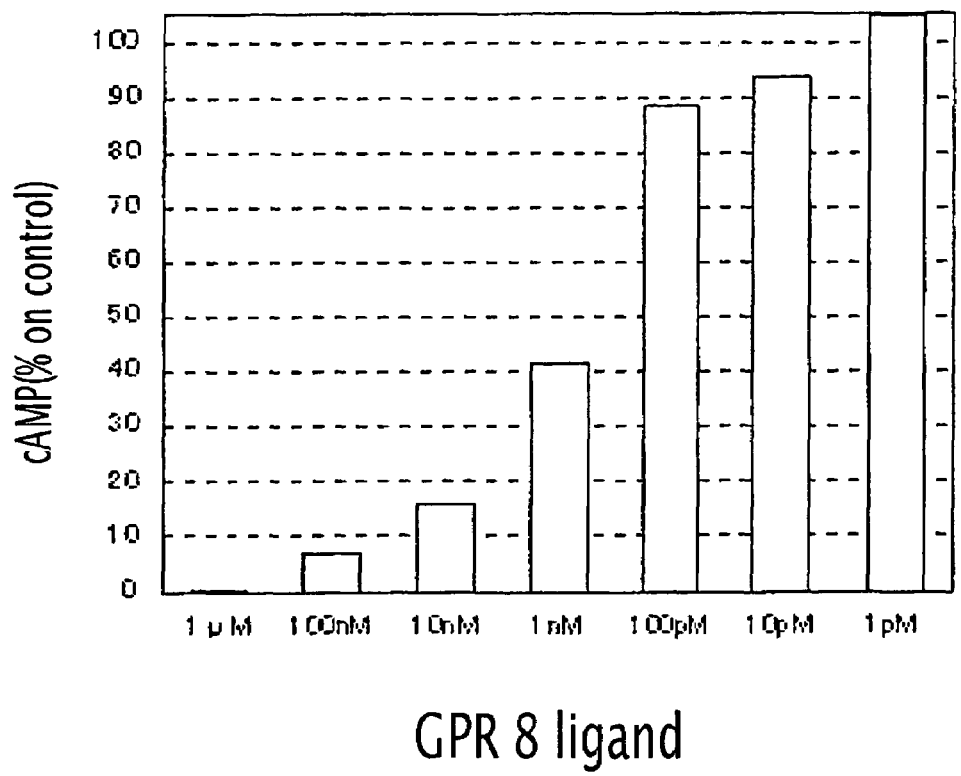
FIG. 4 shows a cAMP production inhibiting activity for various concentrations of human derived GPR8 ligand peptide homologue consisting of 23 residues against cell membrane fraction of CHO/GPR8.

Inhibiting Activity for Intracellular cAMP Production of Human Homologue of GPR8 Ligand Peptide Consisting of 23 Residues, which was Measured Using GPR8 Expressing CHO Cells The hGPR8L(1-23), which was synthesized in Reference Example 12, was brought into contact with the GPR8 expressing CHO cells at various concentrations by the method described in Reference Example 5, and an inhibiting activity of intracellular cAMP production was measured. The result was shown in FIG. 4. The hGPR8L(1-23) apparently inhibited intracellular cAMP production against the GPR8 expressing CHO cells depending on the concentration. In the figure, when an amount subtracted intracellular cAMP level with the reaction buffer from intracellular cAMP level with the reaction buffer containing forskolin is indicated as 100%, the inhibiting activity of cAMP synthesis is indicated as an amount subtracted intracellular cAMP level with hGPR8L(1-23) from intracellular cAMP level with the reaction buffer by representation of percentage (%).

Reference Example 23

Figure 5:
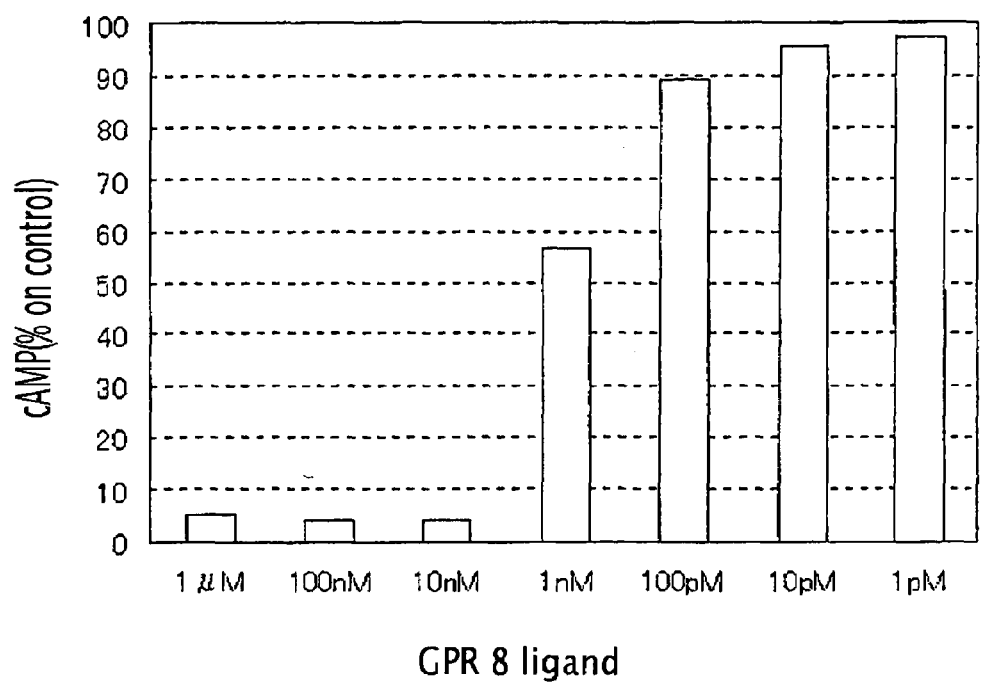
FIG. 5 shows a cAMP production inhibiting activity for various concentrations of human derived GPR8 ligand peptide homologue consisting of 30 residues against cell membrane fraction of CHO/GPR8.

Inhibiting Activity for Intracellular cAMP Production of Human Homologue of GPR8 Ligand Peptide Consisting of 30 Residues, which was Measured Using GPR8 Expressing CHO Cells The hGPR8L(1-30), which was synthesized in Reference Example 13, was brought into contact with the GPR8 expressing CHO cells at various concentrations by the method described in Reference Example 5, and an inhibiting activity of intracellular cAMP production was measured. The result was shown in FIG. 5. The hGPR8L(1-30) apparently inhibited intracellular cAMP production against the GPR8 expressing CHO cells depending on the concentration. In the figure, when an amount subtracted intracellular cAMP level with the reaction buffer from intracellular cAMP level with the reaction buffer containing forskolin is indicated as 100%, the inhibiting activity of cAMP synthesis is indicated as an amount subtracted intracellular cAMP level with hGPR8L(1-30) from intracellular cAMP level with the reaction buffer by representation of percentage (%).

Reference Example 24

Cloning of the cDNA Encoding Mouse TGR26

Using the mouse brain-derived cDNA as a template and the following synthetic DNA primers, namely the synthetic primer shown by SEQ ID NO: 135 and the synthetic primer shown by SEQ ID NO: 136, amplification of mouse TGR26 DNA by PCR method was performed.

The reaction solution in the above reaction comprised of 1 μl of mouse brain cDNA, 0.2 μM each of synthetic DNA primers, 0.8 mM dNTPs, 0.4 μl of Advantage cDNA Polymerase Mix (CLONTECH) and a buffer attached to the enzyme to make the total volume 20 μl. The PCR reaction was carried out using a thermal cycler (Applied Biosystems) by heating of 96° C. for 2 minutes, then a cycle set to include 96° C. for 30 seconds followed by 64° C. for 30 seconds and 72° C. for 1 minute, which was repeated 30 times, and finally, extension reaction at 72° C. for 10 minutes. The amplified DNA fragment in the PCR reaction mixture, of which is about 1100 bases, was cloned to pCR2.1-TOPO in accordance with the protocol of TOPO TA Cloning Kit (Invitrogen). After transformation of *Escherichia coli* TOP 10 competent cell (Invitrogen) by introducing the above-mentioned vector, clones harboring cDNA insert fragment was selected on LB agar medium containing ampicillin and X-gal. All the white-colored clones were isolated with sterilized toothpick, and then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 137, was obtained.

Tlanslation from the base sequence represented by SEQ ID NO: 137 to an amino acid sequence was set as an amino acid sequence of mouse TGR26 and was represented by SEQ ID NO: 138.

When SEQ ID NO: 138 was compared with the amino acid sequence of the rat-derived TGR26, it was found that 96.0% of amino acids are identical.

*Escherichia coli* transformed with a plasmid containing the DNA having the base sequence shown by SEQ ID NO: 137 was designated *Escherichia coli* TOP10/pCR2.1-TOPO mouse GPR7.

Reference Example 25

Cloning of 5' Upstream End of the cDNA Encoding Human TGR8 Ligand Precursor Protein By 5' RACE PCR using primers prepared based on human cDNA sequence (SEQ ID NO: 14) encoding a portion of the precursor protein of human homologue of GPR8 ligand peptide described in Reference Example 11 (hereafter, sometimes referred to as human GPR8 ligand), and human hypothalamus cDNA as a template, a base sequence of 5' upstream region of cDNA encoding human GPR8 ligand precursor protein was elucidated. The 5' RACE PCR cloning was accomplished by PCR reaction using human hypothalamus Marathon-Ready cDNA (CLONTECH) as a template, AP1 primer attached to the kit, and synthetic primer represented by SEQ ID NO: 33 followed by PCR reaction using the above PCR reaction mixture as a template, AP2 primer attached to the kit, and synthetic primer represented by SEQ ID NO: 34. The composition of the reaction solution and the conditions for PCR are as follows. The reaction solution comprised of 4 μl of human hypothalamus cDNA, 0.5 μM of AP1 primer, 0.5 μM of synthetic DNA primer represented by SEQ ID NO: 33, 0.4 mM dNTPs, 0.2 μl of LATaq Polymerase (Takara Shuzo) and a GC (I) buffer attached to the enzyme to make the total volume 20 μl. The PCR reaction was carried out using a thermal cycler (PE Biosystems) by heating of 96° C. for 120 seconds, then a cycle set to include 96° C. for 30 seconds followed by 68° C. for 240 seconds, which was repeated 30 times, and finally, incubation at 72° C. for 10 minutes. Subsequently, the reaction solution comprised of 2 μl of the above PCR reaction solution diluted to 50-fold with Tricine-EDTA Buffer attached to the kit, 0.5 μM of AP2 primer; 0.5 μM of synthetic DNA primer represented by SEQ ID NO: 34, 0.4 mM dNTPs, 0.2 μl of LATaq Polymerase (Takara Shuzo) and GC (I) buffer attached to the enzyme to make the total volume 20 μl. The PCR reaction was carried out using a thermal cycler (PE Biosystems) by heating of 96° C. for 120 seconds, then a cycle set to include 96° C. for 30 seconds followed by 72° C. for 180 seconds, which was repeated 4 times, 96° C. for 30 seconds followed by 70° C. for 180 seconds, which was repeated 4 times, 96° C. for 30 seconds followed by 68° C. for 180 seconds, which was repeated 17 times, and finally, incubation at 72° C. for 10 minutes. After isolating the amplified DNA by 1.2% agarose gel electrophoresis, DNA having about 1200 bases length was excised with razor, and was recovered using QIAquick Gel Extraction Kit (Qiagen). This DNA was cloned into pCR2.1-TOPO vector according to the protocol attached to the TOPO TA Cloning Kit (Invitrogen). After transformation of *Escherichia coli* TOP10 competent cell (Invitrogen) by introducing the above-mentioned vector, clones harboring cDNA insert fragment was selected on LB agar medium containing ampicillin and X-gal. All the white-colored clones were isolated with sterilized toothpick, and then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 35, was obtained.

Reference Example 26

Preparation of Human Brain cDNA

Human brain cDNA was prepared from human brain poly A(+) RNA (CLONTECH) using Marathon™ cDNA Amplification Kit (CLONTCH). The cDNA used for PCR was prepared according to protocol attached to the kit except 1st strand cDNA synthesis. The 1st strand cDNA was synthesized using reverse transcriptase MMLV (-RNAse H) (RevTraAce, TOYOBO) as substitute for reverse transcriptase AMV attached to the kit from 1 μg of human brain poly A(+) RNA.

Reference Example 27

Cloning of 3' Downstream End of the cDNA Encoding Human TGR8 Ligand Precursor Protein By 3' RACE PCR using a primer prepared based on the base sequence of human cDNA encoding a portion of human GPR8 ligand precursor protein (SEQ ID NO: 14), a base sequence of 3' downstream region of cDNA encoding human GPR8 ligand precursor protein was elucidated. The 3' RACE PCR cloning was accomplished by PCR reaction using human brain cDNA as a template, AP1 primer attached to the kit, and synthetic primer represented by SEQ ID NO: 36 followed by PCR reaction using the above PCR reaction mixture as a template, AP2 primer attached to the kit, and synthetic primer represented by SEQ ID NO: 37. The composition of the reaction solution and the conditions for PCR are as follows. The reaction solution comprised of 1 μl of human brain cDNA diluted 50-fold with Tricine-EDTA Buffer attached to the kit, 0.5 μM of AP1 primer, 0.5 μM of synthetic DNA primer represented by SEQ ID NO: 36, 0.4 mM dNTPs, 0.2 μl of LATaq Polymerase (Takara Shuzo) and GC (I) buffer attached to the enzyme to make the total volume 20 μl. The PCR reaction was carried out using a thermal cycler (PE Biosystems) by heating of 96° C. for 120 seconds, then a cycle set to include 96° C. for 30 seconds followed by 68° C. for 240 seconds, which was repeated 30 times, and finally, incubation at 72° C. for 10 minutes. Subsequently, the reaction solution comprised of 1 μl of the above PCR reaction solution diluted to 50-fold with Tricine-EDTA Buffer attached to the kit, 0.5 μM of AP2 primer, 0.5 μM of synthetic DNA primer represented by SEQ ID NO: 37, 0.4 mM dNTPs, 0.2 μl of LATaq Polymerase (Takara Shuzo) and GC (I) buffer attached to the enzyme to make the total volume 20 μl. The PCR reaction was carried out using a thermal cycler (PE Biosystems) by heating of 96° C. for 120 seconds, then a cycle set to include 96° C. for 30 seconds followed by 72° C. for 180 seconds, which was repeated 4 times, 96° C. for 30 seconds followed by 70° C. for 180 seconds, which was repeated 4 times, 96° C. for 30 seconds followed by 68° C. for 180 seconds, which was repeated 17 times, and finally, incubation at 72° C. for 10 minutes. After isolating the amplified DNA by 1.5% agarose gel electrophoresis, DNA having about 600 bases length was excised with razor, and was recovered using QIAquick Gel Extraction Kit (Qiagen). This DNA was cloned into pCR2.1-TOPO vector according to the protocol attached to the TOPO TA Cloning Kit (Invitrogen). After transformation of *Escherichia coli* TOP10 competent cell (Invitrogen) by introducing the above-mentioned vector, clones harboring cDNA insert fragment was selected on LB agar medium containing ampicillin and X-gal. All the white-colored clones were isolated with sterilized toothpick, and then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 38, was obtained.

Reference Example 28

Cloning of cDNA Encoding Human GPR8 Ligand Precursor Protein

By PCR amplification using a human hypothalamus cDNA as a template, a primer based on 5' upstream base sequence of the cDNA encoding human GPR8 ligand precursor protein and a primer based on 3' downstream base sequence of the cDNA encoding human GPR8 ligand precursor protein, cDNA encoding human GPR8 ligand precursor protein was cloned. The composition of the reaction solution and the conditions for PCR are as follows. The reaction solution comprised of 1 μl of human hypothalamus Marathon-Ready cDNA, 0.5 μM of synthetic DNA primer represented by SEQ ID NO: 39, 0.5 μM of synthetic DNA primer represented by SEQ ID NO: 40, 0.4 mM dNTPs, 2.5 mM MgCl$_2$, 5% DMSO, 0.2 μl of LATaq Polymerase (Takara Shuzo) and a buffer attached to the enzyme to make the total volume 20 μl. The PCR reaction was carried out using a thermal cycler (PE Biosystems) by heating of 96° C. for 60 seconds, then a cycle set to include 96° C. for 30 seconds followed by 96° C. for 30 seconds followed by 64° C. for 30 seconds and 72° C. for 120 seconds, which was repeated 35 times, and finally, incubation at 72° C. for 10 minutes. After isolating the amplified DNA by 1.5% agarose gel electrophoresis, DNA having about 700 bases length was excised with razor, and was recovered using QIAquick Gel Extraction Kit (Qiagen). This DNA was cloned into pCR2.1-TOPO vector according to the protocol attached to the TOPO TA Cloning Kit (Invitrogen). After transformation of *Escherichia coli* TOP10 competent cell (Invitrogen) by introducing the above-mentioned vector, clones harboring cDNA insert fragment was selected on LB agar medium containing ampicillin and X-gal. All the white-colored clones were isolated with sterilized toothpick, and then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 41, was obtained.

Since this sequence (SEQ ID NO: 41) is coded for human GPR8 ligand precursor protein, *Escherichia coli* transformed with a plasmid containing this DNA was designated *Escherichia coli* TOP 10/pCR2.1-TOPO human GPR8 Ligand Precursor.

While the DNA sequence shown by SEQ ID NO: 41 has a frame encoding an amino acid sequence of the human GPR8 ligand peptide described in Reference Example 11, there exists no ATG predicted to be an initiation codon for protein translation in the 5' upstream reagion. However, it has been reported that in some proteins, codons other than ATG is predicted to be an initiation codon [human basic fibroblast growth factor (H. Prats et al., Proc. Natl. Acad.

Sci. USA, 86, 1836-1840, 1989; R. Z. Florkiewicz and A. Sommer, Proc. Natl. Acad. Sci. USA, 86, 3978-3981, 1989); mouse retinoic acid receptor β4 (S. Nagpal et al., Proc. Natl. Acad. Sci. USA, 89, 2718, 1992); human phosphoribosyl pyrophosphoric acid synthetase (M. Taira et al., J. Biol. Chem., 265, 16491-16497, 1990); *drosophila* choline acetyltransferase (H. Sugihara et al., J. Biol. Chem., 265, 21714-21719, 1990)].

In many of these cases, CTG encoding Leu is assumed to be an initiation codon instead of ATG Then, in the human GPR8 ligand precursor protein, it was also considered to be the same. Thus, by contrast with porcine or rat homologue of the GPR8 ligand precursor protein, CTG codon presented in the position nearly corresponding to ATG, which is predicted to be an initiation codon in these precursor protein, was assumed to be an initiation codon, and a sequence of the precursor protein was presumed. A virtual amino acid sequence of the human GPR8 ligand precursor protein was shown in SEQ ID NO: 42. In addition, the virtual amino acid sequence and DNA sequence of the human GPR8 ligand precursor protein was shown in FIG. 6.

Reference Example 29

Preparation of Porcine Spinal Cord cDNA

Porcine spinal cord cDNA was prepared using Marathon™ cDNA Amplification Kit (CLONTECH) from porcine spinal cord poly A(+) RNA. The porcine spinal cord poly A(+) RNA was prepared as follows. Porcine spinal cord was perfectly disrupted with Polytron homogenizer in ISOGEN (Nippon Gene). From this disrupted solution, porcine spinal cord total RNA was obtained according to the preparation method for total RNA using ISOGEN solution. Then, from the porcine total RNA, 7 µg of porcine spinal cord poly A(+) RNA was obtained by performing twice chromatography with oligo dT cellulose column attached to the mRNA Purification Kit (Amersham Pharmacia Biotech). The cDNA used for PCR was prepared according to protocol attached to the kit except 1st strand cDNA synthesis. The 1st strand cDNA was synthesized using reverse transcriptase MMLV (-RNAse H) (RevTraAce, TOYOBO) as substitute for reverse transcriptase AMV attached to the kit from 1 µg of porcine spinal cord poly A(+) RNA.

Reference Example 30

Cloning of 5' Upstream End of the cDNA Encoding Porcine TGR8 Ligand Precursor Protein By the first 5' RACE PCR cloning and the second 5' RACE PCR cloning, for which a base sequence of the PCR amplified DNA was utilized, a base sequence of 5' upstream region of cDNA encoding a precursor protein of porcine homologue of GPR8 ligand peptide (hereafter, sometimes referred to as porcine GPR8 ligand) was elucidated.

The first 5' RACE PCR cloning was accomplished by PCR reaction using porcine spinal cord cDNA as a template, AP1 primer attached to the kit, and synthetic primer represented by SEQ ID NO: 43 followed by PCR reaction using the above PCR reaction mixture as a template, AP2 primer attached to the kit, and synthetic primer represented by SEQ ID NO: 44. The composition of the reaction solution and the conditions for PCR are as follows. The reaction solution comprised of 4 µl of porcine spinal cord cDNA diluted 50-fold with Tricine-EDTA Buffer attached to the kit, 0.5 µM of AP1 primer, 0.5 µM of synthetic DNA primer represented by SEQ ID NO: 43, 0.4 mM dNTPs, 0.2 µl of LATaq Polymerase (Takara Shuzo) and a GC (I) buffer attached to the enzyme to make the total volume 20 µL]. The PCR reaction was carried out using a thermal cycler (PE Biosystems) by heating of 96° C. for 120 seconds, then a cycle set to include 96° C. for 30 seconds followed by 68° C. for 180 seconds, which was repeated 30 times, and finally, incubation at 72° C. for 10 minutes. Subsequently, the reaction solution comprised of 1 µl of the above PCR reaction solution diluted to 100-fold with Tricine-EDTA Buffer attached to the kit, 0.5 µM of AP2 primer, 0.5 µM of synthetic DNA primer represented by SEQ ID NO: 44, 0.4 mM dNTPs, 0.2 µl of Advantage-GC 2 Polymerase (CLONTECH) and a buffer attached to the enzyme to make the total volume 20 µl. The PCR reaction was carried out using a thermal cycler (PE Biosystems) by heating of 96° C. for 60 seconds, then a cycle set to include 96° C. for 30 seconds followed by 72° C. for 180 seconds, which was repeated 3 times, 96° C. for 30 seconds followed by 70° C. for 180 seconds, which was repeated 3 times, 96° C. for 30 seconds followed by 68° C. for 180 seconds, which was repeated 4 times, 96° C. for 30 seconds followed by 64° C. for 30 seconds and 72° C. for 180 seconds, which was repeated 15 times, and finally, incubation at 72° C. for 10 minutes. After isolating the amplified DNA by 1.2% agarose gel electrophoresis, DNA having about 300 bases length was excised with razor, and was recovered using QIAquick Gel Extraction Kit (Qiagen). This DNA was cloned into pCR2.1-TOPO vector according to the protocol attached to the TOPO TA Cloning Kit (Invitrogen). After transformation of *Escherichia coli* TOP10F' competent cell (Invitrogen) by introducing the above-mentioned vector, clones harboring cDNA insert fragment was selected on LB agar medium containing ampicillin, IPTG and X-gal. All the white-colored clones were isolated with sterilized toothpick, and then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 45, was obtained.

The second 5' RACE PCR cloning was accomplished by PCR reaction using porcine spinal cord cDNA as a template, AP1 primer attached to the kit, and synthetic primer represented by SEQ ID NO: 46 followed by PCR reaction using the above PCR reaction mixture as a template, AP2 primer attached to the kit, and synthetic primer represented by SEQ ID NO: 47. The composition of the reaction solution and the conditions for PCR are as follows. The reaction solution comprised of 1 µl of porcine spinal cord cDNA diluted 50-fold with Tricine-EDTA Buffer attached to the kit, 0.5 µM of AP1 primer, 0.5 µM of synthetic DNA primer represented by SEQ ID NO: 46, 0.4 mM dNTPs, 0.2 µl of Advantage-GC 2 Polymerase (CLONTECH) and a buffer attached to the enzyme to make the total volume 20 µl. The PCR reaction was carried out using a thermal cycler (PE Biosystems) by heating of 96° C. for 60 seconds, then a cycle set to include 96° C. for 30 seconds followed by 72° C. for 180 seconds, which was repeated 5 times, 96° C. for 30 seconds followed by 70° C. for 180 seconds, which was repeated 5 times, 96° C. for 30 seconds followed by 68° C. for 180 seconds, which was repeated 20 times, and finally, incubation at 72° C. for 10 minutes. Subsequently, the reaction solution comprised of 1 µl of the above PCR reaction solution diluted to 100-fold with Tricine-EDTA Buffer attached to the kit, 0.5 µM of AP2 primer, 0.5 µM of synthetic DNA primer represented by SEQ ID NO: 47, 0.4 mM dNTPs, 0.2 µl of Advantage-GC 2 Polymerase (CLONTECH) and a buffer attached to the enzyme to make the total volume 20 µl. The PCR reaction was carried out using a thermal cycler (PE Biosystems) by heating of 96° C. for 60 seconds, then a cycle set to include 96° C. for 30 seconds followed by 68° C. for 180 seconds, which was repeated 31 times, and finally, incubation at 72° C. for 10 minutes. After isolating the amplified DNA by 2.0% agarose gel electrophoresis, DNA having about 200 bases length was excised with razor, and was recovered using QIAquick Gel Extraction Kit (Qiagen). This DNA was cloned into pCR2.1-TOPO vector according to the protocol attached to the TOPO TA Cloning Kit (Invitrogen). After transformation of *Escherichia coli* TOP10F' competent cell (Invitrogen) by introducing the above-mentioned vector, clones harboring cDNA insert fragment was selected on LB agar medium containing ampicillin, IPTG and X-gal. All the white-colored clones were isolated with sterilized toothpick, and then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 48, was obtained.

Reference Example 31

Cloning of 3' Downstream End of the cDNA Encoding Porcine TGR8 Ligand Precursor Protein By 3' RACE PCR cloning using a primer prepared based on the base sequence of 5' upstream region of cDNA encoding porcine GPR8 ligand precursor protein, a base sequence of 3' downstream region of cDNA encoding porcine TGR8 ligand precursor protein was elucidated. The 3' RACE PCR cloning was accomplished by PCR reaction using porcine spinal cord cDNA as a template, AP1 primer attached to the kit, and synthetic primer represented by SEQ ID NO: 49 followed by PCR reaction using the above PCR reaction mixture as a template, AP2 primer attached to the kit, and synthetic primer represented by SEQ ID NO: 50. The composition of the reaction solution and the conditions for PCR are as follows. The reaction solution comprised of 1 µl of porcine spinal cord cDNA diluted 50-fold with Tricine-EDTA Buffer attached to the kit, 0.5 µM of AP1 primer, 0.5 µM of synthetic DNA primer represented by SEQ ID NO: 49, 0.4 mM dNTPs, 0.2 µl of Advantage-GC 2 Polymerase (CLONTECH) and a buffer attached to the enzyme to make the total volume 20 µl. The PCR reaction was carried out using a thermal cycler (PE Biosystems) by heating of 96° C. for 60 seconds, then a cycle set to include 96° C. for 30 seconds followed by 72° C. for 120 seconds, which was repeated 5 times, 96° C. for 30 seconds followed by 70° C. for 120 seconds, which was repeated 5 times, 96° C. for 30 seconds followed by 68° C. for 120 seconds, which was repeated 20 times, and finally, incubation at 72° C. for 10 minutes. Subsequently, the reaction solution comprised of 1 µl of the above PCR reaction solution diluted to 100-fold with Tricine-EDTA Buffer attached to the kit, 0.5 µM of AP2 primer, 0.5 µM of synthetic DNA primer represented by SEQ ID NO: 50, 0.4 mM dNTPs, 0.2 µl of Advantage-GC 2 Polymerase (CLONTECH) and a buffer attached to the enzyme to make the total volume 20 µl. The PCR reaction was carried out using a thermal cycler (PE Biosystems) by heating of 96° C. for 120 seconds, then a cycle set to include 96° C. for 30 seconds followed by 68° C. for 120 seconds, which was repeated 31 times, and finally, incubation at 72° C. for 10 minutes. After isolating the amplified DNA by 2.0% agarose gel electrophoresis, DNA having about 650 bases length was excised with razor, and was recovered using QIAquick Gel Extraction Kit (Qiagen). This DNA was cloned into pCR2.1-TOPO vector according to the protocol attached to the TOPO TA Cloning Kit (Invitrogen). After transformation of *Escherichia coli* TOP10F' competent cell (Invitrogen) by introducing the above-mentioned vector, clones harboring cDNA insert fragment was selected on LB agar medium containing ampicillin, X-gal and IPTG. All the white-colored clones were isolated with sterilized toothpick, and then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 51, was obtained.

Reference Example 32

Cloning of cDNA Encoding Porcine GPR8 Ligand Precursor Protein

By PCR amplification using a porcine spinal cord cDNA as a template, a primer based on 5' upstream base sequence of the cDNA encoding porcine GPR8 ligand precursor protein and a primer based on 3' downstream base sequence of the cDNA encoding porcine GPR8 ligand precursor protein, cDNA encoding porcine GPR8 ligand precursor protein was cloned. The composition of the reaction solution and the conditions for PCR are as follows. The reaction solution comprised of 1 µl of porcine spinal cord cDNA diluted 50-fold with Tricine-EDTA Buffer attached to the kit, 0.5 µM of synthetic DNA primer represented by SEQ ID NO: 52, 0.5 µM of synthetic DNA primer represented by SEQ ID NO: 53, 0.4 mM dNTPs, 0.2 µl of Advantage 2 Polymerase (CLONTECH) and a buffer attached to the enzyme to make the total volume 20 µl. The PCR reaction was carried out using a thermal cycler (PE Biosystems) by heating of 96° C. for 60 seconds, then a cycle set to include 96° C. for 30 seconds followed by 72° C. for 75 seconds, which was repeated 4 times, 96° C. for 30 seconds followed by 70° C. for 75 seconds, which was repeated 4 times, 96° C. for 30 seconds followed by 68° C. for 75 seconds, which was repeated 4 times, 96° C. for 30 seconds followed by 64° C. for 30 seconds and 72° C. for 45 seconds, which was repeated 5 times, 96° C. for 30 seconds followed by 60° C. for 30 seconds and 72° C. for 45 seconds, which was repeated 20 times, and finally, incubation at 72° C. for 10 minutes. After isolating the amplified DNA by 1.2% agarose gel electrophoresis, DNA having about 600 bases length was excised with razor, and was recovered using QIAquick Gel Extraction Kit (Qiagen). This DNA was cloned into pCR2.1-TOPO vector according to the protocol attached to the TOPO TA Cloning Kit (Invitrogen). After transformation of *Escherichia coli* TOP10 competent cell (Invitrogen) by introducing the above-mentioned vector, clones harboring cDNA insert fragment was selected on LB agar medium containing ampicillin and X-gal. All the white-colored clones were isolated with sterilized toothpick, and then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 54, was obtained. Since this sequence (SEQ ID NO: 54) is coded for porcine GPR8 ligand precursor protein, *Escherichia coli* transformed with a plasmid containing this DNA was designated *Escherichia coli* TOP10/pCR2.1-TOPO Porcine GPR8 Ligand Precursor.

An amino acid sequence of porcine GPR8 ligand precursor protein encoded by the DNA sequence represented by SEQ ID NO: 54 was shown in SEQ ID NO: 55. In this amino acid sequence of the precursor protein, there is a sequence from the amino-terminus to the 17th residue, which was elucidated by analysis of amino acid sequence of the GPR8 ligand peptide isolated from porcine hypothalamus by assaying a GTPγS binding activity to the membrane fraction of GPR8 expressing CHO cells as an index as described in Reference Example 10. Further, as well as the case of human homologue of the GPR8 ligand peptide precursor protein, at the carboxyl-terminus, 2 sites of Arg-Arg sequence (Seidah, N. G. et al., Ann. N.Y. Acad. Sci., 839, 9-24, 1998), which is predicted to be a site where, in general, physiologically active peptide is excised, were present. From this fact, it was presumed that the amino acid sequence of porcine homologue of GPR8 ligand peptide is either SEQ ID NO: 56 or SEQ ID NO: 57, or both. The amino acid sequence and the DNA sequence of the porcine GPR8 ligand precursor protein were shown in FIG. 7.

Reference Example 33

Cloning of cDNA Encoding a Portion of Rat GPR8 Ligand Precursor Protein

As described in Reference Example 10, where based on the sequence consisting of 17 amino acid residues (SEQ ID NO: 6) from the amino-terminus of peptide purified from porcine hypothalamus by GTPγS binding activity to the membrane fraction of GPR8 expressing cells as an index, database retrieval was done, rat EST base sequence (accession number: H31598) identical to the base sequence represented by SEQ ID NO: 11 was found. This DNA sequence has a translation frame, wherein a sequence of 15 amino acids is identical to the amino acid sequence (SEQ ID NO: 6) of the peptide purified from porcine hypothalamus. The H31598 is an EST sequence derived from cDNA library prepared from rat PC12 cells, and consists of 260 bases containing 7 unidentified bases. The H31598 was predicted to be coding for a portion of precursor protein of homologue of rat GPR8 ligand peptide (hereafter, referred to as rat GPR8 ligand). Therefore, in order to determine a precise sequence, using respective primers prepared based on the 5' base sequence and the 3' base sequence of H31598 and rat brain Marathon-Ready cDNA (CLONTECH) as a template, PCR cloning was carried out. The composition of the reaction solution and the conditions for PCR are as follows. The reaction solution comprised of 21 µl of rat brain Marathon cDNA, 0.5 µM of synthetic DNA primer represented by SEQ ID NO: 60, 0.5 µM of synthetic DNA primer represented by SEQ ID NO: 61, 0.4 mM dNTPs, 0.2 µl of Advantage-GC 2 Polymerase (CLONTECH) and a buffer attached to the enzyme to make the total volume 20 µl. The PCR reaction was carried out using a thermal cycler (PE Biosystems) by heating of 96° C. for 60 seconds, then a cycle set to include 96° C. for 30 seconds followed by 60° C. for 30 seconds and 72° C. for 60 seconds, which was repeated 35 times, and finally, incubation at 72° C. for 10 minutes. After isolating the amplified DNA by 4.0% agarose gel electrophoresis, DNA having about 250 bases length was excised with razor, and was recovered using QIAquick Gel Extraction Kit (Qiagen). This DNA was cloned into pCR2.1-TOPO vector according to the protocol attached to the TOPO TA Cloning Kit (Invitrogen). After transformation of *Escherichia coli* TOP10 competent cell (Invitrogen) by introducing the above-mentioned vector, clones harboring cDNA insert fragment was selected on LB agar medium containing ampicillin and X-gal. All the white-colored clones were isolated with sterilized toothpick, and then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 62, was obtained. By comparison between the base sequence of DNA by PCR cloning (SEQ ID NO: 62) and the base sequence of H31598, it was found that the base sequence of H31598 has an error for one base deletion.

Reference Example 34

Cloning of 5' Upstream End of the cDNA Encoding Rat GPR8 Ligand Precursor Protein By 5' RACE PCR cloning, a base sequence of 5' upstream region of cDNA encoding rat GPR8 ligand precursor protein was elucidated. The 5' RACE PCR cloning was accomplished by PCR reaction using rat brain Marathon-Ready cDNA (CLONTECH) as a template, AP1 primer attached to the kit, and synthetic primer represented by SEQ ID NO: 63 followed by PCR reaction using the above PCR reaction mixture as a template, AP2 primer attached to the kit, and synthetic primer represented by SEQ ID NO: 64. The composition of the reaction solution and the conditions for PCR are as follows. The reaction solution comprised of 2 µl of rat brain Marathon cDNA, 0.5 µM of AP1 primer, 0.5 µM of synthetic DNA primer represented by SEQ ID NO: 63, 0.4 mM dNTPs, 0.2 µl of LATaq Polymerase (Takara Shuzo) and a GC (I) buffer attached to the enzyme to make the total volume 20 µl. The PCR reaction was carried out using a thermal cycler (PE Biosystems) by heating of 96° C. for 60 seconds, then a cycle set to include 96° C. for 30 seconds followed by 68° C. for 120 seconds, which was repeated 30 times, and finally, incubation at 72° C. for 10 minutes. Subsequently, the reaction solution comprised of 2 µl of the above PCR reaction solution diluted to 200-fold with Tricine-EDTA Buffer attached to the kit, 0.5 µM of AP2 primer, 0.5 µM of synthetic DNA primer represented by SEQ ID NO: 64, 0.4 mM dNTPs, 0.2 µl of Advantage-GC 2 Polymerase (CLONTECH) and a buffer attached to the enzyme to make the total volume 20 µl. The PCR reaction was carried out using a thermal cycler (PE Biosystems) by heating of 96° C. for 60 seconds, then a cycle set to include 96° C. for 30 seconds followed by 68° C. for 120 seconds, which was repeated 31 times, and finally, incubation at 72° C. for 10 minutes. After isolating the amplified DNA by 1.2% agarose gel electrophoresis, DNA having about 600 bases length was excised with razor, and was recovered using QIAquick Gel Extraction Kit (Qiagen). This DNA was cloned into pCR2.1-TOPO vector according to the protocol attached to the TOPO TA Cloning Kit (Invitrogen). After transformation of *Escherichia coli* TOP10 competent cell (Invitrogen) by introducing the above-mentioned vector, clones harboring cDNA insert fragment was selected on LB agar medium containing ampicillin and X-gal. All the white-colored clones were isolated with sterilized toothpick, and then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 65, was obtained.

Reference Example 35

Cloning of 3' Downstream End of the cDNA Encoding Rat GPR8 Ligand Precursor Protein By 3' RACE PCR cloning using a primer prepared based on the base sequence of 5' upstream end of cDNA encoding rat GPR8 ligand precursor protein and the sequence of cDNA fragment encoding a portion of rat GPR8 ligand precursor protein, a base sequence of 3' downstream region of cDNA encoding rat GPR8 ligand precursor protein was elucidated. The 3' RACE PCR cloning was accomplished by PCR reaction using rat brain Marathon-Ready cDNA as a template, AP1 primer attached to the kit, and synthetic primer represented by SEQ ID NO: 66 followed by PCR reaction using the above PCR reaction mixture as a template, AP2 primer attached to the kit, and synthetic primer represented by SEQ ID NO: 67. The composition of the reaction solution and the conditions for PCR are as follows. The reaction solution comprised: of 2 µl of rat brain Marathon-Ready cDNA, 0.5 µM of AP1 primer, 0.5 µM of synthetic DNA primer represented by SEQ ID NO: 66, 0.4 mM dNTPs, 0.4 µl of Advantage-GC 2 Polymerase (CLONTECH) and a buffer attached to the enzyme to make the total volume 20 µl. The PCR reaction was carried out using a thermal cycler (PE Biosystems) by heating of 96° C. for 60 seconds, then a cycle set to include 96° C. for 30 seconds followed by 68° C. for 180 seconds, which was repeated 30 times, and finally, incubation at 72° C. for 10 minutes. Subsequently, the reaction solution comprised of 2 µl of the above PCR reaction solution diluted to 200-fold with Tricine-EDTA Buffer attached to the kit, 0.5 µM of AP2 primer, 0.5 µM of synthetic DNA primer represented by SEQ ID NO: 67, 0.4 mM dNTPs, 0.4 [l of Advantage-GC 2 Polymerase (CLONTECH) and a buffer attached to the enzyme to make the total volume 20 µl. The PCR reaction was carried out using a thermal cycler (PE Biosystems) by heating of 96° C. for 60 seconds, then a cycle set to include 96° C. for 30 seconds followed by 68° C. for 180 seconds, which was repeated 30 times, and finally, incubation at 72° C. for 10 minutes. After isolating the amplified DNA by 1.2% agarose gel electrophoresis, DNA having about 600 bases length was excised with razor, and was recovered using QIAquick Gel Extraction Kit (Qiagen). This DNA was cloned into pCR2.1-TOPO vector according to the protocol attached to the TOPO TA Cloning Kit (Invitrogen). After transformation of *Escherichia coli* TOP10 competent cell (Invitrogen) by introducing the above-mentioned vector, clones harboring cDNA insert fragment was selected on LB agar medium containing ampicillin and X-gal. All the white-colored clones were isolated with sterilized toothpick, and then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 68, was obtained.

Reference Example 36

Cloning of cDNA Encoding Rat GPR8 Ligand Precursor Protein

By PCR amplification using a rat brain cDNA as a template, a primer based on 5' upstream base sequence of the cDNA encoding rat GPR8 ligand precursor protein and a primer based on 3' downstream base sequence of the cDNA encoding rat GPR8 ligand precursor protein, cDNA encoding rat GPR8 ligand precursor protein was cloned. The composition of the reaction solution and the conditions for PCR are as follows. The reaction solution comprised of 1 µl of rat brain Marathon-Ready cDNA, 0.5 µM of synthetic DNA primer represented by SEQ ID NO: 69, 0.5 µM of synthetic DNA primer represented by SEQ ID NO: 70, 0.4 mM dNTPs, 0.4 µl of Advantage-GC 2 Polymerase (CLONTECH) and a buffer attached to the enzyme to make the total volume 20 µl. The PCR reaction was carried out using a thermal cycler (PE Biosystems) by heating of 96° C. for 60 seconds, then a cycle set to include 96° C. for 30 seconds followed by 60° C. for 30 seconds and 72° C. for 60 seconds, which was repeated 35 times, and finally, incubation at 72° C. for 10 minutes. After isolating the amplified DNA by 1.2% agarose gel electrophoresis, DNA having about 750 bases length was excised with razor, and was recovered using QIAquick Gel Extraction Kit (Qiagen). This DNA was cloned into pCR2.1-TOPO vector according to the protocol attached to the TOPO TA Cloning Kit (Invitrogen). After transformation of *Escherichia coli* TOP10 competent cell (Invitrogen) by introducing the above-mentioned vector, clones harboring cDNA insert fragment was selected on LB agar medium containing ampicillin and X-gal. All the white-colored clones were isolated with sterilized toothpick, and then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 71, was obtained. Since this sequence (SEQ ID NO: 71) is coded for rat GPR8 ligand precursor protein, *Escherichia coli* transformed with a plasmid containing this DNA was designated *Escherichia coli* TOP10/pCR2.1-TOPO Rat GPR8 Ligand Precursor.

An amino acid sequence of rat GPR8 ligand precursor protein encoded by the DNA sequence represented by SEQ ID NO: 71 was shown in SEQ ID NO: 72. In this amino acid sequence of the precursor protein, there are a sequence from the amino-terminus to the 17th residue, which was elucidated by analysis of amino acid sequence of the GPR8 ligand peptide isolated from porcine hypothalamus by assaying a GTPγS binding activity to the membrane fraction of GPR8 expressing CHO cells as an index as described in Reference Example 10, and a similar sequence including different amino acid residues at the 5th and 17th positions. In addition, as well as the case of human or porcine homologue of the GPR8 ligand peptide precursor protein, at the carboxyl-terminus, 2 sites of Arg-Arg sequence (Seidah, N. G, et al., Ann. N.Y. Acad. Sci., 839, 9-24, 1998), which is predicted to be a site where, in general, physiologically active peptide is excised, were present. From this fact, it was presumed that the amino acid sequence of human homologue of GPR8 ligand peptide is either SEQ ID NO: 73 or SEQ ID NO: 74, or both. The amino acid sequence and the DNA sequence of the rat GPR8 ligand precursor protein were shown in FIG. 8.

Reference Example 37

Cloning of cDNA Encoding a Portion of Mouse GPR8 Ligand Precursor Protein

In order to obtain a precursor protein of mouse homologue of the GPR8 ligand peptide (hereinafter, sometimes referred to as mouse GPR8 ligand), using mouse testis cDNAa as a template, PCR amplification was performed. Then, a base sequence of the amplified DNA was determined. The composition of reaction solution and the reaction conditions for PCR are as follows. The reaction solution comprised of 1 μl of mouse testis cDNA (CLONTECH), 0.5 μM of synthetic DNA primer represented by SEQ ID NO: 78, 0.5 μM of synthetic DNA primer represented by SEQ ID NO: 79, 0.4 mM dNTPs, 0.2 μl of LATaq Polymerase (Takara Shuzo) and GC (I) buffer attached to the enzyme to make the total volume 20 μl. The PCR reaction was carried out using a thermal cycler (PE Biosystems) by heating of 96° C. for 120 seconds, then a cycle set to include 96° C. for 30 seconds followed by 68° C. for 120 seconds, which was repeated 10 times, 96° C. for 30 seconds followed by 64° C. for 30 seconds and 72° C. for 120 seconds, which was repeated 25 times, and finally, incubation at 72° C. for 10 minutes. After isolating the amplified DNA by 1.5% agarose gel electrophoresis, DNA having about 350 bases length was excised with razor, and was recovered using QIAquick Gel Extraction Kit (Qiagen). This DNA was cloned into pCR2.1-TOPO vector according to the protocol attached to the TOPO TA Cloning Kit (Invitrogen). After transformation of Escherichia coli TOP10 competent cell (Invitrogen) by introducing the above-mentioned vector, clones harboring cDNA insert fragment was selected on LB agar medium containing ampicillin and X-gal. All the white-colored clones were isolated with sterilized toothpick, and then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence was obtained (SEQ ID NO: 80).

Reference Example 38

Preparation of Mouse Brain cDNA

The mouse brain cDNA was prepared from mouse brain poly A(+) RNA (CLONTECH) using SMART™ RACE cDNA Amplification Kit (CLONTECH) in accordance with the protocol attached the kit. The solution containing the synthesized 1st strand cDNA was diluted to 10-fold with Tricine-EDTA Buffer attached to the kit, and used for RACE PCR reaction.

Reference Example 39

Cloning of 5' Upstream End of the cDNA Encoding Mouse GPR8 Ligand Precursor Protein By 5' RACE PCR cloning, a base sequence of 5' upstream region of cDNA encoding mouse TGR8 ligand precursor protein was elucidated. The 5' RACE PCR cloning was accomplished by PCR reaction using mouse brain cDNA as a template, Universal Primer Mix attached to SMART™ RACE cDNA Amplification Kit, and synthetic primer represented by SEQ ID NO: 81 followed by PCR reaction using the above PCR reaction mixture as a template, Nested Universal Primer attached to the kit, and synthetic primer represented by SEQ ID NO: 82. The composition of the reaction solution and the conditions for PCR are as follows. The reaction solution comprised of 1 μl of mouse brain cDNA, 2 μl of Universal Primer Mix, 0.2 μM of synthetic DNA primer represented by SEQ ID NO: 81, 0.8 mM dNTPs, 0.4 μl of Advantage-GC 2 Polymerase (CLONTECH) and a buffer attached to the enzyme to make the total volume 20 μl. The PCR reaction was carried out using a thermal cycler (PE Biosystems) by heating of 96° C. for 120 seconds, then a cycle set to include 96° C. for 30 seconds followed by 68° C. for 120 seconds, which was repeated 30 times, and finally, incubation at 72° C. for 10 minutes. Subsequently, the reaction solution comprised of 0.5 μl of the above PCR reaction solution diluted to 50-fold with Tricine-EDTA Buffer attached to the kit, 0.5 μM of Nested Universal Primer, 0.5 μM of synthetic DNA primer represented by SEQ ID NO: 82, 0.8 mM dNTPs, 0.4 μl of Advantage-GC 2 Polymerase (CLONTECH) and a buffer attached to the enzyme to make the total volume 20 μl. The PCR reaction was carried out using a thermal cycler (PE Biosystems) by heating of 96° C. for 120 seconds, then a cycle set to include 96° C. for 30 seconds followed by 68° C. for 30 seconds and 72° C. for 120 seconds, which was repeated 30 times, and finally, incubation at 72° C. for 10 minutes. After isolating the amplified DNA by 1.5% agarose gel electrophoresis, DNA having about 300 bases length was excised with razor, and was recovered using QIAquick Gel Extraction Kit (Qiagen). This DNA was cloned into pCR2.1-TOPO vector according to the protocol attached to the TOPO TA Cloning Kit (Invitrogen). After transformation of Escherichia coli TOP10 competent cell (Invitrogen) by introducing the above-mentioned vector, clones harboring cDNA insert fragment was selected on LB agar medium containing ampicillin and X-gal. All the white-colored clones were isolated with sterilized toothpick, and then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 83, was obtained.

Reference Example 40

Cloning of 3' Downstream End of the cDNA Encoding Mouse TGR8 Ligand Precursor Protein By 3' RACE PCR cloning, a base sequence of 3' downstream region of cDNA encoding mouse TGR8 ligand precursor protein was elucidated. The 3' RACE PCR cloning was accomplished by PCR reaction using mouse brain cDNA as a template, Universal Primer Mix attached to SMART™ RACE cDNA Amplification Kit, and synthetic primer represented by SEQ ID NO: 84 followed by PCR reaction using the above PCR reaction mixture as a template, Nested Universal Primer attached to the kit, and synthetic primer represented by SEQ ID NO: 85. The composition of the reaction solution and the conditions for PCR are as follows. The reaction solution comprised of 1 µl of mouse brain cDNA, 2 µl of Universal Primer Mix, 0.2 µM of synthetic DNA primer represented by SEQ ID NO: 84, 0.8 mM dNTPs, 0.4 [of Advantage-GC 2 Polymerase (CLONTECH) and a buffer attached to the enzyme to make the total volume 20 µl. The PCR reaction was carried out using a thermal cycler (PE Biosystems) by heating of 96° C. for 120 seconds, then a cycle set to include 96° C. for 30 seconds followed by 68° C. for 120 seconds, which was repeated 30 times, and finally, incubation at 72° C. for 10 minutes. Subsequently, the reaction solution comprised of 0.5 µl of the above PCR reaction solution diluted to 50-fold with Tricine-EDTA Buffer attached to the kit, 0.5 µM of Nested Universal Primer, 0.5 µM of synthetic DNA primer represented by SEQ ID NO: 85, 0.8 mM dNTPs, 0.4 µl of Advantage-GC 2 Polymerase (CLONTECH) and a buffer attached to the enzyme to make the total volume 20 µl. The PCR reaction was carried out using a thermal cycler (PE Biosystems) by heating of 96° C. for 120 seconds, then a cycle set to include 96° C. for 30 seconds followed by 68° C. for 30 seconds and 72° C. for 120 seconds, which was repeated 30 times, and finally, incubation at 72° C. for 10 minutes. After isolating the amplified DNA by 1.5% agarose gel electrophoresis, DNA having about 700 bases length was excised with razor, and was recovered using QIAquick Gel Extraction Kit (Qiagen). This DNA was cloned into pCR2.1-TOPO vector according to the protocol attached to the TOPO TA Cloning Kit (Invitrogen). After transformation of *Escherichia coli* TOP10 competent cell (Invitrogen) by introducing the above-mentioned vector, clones harboring cDNA insert fragment was selected on LB agar medium containing ampicillin and X-gal. All the white-colored clones were isolated with sterilized toothpick, and then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 86, was obtained.

Reference Example 41

Cloning of cDNA Encoding Mouse GPR8 Ligand Precursor Protein

By PCR amplification using a mouse brain cDNA as a template, a primer based on 5' upstream base sequence of the cDNA encoding mouse GPR8 ligand precursor protein and a primer based on 3' downstream base sequence of the cDNA encoding mouse GPR8 ligand precursor protein, cDNA encoding mouse GPR8 ligand precursor protein was cloned. The composition of the reaction solution and the conditions for PCR are as follows. The reaction solution comprised of 1 µl of mouse brain cDNA, 0.5 µM of synthetic DNA primer represented by SEQ ID NO: 87, 0.5 µM of synthetic DNA primer represented by SEQ ID NO: 88, 1.6 mM dNTPs, 0.2 µl of LATaq Polymerase (Takara Shuzo) and GC (I) buffer attached to the enzyme to make the total volume 20 µl. The PCR reaction was carried out using a thermal cycler (PE Biosystems) by heating of 96° C. for 120 seconds, then a cycle set to include 96° C. for 30 seconds followed by 64° C. for 30 seconds and 72° C. for 120 seconds, which was repeated 40 times, and finally, incubation at 72° C. for 10 minutes. After isolating the amplified DNA by 1.5% agarose gel electrophoresis, DNA having about 700 bases length was excised with razor, and was recovered using QIAquick Gel Extraction Kit (Qiagen). This DNA was cloned into pCR2.1-TOPO vector according to the protocol attached to the TOPO TA Cloning Kit (Invitrogen). After transformation of *Escherichia coli* TOP10 competent cell (Invitrogen) by introducing the above-mentioned vector, clones harboring cDNA insert fragment was selected on LB agar medium containing ampicillin and X-gal. All the white-colored clones were isolated with sterilized toothpick, and then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 89, was obtained. Since this sequence (SEQ ID NO: 89) is coded for rat GPR8 ligand precursor protein, *Escherichia coli* transformed with a plasmid containing this DNA was designated *Escherichia coli* TOP10/pCR2.1-TOPO Mouse GPR8 Ligand Precursor.

In the DNA sequence shown by SEQ ID NO: 89, there are frames coding for a sequence from the amino-terminus to the 17th residue, which was elucidated by analysis of amino acid sequence of the GPR8 ligand peptide isolated from porcine hypothalamus by assaying a GTPγS binding activity to the membrane fraction of GPR8 expressing CHO cells as an index as described in Reference Example 10, and a similar sequence including different amino acid residues at the 5th and 17th positions. However, as well as the case of human GPR8 ligand precursor, at the 5' upstream, there exists no ATG, which is predicted to be an initiation codon of the protein translation. Thus, as presumed in the case of human GPR8 ligand precursor protein, by comparison with porcine or rat homologue of GPR8 ligand precursor protein, CTG codon, which exists in the position nearly corresponding to that of ATG predictable to be an initiation codon of the precursor protein, was assumed to be an initiation codon. Then, a sequence of the mouse GPR8 ligand precursor protein was presumed. The assumptive amino acid sequence of the mouse GPR8 ligand precursor protein was shown in SEQ ID NO: 90. As well as the case of human, porcine or rat homologue of the GPR8 ligand peptide precursor protein, at the carboxyl-terminus, 2 sites of Arg-Arg sequence (Seidah, N. G. et al., Ann. N.Y. Acad. Sci., 839, 9-24, 1998), which is predicted to be a site where, in general, physiologically active peptide is excised, were present. From these facts, it was presumed that the amino acid sequence of mouse homologue of GPR8 ligand peptide is either SEQ ID NO: 91 or SEQ ID NO: 92, or both. In addition, an amino acid sequence of the mouse GPR8 ligand consisting of 23 residues, which is represented by SEQ ID NO: 91, is identical to the amino acid sequence of the rat GPR8 ligand consisting of 23 residues (SEQ ID NO: 73). The assumptive amino acid sequence and the DNA sequence of mouse GPR8 ligand precursor protein were shown in FIG. 9.

Reference Example 42

Preparation of [$^{125}$I-Tyr$^2$]-hGPR8L (1-23) and [$^{125}$I-Tyr$^{10}$]-hGPR8L (1-23) Using the Lactoperoxidase Method One nmol of hGPR8L (1-23) (the polypeptide consisting of the amino acid sequence represented by SEQ ID NO: 16) dissolved in 5 μl of DMSO was mixed with 5 μl of 1 M nickel chloride, 10 μl of 0.001% hydrogen peroxide dissolved in 0.1 M HEPES (pH7), 10 μl of 10 μg/ml lactoperoxidase (Sigma) dissolved in 0.1 M HEPES (pH7), and 10 μl of NaI (37 MBq, NEN Life Science Products). The reaction mixture was incubated at room temperature for 60 minutes, and then was fractionated by HPLC under the following conditions.

As a column, ODS-80™ (4.6 mm×15 cm) (Toso) was used, and as an eluent A and eluent B, 10% acetonitrile/0.1% TFA and 60% acetonitrile/0.1% TFA were used, respectively. Elution was performed by gradient elution of 0-0 (2 minutes), 0-30 (3 minutes), 30-38 (5 minutes), and 38-43 (55 minutes) of % B/A+B. Flow rate was 1 mL/min. Column temperature was 25° C. Detection of absorbance at 220 nm was used.

Since hGPR8L (1-23) has two tyrosine residues, by iodization, [$^{125}$I-Tyr$^2$]-hGPR8L (1-23) and [$^{125}$I-Tyr$^{10}$]-hGPR8L (1-23) were formed. Under the HPLC condition utilized, [$^{125}$I-Tyr$^2$]-hGPR8L (1-23) was eluted at around 30 minutes and [$^{125}$-Tyr$^{10}$]-hGPR8L (1-23) at around 32 minutes.

Reference Example 43

Experiment for Receptor Binding Using [$^{125}$I-Tyr$^{10}$]-hGPR8L(1-23)

Using [$^{125}$I]-labeled hGPR8L(1-23) prepared as described in Reference Example 42 and a cell membrane fraction prepared from human GPR8 expressing cells by the similar manner as described in Reference Example 6, a receptor binding assay was carried out as follows.

Figure 10:
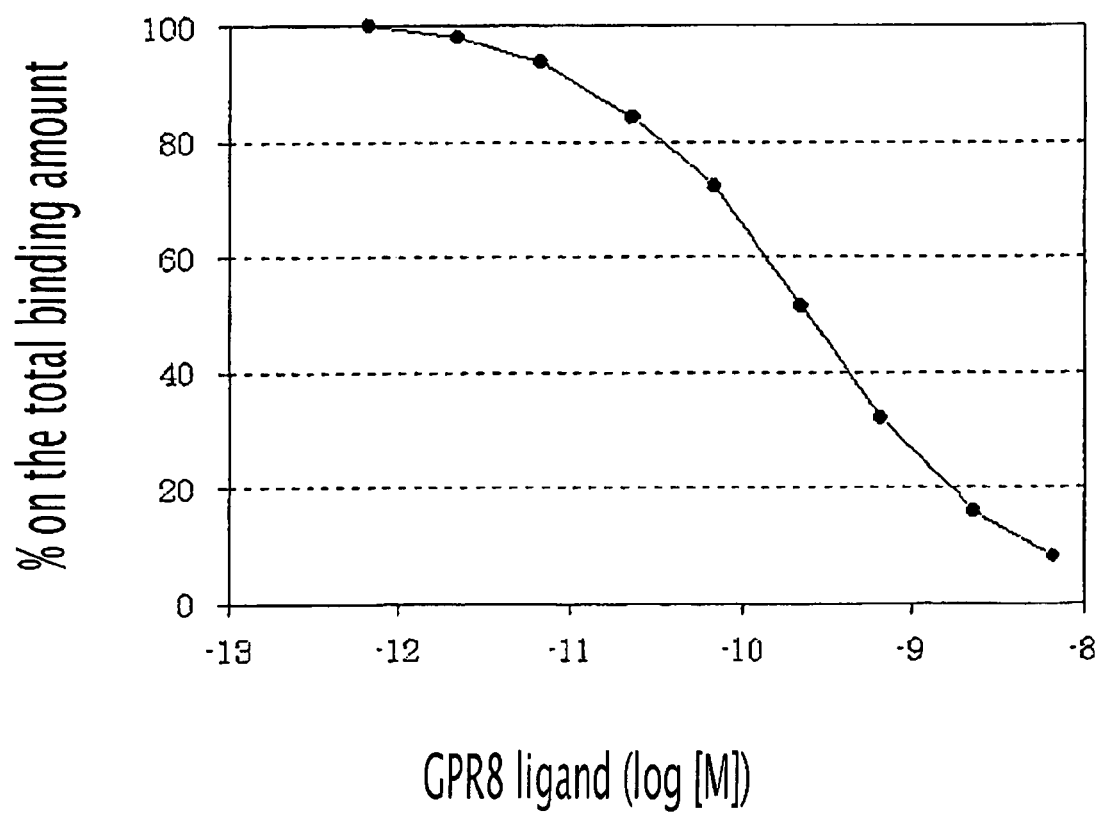
FIG. 10 shows a binding inhibiting activity of human GPR8 ligand, which consists of 23 residues, against [$^{125}$I] labeled human GPR8 ligand, which consists of 23 residues, using a cell membrane fraction prepared from human GPR8-expressing CHO cells.

Cell membrane fraction prepared from human GPR8 expressing cells was diluted to various concentration with assay buffer (25 mM Tris-HCl, 5 mM EDTA, 0.05% CHAPS (3-[(3-Cholamidopropyl) Dimethyl-Ammonio]-1-Propanesulfonate), 0.1% BSA, 0.25 mM PMSF, 1 μg/ml Pepstatin, 20 μg/ml Leupeptin, pH7.4), and 200 μl each of the diluent was dispensed into polypropilene test tube (Falcon 2053). In order to determine an amount of maximum binding (TB), 21 μl of DMSO and 2 μl of 7 nM [$^{125}$I-Tyr$^2$]-hGPR8L(1-23) or [$^{125}$I-Tyr$^{10}$]-hGPR8L(1-23) were added to the membrane fraction solution. Further, in order to determine a non-specific binding (NSB), 2 μt of 100 μM hGPR8L(1-23)/DMSO solution and 2 μl of 7 nM [$^{125}$I]-Tyr$^2$]-hGPR8L(1-23) or [$^{125}$I-Tyr$^{10}$]-hGPR8L(1-23) were added to the membrane fraction solution. The reaction was done at 25° C. for 60 minutes, and the reaction mixture was filtered by suction filtration using Whatman glassfilter (GF-F) treated with polyethyleneimine. After filtration, a radioactivity remaining on the filter was counted using γ-counter, and an amount of specific binding (SB) was estimated by subtracting an amount of non-specific binding from an amount of maximum binding. Since the specific binding in the case where [$^{125}$I-Tyr$^{10}$]-hGPR8L(1-23) was used, was twice as much as that in the case where [$^{125I-Tyr2}$]-hGPR8L(1-23) was used, in practice, [$^{125}$I-Tyr$^{10}$]-hGPR8L(1-23) was used in the assay. When the concentration of membrane fraction was changed, a specific binding of [$^{125}$I-Tyr$^{10}$]-hGPR8L(1-23) was perceived depending on the concentration of membrane fraction. Where the concentration of membrane fraction was set to 5 μg/ml, concentration of 50% inhibition (IC$_{50}$ values) of hGPR8L(1-23) was calculated from the inhibition rate. It was found that the IC$_{50}$ value was 0.25 nM. FIG. 10 shows the inhibition of hGPR8L(1-23) binding at various concentration.

Reference Example 44

Production of Human GPR8 Ligand (1-23) Oxidant: Trp-Tyr-Lys-His-Val-Ala-Ser-Pro-Arg-Tyr-His-Thr-Val-Gly-Arg-Ala-Ala-Gly-Leu-Leu-Met(O)-Gly-Leu (SEQ ID NO: 95)

The compound in Reference Example 12, 0.45 mg was dissolved in 0.5 ml of 50% acetic acid water, and further 0.3% hydrogen peroxide solution was added followed by leaving to stand at room temperature for 8 hours. After vacuum concentration, the solution was purified by SepPak to give 0.443 mg of a white-colored powder.

(M+H)$^+$ by mass spectrometry: 2599.2 (calculated value 2599.4) Elution time on HPLC: 19.1 minutes Conditions for elution Column: Wakosil-II 5C18HG (4.6×100 mm) Eluant: using Solution A: 0.1% TFA-water and Solution B: acetonitrile containing 0.1% TFA, elution by linear concentration gradient from A/B: 100/0 to 0/70 (35 minutes) Flow rate: 1.0 ml/minute Reference Example 45

Production of Human GPR8 Ligand (1-22): Trp-Tyr-Lys-His-Val-Ala-Ser-Pro-Arg-Tyr-His-Thr-Val-Gly-Arg-Ala-Ala-Gly-Leu-Leu-Met-Gly (SEQ ID NO: 96)

Fmoc-Gly was introduced to commercially available 2-chlorotrityl resin (Clt resin, 1.33 mmol/g). Then, just like Reference Example 13, condensation of amino acids and excision from the resin in the sequence order, and purification were carried out to give a target.

Reference Example 46

Production of Human GPR8 Ligand (1-21): Trp-Tyr-Lys-His-Val-Ala-Ser-Pro-Arg-Tyr-His-Thr-Val-Gly-Arg-Ala-Ala-Gly-Leu-Leu-Met (SEQ ID NO: 97)

Fmoc-Met was introduced to commercially available 2-chlorotrityl resin (Clt resin, 1.33 mmol/g). Then, just like Reference Example 13, condensation of amino acids and excision from the resin in the sequence order, and purification were carried out to give a target.

Reference Example 47

Production of Human GPR8 Ligand (1-20): Trp-Tyr-Lys-His-Val-Ala-Ser-Pro-Arg-Tyr-His-Thr-Val-Gly-Arg-Ala-Ala-Gly-Leu-Leu (SEQ ID NO: 98)

Fmoc-Leu was introduced to commercially available 2-chlorotrityl resin (Clt resin, 1.33 mmol/g). Then, just like Reference Example 13, condensation of amino acids and excision from the resin in the sequence order, and purification were carried out to give a target.

(M+H)$^+$ by mass spectrometry: 2282.8 (calculated value 2282.6) Elution time on HPLC: 17.2 minutes Conditions for elution Column: Wakosil-II 5C18HG (4.6×100 mm) Eluant:

using Solution A: 0.1% TFA-water and Solution B: acetonitrile containing 0.1% TFA, elution by linear concentration gradient from A/B: 100/0 to 0/70 (35 minutes) Flow rate: 1.0 ml/minute

Reference Example 48

Production of Human GPR8 Ligand (1-19): Trp-Tyr-Lys-His-Val-Ala-Ser-Pro-Arg-Tyr-His-Thr-Val-Gly-Arg-Ala-Ala-Gly-Leu (SEQ ID NO: 99)

Fmoc-Leu was introduced to commercially available 2-chlorotrityl resin (Clt resin, 1.33 mmol/g). Then, just like Reference Example 13, condensation of amino acids and excision from the resin in the sequence order, and purification were carried out to give a target.

$(M+H)^+$ by mass spectrometry: 2169.6 (calculated value 2169.5) Elution time on HPLC: 16.4 minutes Conditions for elution Column: Wakosil-II 5C18HG (4.6×100 mm) Eluant: using Solution A: 0.1% TFA-water and Solution B: acetonitrile containing 0.1% TFA, elution by linear concentration gradient from A/B: 100/0 to 0/70 (35 minutes) Flow rate: 1.0 ml/minute

Reference Example 49

Production of Human GPR8 Ligand (1-18): Trp-Tyr-Lys-His-Val-Ala-Ser-Pro-Arg-Tyr-His-Thr-Val-Gly-Arg-Ala-Ala-Gly (SEQ ID NO: 100)

Fmoc-Gly was introduced to commercially available 2-chlorotrityl resin (Clt resin, 1.33 mmol/g). Then, just like Reference Example 13, condensation of amino acids and excision from the resin in the sequence order, and purification were carried out to give a target.

$(M+H)^+$ by mass spectrometry: 2056.8 (calculated value 2056.3) Elution time on HPLC: 14.2 minutes Conditions for elution Column: Wakosil-II 5C18HG (4.6×100 mm) Eluant: using Solution A: 0.1% TFA-water and Solution B: acetonitrile containing 0.1% TFA, elution by linear concentration gradient from A/B: 100/0 to 0/70 (35 minutes) Flow rate: 1.0 ml/minute

Reference Example 50

Production of Human GPR8 Ligand (1-17): Trp-Tyr-Lys-His-Val-Ala-Ser-Pro-Arg-Tyr-His-Thr-Val-Gly-Arg-Ala-Ala (SEQ ID NO: 101)

Fmoc-Ala was introduced to commercially available 2-chlorotrityl resin (Clt resin, 1.33 mmol/g). Then, just like Reference Example 13, condensation of amino acids and excision from the resin in the sequence order, and purification were carried out to give a target.

Reference Example 51

Production of Human GPR8 Ligand (1-16): Trp-Tyr-Lys-His-Val-Ala-Ser-Pro-Arg-Tyr-His-Thr-Val-Gly-Arg-Ala (SEQ ID NO: 102)

Fmoc-Ala was introduced to commercially available 2-chlorotrityl resin (Clt resin, 1.33 mmol/g). Then, just like Reference Example 13, condensation of amino acids and excision from the resin in the sequence order, and purification were carried out to give a target.

Reference Example 52

Production of porcine GPR8 Ligand (1-23): Trp-Tyr-Lys-His-Val-Ala-Ser-Pro-Arg-Tyr-His-Thr-Val-Gly-Arg-Ala-Ala-Gly-Leu-Leu-Met-Gly-Leu (SEQ ID NO: 56)

Fmoc-Leu was introduced to commercially available 2-chlorotrityl resin (Clt resin, 1.33 mmol/g). Then, just like Reference Example 13, condensation of amino acids and excision from the resin in the sequence order, and purification were carried out to give a target.

$(M+H)^+$ by mass spectrometry: 2585.2 (calculated value 2585.4) Elution time on HPLC: 20.2 minutes Conditions for elution Column: Wakosil-II 5C18HG (4.6×100 mm) Eluant: using Solution A: 0.1% TFA-water and Solution B: acetonitrile containing 0.1% TFA, elution by linear concentration gradient from A/B: 100/0 to 0/70 (35 minutes) Flow rate: 1.0 ml/minute

Reference Example 53

Production of Rat/Mouse GPR8 Ligand (1-23): Trp-Tyr-Lys-His-Val-Ala-Ser-Pro-Arg-Tyr-His-Thr-Val-Gly-Arg-Ala-Ala-Gly-Leu-Leu-Met-Gly-Leu (SEQ ID NO: 73 and SEQ ID NO: 91)

Just like Reference Example 52, condensation of amino acids and excision from the resin in the sequence order, and purification were carried out to give a target.

Reference Example 54

Production of Porcine GPR8 Ligand (1-23) Oxidant: Trp-Tyr-Lys-His-Val-Ala-Ser-Pro-Arg-Tyr-His-Thr-Val-Gly-Arg-Ala-Ala-Gly-Leu-Leu-Met(O)-Gly-Leu (SEQ ID NO: 103)

Using a compound described in Reference Example 52, a compound was oxidized in a similar manner to Reference Example 44 to give a target.

$(M+H)^+$ by mass spectrometry: 2601.3 (calculated value 2601.4) Elution time on HPLC: 18.9 minutes Conditions for elution Column: Wakosil-II 5C18HG (4.6×100 mm) Eluant: using Solution A: 0.1% TFA-water and Solution B: acetonitrile containing 0.1% TFA, elution by linear concentration gradient from A/B: 100/0 to 0/70 (35 minutes) Flow rate: 1.0 ml/minute

Reference Example 55

Production of Rat/Mouse GPR8 Ligand (1-23) Oxidant: Trp-Tyr-Lys-His-Val-Ala-Ser-Pro-Arg-Tyr-His-Thr-Val-Gly-Arg-Ala-Ala-Gly-Leu-Leu-Met(O)-Gly-Leu (SEQ ID NO: 104)

Using a compound described in Reference Example 53, a compound was oxidized in a similar manner to Reference Example 44 to give a target.

Reference Example 56

Production of [N$^\alpha$-Acetyl-Trp$^1$]-Human GPR8 Ligand (1-23): Ac-Trp-Tyr-Lys-His-Val-Ala-Ser-Pro-Arg-Tyr-His-Thr-Val-Gly-Arg-Ala-Ala-Gly-Leu-Leu-Met-Gly-Leu (SEQ ID NO: 106)

Fmoc group was removed from the resin prepared in Reference Example 12, and the terminus was acetylated with acetic anhydride. Then, excision from the resin and removal of protecting group of side chain were simultaneously performed by treatment of TFA/thioanisole/m-cresol/triisopropylsilane/ethanedithiol (85/5/5/2.5/2.5). Crude peptide was purified in a similar manner to Reference Example 12 to give a target.

(M+H)+ by mass spectrometry: 2626.1 2625.8 (calculated value 2627.1 2626.1) Elution time on HPLC: 21.4 minutes Conditions for elution Column: Wakosil-II 5C18HG (4.6× 100 mm) Eluant: using Solution A: 0.1% TFA-water and Solution B: acetonitrile containing 0.1% TFA, elution by linear concentration gradient from A/B: 100/0 to 30/70 (35 minutes) Flow rate: 1.0 ml/minute Reference Example 57

Production of Human GPR8 Ligand (2-23): Tyr-Lys-His-Val-Ala-Ser-Pro-Arg-Tyr-His-Thr-Val-Gly-Arg-Ala-Ala-Gly-Leu-Leu-Met-Gly-Leu (SEQ ID NO: 107)

In a similar manner to Reference Example 12, desired amino acid sequence was introduced to the resin. After removal of the last Tyr, Fmoc group was removed from the resin. Then, by treatment of TFA/thioanisole/m-cresol/triisopropylsilane/ethanedithiol (85/5/5/2.5/2.5), excision from the resin and removal of protecting group of side chain were simultaneously performed. Crude peptide was purified in a similar manner to Reference Example 12 to give a target.

(M+H)+ by mass spectrometry: 2397.1 (calculated value 2397.3) Elution time on HPLC: 19.9 minutes Conditions for elution Column: Wakosil-II 5C18HG (4.6×100 mm) Eluant: using Solution A: 0.1% TFA-water and Solution B: acetonitrile containing 0.1% TFA, elution by linear concentration gradient from A/B: 100/0 to 30/70 (35 minutes) Flow rate: 1.0 ml/minute Reference Example 58

Production of Human GPR8 Ligand (4-23): His-Val-Ala-Ser-Pro-Arg-Tyr-His-Thr-Val-Gly-Arg-Ala-Ala-Gly-Leu-Leu-Met-Gly-Leu (SEQ ID NO: 108)

In a similar manner to Reference Example 12, desired amino acid sequence was introduced to the resin. After removal of the last His, Fmoc group was removed from the resin. Then, by treatment of TFA/thioanisole/m-cresol/triisopropylsilane/ethanedithiol (85/5/5/2.5/2.5), excision from the resin and removal of protecting group of side chain were simultaneously performed. Crude peptide was purified in a similar manner to Reference Example 12 to give a target.

(M+H)+ by mass spectrometry: 2106.0 (calculated value 2106.1) Elution time on HPLC: 20.0 minutes Conditions for elution Column: Wakosil-II 5C18HG (4.6×100 mm) Eluant: using Solution A: 0.1% TFA-water and Solution B: acetonitrile containing 0.1% TFA, elution by linear concentration gradient from A/B: 100/0 to 30/70 (35 minutes) Flow rate: 1.0 ml/minute Reference Example 59

Production of Human GPR8 Ligand (9-23): Arg-Tyr-His-Thr-Val-Gly-Arg-Ala-Ala-Gly-Leu-Leu-Met-Gly-Leu (SEQ ID NO: 109)

In a similar manner to Reference Example 12, desired amino acid sequence was introduced to the resin. After removal of the last Arg, Fmoc group was removed from the resin. Then, by treatment of TFA/thioanisole/m-cresol/triisopropylsilane/ethanedithiol (85/5/5/2.5/2.5), excision from the resin and removal of protecting group of side chain were simultaneously performed. Crude peptide was purified in a similar manner to Reference Example 12 to give a target.

(M+H)+ by mass spectrometry: 1615.0 (calculated value 1614.9) Elution time on HPLC: 20.2 minutes Conditions for elution Column: Wakosil-II 5C18HG (4.6×100 mm) Eluant: using Solution A: 0.1% TFA-water and Solution B: acetonitrile containing 0.1% TFA, elution by linear concentration gradient from A/B: 100/0 to 30/70 (35 minutes) Flow rate: 1.0 ml/minute Reference Example 60

Production of Human GPR8 Ligand (15-23): Arg-Ala-Ala-Gly-Leu-Leu-Met-Gly-Leu (SEQ ID NO: 110)

In a similar manner to Reference Example 12, desired amino acid sequence was introduced to the resin. After removal of the last Arg, Fmoc group was removed from the resin. Then, by treatment of TFA/thioanisole/m-cresol/triisopropylsilane/ethanedithiol (85/5/5/2.5/2.5), excision from the resin and removal of protecting group of side chain were simultaneously performed. Crude peptide was purified in a similar manner to Reference Example 12 to give a target.

(M+H)+ by mass spectrometry: 901.4 (calculated value 901.5) Elution time on HPLC: 20.2 minutes Conditions for elution Column: Wakosil-II 5C18HG (4.6×100 mm) Eluant: using Solution A: 0.1% TFA-water and Solution B: acetonitrile containing 0.1% TFA, elution by linear concentration gradient from A/B: 100/0 to 30/70 (35 minutes) Flow rate: 1.0 ml/minute Reference Example 61

Production of [N-Acetyl-Tyr$^2$]-Human GPR8 Ligand (2-23): Ac-Tyr-Lys-His-Val-Ala-Ser-Pro-Arg-Tyr-His-Thr-Val-Gly-Arg-Ala-Ala-Gly-Leu-Leu-Met-Gly-Leu (SEQ ID NO: 111)

After completion of acetylation of the resin prepared in Reference Example 57 with acetic anhydride, the resin was treated in a similar manner to Reference Example 57 and the peptide was purified to give a target.

(M+H)+ by mass spectrometry: 2439.3 (calculated value 2439.3) Elution time on HPLC: 20.2 minutes Conditions for elution Column: Wakosil-II 5C18HG (4.6×100 mm) Eluant: using Solution A: 0.1% TFA-water and Solution B: acetonitrile containing 0.1% TFA, elution by linear concentration gradient from A/B: 100/0 to 30/70 (35 minutes) Flow rate: 1.0 ml/minute Reference Example 62

Production of [D-Trp$^1$]-human GPR8 Ligand (1-23): D-Trp-Tyr-Lys-His-Val-Ala-Ser-Pro-Arg-Tyr-His-Thr-Val-Gly-Arg-Ala-Ala-Gly-Leu-Leu-Met-Gly-Leu (SEQ ID NO: 112)

Using Fmoc-D-Trp(Boc) instead of Fmoc-Trp(Boc) in Reference Example 12, a target was obtained in a similar manner.

(M+H)+ by mass spectrometry: 2583.4 (calculated value 2583.4) Elution time on HPLC: 20.6 minutes Conditions for elution Column: Wakosil-II 5C18HG (4.6×100 mm) Eluant: using Solution A: 0.1% TFA-water and Solution B: acetonitrile containing 0.1% TFA, elution by linear concentration gradient from A/B: 100/0 to 30/70 (35 minutes) Flow rate: 1.0 ml/minute Reference Example 63

Production of [N-3-Indolepropanoyl-Tyr$^2$]-Human GPR8 Ligand (2-23): 3-Indolepropanoyl-Tyr-Lys-His-Val-Ala-Ser-Pro-Arg-Tyr-His-Thr-Val-Gly-Arg-Ala-Ala-Gly-Leu-Leu-Met-Gly-Leu (SEQ ID NO: 113)

Using 3-Indolepropionic acid instead of Fmoc-Trp(Boc) in Reference Example 12, a target was obtained. By treatment of TFA/thioanisole/m-cresol/triisopropylsilane/ethanedithiol (85/5/5/2.5/2.5), an excision of the peptide from the resin and removal of side chain protecting group were carried out at the same time. The crude peptide was purified in a similar way as described in Reference Example 12 to get a target.

(M+H)$^+$ by mass spectrometry: 2568.4 (calculated value 2568.4) Elution time on HPLC: 21.7 minutes Conditions for elution Column: Wakosil-II 5C18HG (4.6×100 mm) Eluant: using Solution A: 0.1% TFA-water and Solution B: acetonitrile containing 0.1% TFA, elution by linear concentration gradient from A/B: 100/0 to 30/70 (35 minutes) Flow rate: 1.0 ml/minute Reference Example 64

Promoting Activity to GTPγS Binding of Human- and Porcine-Homologue Derivatives of GPR8 Ligand Peptide, which was Measured Using a Membrane Fraction of GPR8 Expressing CHO Cells A promoting activity to GTPγS binding of human- and porcine-homologue derivatives of GPR8 ligand peptide, wherein the synthesis method has been described in the specification, was measured by administering the derivatives at various concentrations via the method described in Reference Example 6 to the membrane fraction of GPR8 expressing CHO cells. SEQ ID NO of the derivatives measured and promoting activity to GTPγS binding thereof are shown in Table 1. The activity is represented by concentration of 50% effective concentrations (EC$_{50}$ value). In addition, the promoting activity to GTPγS binding of hGPR8L(1-23) and hGPR8L(1-30) described in Reference Examples 20 and 21 was also included.

Reference Example 65

Receptor Binding Activity of Human- and Porcine-Homologue Derivatives of GPR8 Ligand Peptide, which was Measured Using a Membrane Fraction of GPR8 Expressing CHO Cells and [$^{125}$I-Tyr$^{10}$]-hGPR8L(1-23)

A receptor binding activity of human- and porcine-homologue derivatives of GPR8 ligand peptide, wherein the synthesis method has been described in the specification, was measured using a membrane fraction of GPR8 expressing CHO cells and [$^{125}$I-Tyr$^{10}$]-hGPR8L(1-23) by the method described in Reference Example 43. SEQ ID NO of the derivatives measured and receptor binding activity thereof are shown in Table 1. The receptor binding activity is represented by concentration of 50% inhibition for binding (IC$_{50}$ value). In addition, the receptor binding activity of hGPR8L(1-23) described in Reference Example 43 was also included.

TABLE 1

The promoting activity to GTPγS binding and the receptor binding activity of human- and porcine-homologue derivatives of GPR8 ligand peptide

| Derivatives | SEQ ID NO | Promoting activity to GTPγS binding (EC$_{50}$ nM) | Receptor binding activity (IC$_{50}$ nM) |
|---|---|---|---|
| hGPR8L(1-23) | 16 | 1.6 | 0.25 |
| hGPR8L(1-30) | 17 | 0.57 | 0.025 |
| [MET(O)]-hGPR8L(1-23) | 95 | 1.4 | 0.31 |
| Fmoc-hGPR8L(1-23) | 105 | 240 | 0.20 |
| Ac-hGPR8L(1-23) | 106 | 14 | 2.4 |
| [D-Trp$^1$]-hGPR8L(1-23) | 112 | 7.1 | 0.82 |
| hGPR8L(2-23) | 107 | 3900 | 160 |
| Ac-hGPR8L(2-23) | 111 | 7200 | 420 |
| IndPr-hGPR8L(2-23) | 113 | 5.0 | 0.28 |
| hGPR8L(4-23) | 108 | 6700 | 1400 |
| hGPR8L(9-23) | 109 | 4200 | 1300 |
| hGPR8L(1-20) | 98 | 0.86 | 0.20 |
| hGPR8L(1-19) | 99 | 1000 | 100 |
| hGPR8L(1-18) | 100 | >10000 | 2700 |
| pGPR8L(1-23) | 56 | 1.5 | 0.38 |
| [MET(O)]-pGPR8L(1-23) | 103 | 0.73 | 0.29 |

Reference Example 66

Cloning of the cDNA Encoding the Rat Whole Brain-Derived G Protein-Coupled Receptor Protein and Determination of the Base Sequence Using rat whole brain-derived cDNA (CLONTECH) as a template and two primers, namely, primer 1 (SEQ ID NO: 128) and primer 2 (SEQ ID NO: 129), which were designed based on the base sequence of the DNA encoding human GPR8, PCR reaction was carried out. The reaction solution in the above reaction comprised of 1/10 volume of the cDNA as a template, 1/50 volume of Advantage-2 cDNA Polymerase Mix (CLONTECH), 0.2 μM of primer 3, 0.2 μM of primer 2, 200 μM of dNTPs, and a buffer attached to the enzyme to make the total volume 25 μl. The PCR reaction was carried out (i) by reaction of 94° C. for 2 minutes, then (ii) a cycle set to include 94° C. for 20 seconds followed by 72° C. for 2 minutes, which was repeated 3 times, (iii) 94° C. for 20 seconds followed by 66° C. for 20 seconds and 68° C. for 2 minutes, which was repeated 3 times, (iv) 94° C. for 20 seconds followed by 60° C. for 20 seconds and 68° C. for 2 minutes, which was repeated 36 times, and finally, extension reaction at 68° C. for 7 minutes. The PCR product was subcloned to plasmid vector pCR2.1-TOPO (Invitrogen) following the instructions attached to the TA Cloning Kit (Invitrogen). The plasmid was then introduced into *Escherichia coli* DH5α, and the clones containing the cDNA were selected on LB agar plates containing ampicillin. As a result of analysis for sequence of each clone, a base sequence of the cDNA encoding the novel G protein-coupled receptor protein was obtained (SEQ ID NO: 127). The novel G protein-coupled receptor protein containing the amino acid sequence (SEQ ID NO: 126) encoded by the base sequence of this DNA was designated TGR26 (in the specification, referred to as rat TGR26).

The amino acid sesquence represented by SEQ ID NO: 126 has an 84.8% homology to GPR7, the well-known human G protein-coupled receptor protein [Genomics, Vol.28, 84-91, 1995].

One clone of the aforementioned transformants harboring a plasmid, in which the DNA encoding TGR26 was inserted, was selected, cultured in LB medium containing ampicillin with shaking. As a result, the plasmid was obtained. The plasmid was treated with restriction enzymes ClaI and SpeI, and the insert encoding TGR26 was excised. Using pAKKO-1.11H treated with restrictionenzymes ClaI and SpeI in a similar manner and Ligaation Expression Kit (CLONTECH), the insert was ligated, and the plasmid obtained was introduced into *Escherichia coli* DH10B by electroporation. A structure of the plasmid used for construction of cells for expression, in which the obtained clone contained, was confirmed by treatment of restriction enzymes and by analysis of the sequence. Then, the clone was designated *Escherichia coli* DH10B/pAK-rGPR7.

Figure 11:
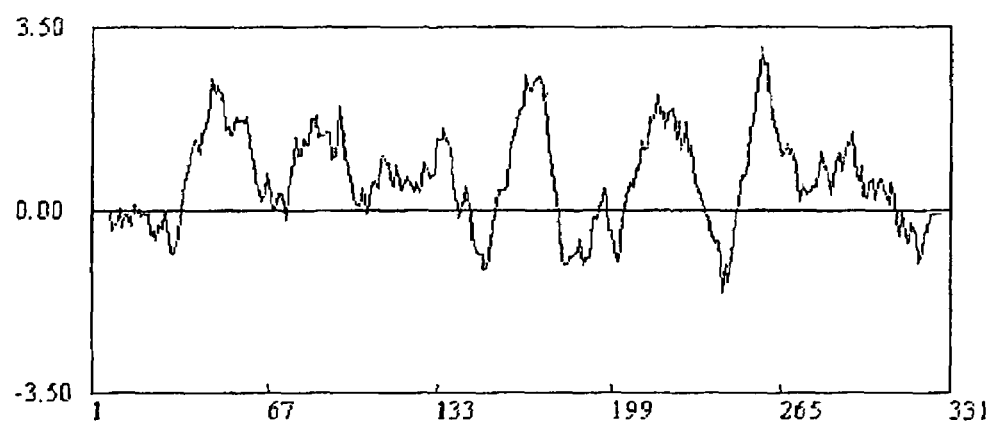
FIG. 11 shows a plot for hydrophobicity of TGR26.

The hydrophobicity plot of TGR26 is indicated in FIG. 11.

Reference Example 67

Preparation of TGR26 Expressing CHO Cells

After completion of culture of *Escherichia coli* DH5α (TOYOBO) transformed with the expression plasmid pAK-rGPR7 described in Reference Example 66, pAK-rGPR7 plasmid DNA was prepared using Plasmid Midi Kit (QIAGEN). This plasmid was introduced into CHO dhfr⁻ cells using CellPhect Transfection Kit (Amersham Pharmacia Biotech) in accordance with the attached protocol. Co-precipitate suspension of 5 µg of DNA with calcium phosphate was prepared and added to each of two 6 cm-diameter dishes, on which $3 \times 10^5$ CHO dhfr⁻ cells were seeded before 48 hours. The cells were cultivated in MEMα medium containing 10% fetal bovine serum for one day and were subcultured. Subsequently, the cells were cultured in the selection medium, MEMα medium containing 10% dialyzed fetal bovine serum and no nucleic acid. The 44 clones of transformant colonies that are TGR26 expressing CHO cells grown in the selection medium were selected.

Reference Example 68

Quantification of an Expression Level of TGR26 in TGR26 Expressing CHO Cell Line Using TaqMan PCR Method The 44 clones of TGR26 expressing cell line obtained in Reference Example 67 were cultured in 25 cm² flask, respectively. After preparation of total RNA using Rneasy Mini Kits (Qiagen), RNA was treated with DNase using RNase-free DNase Set (Qiagen). Four micrograms of total RNA obtained was dissolved in 12 µl of solution containing 500 pmol of random primers (Takara Shuzo), was treated at 70° C. for 10 minutes and was chilled on ice. Further, to the mixture, 1× First Strand Buffer, 10 mM DTT, 500 µM dA/dC/dG/dTTP and 200 units of SUPERSCRIPT II (GIBCO) were added. Subsequently, for 20 µl of the mixture, reverse transcription was carried out by treatment at 30° C. for 10 minutes, followed by 42° C. for 60 minutes, 51° C. for 30 minutes and 70° C. for 15 minute. For 25 µl of the reaction mixture containing the obtained reverse transcripts corresponding to 5 ng of total RNA or 10 to $1 \times 10^7$ copies of standard cDNA prepared by the method described below, 1× Universal PCR Master Mix (PE Biosystems), 100 nM each of primers represented by SEQ ID NO: 130 and SEQ ID NO: 131, and 100 nM TaqMan probe represented by SEQ ID NO: 140 (Fam-tcctctgctg gacaccgtac cacctga-Tamra; in the sequence, Fam and Tamra represent 6-carboxy-fluorescein and 6-carboxy-tetramethyl-rhodamine, respectively), using ABI PRISM 7700 Sequence Detector (PE Biosystems), PCR was carried out. PCR was performed by heating of 50° C. for 2 minutes and 95° C. for 10 minutes, then a cycle set to include 95° C. for 15 seconds followed by 60° C. for 60 seconds, which was repeated 40 times.

The standard cDNA was prepared by PCR amplification, wherein the PCR was performed using 200 µl of the reaction mixture containing 100 pg of TGR26 expressing plasmid DNA (pAK-rGPR7), 500 nM each of primers represented by SEQ ID NO: 130 and SEQ ID NO: 131, 1×PCR Gold Buffer, 2.5 mM MgCl₂, 200 µM dA/dC/dG/dTTP and 200 units of AmpliTaq Gold (PE Biosystems) and GeneAmp PCR System 9700 (PE Biosystems), by treatment at 95° C. for 10 minutes, then a cycle set to include 95° C. for 10 seconds followed by 63° C. for 15 seconds and 72° C. for 10 seconds, which was repeated 40 times. Concentration of the synthetic cDNA purified using QIAquick PCR Purification Kit (Qiagen) was calculated by measurement of absorbance at 260 nm. Further, accurate copy number of standard cDNA was calculated, and subsequently, standard cDNA solution was prepared at the concentration of $1 \times 10^8$ copies/µl by dilution with 10 mM Tris-HCl (pH8.0) containing 1 mM EDTA. Probe and primers for TaqMan PCR were designed by using Primer Express (Version 1.0) (PE Biosystems).

The expression level was calculated by using ABI PRISM 7700 SDS Software. Cycle numbers at the moment when fluorescent intensity of reporter comes to preset values indicated as a vertical axis, and logarithm of an initial concentration of the standard cDNA as a horizontal axis. Subsequently, a standard curve was prepared. By calculating an initial concentration of each reverse transcript from a standard curve, an expression level of TGR26 gene per total RNA of each clone was estimated. As a result, it was found that clone numbers 18 and 28 of the TGR26 expressing cell line exhibit high expression level. Hereafter, these two clones of expression cells were utilized in experiments.

Reference Example 69

Assay for a Level of Intracellular cAMP Production Using TGR26 Expressing CHO Cells TGR26 expressing CHO cells prepared in Reference Example 68, were seeded on 24-well plate at $5 \times 10^4$ cells/well and cultivated for 48 hours. The cells were washed with MEMα buffer (pH7.4) containing 0.2 mM 3-isobutyl-methylxanthine, 0.05% BSA (bovine serum albumine) and 20 mM HEPES [hereafter, MEMα buffer (pH7.4) containing 0.2 mM 3-isobutyl-methylxanthine, 0.05% BSA (bovine serum albumine) and 20 mM HEPES may be referred to as reaction buffer]. Then, 0.5 ml of the reaction buffer was added to the cells and the suspension was incubated for 30 minutes in the incubator. After removal of the reaction buffer and newly adding 0.25 ml of the reaction buffer to the cells, an appropriate concentration of sample in DMSO solution and 0.25 ml of the reaction buffer containing 2 µM forskolin were added to the cells and the mixture was reacted at 37° C. for 30 minutes. For termination of the reaction, 100 µl of 20% perchloric acid was added. Subsequently, the mixture was stood on ice for an hour to extract intracellular cAMP. The cAMP level in the extract was measured using the cAMP EIA Kit (Amersham Pharmacia Biotech).

Reference Example 70

Inhibiting Activity for Intracellular cAMP Production of Human Homologue of GPR8 Ligand Peptide Consisting of 23 or 30 Residues, which was Measured Using TGR26 Expressing CHO Cells The human homologue of GPR8 ligand peptide consisting of 23 residues, which was obtained in Reference Example (hereafter, sometimes referred to as hGPR8L(1-23)), or the human homologue of GPR8 ligand peptide consisting of 30 residues, which was obtained in Reference Example (hereafter, sometimes referred to as hGPR8L(1-30)), was administered at various concentrations to membrane fraction of the TGR26 expressing CHO cells by the method described in Reference Example 69, and an inhibiting activity of intracellular cAMP production was measured.

Figure 12:
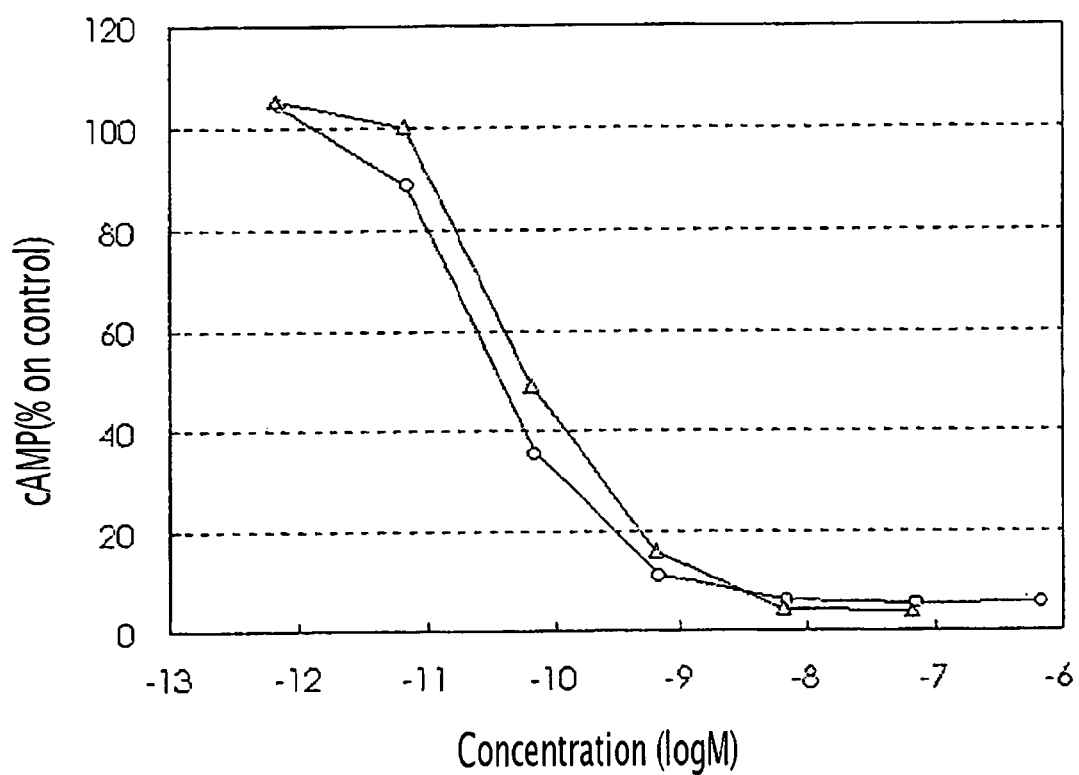
FIG. 12 shows a cAMP production inhibiting activity of hGPR8L(1-23) and hGPR8L(1-30) to CHO/TGR26 cells. In the figure, open circle represents the case where the hGPR8L (1-23) was administered, and open triangle represents the case where the hGPR8L(1-30) was administered.

The result was shown in FIG. 12.

From this result, hGPR8L(1-23) and hGPR8L(1-30) apparently inhibited intracellular cAMP production of TGR26 expressing CHO cells depending on the concentration.

In the figure, when an amount subtracted intracellular cAMP level with the reaction buffer from intracellular cAMP level with the reaction buffer containing forskolin is indicated as 100%, the inhibiting activity of cAMP synthesis is indicated as an amount subtracted intracellular cAMP level with hGPR8L(1-23) or hGPR8L(1-30) from intracellular cAMP level with the reaction buffer by representation of percentage (%).

From this result, it was found that hGPR8L(1-23) or hGPR8L(1-30) is a ligand to TGR26.

When porcine-, rat- and mouse-homologues of hGPR8L (1-23) and porcine-, rat- and mouse-homologues of hGPR8L (1-30) were also used, as described above, it can be confirmed that intracellular cAMP production of the TGR26 expressing CHO cells was inhibited depending on the concentration.

Reference Example 71

Assay for a GTPγS Binding Activity Using a Membrane Fraction of TGR26 Expressing CHO Cells Promoting activity for [$^{35}$S]-guanosine 5'-(γ-thio) triphosphate (GTPγS) binding to a membrane fraction of TGR26 expressing cells was assayed in accordance with the following method.

1) Preparing Method of Membrane Fraction

To 1×10$^8$ of TGR26 expressing CHO cells, 10 ml of homogenating buffer (10 mM NaHCO$_3$, 5 mM EDTA, 0.5 mM PMSF (phenylmethylsulfonyl fluoride), 1 µg/ml Pepstatin, 4 µg/ml E-64, 20 µg/ml Leupeptin) was added, and the cells were disrupted using Polytron (12,000 rpm, 1 minute). Supernatant was obtained from the disrupted cell suspension by centrifugation (1,000 g, 15 minutes). Further, the supernatant was ultracentrifuged (Beckman Type 30 rotor, 30,000 rpm, 1 hour), and precipitate obtained was kept as a membrane fraction of TGR26 expressing CHO cells.

2) Measurement of GTPγS Binding Activity

The membrane fraction of TGR26 expressing CHO cells was diluted with membrane dilution buffer (50 mM Tris HCl buffer (pH7.4), 5 mM MgCl$_2$, 150 mM NaCl, 1 µM GDP, 0.1% BSA) to prepare a cell membrane fraction solution for assay at 30 µg/ml of protein concentration. To 200 µl of membrane fraction solution for assay, 2 µl of 50 nM [$^{35}$S]-guanosine 5'-(γ-thio) triphosphate (NEN) and 2 µl of sample/DMSO solution having an appropriate concentration were added. Then the mixture was incubated at 25° C. for one hour. The mixture was filtrated, and further the filter was washed twice with 1.5 ml of washing buffer (50 mM Tris HCl buffer (pH7.4), 5 mM MgCl$_2$, 1 mM EDTA, 0.1% BSA). Finally, a radioactivity on the filter was determined by liquid scintillation counter.

Reference Example 72

Promoting Activity for GTPγS Binding of Human Homologue of GPR8 Ligand Peptide Consisting of 23 or 30 Residues, which was Measured Using a Membrane Fraction of TGR26 Expressing CHO Cells Various concentration of hGPR8L(1-23) or hGPR8L(1-30) was mixed with a membrane fraction of the TGR26 expressing cell in accordance with the method described in Reference Example 71, and a promoting activity of GTPγS binding was assayed.

Figure 13:
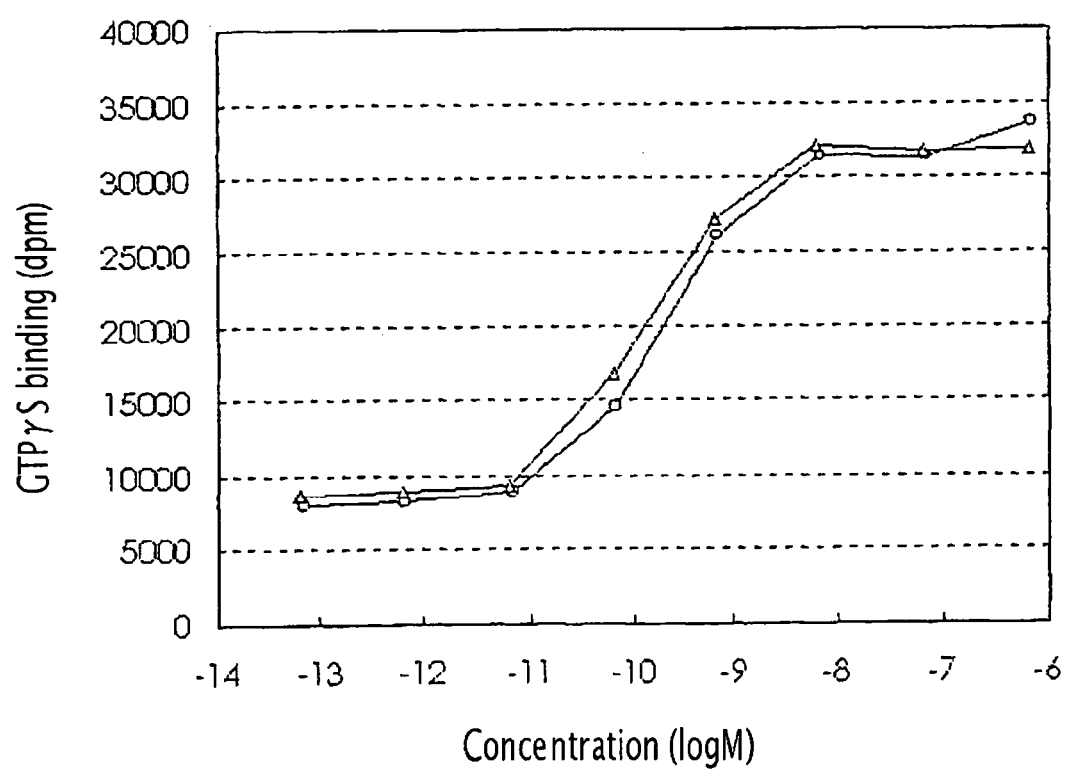
FIG. 13 shows a GTPγS binding stimulating activity of hGPR8L(1-23) and hGPR8L(1-30) to CHO/TGR26 cell membrane fraction. In the figure, open circle represents the case where the hGPR8L(1-23) was administered, and open triangle represents the case where the hGPR8L(1-30) was administered.

The result was shown in FIG. 13.

From this result, hGPR8L(1-23) and hGPR8L(1-30) apparently promoted GTPγS binding of TGR26 expressing CHO cells depending on the concentration.

When porcine-, rat- and mouse-homologues of hGPR8L (1-23) and porcine-, rat- and mouse-homologues of hGPR8L (1-30) were also used, as described above, it can be confirmed that GTPγS binding of the TGR26 expressing CHO cells was promoted depending on the concentration.

Reference Example 73

Experiment for Receptor Binding Using [$^{125}$I-Tyr$^{10}$]-hGPR8L(1-23)

Using [$^{125}$I-Tyr$^{10}$]-hGPR8L(1-23) prepared by the method described in Reference Example 42 and a cell membrane fraction prepared from TGR26 expressing cells as described in Example 6, a receptor binding assay was carried out as follows.

Cell membrane fraction prepared from TGR26 expressing cells was diluted to various concentration with assay buffer (25 mM Tris-HCl, 5 mM EDTA, 0.05% CHAPS (3-[(3-Cholamidopropyl) Dimethyl-Ammonio]-1-Propanesulfonate), 0.1% BSA, 0.5 mM PMSF, 1 µg/ml Pepstatin, 20 µg/ml Leupeptin, 4 µg/ml E-64, pH7.4), and 200 µl each of the diluent was dispensed into polypropylene test tube (Falcon 2053). In order to determine an amount of maximum binding, 2 µl of DMSO and 2 µl of 7 nM [$^{125}$I-Tyr$^{10}$]-hGPR8L(1-23) were added to the membrane fraction solution. Further, in order to determine a non-specific binding, 2 µl of 100 µM hGPR8L(1-23)/DMSO solution and 2 µl of 7 nM [$^{125}$I]-Tyr$^{10}$]-hGPR8L(1-23) were added to the membrane fraction solution. The reaction was done at 25° C. for 75 minutes, and the reaction mixture was filtered by suction filtration using Whatman glassfilter (GF-F) treated with polyethyleneimine. In addition, the filter was washed twice with 1.5 ml of washing buffer (25 mM Tris-HCl, 5 mM EDTA, 0.05% CHAPS, 0.1% BSA, pH7.4). After filtration, a radioactivity remaining on the filter was counted using γ-counter, and an amount of specific binding was estimated by subtracting an amount of non-specific binding from an amount of maximum binding.

When the concentration of membrane fraction was changed, a specific binding of [$^{125}$I-Tyr$^{10}$]-hGPR8L(1-23) was perceived depending on the concentration of membrane fraction. Where the concentration of membrane fraction was set to 3 µg/ml, an inhibition for the specific binding of [$^{125}$I-Tyr$^{10}$]-hGPR8L(1-23) to the membrane fraction of TGR26 expressing cells by hGPR8L(1-23) and hGPR8L(1-30) was investigated. When concentration of 50% inhibition (IC$_{50}$ values) was calculated from the inhibition rate, it was found that the IC$_{50}$ values for hGPR8L(1-23) and hGPR8L (1-30) were 0.12 nM and 0.028 nM, respectively.

From this result, it was shown that both hGPR8L(1-23) and hGPR8L(1-30) have a high affinity for the membrane fraction of TGR26 expressing cells. That is, this means hGPR8L(1-23) and hGPR8L(1-30) is a high affinity ligand for TGR26 receptor.

Figure 14:
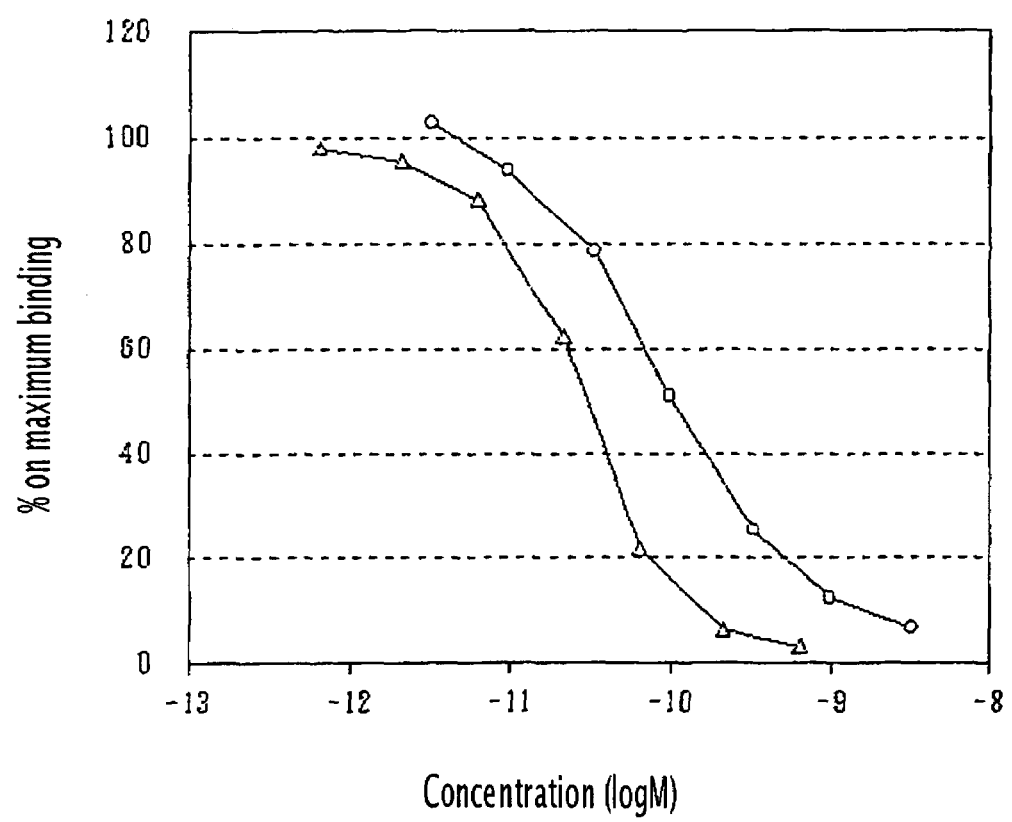
FIG. 14 shows a binding inhibitory activity of various concentrations of hGPR8L(1-23) and hGPR8L(1-30) on the binding of [$^{125}$I] labeled human GPR8 ligand, which consists of 23 residues, to the cell membrane fraction prepared from TGR26 expressing CHO cells. In the figure, open circle represents the case where the hGPR8L(1-23) was administered, and open triangle represents the case where the hGPR8L(1-30) was administered.

An inhibition of binding of hGPR8L(1-23) and hGPR8L (1-30) on the various concentration was shown in FIG. 14.

Using rat and mouse homologues of hGPR8L(1-23) and porcine, rat and mouse homologues of hGPR8L(1-30), as well as the above, an inhibition for the specific binding of [$^{125}$I-Tyr$^{10}$]-hGPR8L(1-23) to the membrane fraction of TGR26 expressing cells can also be confirmed.

Reference Example 74

Receptor Binding Activity of Human- and Porcine-Homologue Derivatives of GPR8 Ligand Peptide, which was Measured Using a Membrane Fraction of TGR26 Expressing CHO Cells and [$^{125}$I-Tyr$^{10}$]-hGPR8L(1-23)

A receptor binding activity of human- and porcine-homologue derivatives of GPR8 ligand peptide obtained in the reference examples was measured using a membrane fraction of TGR26 expressing CHO cells and [$^{125}$I-Tyr$^{10}$]-hGPR8L(1-23) by the method described in Reference Example 73. The derivatives, which has been measured, and receptor binding activity thereof are shown in Table 2. The receptor binding activity is represented by concentration of 50% inhibition for binding (IC$_{50}$ value).

TABLE 2

| Derivatives | Receptor binding activity (IC$_{50}$ nM) |
| --- | --- |
| [MET(O)]-hGPR8L(1-23) | 0.29 |
| Fmoc-hGPR8L(1-23) | 0.23 |
| Ac-hGPR8L(1-23) | 0.27 |
| [D-Trp$^1$]-hGPR8L(1-23) | 1.3 |
| hGPR8L(2-23) | 240 |
| Ac-hGPR8L(2-23) | 570 |
| IndPr-hGPR8L(2-23) | 0.12 |
| hGPR8L(4-23) | 2000 |
| hGPR8L(9-23) | 2500 |
| hGPR8L(1-20) | 0.17 |
| hGPR8L(1-19) | 9.9 |
| hGPR8L(1-18) | 760 |
| pGPR8L(1-23) | 0.12 |
| [MET(O)]-pGPR8L(1-23) | 0.28 |

Reference Example 75

Cloning of 5' Upstream End of the cDNA Encoding Mouse TGR26

By 5' RACE PCR cloning, a base sequence of 5' upstream region of cDNA encoding mouse TGR26 was elucidated.

The 5' RACE PCR cloning was accomplished by PCR reaction using mouse brain cDNA described in Reference Example as a template, Universal Primer Mix attached to SMART™ RACE cDNA Amplification Kit, and synthetic primer represented by SEQ ID NO: 132 followed by PCR reaction using the above PCR reaction mixture as a template, Nested Universal Primer attached to the kit, and synthetic primer represented by SEQ ID NO: 133. The primers represented by SEQ ID NO: 132 and SEQ ID NO: 133 were designed based on the sequence of mouse GPR7 cDNA fragment registered on Genbank (Accession: U23807). The composition of the reaction solution and the conditions for PCR are as follows. The reaction solution comprised of 1 µl of mouse brain cDNA, 2 µl of Universal Primer Mix, 0.2 µM of synthetic DNA primer represented by SEQ ID NO: 132, 0.8 mM dNTPs, 0.4 µl of Advantage-GC 2 Polymerase (CLONTECH) and a buffer attached to the enzyme to make the total volume 20 µl. The PCR reaction was carried out using a thermal cycler (PE Biosystems) by heating of 96° C. for 120 seconds, then a cycle set to include 96° C. for 30 seconds followed by 68° C. for 120 seconds, which was repeated 30 times, and finally, incubation at 72° C. for 10 minutes. Subsequently, the reaction solution comprised of 0.5 µl of the above PCR reaction solution diluted to 50-fold with Tricine-EDTA Buffer attached to the kit, 0.5 µM of Nested Universal Primer, 0.5 µM of synthetic DNA primer represented by SEQ ID NO: 133, 0.8 mM dNTPs, 0.4 µl of Advantage-GC 2 Polymerase (CLONTECH) and a buffer attached to the enzyme to make the total volume 20 µl. The PCR reaction was carried out using a thermal cycler (PE Biosystems) by heating of 96° C. for 120 seconds, then a cycle set to include 96° C. for 30 seconds followed by 68° C. for 30 seconds and 72° C. for 60 seconds, which was repeated 30 times, and finally, incubation at 72° C. for 10 minutes. After isolating the amplified DNA by 1.5% agarose gel electrophoresis, DNA having about 450 bases length was excised with razor, and was recovered using QIAquick Gel Extraction Kit (Qiagen). This DNA was cloned into pCR2.1-TOPO vector according to the protocol attached to the TOPO TA Cloning Kit (Invitrogen). After transformation of Escherichia coli TOP10 competent cell (Invitrogen) by introducing the above-mentioned vector, clones harboring cDNA insert fragment was selected on LB agar medium containing ampicillin and X-gal. All the white-colored clones were isolated with sterilized toothpick, and then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 134, was obtained.

Reference Example 76

Amplification of Human GPR7 DNA Using Human Chromosomal DNA by PCR Method

Using human chromosomal DNA as a template and two synthetic DNA primers (SEQ ID NO: 141 and SEQ ID NO: 142), DNA amplification by PCR method was performed. The synthetic primers were constructed to allow a region of the gene to be translated to the receptor protein to amplify. Therewith, at the 5' end of the gene, the base sequence recognized by restriction enzyme ClaI was added, and at the 3' end, the base sequence recognized by restriction enzyme SpeI was added. The reaction solution in the above reaction comprised of 0.5 µg of human chromosomal DNA (Takara), 1 µM each of synthetic DNA primers, 0.8 mM dNTPs, 1 mM MgCl$_2$, 1 µl of KOD Polymerase (TOYOBO) and a buffer attached to the enzyme to make the total volume 50 µl. The PCR reaction was carried out using a thermal cycler (Takara) by heating of 94° C. for 60 seconds, then a cycle set to include 98° C. for 15 seconds followed by 65° C. for 2 seconds and 74° C. for 30 seconds, which was repeated 35 times. The amplified product was confirmed by 0.8% agarose gel electrophoresis follwed by ethidium bromide staining.

Reference Example 77

Subcloning of the PCR Product into Plasmid Vector and Confirmation of a Sequence of the Amplified DNA by Decoding of the Base Sequence of Inserted DNA Region Using the PCR reaction solution described in Reference Example 76, DNA was isolated by 0.8% low melting agarose gel electrophoresis. The DNA band was excised from the gel with razor, and was recovered by crashing the pieces of agarose, phenol extraction, phenol-chroloform extraction and ethanol precipitation. In the manner prescribed in PCR-SCRIPT™ Amp SK(+) Cloning Kit (Stratagene), the recovered DNA was subcloned to plasmid vector pCR-Script Amp SK(+). After transformation of *Escherichia coli* DH5α competent cell (TOYOBO) by introducing the above-mentioned vector, clones harboring cDNA insert fragment was selected on LB agar medium containing ampicillin, IPTG and X-gal. All the white-colored clones were isolated with sterilized toothpick, and then the transformant *E. coli* DH5α/GPR7 was obtained. Respective clones were cultured in LB medium containing ampicillin for overnight. Subsequently, the plasmid DNA was prepared using QIAwell 8 Plasmid Kit (Qiagen). A portion of the prepared DNA was cleaved with the restriction enzymes ClaI and SpeI, and a size of the receptor cDNA fragment inserted was confirmed. The reaction for determination of the base sequence was carried out using DyeDeoxy Terminator Cycle Sequence Kit (PE Biosystems PE Biosystems). As a result, after decoding with the fluorescent automated sequencer, the DNA sequence was obtained (SEQ ID NO: 143). The pCR-Script Amp SK(+) plasmid harboring a DNA having the base sequence represented by SEQ ID NO: 143 was designated pCR-Script human GPR7. An amino acid sequence of human GPR7 encoded by DNA having the base sequence represented by SEQ ID NO: 143 was shown by SEQ ID NO: 144. Two bases in the DNA sequence of human GPR7 determined hereinabove was different from the DNA sequence described in O'Dowd's report (O'Dowd, B. F., et al., Genomics 28, 84-91, 1995). These two bases correspond to the 893rd and the 894th base in the sequence of SEQ ID NO: 143. These are C and G in O'Dowd's report, respectively, whereas G and C in the reference example, respectively. Therefore, for the amino acid sequence to be translated, the 296th amino acid of SEQ ID NO: 144 changes Thr in O'Dowd's report to Ser in the example.

Reference Example 78

Preparation of Human GPR7-expressing CHO Cells

Using Plasmid Midi Kit (Qiagen), plasmid DNA was prepared from clones of *E. coli* transformed by the plasmid encoding the human GPR7 full-length amino acid sequence, which sequence was confirmed in Reference Example 77, with the ClaI recognition sequence added at the 5' side and with the SpeI recognition sequence added at the 3' side. The plasmid DNA was digested with restriction enzymes ClaI and SpeI to excise the insert part out. After electrophoresis, the insert DNA was excised from the agarose gel with a razor and then homogenized. The homogenate was extracted with phenol and then with phenol/chloroform, followed by precipitation in ethanol. Thus, the insert DNA was recovered. The insert DNA was added to ClaI- and SpeI-cleaved expression vector plasmid pAKK0-111H for animal cell (the same as the vector plasmid pAKK01.11G described in Hinuma, S. et al., Biochim. Biophys. Acta, Vol. 1219, pp. 251-259 (1994)) followed by ligation using T4 ligase (Takara). Thus, plasmid pAKKO-Human GPR7 for protein expression was constructed. *Escherichia coli* transformed with the plasmid pAKKO-Human GPR7 was designated DH5α/pAKKO-Human GPR7.

After *E. coli* DH5α (TOYOBO) transformed by pAKKO-Human GPR7 was cultured, pAKKO-Human GPR7 plasmid DNA was prepared using Plasmid Midi Kit (Qiagen). Using CellPhect Transfection Kit (Amersham Pharmacia Biotech Co.), the plasmid DNA was introduced into CHO dhfr⁻ cells in accordance with the protocol attached to the kit. The DNA, 3 μg, was co-precipitated with calcium phosphate in suspension. The resulting suspension was added to a 6 cm Petri dish in which $5\times10^5$ or $1\times10^6$ CHO dhfr⁻ cells had been seeded before 24 hours. The cells were cultured in MEMα containing 10% fetal calf serum for one day. After passage, the cells were cultured in nucleic acid-free selection medium MEMα containing 10% dialyzed fetal calf serum and 24 clones of the transformant GPR8 expressing CHO cells, growing in the selection medium, were selected.

Reference Example 79

Quantification of an Expression Level of Human GPR7 Gene in Human GPR7 Expressing CHO Cell Line Using TaqMan PCR Method The 24 clones of human GPR7 expressing cell line obtained in Reference Example 78 were cultured in 25 cm² flask, respectively. From the cultured cells, using ISOGEN (Nippon Gene), total RNA fraction was prepared. The total RNA fraction was treated with Dnase I using Message Clean (Gen Hunter). Then total RNA containing no DNA was obtained.

The cDNA synthesis using a total RNA as a template was performed using TaqMan Reverse Transcription Reagents Kit (Applied Biosystems). The reaction mixture comprised of 4 μg of total RNA treated with DnaseI, one microliter of random primer, 4.4 μl of 25 mM $MgCl_2$ solution, 2 μl of 10 mM dNTP mix, 0.4 μl of Rnase Inhibitor, 0.5 μl of reverse transcriptase and the reaction buffer attached with the kit to make the volume 20 μl. The reverse transcription reaction was carried out with a thermal cycler in the conditions of 25° C. for 10 minutes, followed by 48° C. for 30 minutes and 95° C. for 5 minutes.

The standard human GPR7 DNA was prepared by purification of the PCR amplified DNA using the full length human GPR7 DNA as a template. The reaction mixture comprised of 5 pg of pCR-Script human GPR7, 0.5 μM each of synthetic primers represented by SEQ ID NO: 145 and SEQ ID NO: 146, 1.6 mM dNTPs, 2.5 mM $MgCl_2$, 0.5 μl of LATaq polymerase (Takara) and the buffer attached with the enzyme to make the volume 50 μl. The reaction for amplification was carried out with a thermal cycler (Applied Biosystems), by treatment at 94° C. for 120 seconds, then a cycle set to include 94° C. for 30 seconds followed by 60° C. for 30 seconds and 72° C. for 60 seconds, which was repeated 25 times, and finally incubation at 72° C. for 10 minutes. The PCR reaction mixture was subjected to 0.8% agarose gel electrophoresis to isolate the products. The band was excised with razor, and the PCR-amplified DNA was recovered using QIAquick PCR Purification Kit (Qiagen). In order to remove the primer DNA and dNTPs, which are contaminated in the DNA solution, the DNA solution was subjected to Chromospin column 400 (Clontech) gel chromatography to give an eluate for the amplified human GPR7 DNA. From amounts of the DNA calculated by absorbance at 260 nm of the amplified human GPR7 DNA solution and the base compositions of the amplified human GPR7 DNA, copy number of the DNA, which is contained in the amplified human GPR7 DNA solution, was calculated. Using the amplified human GPR7 DNA with obvious copy number as a standard human GPR7 DNA, TaqMan PCR for quantification was carried out.

A copy number of the human GPR7 gene, which has expressed in the human GPR7 expressing CHO cell line, was determined by TaqMan PCR method. The reaction mixture for TaqMan PCR comprised of one (1) μl of reverse transcribed cDNA diluted to 1/100 with distilled water or one (1) μl of various copy number of the standard human GPR7 DNA solution, 0.2 μM each of synthetic DNA primers (SEQ ID NO: 147 and SEQ ID NO: 148), 0.2 μM human TaqMan probe [the probe having the base sequence represented by SEQ ID NO: 77 (Fam-TTCATCCTCAACCTGGCCAT CGC-Tamra; in the sequence, Fam and Tamra represent 6-carboxy-fluorescein and 6-carboxy-tetramethyl-rhodamine, respectively)] and TaqMan Universal PCR Master Mix (Applied Biosystems) to make the volume 25 μl. The PCR reaction was performed with ABI PRISM 7700 Sequence Detector System (Applied Biosystems) by treatment at 50° C. for 2 minutes and 95° C. for 10 minutes, then a cycle set to include 95° C. for 15 seconds followed by 60° C. for 60 seconds, which was repeated 40 times. The expression level of human GPR7 gene was calculated by using ABI PRISM 7700 SDS Software. Cycle numbers at the moment when fluorescent intensity of reporter comes to preset values indicated as a vertical axis, and logarithm of an initial concentration of the standard human GPR7 DNA as a horizontal axis. Subsequently, a standard curve was prepared. By calculating a copy number of human GPR7 cDNA, which is contained in each reverse transcript, from a standard curve, an expression level of human GPR7 gene per one nanogram of total RNA was estimated. The clone numbers 7, 8 and 14, which exhibit high expression level, were selected as human GPR7 gene-highly expressing cell lines.

Reference Example 80

Assay for a Level of Intracellular cAMP Production Using Human GPR7 Expressing CHO Cells The human GPR7 expressing CHO cells, which are prepared in Reference Example 78 and selected as described in Reference Example 79, were seeded on 24-well plate at $5 \times 10^4$ cells/well and cultivated for 48 hours. The cells were washed with MEMα buffer (pH7.4) containing 0.2 mM 3-isobutyl-methylxanthine, 0.05% BSA (bovine serum albumine) and 20 mM HEPES [hereafter, MEMα buffer (pH7.4) containing 0.2 mM 3-isobutyl-methylxanthine, 0.05% BSA (bovine serum albumine) and 20 mM HEPES may be referred to as reaction buffer]. Then, 0.5 ml of the reaction buffer was added to the cells and the suspension was incubated for 30 minutes in the incubator. After removal of the reaction buffer and newly adding 0.25 ml of the reaction buffer to the cells, an appropriate concentration of sample in DMSO solution and 0.25 ml of the reaction buffer containing 2 μM forskolin were added to the cells and the mixture was reacted at 37° C. for 30 minutes. For termination of the reaction, 100 μl of 20% perchloric acid was added. Subsequently, the mixture was stood on ice for an hour to extract intracellular cAMP. The cAMP level in the extract was measured using the cAMP EIA Kit (Amersham Pharmacia Biotech).

Reference Example 81

Figure 15:
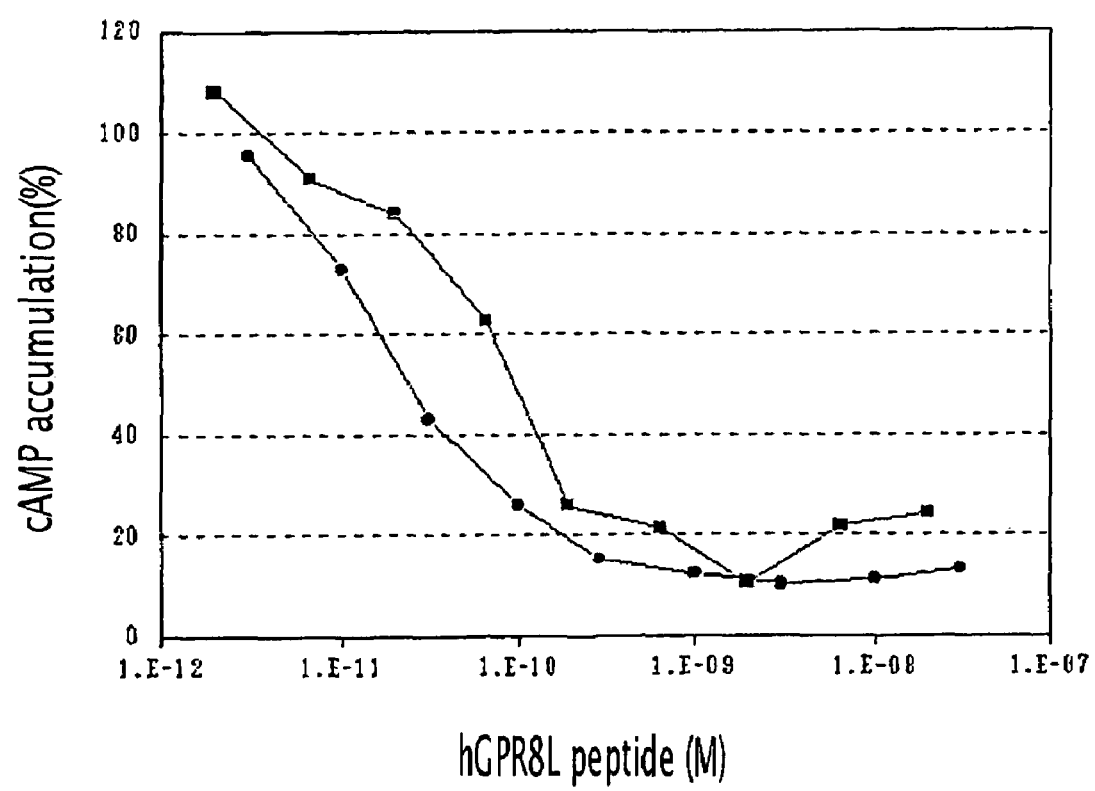
FIG. 15 shows a cAMP production inhibiting activity of various concentrations of human homologue of GPR8 ligand peptide, which consists of 23 residues or 30 residues, on CHO/GPR7 cells. In the figure, closed circle represents the case where the hGPR8L(1-23) was administered, and closed square represents the case where the hGPR8L(1-30) was administered.

Inhibiting Activity for Intracellular cAMP Production of Human Homologue of GPR8 Ligand Peptide Consisting of 23 or 30 Residues, which was Measured Using Human GPR7 Expressing CHO Cells The hGPR8L(1-23) or the hGPR8L(1-30) was administered at various concentrations to the human GPR7 expressing CHO cells by the method described in Reference Example 80, and an inhibiting activity of intracellular cAMP production was measured. The result was shown in FIG. 15. In the figure, when an amount subtracted intracellular cAMP level with the reaction buffer from intracellular cAMP level with the reaction buffer containing forskolin is indicated as 100%, the inhibiting activity of cAMP synthesis is indicated as an amount subtracted intracellular cAMP level with hGPR8L(1-23) or hGPR8L(1-30) from intracellular cAMP level with the reaction buffer by representation of percentage (%).

The hGPR8L(1-23) and the hGPR8L(1-30) apparently inhibited intracellular cAMP production of human GPR7 expressing CHO cells depending on the concentration. From this result, it was found that hGPR8L(1-23) or hGPR8L(1-30) is a ligand to human GPR7. When concentration of 50% inhibition ($IC_{50}$ values) was calculated from the level of cAMP production, it was found that the $IC_{50}$ values for hGPR8L(1-23) and hGPR8L(1-30) were 0.025 nM and 0.13 nM, respectively.

When porcine-, rat- and mouse-homologues of hGPR8L (1-23) and porcine-, rat- and mouse-homologues of hGPR8L (1-30) were also used, as described above, it can be confirmed that intracellular cAMP production of the TGR26 expressing CHO cells was inhibited depending on the concentration.

Reference Example 82

Experiment for Receptor Binding by Using [$^{125}$I-Tyr$^{10}$]-hGPR8L(1-23)

Using [$^{125}$I-Tyr$^{10}$]-hGPR8L(1-23) prepared by the method described in Reference Example 42 and the membrane fraction prepared from human GPR7 expressing CHO cells, the receptor binding assay was performed.

Firstly, the preparing method of the membrane fraction was described as follows.

To $1 \times 10^8$ of human GPR7 expressing CHO cells was added 10 ml of a homogenate buffer (10 mM NaHCO$_3$, 5 mM EDTA, 0.5 mM PMSF (phenylmethylsulfonyl fluoride), 1 μg/ml pepstatin, 4 μg/ml E64, 20 μg/ml leupeptin), followed by cell disruption with a polytron (12,000 rpm, 1 minute). The disrupted cells were then centrifuged (1,000 g, 15 minutes) to give the supernatant. Next, the supernatant was subjected to ultracentrifugation (Beckman type 30 rotor, 30,000 rpm, one (1) hour). The resulting precipitate was used as a membrane fraction of human GPR7 expressing CHO cell.

Cell membrane fraction thus obtained was diluted to various concentrations with assay buffer (25 mM Tris-HCl, 5 mM EDTA, 0.05% CHAPS (3-[(3-Cholamidopropyl) Dimethyl-Ammonio]-1-Propanesulfonate), 0.1% BSA, 0.5 mM PMSF, 1 μg/ml Pepstatin, 20 μg/ml Leupeptin, 4 μg/ml E-64, pH7.4), and 200 μl each of the diluent was dispensed into polypropylene test tube (Falcon 2053). In order to determine an amount of maximum binding, 2 μl of DMSO and 2 μl of 8 nM [$^{125}$I-Tyr$^{10}$]-hGPR8L(1-23) were added to the membrane fraction solution. Further, in order to determine a non-specific binding, 2 μl of 1 mM hGPR8L(1-23)/DMSO solution and 2 μl of 8 nM [$^{125}$I-Tyr$^{10}$]-hGPR8L(1-23) were added to the membrane fraction solution. The reaction was done at 25° C. for 75 minutes, and the reaction mixture was filtered by suction filtration using Whatman glassfilter (GF-F) treated with polyethyleneimine. Subsequently, the filter was washed twice with 1.5 ml of the washing buffer (25 mM Tris-HCl, 5 mM EDTA, 0.05% CHAPS, 0.1% BSA, ph7.4). After filtration, a radioactivity remaining on the filter was counted using γ-counter, and an amount of specific binding was estimated by subtracting an amount of non-specific binding from an amount of maximum binding.

When the concentration of membrane fraction was changed, a specific binding of [$^{125}$I-Tyr$^{10}$]-hGPR8L(1-23) was perceived depending on the concentration of membrane fraction. Where the concentration of membrane fraction was set to 10 μg/ml for the membrane fraction, the binding inhibition by hGPR8L(1-23) and hGPR8L(1-30) for the specific binding of [$^{125}$I-Tyr$^{10}$]-hGPR8L(1-23) to the membrane fraction of human GPR7 expressing cells was investigated. When the concentration of 50% inhibition (IC$_{50}$ values) was calculated from the inhibition rate, the IC$_{50}$ values for hGPR8L(1-23) and hGPR8L(1-30) were 0.099 nM and 0.025 nM, respectively.

Figure 16:
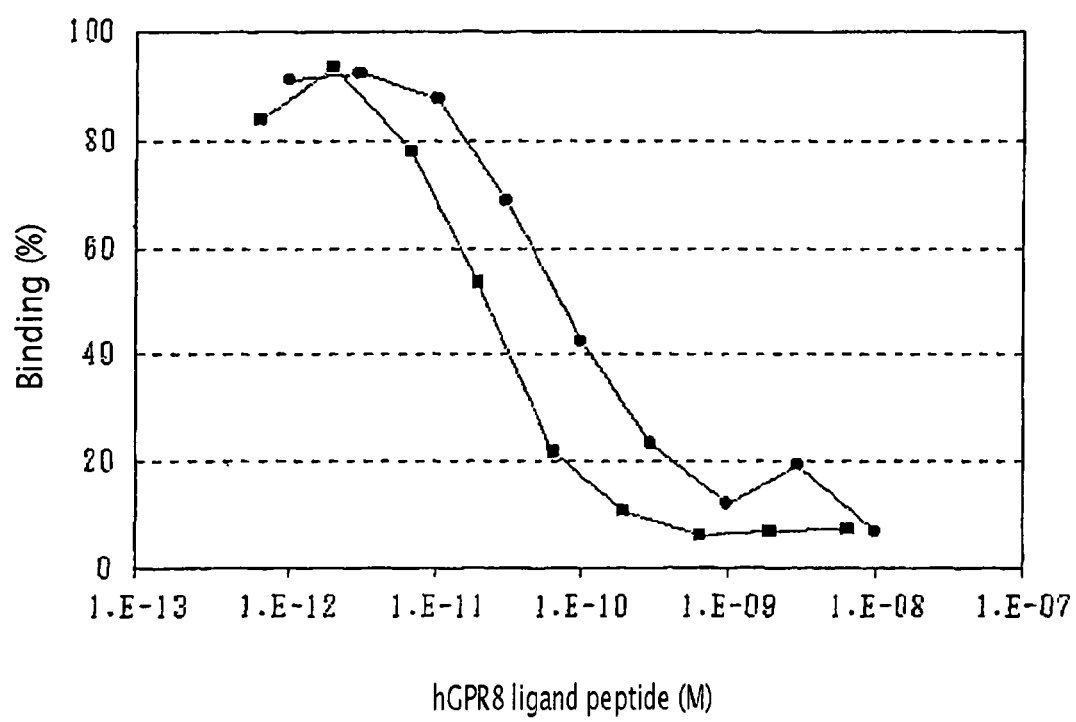
FIG. 16 shows a binding inhibitory activity of various concentrations of hGPR8L(1-23) and hGPR8L(1-30) on the binding of [$^{125}$I] labeled human GPR8 ligand, which consists of 23 residues, to the cell membrane fraction prepared from human GPR7 expressing CHO cells. In the figure, closed circle represents the case where the hGPR8L(1-23) was administered, and closed square represents the case where the hGPR8L(1-30) was administered.

From this result, it was indicated that hGPR8L(1-23) and hGPR8L(1-30) have a high affinity to the membrane fraction of human GPR7 expressing cells. This means that hGPR8L(1-23) and hGPR8L(1-30) is a high affinity ligand to human GPR7 receptor. FIG. 16 shows the inhibition of binding for human GPR8 ligand (1-23) and human GPR8 ligand (1-30) at various concentrations. As described above, when rat- and mouse homologue of hGPR8L(1-23) and porcine-, rat- and mouse-homologue of hGPR8L(1-30) were used, the binding inhibition for the specific binding of [$^{125}$I-Tyr$^{10}$]-hGPR8L(1-23) to the membrane fraction of human GPR7 expressing cells can be confirmed.

Reference Example 83

1) Assay for GTPγS Binding Activity Using the Membrane Fraction of GPR7 Expressing CHO Cells Promoting activity for [$^{35}$S]-guanosine 5'-(γ-thio) triphosphate (GTPγS) binding to the membrane fraction of GPR7 expressing CHO cells was assayed as follows.

The membrane fraction of the GPR7 expressing CHO cell, which was prepared by the method described in Reference Example 82, was diluted with a buffer for membrane dilution (50 mM Tris-hydrochloride buffer (pH 7.4), 5 mM MgCl$_2$, 150 mM NaCl, 1 μM GDP) to make a cell membrane fraction solution for assay having a protein concentration of 30 mg/ml. To 200 μl of the cell membrane fraction solution for assay were added 2 μl of 50 nM [$^{35}$S]-guanosine 5'-(γ-thio) triphosphate (NEN) and 2 μl of sample, which was prepared at an appropriate concentration with DMSO solution. The resulting solution mixture was kept at 25° C. for an hour. The mixture was filtrated through a filter. After washing twice with 1.5 ml of a washing buffer (50 mM Tris-hydrochloride buffer (pH 7.4), 5 mM MgCl$_2$, 1 mM EDTA, 0.1% BSA), radioactivity of the filter was measured using a liquid scintillation counter.

2) Promoting Activity to GTPγS Binding of hGPR8L(1-23) and hGPR8L(1-30), which was Measured Using a Membrane Fraction of GPR7 Expressing CHO Cells By administering hGPR8L(1-23) and hGPR8L(1-30) at various concentrations to the membrane fraction of GPR7 expressing CHO cells in accordance with the method described in I) above, a promoting activity to GTPγS binding was measured.

Figure 17:
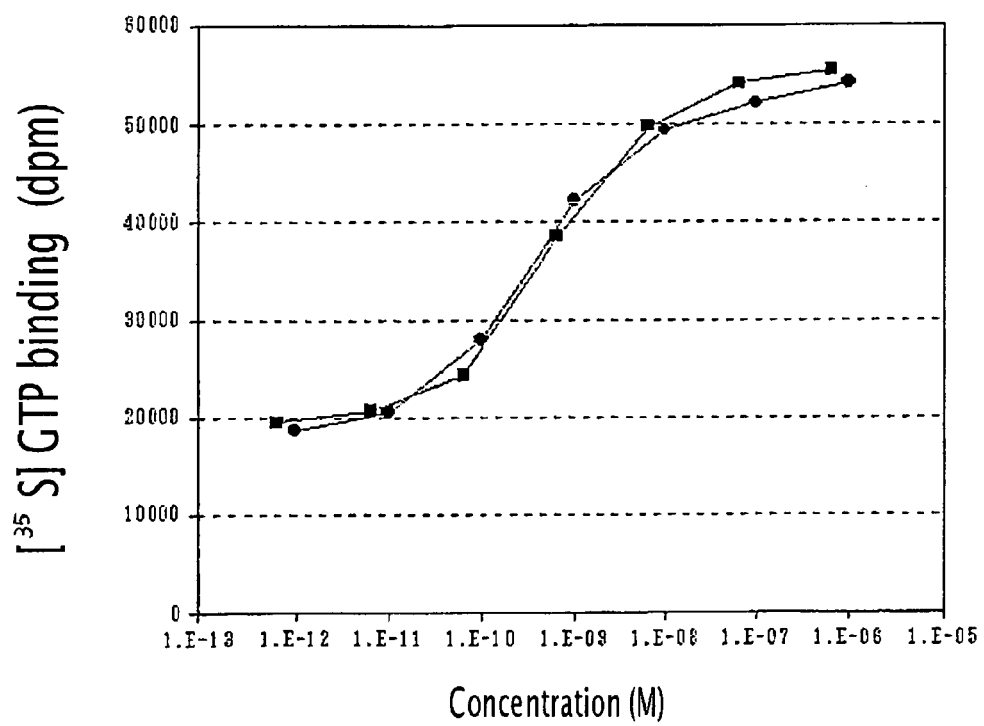
FIG. 17 shows a GTPγS binding inhibitory activity of hGPR8L(1-23) and hGPR8L(1-30) to CHO/GPR7 cell membrane fraction. In the figure, closed circle represents the case where the hGPR8L(1-23) was administered, and closed square represents the case where the hGPR8L(1-30) was administered.

The result was shown in FIG. 17.

The hGPR8L(1-23) and the hGPR8L(1-30) apparently promote GTPγS binding of the membrane fraction of GPR7 expressing CHO cells depending on the concentrations.

When 50% effective concentration (EC$_{50}$) was calculated from the promoting activity to GTPγS binding, EC$_{50}$ for hGPR8L(1-23) is 0.74 nM, whereas EC$_{50}$ for hGPR8L(1-30) is 0.67 nM (Table 3).

When rat- and mouse homologue of hGPR8L(1-23) and porcine-, rat- and mouse-homologue of hGPR8L(1-30) were used, as described above, the reaction for human GPR7 expressing CHO cells can be perceived.

Reference Example 84

Promoting Activity to GTPγS Binding of Human- and Porcine-Homologue Derivatives of GPR8 Ligand Peptide, which was Measured Using a Membrane Fraction of GPR7 Expressing CHO Cells A promoting activity to GTPγS binding was measured by administering at various concentrations the human- and porcine-homologue derivatives of GPR8 ligand peptide obtained in Reference Example to the membrane fraction of GPR7 expressing CHO cells. The derivatives measured and promoting activity to GTPγS binding thereof are shown in Table 3. The activity is represented by concentration of 50% effective concentrations (EC$_{50}$ value).

TABLE 3

The promoting activity to GTPγS binding and the receptor binding activity of human- and porcine-homologue derivatives of GPR8 ligand peptide

| Derivatives | Promoting activity to GTPγS binding (EC$_{50}$ nM) | Receptor binding activity (IC$_{50}$ nM) |
|---|---|---|
| hGPR8L(1-23) | 0.74 | 0.072 |
| hGPR8L(1-30) | 0.67 | 0.025 |
| [MET(O)]-hGPR8L(1-23) | 1.6 | 0.17 |
| Fmoc-hGPR8L(1-23) | 6.6 | 0.14 |
| Ac-hGPR8L(1-23) | 1.5 | 0.077 |
| [D-Trp$^1$]-hGPR8L(1-23) | 2.3 | 0.63 |
| hGPR8L(2-23) | 7410 | 140 |
| Ac-hGPR8L(2-23) | 7000 | 570 |
| IndPr-hGPR8L(2-23) | 0.85 | 0.044 |
| hGPR8L(4-23) | >10000 | 1200 |
| hGPR8L(9-23) | >10000 | 2200 |
| hGPR8L(1-20) | 0.88 | 0.094 |
| hGPR8L(1-19) | 84 | 1.7 |
| hGPR8L(1-18) | 6200 | 2400 |
| pGPR8L(1-23) | 0.35 | 0.066 |
| [MET(O)]-pGPR8L(1-23) | 1.2 | 0.22 |

Reference Example 85

Receptor Binding Activity of Human- and Porcine-Homologue Derivatives of GPR8 Ligand Peptide, which was Measured Using a Membrane Fraction of GPR7 Expressing CHO Cells and [$^{125}$I-Tyr$^{10}$]-hGPR8L(1-23)

A receptor binding activity of human- and porcine-homologue derivatives of GPR8 ligand peptide, which are obtained in Reference Examples, was measured using a membrane fraction of GPR7 expressing CHO cells and [$^{125}$I-Tyr$^{10}$]-hGPR8L(1-23) by the method described in Reference Example 82.

The derivatives measured, and receptor binding activity thereof, are shown in Table 3. The receptor binding activity is represented by concentration of 50% inhibition for binding ($IC_{50}$ value).

Example 1

Actions for Food Consumption and Body Weight Gain in Rat by Continuous Administration of hGPR8L(1-23) Under the Skin (1) Actions for Food Consumption and Body Weight Gain Wistar male rats (eight weeks age, Charles River Japan, Inc.) were naturalized with MF powdered food (Oriental Yeast, Co., Ltd.) for about one week. An osmotic pump (alzet, MINI-OSMOTIC PUMP Model 2001, release rate: 24 µl/day), wherein 200 µl of hGPR8L(1-23) [human GPR8 ligand (1-23)] dissolved in saline at the concentration of 1 mM, or 200 µl of saline was filled, was loaded under the skin (at the center of back) of the above rats anesthetized by pentobarbital (each n=6). The next day on loading was set to zero. Under free feeding of MF powdered food, until the eighth day, food consumption and body weight were measured at 8:00 and 20:00. The light period was set from 8:00 to 20:00, and the dark period was set from 20:00 to next 8:00. After measurement at 8:00 on the eighth day, the rats were slaughtered by decapitation. The weight of liver, kidney, heart, spleen, testis, fat around kidney, fat around genitals and brown fat was measured. All animals were bred for the light period of 12 hours (the light period was set from 8:00 to 20:00).

Figure 18:
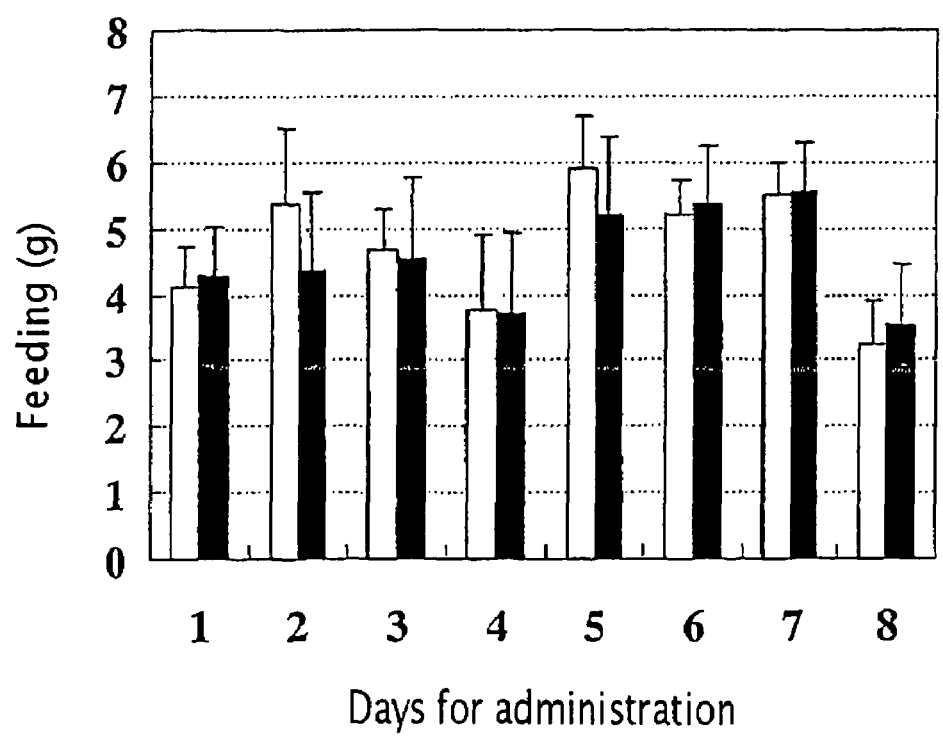
FIG. 18 shows an action of the hGPR8L(1-23), which was continuously administered under the skin, on a food intake during light period for rat. In the figure, open square and closed square represent the vehicle group and the hGPR8L (1-23) group, respectively.
Figure 19:
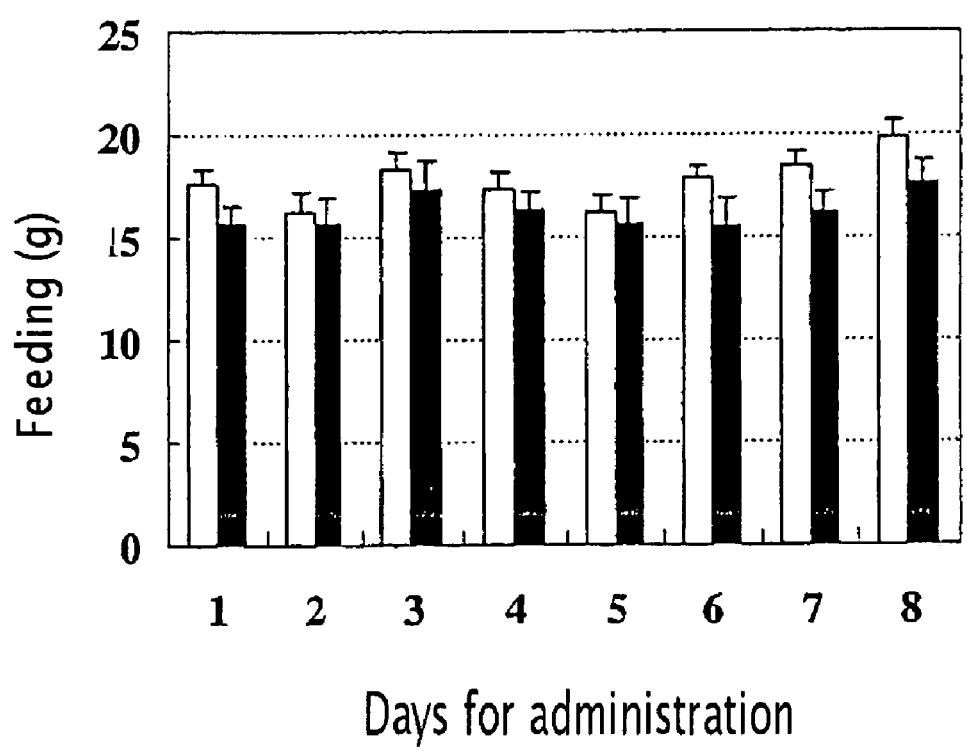
FIG. 19 shows an action of the hGPR8L(1-23), which was continuously administered under the skin, on a food intake during dark period for rat. In the figure, open square and closed square represent the vehicle group and the hGPR8L (1-23) group, respectively.
Figure 20:
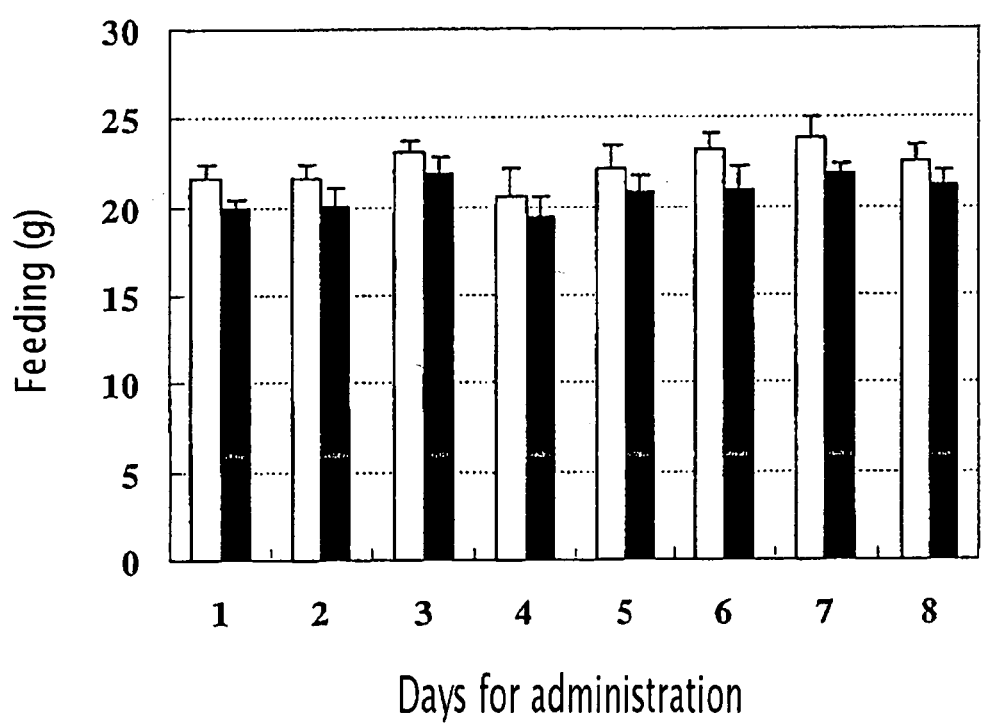
FIG. 20 shows an action of the hGPR8L(1-23), which was continuously administered under the skin, on a food intake during a day for rat. In the figure, open square and closed square represent the vehicle group and the hGPR8L(1-23) group, respectively.
Figure 21:
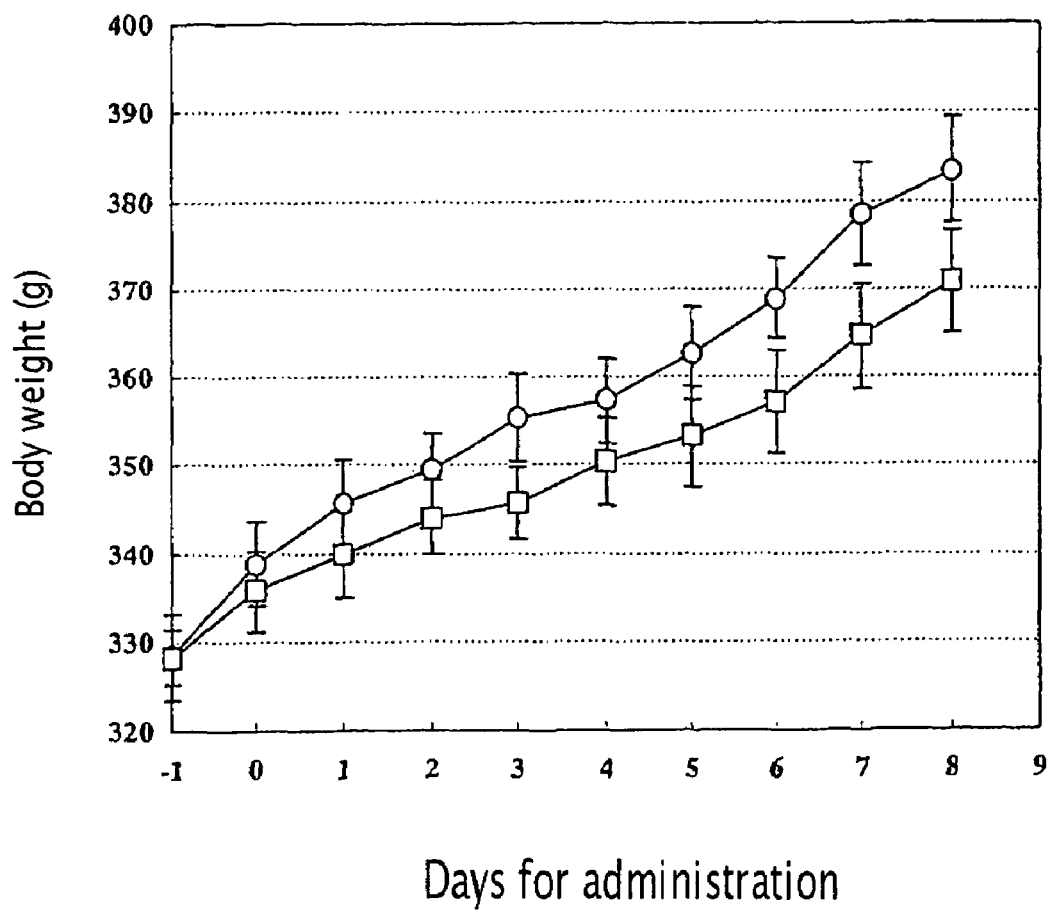
FIG. 21 shows an action of the hGPR8L(1-23), which was continuously administered under the skin, on a body weight gain for rat. In the figure, open circle and open square represent the vehicle group and the hGPR8L(1-23) group, respectively.
Figure 22:
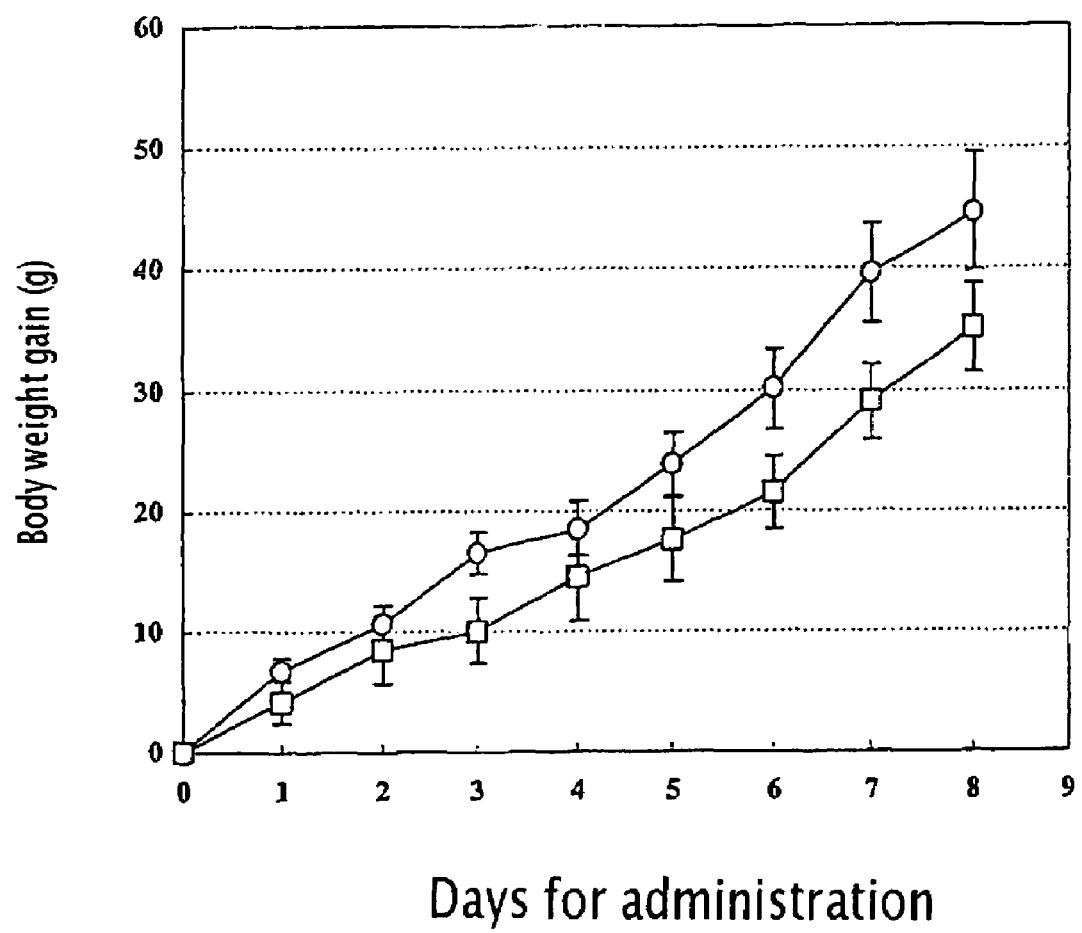
FIG. 22 shows an action of the hGPR8L(1-23), which was continuously administered under the skin, on a body weight gain for rat. In the figure, open circle and open square represent the vehicle group and the hGPR8L(1-23) group, respectively.

For food consumption, in the light period, no difference between both groups was observed, whereas in the dark period, a tendency to decrease in the group of hGPR8L(1-23) was observed in any measuring point compared to the vehicle group (FIGS. 18 and 19). In the total food consumption of a day, a decrease was found (FIG. 20). For the body weight (means±standard error), the difference between both groups was steadily increased on and after the second day. On the seventh day, the vehicle group exhibits 378.4±5.8 g, whereas the group of hGPR8L(1-23) exhibits 364.6±6.0 g (FIG. 21). The body weght gain from zero day to the seventh day is 39.6±4.1 g for the vehicle group and 28.9±3.2 g for the group of hGPR8L(1-23). That is, by continuous administration of the hGPR8L(1-23) under skin for one week, the body weight gain of about 10.7 g was suppressed (FIG. 22).

When the weight of organs on the eighth day was compared, in the group of hGPR8L(1-23), at least 0.5 g of decrease was found in liver (1.6 g of decrease), fat around kidney, which is white fat tissue (1.2 g of decrease) and fat around genitals (0.7 g of decrease) (Table 4).

TABLE 4

The weight of organs on the eighth day

| | Vehicle group (g) | GPR8 ligand (1-23) (g) |
|---|---|---|
| Liver | 15.8 ± 0.2 | 14.2 ± 0.7 |
| Kidney | 2.8 ± 0.09 | 2.6 ± 0.09 |
| Heart | 1.2 ± 0.03 | 1.1 ± 0.04 |
| Spleen | 1.0 ± 0.02 | 1.0 ± 0.06 |
| Testis | 3.7 ± 0.14 | 3.4 ± 0.12 |
| Fat around kidney | 5.0 ± 0.29 | 3.8 ± 0.53 |
| Fat around genitals | 6.2 ± 0.26 | 5.5 ± 0.38 |
| Brown fat | 0.32 ± 0.03 | 0.45 ± 0.05 |

(means ± standard error, n = 6)

From the results, it was perceived that food consumption is decreased by intraperisteneal administration of hGPR8L (1-23) and the hGPR8L(1-23) has an effect on the body weight gain inhibition accompanied with adipose weight loss.

(2) Actions for Glucose in Blood, Total Cholesterol and Triglyceride

Glucose in blood, total cholesterol and triglyceride on the eighth day after administration of hGPR8L(1-23) and vehicle described in (1) was measured using Fuji DRI CHEM. For glucose in blood (the vehicle group: 150±4.9 mg/dl; the hGPR(L(1-23) group: 155±4.5 mg/dl) and total cholesterol in blood (the vehicle group: 73.6±2.4 mg/dl; the hGPR(L(1-23) group: 69.1±1.8 mg/dl), no difference was perceived in both groups. On the other hand, for triglyceride in blood (the vehicle group: 168±8.9 mg/dl; the hGPR(L(1-23) group: 134±28 mg/dl), in the group of hGPR8L(1-23), a lower value, in which the difference was at least 30 mg/dl, was demonstrated (FIG. 23).

From the result, it was perceived that triglyceride in blood is lowered by subcutaneous administration of the hGPR8L (1-23).

Example 2

Actions for Food Consumption and Body Weight Gain in Rat by Intraperitoneal Administration of hGPR8L(1-23)

As Example 1, Wistar male rats (eight weeks age, Charles River Japan, Inc.) were naturalized with MF powdered food (Oriental Yeast, Co., Ltd.) for about one week. The hGPR8L (1-23) [human GPR8 ligand (1-23)] dissolved in saline at the concentration of 0.2 mg/ml and 2 mg/ml, or saline as a vehicle group was intraperistoneally administered at the ratio of 1 ml/kg just before dark period (between 19:45 and 20:00). This administration was carried out for three days (each n=10). At eight o'clock on the day after administration, food consumption and body weight were measured. All animals were bred for the light period of 12 hours, wherein the light period was set from 8:00 to 20:00, and the dark period was set from 20:00 to next 8:00.

Figure 24:
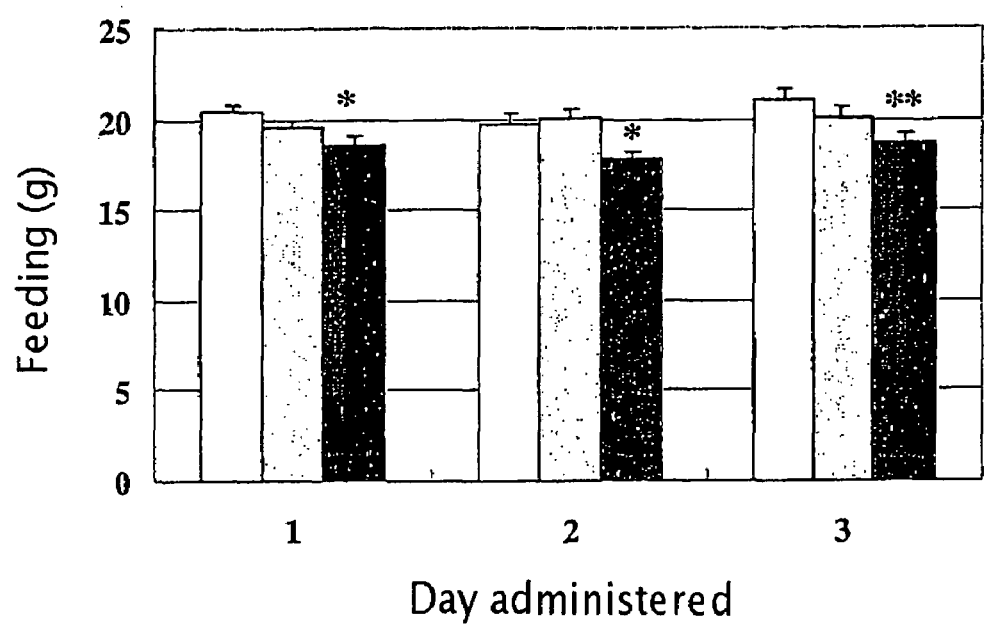
FIG. 24 shows an action of the hGPR8L(1-23), which was administered to interperitoneal, on a food intake for rat. In the figure, white, gray and black represent the vehicle group, the 0.2 mg-administration group and the 2 mg-administration group, respectively. * means to be significant with 5% of risk rate, and ** means to be significant with 1% of risk rate.

For food consumption, a tendency to decrease was demonstrated depending on dose in the group of hGPR8L(1-23); eapecially in the group of 2 mg/kg administration, significant decrease ($p<=0.05$ or $p<=0.01$) was demonstrated for all three days after administration compared to the vehicle group (FIG. 24).

Figure 25:
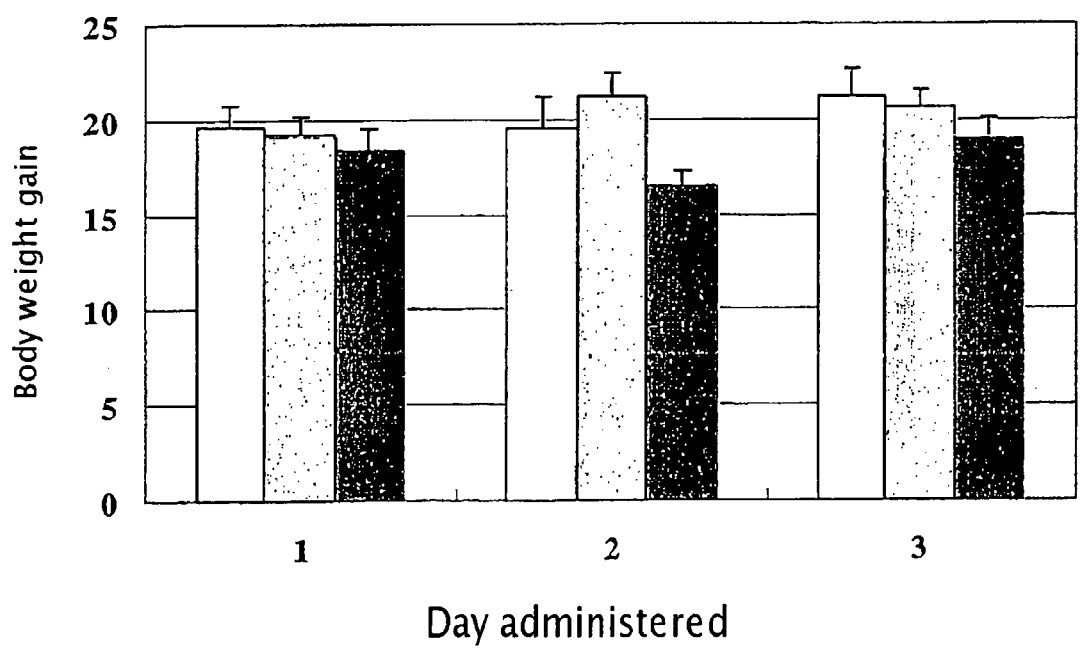
FIG. 25 shows an action of the hGPR8L(1-23), which was administered to interperitoneal, on a body weight gain for rat. In the figure, white, gray and black represent the vehicle group, the 0.2 mg-administration group and the 2 mg-administration group, respectively.

For body weight gain, in the group of 2 mg/kg administration, a tendency to decrease was demonstrated for all three days compared to the vehicle group (the differences among the means: the first day, 1.2 g; the second day, 3.1 g; the third day, 2.3 g) (FIG. 25).

From the results, it was perceived that by intraperistoneal administration of the hGPR8L(1-23), during dark period, food consumption was decreased, and the hGPR8L(1-23) has an effect on the body weight gain inhibition.

Example 3

Production of [Phe2] Human GPR8 Ligand (1-20): Trp-Phe-Lys-His-Val-Ala-Ser-Pro-Arg-Tyr-His-Thr-Val-Gly-Arg-Ala-Ala-Gly-Leu-Leu (SEQ ID NO: 149)

Using the peptide automated synthesizer (ABI model 433) manufactured by Applied Biosystems, according to programme, a peptide chain was successively extended from the C-terminus by Fmoc method. Then the protected peptide resin of interest was synthesized.

Using Wang (p-benzyloxybenzyl alcohol) resin (0.25 mmol) as a starting amino acid resin carrier, Fmoc amino acid derivatives, namely Fmoc-Leu, Fmoc-Gly, Fmoc-Ala, Fmoc-Arg(Pbf), Fmoc-Val, Fmoc-Thr(Bu$^t$), Fmoc-His(Trt), Fmoc-Pro, Fmoc-Ser(Bu$^t$), Fmoc-Lys(Boc), Fmoc-Phe and Fmoc-Trp(Boc) were successively condensed by HBTU (2-(1H-Benzotriazol-1-yl)-1,1,3,3-tetramethyluronium hexafluorophosphate) in accordance with the sequence.

After completion of the construction of peptide on the resin, the protective peptide resin was dried. Deprotection treatment of the obtained protective peptide and separation of peptide from the resin carrier was performed by TFA treatment. Crude peptide obtained was extracted with 0.1% TFA water and lyophilized to get a powder. Subsequently, the crude peptide was fractionated and purified by reverse phase high performance liquid chromatography (Shimadzu Corporation, fractionator: model LC8A) using acetonitrile-0.1% TFA water system (15-35%, 80 minutes) to get 35 mg of the purified peptide of interest.

Analytical values (theoretical values in parentheses) of amino acid for hydrolysate, which was obtained by hydrolysis of the purified product with 4N methanesulfonic acid containing 0.2% 3-(2-aminoethyl) indol at 110° C. for 22 hours, are as follows:

Thr (1) 0.93; Ser (1) 0.92; Gly (2) 2.03; Ala (3) 3.09; Val (2) 1.90; Leu (2) 2.02; Tyr (1) 1.02; Phe (1) 1.00; His (2) 1.91; Lys (1) 0.98; Trp (1) 0.88; Arg (2) 2.06; and Pro (1) 1.02.

The purity was calculated as 98.8% by HPLC. In addition, the value of mass spectrometry was 2266.6 (theoretical value: 2266.6).

Example 4

Preparation of [Phe$^2$, $^{125}$I-Tyr$^{10}$]-Human GPR8 Ligand (1-20) Using the Lactoperoxidase Method Ten (10) nmol of [Phe$^2$] human GPR8 ligand (1-20) dissolved in 10 μl of DMSO, which was obtained in accordance with the method described in Example 3, was mixed with 10 μl of 1 M nickel chloride, 10 μl of 0.001% hydrogen peroxide dissolved in 0.1 M HEPES (pH7), 10 μl of 10 μg/ml lactoperoxidase (Sigma) dissolved in 0.1 M HEPES (pH7), and 10 μl of [$^{125}$I] NaI (40 MBq, NEN Life Science Products). The reaction mixture was incubated at room temperature for 50 minutes, and then the [Phe$^2$, $^{125}$I-Tyr$^{10}$]-human GPR8 ligand (1-20) formed, was fractionated by HPLC under the following conditions.

As a column, ODS-80™ (4.6 mm×15 cm) (Toso) was used, and as an eluent A and eluent B, 10% acetonitrile/0.1% TFA and 60% acetonitrile/0.1% TFA were used, respectively. Elution was performed by gradient elution of 0-0 (2 minutes), 0-27 (5 minutes), and 27-32 (40 minutes) of % B/A+B. Flow rate was 1 mL/min. Column temperature was 40° C. Detection of absorbance at 215 nm was used. Under the HPLC condition utilized, [Phe$^2$, $^{125}$I-Tyr$^0$]-human GPR8 ligand (1-20) was eluted at around 25 minutes.

Example 5

Experiment for Receptor Binding Using [Phe$^2$, $^{125}$I-Tyr$^{10}$]-Human GPR8 Ligand (1-20)

Using [Phe$^2$, $^{125}$I-Tyr$^{10}$]-human GPR8 ligand (1-20) prepared as described in Example 4, the membrane fraction from GPR7 expressing CHO cells prepared by the method as described in Reference Example 82 and the cell membrane fraction from GPR8 expressing cells prepared by the method as described in Reference Example 6, a receptor binding assay was carried out.

Cell membrane fractions prepared from GPR7 expressing CHO cells and GPR8 expressing CHO cells, were diluted to various concentration with assay buffer (25 mM Tris-HCl, 5 mM EDTA, 0.05% CHAPS, 0.1% BSA, 0.5 mM PMSF, 1 μg/ml Pepstatin, 4 μg/ml E-64, 20 μg/ml Leupeptin, pH7.4), and 200 μl each of the diluent was dispensed into polypropilene test tube (Falcon 2053). In order to determine an amount of maximum binding, 2 μl of DMSO and 2 μl of 7 nM [Phe$^2$, $^{125}$I-Tyr$^{10}$]-human GPR8 ligand (1-20) were added to the membrane fraction solution. Further, in order to determine a non-specific binding, 2 μl of 100 μM hGPR8L (1-23)/DMSO solution and 2 μl of 7 nM [Phe$^2$, $^{125}$I-Tyr$^{10}$]-human GPR8 ligand (1-20) were added to the membrane fraction solution. The reaction was done at 25° C. for 75 minutes, and the reaction mixture was filtered by suction filtration using Whatman glassfilter (GF-F) treated with polyethyleneimine. After filtration, a radioactivity remaining on the filter was counted using γ-counter, and an amount of specific binding was estimated by subtracting an amount of non-specific binding from an amount of maximum binding. When the concentration of membrane fraction was changed, a specific binding of [Phe$^2$, $^{125}$I-Tyr$^{10}$]-human GPR8 ligand (1-20) was perceived depending on the concentration of membrane fraction.

Figure 26:
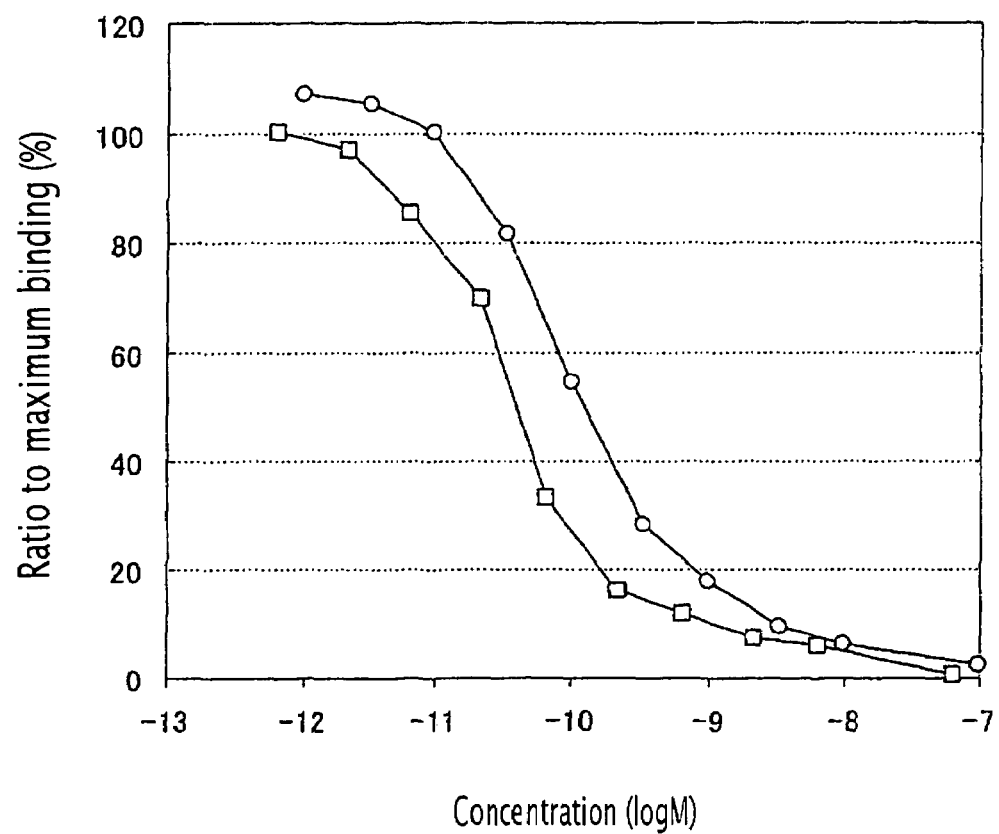
FIG. 26 shows a binding inhibitory activity of various concentrations of hGPR8L(1-23) and hGPR8L(1-30) on the binding of [Phe$^2$, $^{125}$I-Tyr$^{10}$] human GPR8 ligand(1-20) to the cell membrane fraction prepared from human GPR7 expressing CHO cells. In the figure, open circle represents the case where the hGPR8L(1-23) was administered, and open square represents the case where the hGPR8L(1-30) was administered.
Figure 27:
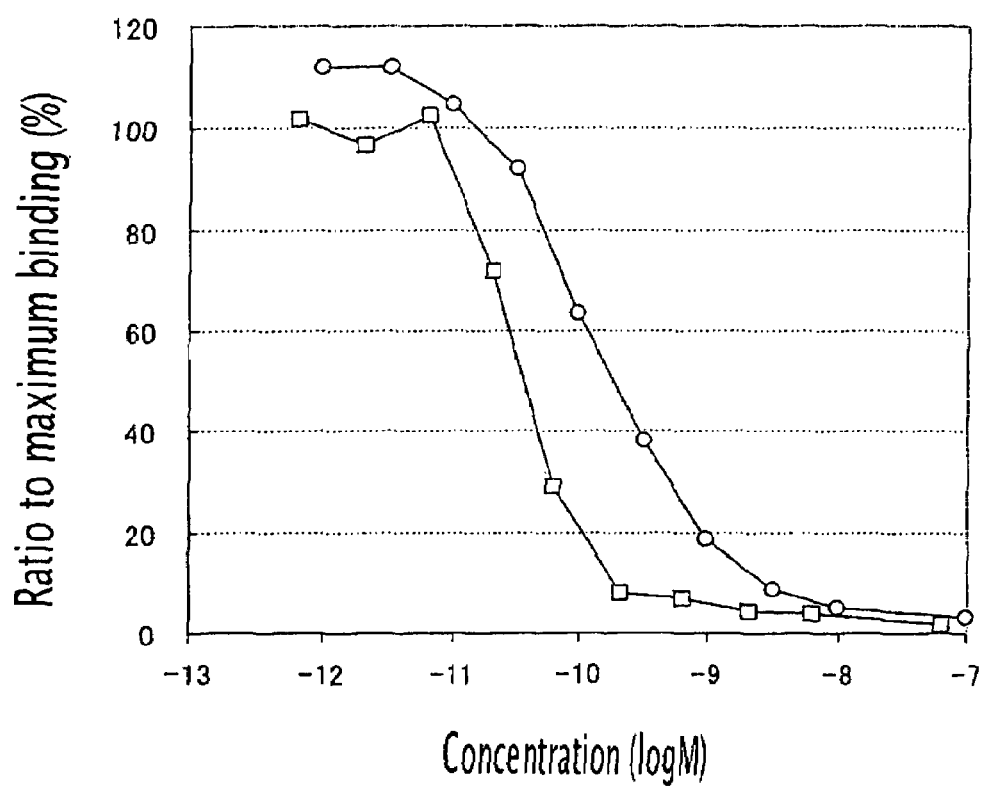
FIG. 27 shows a binding inhibitory activity of various concentrations of hGPR8L(1-23) and hGPR8L(1-30) on the binding of [Phe$^2$, $^{125}$I-Tyr$^{10}$] human GPR8 ligand(1-20) to the cell membrane fraction prepared from human GPR8 expressing CHO cells. In the figure, open circle represents the case where the hGPR8L(1-23) was administered, and open square represents the case where the hGPR8L(1-30) was administered.

The inhibition of binding for GPR7 receptor or GPR8 receptor in the test sample (the inhibition rate (%)) is represented by the ratio of the values obtained by subtracting a radioactivity (X) remaining on the filter in the case where the test sample and of [Phe$^2$, $^{125}$I-Tyr$^{10}$]-human GPR8 ligand (1-20) were added from the maximum binding (TB) to the specific binding (SB) ((TB−X)/SB×100(%)).

Where the concentration of membrane fraction was set to 15 μg/ml for the membrane fraction prepared from GPR7 expressing CHO cells, concentration of 50% inhibition (IC$_{50}$ values) of human GPR8 ligand (1-23) and human GPR8 ligand (1-30) was calculated from the inhibition rate. The IC$_{50}$ values were 0.13 nM and 0.039 nM, respectively. FIG. 26 shows the inhibition of binding for human GPR8 ligand (1-23) and human GPR8 ligand (1-30) at various concentrations. Where the concentration of membrane fraction was set to 5 μg/ml for the membrane fraction prepared from GPR8 expressing CHO cells, concentration of 50% inhibition (IC$_{50}$ values) of human GPR8 ligand (1-23) and human GPR8 ligand (1-30) was calculated from the inhibition rate. The IC$_{50}$ values were 0.19 nM and 0.037 nM, respectively. FIG. 27 shows the inhibition of binding for human GPR8 ligand (1-23) and human GPR8 ligand (1-30) at various concentrations.

Example 6

Method for Screening a Compound that Alters the Binding Property between GPR7 and GPR8 Ligand, which Comprises Using [Phe$^2$, $^{125}$I-Tyr$^{10}$]-Human GPR8 Ligand (1-20) and the Membrane Fraction of Human GPR7 Expressing CHO Cells By the experiment for receptor binding with [Phe$^2$, $^{125}$I-Tyr$^{10}$]-human GPR8 ligand (1-20) prepared by the method described in Example 4 and the membrane fraction of GPR7 expressing CHO cells prepared by the method described in Reference Example 82, a compound that alters the binding property between GPR7 and GPR8 ligand was screened.

In Example 5 using the membrane fraction prepared from the GPR7 expressing CHO cells, 2 μl of test compound dissolved in DMSO solution and 2 μl of 7 nM [Phe², ¹²⁵I-Tyr¹⁰]-human GPR8 ligand (1-20) were added to membrane fraction solution. The reaction was done at 25° C. for 75 minutes, and the reaction mixture was filtered by suction filtration using Whatman glassfilter (GF-F) treated with polyethyleneimine. After filtration, a radioactivity remaining on the filter was counted using γ-counter, and an amount of binding in the case where the test compound was added, was estimated. Percentage was calculated by dividing the value obtained by subtracting an amount of binding in the case where the test compound was added, from an amount of maximum binding with the value from the specific binding. Then the binding inhibition activity for the test compound (%) was estimated.

For the test compound exhibiting the binding inhibition activity, by measuring the activity using the test compound at various concentrations, concentration of 50% inhibition ($IC_{50}$ value) was calculated. The compounds having lower $IC_{50}$ was selected as compounds that extremely inhibit the binding between GPR7 and GPR8 ligand.

On the other hand, the compounds having negative values as the binding inhibition activity was selected as compounds that promote the binding between GPR7 and GPR8 ligand.

INDUSTRIAL APPLICABILITY

The DNA of the present invention or the polypeptide of the present invention is useful for the screening of, for example, a body weight gain inhibitor, a body weight loss agent, an adipose gain inhibitor, a feeding inhibitor or a body weight gain product, or as a body weight gain inhibitor, a body weight loss agent, an adipose gain inhibitor, a feeding inhibitor or a body weight gain product. The body weight gain inhibitor, the body weight loss agent, the adipose gain inhibitor, and the feeding inhibitor, which are obtained by the screening using the polypptide of the present inhibition, preferably the screening using also the receptor of the present invention, can be used as a safe and superior medicine.

The invention claimed is:

1. A method for body weight gain inhibition, body weight loss promotion, or adipose gain inhibition, wherein said method is characterized by administering to a mammal in need thereof an effective amount of a polypeptide comprising the amino acid sequence represented by SEQ ID NO: 16, its amide or ester, or salts thereof; wherein said administering is parenteral administration.

2. A method for inhibiting body weight gain, which comprises administering to a mammal in need thereof an effective amount of a polypeptide comprising the amino acid sequence represented by SEQ ID NO: 16, its amide or ester, or salts thereof wherein said administering is parenteral administration.

3. A method for losing body weight, which comprises administering to a mammal in need thereof an effective amount of a polypeptide comprising the amino acid sequence represented by SEQ ID NO: 16, its amide or ester, or salts thereof wherein said administering is parenteral administration.

4. A method for inhibiting adipose gain, which comprises administering to a mammal in need thereof an effective amount of a polypeptide comprising the amino acid sequence represented by SEQ ID NO: 16, its amide or ester, or salt thereof wherein said administering is parenteral administration.

* * * * *

SEQUENCE LISTING

```
<160> NUMBER OF SEQ ID NOS: 150

<210> SEQ ID NO 1
<211> LENGTH: 32
<212> TYPE: DNA
<213> ORGANISM: Artificial Sequence
<220> FEATURE:
<223> OTHER INFORMATION: Primer

<400> SEQUENCE: 1
atcgattaca atgcaggccg ctgggcaccc ag                              32

<210> SEQ ID NO 2
<211> LENGTH: 32
<212> TYPE: DNA
<213> ORGANISM: Artificial Sequence
<220> FEATURE:
<223> OTHER INFORMATION: Primer

<400> SEQUENCE: 2
actagtgccc ttcagcaccg caatatgctg cg                              32

<210> SEQ ID NO 3
<211> LENGTH: 1023
<212> TYPE: DNA
<213> ORGANISM: Homo sapiens

<400> SEQUENCE: 3
atcgattaca atgcaggccg ctgggcaccc agagcccctt gacagcaggg gctccttctc     60
cctccccacg atgggtgcca acgtctctca ggacaatggc actggccaca atgccacctt    120
ctccgagcca ctgccgttcc tctatgtgct cctgcccgcc gtgtactccg ggatctgtgc    180
tgtggggctg actggcaaca cggccgtcat ccttgtaatc ctaagggcgc ccaagatgaa    240
gacggtgacc aacgtgttca tcctgaacct ggccgtcgcc gacgggctct tcacgctggt    300
actgcccgtc aacatcgcgg agcacctgct gcagtactgg cccttcgggg agctgctctg    360
caagctggtg ctggccgtcg accactacaa catcttctcc agcatctact tcctagccgt    420
gatgagcgtg gaccgatacc tggtggtgct ggccaccgtg aggtcccgcc acatgccctg    480
gcgcacctac cgggggggcga aggtcgccag cctgtgtgtc tggctgggcg tcacggtcct    540
```

-continued

```
ggttctgccc ttcttctctt tcgctggcgt ctacagcaac gagctgcagg tcccaagctg      600
tgggctgagc ttcccgtggc ccgagcaggt ctggttcaag gccagccgtg tctacacgtt      660
ggtcctgggc ttcgtgctgc ccgtgtgcac catctgtgtg ctctacacag acctcctgcg      720
caggctgcgg gccgtgcggc tccgctctgg agccaaggct ctaggcaagg ccaggcggaa      780
ggtgaccgtc ctggtcctcg tcgtgctggc cgtgtgcctc ctctgctgga cgccttcca       840 cctggcctct gtcgtggccc tgaccacgga cctgccccag accccactgg tcatcagtat      900
gtcctacgtc atcaccagcc tcagctacgc caactcgtgc ctgaacccct tcctctacgc      960
ctttctagat gacaacttcc ggaagaactt ccgcagcata ttgcggtgct gaagggcact     1020
agt                                                                   1023
```

<210> SEQ ID NO 4
<211> LENGTH: 333
<212> TYPE: PRT
<213> ORGANISM: Homo sapiens

<400> SEQUENCE: 4

```
Met Gln Ala Ala Gly His Pro Glu Pro Leu Asp Ser Arg Gly Ser Phe
1               5                   10                  15

Ser Leu Pro Thr Met Gly Ala Asn Val Ser Gln Asp Asn Gly Thr Gly
            20                  25                  30

His Asn Ala Thr Phe Ser Glu Pro Leu Pro Phe Leu Tyr Val Leu Leu
        35                  40                  45

Pro Ala Val Tyr Ser Gly Ile Cys Ala Val Gly Leu Thr Gly Asn Thr
    50                  55                  60

Ala Val Ile Leu Val Ile Leu Arg Ala Pro Lys Met Lys Thr Val Thr
65                  70                  75                  80

Asn Val Phe Ile Leu Asn Leu Ala Val Ala Asp Gly Leu Phe Thr Leu
                85                  90                  95

Val Leu Pro Val Asn Ile Ala Glu His Leu Leu Gln Tyr Trp Pro Phe
            100                 105                 110

Gly Glu Leu Leu Cys Lys Leu Val Leu Ala Val Asp His Tyr Asn Ile
        115                 120                 125

Phe Ser Ser Ile Tyr Phe Leu Ala Val Met Ser Val Asp Arg Tyr Leu
    130                 135                 140

Val Val Leu Ala Thr Val Arg Ser Arg His Met Pro Trp Arg Thr Tyr
145                 150                 155                 160

Arg Gly Ala Lys Val Ala Ser Leu Cys Val Trp Leu Gly Val Thr Val
                165                 170                 175

Leu Val Leu Pro Phe Phe Ser Phe Ala Gly Val Tyr Ser Asn Glu Leu
            180                 185                 190

Gln Val Pro Ser Cys Gly Leu Ser Phe Pro Trp Pro Glu Gln Val Trp
        195                 200                 205

Phe Lys Ala Ser Arg Val Tyr Thr Leu Val Leu Gly Phe Val Leu Pro
    210                 215                 220

Val Cys Thr Ile Cys Val Leu Tyr Thr Asp Leu Leu Arg Arg Leu Arg
225                 230                 235                 240

Ala Val Arg Leu Arg Ser Gly Ala Lys Ala Leu Gly Lys Ala Arg Arg
                245                 250                 255

Lys Val Thr Val Leu Val Leu Val Val Leu Ala Val Cys Leu Leu Cys
            260                 265                 270

Trp Thr Pro Phe His Leu Ala Ser Val Val Ala Leu Thr Thr Asp Leu
```

```
                   275                 280                 285
Pro Gln Thr Pro Leu Val Ile Ser Met Ser Tyr Val Ile Thr Ser Leu
    290                 295                 300

Ser Tyr Ala Asn Ser Cys Leu Asn Pro Phe Leu Tyr Ala Phe Leu Asp
305                 310                 315                 320

Asp Asn Phe Arg Lys Asn Phe Arg Ser Ile Leu Arg Cys
                325                 330

<210> SEQ ID NO 5
<211> LENGTH: 687
<212> TYPE: RNA
<213> ORGANISM: Artificial Sequence
<220> FEATURE:
<223> OTHER INFORMATION: Riboprobe

<400> SEQUENCE: 5
caaaagcugg agcuccaccg cgguggcggc cgcucuagcc cacuagugcc cuucagcacc      60
gcaauaugcu gcggaaguuc uuccggaagu ugucaucuag aaaggcguag aggaaggggu     120
ucaggcacga guuggcguag cugaggcugg ugaugacgua ggacauacug augaccagug     180
gggucugggg cagguccgug gucagggcca cgacagaggc caggugga ag ggcguccagc    240 agaggaggca cacggccagc acgacgagga ccaggacggu caccuuccgc cuggccuugc    300
cuagagccuu ggcuccagag cggagccgca cggcccgcag ccugcgcagg aggucugugu    360
agagcacaca gauggugcac acgggcagca cgaagcccag gaccaacgug uagacacggc    420
uggccuugaa ccagaccugc ucgggccacg ggaagcucac cccacagcuu gggaccugca    480
gcucguugcu guagacgcca gcgaaagaga agaagggcag aaccaggacc gugacgccca    540
gccagacaca caggcuggcg accuucgccc ccgguaggu gcgccagggc augugg cggg    600 accucacggu ggccagcacc accagguauc gguccacgcu caucacggcu aggaaguaga    660
ugcuggagaa gauguuguag uggucga                                        687

<210> SEQ ID NO 6
<211> LENGTH: 17
<212> TYPE: PRT
<213> ORGANISM: Sus scrofa

<400> SEQUENCE: 6

Trp Tyr Lys His Thr Ala Ser Pro Arg Tyr His Thr Val Gly Arg Ala
1               5                   10                  15
Ala

<210> SEQ ID NO 7
<211> LENGTH: 438
<212> TYPE: DNA
<213> ORGANISM: Homo sapiens
<220> FEATURE:
<221> NAME/KEY: misc_feature
<222> LOCATION: 408
<223> OTHER INFORMATION: n is a, c, g, or t

<400> SEQUENCE: 7
gccccatgag caggccagcg gcgcggccca ccgtgtggta gcgggactc gccacgtgct       60 tgtaccacgc gccggagggc agcggcagca ggagcagaag cagcagcagt gccagccgcg    120
gccggctcgc gggagccccc cgctcccctg gcgccacgc cagggcgctc gcgtcgacgg     180
ccgcccggcg gggcgggcca cgaaccggct cggctggggt tgggcgcgca gtggagttgg   240
gacgcccagg taccggagcg caggaggctg gaggcgagcc gtgggtcccc tgcaggccca   300
```

-continued

```
gctataaccg ctcggtggcc ccgcctcgtt ccgcccccte agtaccgctg ggctccccag    360 atgggggggag ggacggaggg aggagaggga accctggcag ctggcggngg acgtgggtac   420
ttgagcacct cactgagt                                                  438

<210> SEQ ID NO 8
<211> LENGTH: 264
<212> TYPE: DNA
<213> ORGANISM: Homo sapiens

<400> SEQUENCE: 8
gatagggtga gcgacgcagc cccatgagca ggccagcggc gcggcccacc gtgtggtagc    60
ggggactcgc cacgtgcttg taccacgcgc cggaggcag cggcagcagg agcagaagca    120
gcagcagtgc cagccgcggc cggctcgcgg gagcccccg ctcccctggg cgccacgcca    180
gggcgctcgc gtcgacggcc gcccggcggg gcgggccacg aaccggctcg gctgggtttg   240
ggcgcgcagt ggagttggga cgcc                                           264

<210> SEQ ID NO 9
<211> LENGTH: 424
<212> TYPE: DNA
<213> ORGANISM: Homo sapiens

<400> SEQUENCE: 9
gatagggtga gcgacgcagc cccatgagca ggccagcggc gcggcccacc gtgtggtagc    60
ggggactcgc cacgtgcttg taccacgcgc cggaggcag cggcagcagg agcagaagca    120
gcagcagtgc cagccgcggc cggctcgcgg gagcccccg ctcccctggg cgccacgcca    180
gggcgctcgc gtcgacggcc gcccggcggg gcgggccacg aaccggctcg gctgggtttg   240
ggcgcgcagt ggagttggga cgcccaggta ccggagcgca ggaggctgga ggcgagccgt   300
gggtcccctg caggcccagc tataaccgct cggtggcccc gctcgttcc gcccctcag    360 taccgctggg ctccccagat ggggggaggg acggagggag gagagggaac cctggcagct   420
ggcg                                                                 424

<210> SEQ ID NO 10
<211> LENGTH: 375
<212> TYPE: DNA
<213> ORGANISM: Homo sapiens

<400> SEQUENCE: 10
gcgcctcacc gtgtggtagc ggggactcgc cacgtgcttg taccacgcgc cggaggcagc    60
ggcacgagga gcagaagcag cagcagtgcc agccgcggcc ggctcgcggg agccccccgc   120
tcccctgggc gccacgcagg gctacagcgt cgacggccgc ccgcggggcc atcgcaaccg   180
gctcggctgg gtttgggcgc gcagtggagt tgggacgccc aggtaccgga gcgcaggagg   240
ctggaggcga gccgtgggtc ccctgcaggc ccagctataa ccgctcggtg gccccgcctc   300
gttccgcccc ctcagtaccg ctgggctccc cagaatgggg gagggacgga gggaggagag   360
ggaaccctgg cagct                                                    375

<210> SEQ ID NO 11
<211> LENGTH: 260
<212> TYPE: DNA
<213> ORGANISM: Homo sapiens
<220> FEATURE:
<221> NAME/KEY: misc_feature
<222> LOCATION: 2, 61, 147, 189, 213, 237, 249
```

<223> OTHER INFORMATION: n is a, c, g, or t

<400> SEQUENCE: 11

```
cnacgttctc ggggacataa accctgttct tgtcctaacc cgccaagggg ccatggactt      60
nagcgcgctg gcgtcgagca gagaagtacg gggccctggg ccggggctcc ggtgaaccgg     120
cccctgctac cgctactgct gcttctnctc ttgctacctc tgcccgccag cgcctggtac     180
aagcacgtng cgagccctcg ctatcacaca gtnggtcgtg cctccgggct gctcatnggg     240
ctgcgccgnt cgtcctacct                                                  260
```

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12

```
aactccactg cgcgcccaaa ccca                                             24
```

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13

```
tctcccacag ctcctgaacc cacg                                             24
```

<210> SEQ ID NO 14
<211> LENGTH: 375
<212> TYPE: DNA
<213> ORGANISM: Homo sapiens

<400> SEQUENCE: 14

```
aactccactg cgcgcccaaa cccagccgag ccggttcgtg gcccgccccg ccgggcggcc      60
gtcgacgcga gcgccctggc gtggcgccca ggggagcggg gggctcccgc gagccggccg     120
cggctggcac tgctgctgct tctgctcctg ctgccgctgc cctccggcgc gtggtacaag     180
cacgtggcga gtccccgcta ccacacggtg gccgcgccgc tggcctgct catggggctg     240
cgtcgctcac cctatctgtg gcgccgcgcg ctgcgcgcgg ccgccgggcc cctggccagg     300
gacaccctct cccccgaacc cgcagcccgc gaggctcctc tcctgctgcc ctcgtgggtt     360
caggagctgt gggag                                                      375
```

<210> SEQ ID NO 15
<211> LENGTH: 125
<212> TYPE: PRT
<213> ORGANISM: Homo sapiens

<400> SEQUENCE: 15

```
Asn Ser Thr Ala Arg Pro Asn Pro Ala Glu Pro Val Arg Gly Pro Pro
1               5                   10                  15

Arg Arg Ala Ala Val Asp Ala Ser Ala Leu Ala Trp Arg Pro Gly Glu
            20                  25                  30

Arg Gly Ala Pro Ala Ser Arg Pro Arg Leu Ala Leu Leu Leu Leu Leu
        35                  40                  45

Leu Leu Leu Pro Leu Pro Ser Gly Ala Trp Tyr Lys His Val Ala Ser
    50                  55                  60
```

```
Pro Arg Tyr His Thr Val Gly Arg Ala Ala Gly Leu Leu Met Gly Leu
65                  70                  75                  80

Arg Arg Ser Pro Tyr Leu Trp Arg Arg Ala Leu Arg Ala Ala Gly
                85                  90                  95

Pro Leu Ala Arg Asp Thr Leu Ser Pro Glu Pro Ala Ala Arg Glu Ala
            100                 105                 110

Pro Leu Leu Leu Pro Ser Trp Val Gln Glu Leu Trp Glu
        115                 120                 125

<210> SEQ ID NO 16
<211> LENGTH: 23
<212> TYPE: PRT
<213> ORGANISM: Homo sapiens

<400> SEQUENCE: 16

Trp Tyr Lys His Val Ala Ser Pro Arg Tyr His Thr Val Gly Arg Ala
1               5                   10                  15

Ala Gly Leu Leu Met Gly Leu
            20

<210> SEQ ID NO 17
<211> LENGTH: 30
<212> TYPE: PRT
<213> ORGANISM: Homo sapiens

<400> SEQUENCE: 17

Trp Tyr Lys His Val Ala Ser Pro Arg Tyr His Thr Val Gly Arg Ala
1               5                   10                  15

Ala Gly Leu Leu Met Gly Leu Arg Arg Ser Pro Tyr Leu Trp
            20                  25                  30

<210> SEQ ID NO 18
<211> LENGTH: 69
<212> TYPE: DNA
<213> ORGANISM: Homo sapiens

<400> SEQUENCE: 18
tggtacaagc acgtggcgag tccccgctac cacacggtgg gccgcgccgc tggcctgctc     60
atggggctg                                                            69

<210> SEQ ID NO 19
<211> LENGTH: 90
<212> TYPE: DNA
<213> ORGANISM: Homo sapiens

<400> SEQUENCE: 19
tggtacaagc acgtggcgag tccccgctac cacacggtgg gccgcgccgc tggcctgctc     60
atggggctgc gtcgctcacc ctatctgtgg                                     90

<210> SEQ ID NO 20
<211> LENGTH: 29
<212> TYPE: PRT
<213> ORGANISM: Homo sapiens

<400> SEQUENCE: 20

Trp Tyr Lys His Val Ala Ser Pro Arg Tyr His Thr Val Gly Arg Ala
1               5                   10                  15

Ala Gly Leu Leu Met Gly Leu Arg Arg Ser Pro Tyr Leu
            20                  25
```

<210> SEQ ID NO 21
<211> LENGTH: 28
<212> TYPE: PRT
<213> ORGANISM: Homo sapiens

<400> SEQUENCE: 21

Trp Tyr Lys His Val Ala Ser Pro Arg Tyr His Thr Val Gly Arg Ala
1               5                   10                  15

Ala Gly Leu Leu Met Gly Leu Arg Arg Ser Pro Tyr
            20                  25

<210> SEQ ID NO 22
<211> LENGTH: 27
<212> TYPE: PRT
<213> ORGANISM: Homo sapiens

<400> SEQUENCE: 22

Trp Tyr Lys His Val Ala Ser Pro Arg Tyr His Thr Val Gly Arg Ala
1               5                   10                  15

Ala Gly Leu Leu Met Gly Leu Arg Arg Ser Pro
            20                  25

<210> SEQ ID NO 23
<211> LENGTH: 26
<212> TYPE: PRT
<213> ORGANISM: Homo sapiens

<400> SEQUENCE: 23

Trp Tyr Lys His Val Ala Ser Pro Arg Tyr His Thr Val Gly Arg Ala
1               5                   10                  15

Ala Gly Leu Leu Met Gly Leu Arg Arg Ser
            20                  25

<210> SEQ ID NO 24
<211> LENGTH: 25
<212> TYPE: PRT
<213> ORGANISM: Homo sapiens

<400> SEQUENCE: 24

Trp Tyr Lys His Val Ala Ser Pro Arg Tyr His Thr Val Gly Arg Ala
1               5                   10                  15

Ala Gly Leu Leu Met Gly Leu Arg Arg
            20                  25

<210> SEQ ID NO 25
<211> LENGTH: 24
<212> TYPE: PRT
<213> ORGANISM: Homo sapiens

<400> SEQUENCE: 25

Trp Tyr Lys His Val Ala Ser Pro Arg Tyr His Thr Val Gly Arg Ala
1               5                   10                  15

Ala Gly Leu Leu Met Gly Leu Arg
            20

<210> SEQ ID NO 26
<211> LENGTH: 87
<212> TYPE: DNA
<213> ORGANISM: Homo sapiens

<400> SEQUENCE: 26
tggtacaagc acgtggcgag tccccgctac cacacggtgg gccgcgccgc tggcctgctc    60

```
atggggctgc gtcgctcacc ctatctg                                          87

<210> SEQ ID NO 27
<211> LENGTH: 84
<212> TYPE: DNA
<213> ORGANISM: Homo sapiens

<400> SEQUENCE: 27
tggtacaagc acgtggcgag tccccgctac cacacggtgg gccgcgccgc tggcctgctc      60
atggggctgc gtcgctcacc ctat                                             84

<210> SEQ ID NO 28
<211> LENGTH: 81
<212> TYPE: DNA
<213> ORGANISM: Homo sapiens

<400> SEQUENCE: 28
tggtacaagc acgtggcgag tccccgctac cacacggtgg gccgcgccgc tggcctgctc      60
atggggctgc gtcgctcacc c                                                81

<210> SEQ ID NO 29
<211> LENGTH: 78
<212> TYPE: DNA
<213> ORGANISM: Homo sapiens

<400> SEQUENCE: 29
tggtacaagc acgtggcgag tccccgctac cacacggtgg gccgcgccgc tggcctgctc      60
atggggctgc gtcgctca                                                    78

<210> SEQ ID NO 30
<211> LENGTH: 75
<212> TYPE: DNA
<213> ORGANISM: Homo sapiens

<400> SEQUENCE: 30
tggtacaagc acgtggcgag tccccgctac cacacggtgg gccgcgccgc tggcctgctc      60
atggggctgc gtcgc                                                       75

<210> SEQ ID NO 31
<211> LENGTH: 72
<212> TYPE: DNA
<213> ORGANISM: Homo sapiens

<400> SEQUENCE: 31
tggtacaagc acgtggcgag tccccgctac cacacggtgg gccgcgccgc tggcctgctc      60
atggggctgc gt                                                          72

<210> SEQ ID NO 32
<211> LENGTH: 999
<212> TYPE: DNA
<213> ORGANISM: Homo sapiens

<400> SEQUENCE: 32
atgcaggccg ctgggcaccc agagcccctt gacagcaggg gctccttctc cctccccacg      60
atgggtgcca acgtctctca ggacaatggc actggcacca atgccacctt ctccgagcca     120
ctgccgttcc tctatgtgct cctgcccgcc gtgtactccg ggatctgtgc tgtggggctg     180
actggcaaca cggccgtcat ccttgtaatc ctaagggcgc ccaagatgaa gacggtgacc     240
```

```
aacgtgttca tcctgaacct ggccgtcgcc gacgggctct tcacgctggt actgcccgtc    300
aacatcgcgg agcacctgct gcagtactgg cccttcgggg agctgctctg caagctggtg    360
ctggccgtcg accactacaa catcttctcc agcatctact tcctagccgt gatgagcgtg    420
gaccgatacc tggtggtgct ggccaccgtg aggtcccgcc acatgccctg gcgcacctac    480 cgggggggcga aggtcgccag cctgtgtgtc tggctgggcg tcacggtcct ggttctgccc    540
ttcttctctt tcgctggcgt ctacagcaac gagctgcagg tcccaagctg tgggctgagc    600
ttcccgtggc ccgagcgggt ctggttcaag gccagccgtg tctacacttt ggtcctgggc    660
ttcgtgctgc ccgtgtgcac catctgtgtg ctctacacag acctcctgcg caggctgcgg    720
gccgtgcggc tccgctctgg agccaaggct ctaggcaagg ccaggcggaa ggtgaccgtc    780
ctggtcctcg tcgtgctggc cgtgtgcctc tctgctggga cgcccttcca cctgcctct     840 gtcgtggccc tgaccacgga cctgccccag accccactgg tcatcagtat gtcctacgtc    900
atcaccagcc tcacgtacgc caactcgtgc ctgaacccct tcctctacgc ctttctagat    960
gacaacttcc ggaagaactt ccgcagcata ttgcggtgc                            999

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
tctcccacag ctcctgaacc cacg                                             24

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
acagataggg tgagcgacgc agcc                                             24

<210> SEQ ID NO 35
<211> LENGTH: 1102
<212> TYPE: DNA
<213> ORGANISM: Homo sapiens

<400> SEQUENCE: 35
gccatttaag tggagtcttg aaggatgagt aggtgttagg cacagacgca cagaggcagg     60
caaagccaca ggctgttggt ttaggcaaaa attgagactg gctggataaa gtggtcttgg    120
gggaccatca ccagagagga ggcgctggag gtctgcaagg ccttgtcctg cccctccagg    180
ggtagaggtt ccaggagggg ctgacttttt tcctgaaag cctcacagaa ctgcagaccc     240
cacggatggc ttggtgttgc caacatgagg cttctaaggc ttctgcgggg agatgggttg    300
gtggggagaa gctgggggtg gcagtggaca ggacagggtg tggggacagc tttgggagct    360
atgctaggca aggacaaggg acaactcttg ggggactca cccagagggg tcttgaatgg     420
tgctgaaggc ccccgacagc cctcctgcaa tagccactgt agctctgcct gcacctgggc    480
cttcgctctg ctgtcgtccc accggcagga gtctggctaa aggggcatcc ctcagcccta    540
ctccctcatc agtgttccca gtacccactc cctggcactt ccactcctag agggaggagg    600
ctgagcaggc agagaatggg acgtgtcccc tcagaggagc ctcgagccca gttccagcca    660
```

```
gcggcccact cagtgaggtg ctcaagtacc cacgtccccc gccagctgcc agggttccct    720
ctcctccctc cgtccctccc cccatctggg gagcccagcg gtactgaggg ggcggaacga    780
ggcggggcca ccgagcggtt atagctgggc ctgcagggga cccacggctc gcctccagcc    840
tcctgcgctc cggtacctgg gcgtcccaac tccactgcgc gcccaaaccc agccgagccg    900
gttcgtggcc cgccccgccg ggcggccgtc gacgcgagcg ccctggcgtg gcgcccaggg    960
gagcgggggg ctcccgcgag ccggccgcgg ctggcactgc tgctgcttct gctcctgctg   1020
ccgctgccct ccggcgcgtg gtacaagcac gtggcgagtc cccgctacca cacggtgggc   1080
cgcgccgctg gcctgctcat gg                                            1102
```

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36

```
aactccactg cgcgcccaaa ccca                                            24
```

<210> SEQ ID NO 37
<211> LENGTH: 24
<212> TYPE: DNA
<213> ORGANISM: Artificial Sequence
<220> FEATURE:
<223> OTHER INFORMATION: Primer

<400> SEQUENCE: 37

```
ctggcactgc tgctgcttct gctc                                            24
```

<210> SEQ ID NO 38
<211> LENGTH: 609
<212> TYPE: DNA
<213> ORGANISM: Homo sapiens

<400> SEQUENCE: 38

```
ctgctgccgc tgccctccgg cgcgtggtac aagcacgtgg cgagtccccg ctaccacacg     60
gtgggccgcg ccgctggcct gctcatgggg ctgcgtcgct cacccctatct gtggcgccgc   120 gcgctgcgcg cggccgccgg gcccctggcc agggacaccc tctccccccga acccgcagcc   180 cgcgaggctc ctctcctgct gccctcgtgg gttcaggagc tgtgggagac gcgacgcagg   240
agctcccagg cagggatccc cgtccgtgcg ccccggagcc cgcgcgcccc agagcctgcg   300
ctggaaccgg agtccctgga cttcagcgga gctggccaga gacttcggag agacgtctcc   360
cgcccagcgg tggaccccgc agcaaaccgc cttggcctgc cctgcctggc ccccggaccg   420
ttctgacagc gtccccgcc cgcccgtggc gcctccgcgc ctgacccagg aggagtggcc   480
gcgcgcttcc aggagccgct catagacccc gcctgccgtc cggtcaataa aatccgcctg   540
actcctgcgc ccccgcatgc gtaaaaaaaa aaaaaaaaa aaaaaaaaaa agcggccgct   600
gaattctag                                                           609
```

<210> SEQ ID NO 39
<211> LENGTH: 24
<212> TYPE: DNA
<213> ORGANISM: Artificial Sequence
<220> FEATURE:
<223> OTHER INFORMATION: Primer

```
<400> SEQUENCE: 39
agcggtactg aggggcgga acga                                              24

<210> SEQ ID NO 40
<211> LENGTH: 24
<212> TYPE: DNA
<213> ORGANISM: Artificial Sequence
<220> FEATURE:
<223> OTHER INFORMATION: Primer

<400> SEQUENCE: 40
gggtctatga gcggctcctg gaag                                             24

<210> SEQ ID NO 41
<211> LENGTH: 719
<212> TYPE: DNA
<213> ORGANISM: Homo sapiens

<400> SEQUENCE: 41 ggcgggcca ccgagcggtt atagctgggc ctgcagggga cccacggctc gcctccagcc        60
tcctgcgctc cggtacctgg gcgtcccaac tccactgcgc gcccaaaccc agccgagccg      120
gttcgtggcc cgccccgccg ggcggccgtc gacgcgagcg ccctggcgtg cgcccagggg      180
gagcgggggg ctcccgcgag ccggccgcgg ctggcactgc tgctgcttct gctcctgctg      240
ccgctgccct ccggcgcgtg gtacaagcac gtggcgagtc cccgctacca cacggtgggc      300
cgcgccgctg gcctgctcat ggggctgcgt cgctcaccct atctgtggcg ccgcgcgctg      360
cgcgcggccg ccgggcccct ggccagggac accctctccc ccgaacccgc agcccgcgag      420
gctcctctcc tgctgccctc gtgggttcag gagctgtggg agacgcgacg caggagctcc      480
caggcaggga tccccgtccg tgcgccccgg agcccgcgcg cccagagccc tgcgctggaa      540
ccggagtccc tggacttcag cggagctggc cagagacttc ggagagacgt ctcccgccca      600
gcggtggacc ccgcagcaaa ccgccttggc ctgccctgcc tggccccggg accgttctga      660
cagcgtcccc cgcccgcccg tggcgcctcc gcgcctgacc caggaggagt ggccgcgcg      719

<210> SEQ ID NO 42
<211> LENGTH: 165
<212> TYPE: PRT
<213> ORGANISM: Homo sapiens

<400> SEQUENCE: 42

Leu Ala Trp Arg Pro Gly Glu Arg Gly Ala Pro Ala Ser Arg Pro Arg
 1               5                  10                  15

Leu Ala Leu Leu Leu Leu Leu Leu Leu Pro Leu Pro Ser Gly Ala
             20                  25                  30

Trp Tyr Lys His Val Ala Ser Pro Arg Tyr His Thr Val Gly Arg Ala
         35                  40                  45

Ala Gly Leu Leu Met Gly Leu Arg Arg Ser Pro Tyr Leu Trp Arg Arg
     50                  55                  60

Ala Leu Arg Ala Ala Ala Gly Pro Leu Ala Arg Asp Thr Leu Ser Pro
 65                  70                  75                  80

Glu Pro Ala Ala Arg Glu Ala Pro Leu Leu Leu Pro Ser Trp Val Gln
                 85                  90                  95

Glu Leu Trp Glu Thr Arg Arg Arg Ser Ser Gln Ala Gly Ile Pro Val
            100                 105                 110

Arg Ala Pro Arg Ser Pro Arg Ala Pro Glu Pro Ala Leu Glu Pro Glu
        115                 120                 125
```

Ser Leu Asp Phe Ser Gly Ala Gly Gln Arg Leu Arg Arg Asp Val Ser
    130                 135                 140

Arg Pro Ala Val Asp Pro Ala Ala Asn Arg Leu Gly Leu Pro Cys Leu
145                 150                 155                 160

Ala Pro Gly Pro Phe
            165

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
acagataggg tgagcgacgc agcc                                        24

<210> SEQ ID NO 44
<211> LENGTH: 24
<212> TYPE: DNA
<213> ORGANISM: Artificial Sequence
<220> FEATURE:
<223> OTHER INFORMATION: Primer

<400> SEQUENCE: 44
tgagcgacgc agccccatga gcag                                        24

<210> SEQ ID NO 45
<211> LENGTH: 235
<212> TYPE: DNA
<213> ORGANISM: Sus scrofa

<400> SEQUENCE: 45
cgacacccct gcgcccagac cctccggagc cagttcctgg tccgccccgc cgggagccgt    60
cagcatgaac ccccgggcac gcggcatggg agcgcggggc ccgggaccgg ggccactgc   120 gaggcgccgg ctgctggcat tgctgttact gctgctgctg ctgccgctgc ccgcccgtgc   180
ctggtacaag cacacggcga gtccccgcta ccacacggtg ggccgcgccg cgggc        235

<210> SEQ ID NO 46
<211> LENGTH: 24
<212> TYPE: DNA
<213> ORGANISM: Artificial Sequence
<220> FEATURE:
<223> OTHER INFORMATION: Primer

<400> SEQUENCE: 46
cagcggcagc agcagcagca gtaa                                        24

<210> SEQ ID NO 47
<211> LENGTH: 24
<212> TYPE: DNA
<213> ORGANISM: Artificial Sequence
<220> FEATURE:
<223> OTHER INFORMATION: Primer

<400> SEQUENCE: 47
cagcagtaac agcaatgcca gcag                                        24

<210> SEQ ID NO 48
<211> LENGTH: 156
<212> TYPE: DNA
<213> ORGANISM: Sus scrofa

<400> SEQUENCE: 48

```
ctgtagcctc cgcgctgcg gcttcccgac acccctgcgc ccagaccctc cggagccagt    60
tcctggtccg ccccgccggg agccgtcagc atgaaccccc gggcacgcgg catgggagcg   120
cggggcccgg gaccggggggc cactgcgagg cgccgg                            156
```

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49

```
cggctgctgg cattgctgtt actg                                          24
```

<210> SEQ ID NO 50
<211> LENGTH: 23
<212> TYPE: DNA
<213> ORGANISM: Artificial Sequence
<220> FEATURE:
<223> OTHER INFORMATION: Primer

<400> SEQUENCE: 50

```
cgcccgtgcc tggtacaagc aca                                           23
```

<210> SEQ ID NO 51
<211> LENGTH: 588
<212> TYPE: DNA
<213> ORGANISM: Sus scrofa

<400> SEQUENCE: 51

```
cggcgagtcc ccgctaccac acggtgggcc gcgccgcggg cctgctcatg gggctgcgcc    60
gctcgcccta catgtggcgc gcgcgctgc gcccggcggc cgggcccctg gcctgggaca   120
cttctcggcca ggacgtgccc cctcggggac cctccgccag gaacgccctc tctccggggc   180
ccgcccctcg cgacgctccg ctgcttcccc ccggggttca gacactgtgg caggtgcgac   240
gcggaagctt ccgctccggg atcccggtca gtgcgccccg cagcccgcgc gcccggggt   300
ccgagccgca accggaattg ggcgcctctt cctggacctc ggcggagtag accagagcct   360
tcggagagtc ttcagctcag cggtggtctg cgcagggaac cgccttcgcc agccccgcc   420
tcgcccagc gtcagagccg acctgatcgc ggccccggcg gcgcggcccc cgcgcctggcc   480
cccgcggagt ctcttcgcgc cccaggccg gccgtctggt caataaaacc cgcctagttc   540
ctgcgaaaaa aaaaaaaaaa aaaaaaaaaa aaaaaaaaaa aaaaaaaa                588
```

<210> SEQ ID NO 52
<211> LENGTH: 24
<212> TYPE: DNA
<213> ORGANISM: Artificial Sequence
<220> FEATURE:
<223> OTHER INFORMATION: Primer

<400> SEQUENCE: 52

```
ttcccgacac ccctgcgccc agac                                          24
```

<210> SEQ ID NO 53
<211> LENGTH: 24
<212> TYPE: DNA
<213> ORGANISM: Artificial Sequence
<220> FEATURE:

<223> OTHER INFORMATION: Primer

<400> SEQUENCE: 53
gggctggcga aggcggttcc ctgc                                              24

<210> SEQ ID NO 54
<211> LENGTH: 565
<212> TYPE: DNA
<213> ORGANISM: Sus scrofa

<400> SEQUENCE: 54
cctccggagc cagttcctgg tccgccccgc cgggagccgt cagcatgaac ccccgggcac        60
gcggcatggg agcgcggggc ccgggaccgg ggccactgc gaggcgccgg ctgctggcat       120
tgctgttact gctgctgctg ctgccgctgc ccgcccgtgc ctggtacaag cacacggcga       180
gtccccgcta ccacacggtg ggccgcgccg cgggcctgct catggggctg cgccgctcgc       240
cctacatgtg gcgccgcgcg ctgcgcccgg cggccgggcc cctggcctgg gacactttcg       300
gccaggacgt gccccctcgg ggaccctccg ccaggaacgc cctctctccg ggcccgccc       360 ctcgcgacgc tccgctgctt cccccgggg ttcagacact gtggcaggtg cgacgcggaa       420
gcttccgctc cgggatcccg gtcagtgcgc cccgcagccc gcgcgccgg gggtccgagc       480 cgcaaccgga attgggcgcc tcttcctgga cctcggcgga gtagaccaga gccttcggag       540
agtcttcagc tcagcggtgg tctgc                                            565

<210> SEQ ID NO 55
<211> LENGTH: 159
<212> TYPE: PRT
<213> ORGANISM: Sus scrofa

<400> SEQUENCE: 55

Met Asn Pro Arg Ala Arg Gly Met Gly Ala Arg Gly Pro Gly Pro Gly
1               5                   10                  15

Ala Thr Ala Arg Arg Arg Leu Leu Ala Leu Leu Leu Leu Leu Leu Leu
                20                  25                  30

Leu Pro Leu Pro Ala Arg Ala Trp Tyr Lys His Thr Ala Ser Pro Arg
        35                  40                  45

Tyr His Thr Val Gly Arg Ala Ala Gly Leu Leu Met Gly Leu Arg Arg
    50                  55                  60

Ser Pro Tyr Met Trp Arg Arg Ala Leu Arg Pro Ala Ala Gly Pro Leu
65                  70                  75                  80

Ala Trp Asp Thr Phe Gly Gln Asp Val Pro Pro Arg Gly Pro Ser Ala
                85                  90                  95

Arg Asn Ala Leu Ser Pro Gly Pro Ala Pro Arg Asp Ala Pro Leu Leu
            100                 105                 110

Pro Pro Gly Val Gln Thr Leu Trp Gln Val Arg Arg Gly Ser Phe Arg
        115                 120                 125

Ser Gly Ile Pro Val Ser Ala Pro Arg Ser Pro Arg Ala Arg Gly Ser
    130                 135                 140

Glu Pro Gln Pro Glu Leu Gly Ala Ser Ser Trp Thr Ser Ala Glu
145                 150                 155

<210> SEQ ID NO 56
<211> LENGTH: 23
<212> TYPE: PRT
<213> ORGANISM: Sus scrofa

<400> SEQUENCE: 56

Trp Tyr Lys His Thr Ala Ser Pro Arg Tyr His Thr Val Gly Arg Ala
1               5                   10                  15

Ala Gly Leu Leu Met Gly Leu
            20

<210> SEQ ID NO 57
<211> LENGTH: 30
<212> TYPE: PRT
<213> ORGANISM: Sus scrofa

<400> SEQUENCE: 57

Trp Tyr Lys His Thr Ala Ser Pro Arg Tyr His Thr Val Gly Arg Ala
1               5                   10                  15

Ala Gly Leu Leu Met Gly Leu Arg Arg Ser Pro Tyr Met Trp
            20                  25                  30

<210> SEQ ID NO 58
<211> LENGTH: 69
<212> TYPE: DNA
<213> ORGANISM: Sus scrofa

<400> SEQUENCE: 58
tggtacaagc acacggcgag tccccgctac cacacggtgg gccgcgccgc gggcctgctc      60
atggggctg                                                              69

<210> SEQ ID NO 59
<211> LENGTH: 90
<212> TYPE: DNA
<213> ORGANISM: Sus scrofa

<400> SEQUENCE: 59
tggtacaagc acacggcgag tccccgctac cacacggtgg gccgcgccgc gggcctgctc      60
atggggctgc gccgctcgcc ctacatgtgg                                       90

<210> SEQ ID NO 60
<211> LENGTH: 23
<212> TYPE: DNA
<213> ORGANISM: Artificial Sequence
<220> FEATURE:
<223> OTHER INFORMATION: Primer

<400> SEQUENCE: 60
cgttctcggg gacataaacc ctg                                              23

<210> SEQ ID NO 61
<211> LENGTH: 23
<212> TYPE: DNA
<213> ORGANISM: Artificial Sequence
<220> FEATURE:
<223> OTHER INFORMATION: Primer

<400> SEQUENCE: 61
atgagcagcc cggaggcacg acc                                              23

<210> SEQ ID NO 62
<211> LENGTH: 188
<212> TYPE: DNA
<213> ORGANISM: Rattus norvegicus

<400> SEQUENCE: 62
ttcttgtcct aacccgccaa ggggccatgg acttgagcgc gctggcgtcg agcagagaag      60

```
tacggggccc tgggcccggg gctccggtga accggcccct gctaccgcta ctgctgcttc    120
tgctcttgct acctctgccc gccagcgcct ggtacaagca cgtggcgagc cctcgctatc    180
acacagtg                                                              188

<210> SEQ ID NO 63
<211> LENGTH: 23
<212> TYPE: DNA
<213> ORGANISM: Artificial Sequence
<220> FEATURE:
<223> OTHER INFORMATION: Primer

<400> SEQUENCE: 63
atgagcagcc cggaggcacg acc                                              23

<210> SEQ ID NO 64
<211> LENGTH: 23
<212> TYPE: DNA
<213> ORGANISM: Artificial Sequence
<220> FEATURE:
<223> OTHER INFORMATION: Primer

<400> SEQUENCE: 64
actgtgtgat agcgagggct cgc                                              23

<210> SEQ ID NO 65
<211> LENGTH: 615
<212> TYPE: DNA
<213> ORGANISM: Rattus norvegicus

<400> SEQUENCE: 65
ctcagagctg tactaggcag gaagagggac ggccctcagg gaagggtggc cctatgctta     60
aaactttcct gtctcctctc cataagtgct ccacttgtag caactcctac caaggggca    120 tccttttgcc cctggcagcc catccttgta ttctgagacc atgcatggta ccagaactcc   180
ctccctgaca gttcccttcc tggggcgag gaaagggtaa gcaaggagat cccccactaa    240
agcttcaagc gcagtccagc ttgcgatcta ctcattggga ggcttctagc tacccgggtt    300
ccctcttctc cctccctctc catcctcctc tcccttgggc atgtgccgcg ggggcgagcc    360 ggggcgggc cattgagaag ctgtagtcgc accaactgac tagtctcttc catcctccgg    420
agctccgacg ttctcgggga cataaaccct gttcttgtcc taacccgcca aggggccatg    480
gacttgagcg cgctggcgtc gagcagagaa gtacggggcc ctgggccgg ggctccggtg    540 aaccggcccc tgctaccgct actgctgctt ctgctcttgc tacctctgcc cgccagcgcc    600
tggtacaagc acgtg                                                     615

<210> SEQ ID NO 66
<211> LENGTH: 23
<212> TYPE: DNA
<213> ORGANISM: Artificial Sequence
<220> FEATURE:
<223> OTHER INFORMATION: Primer

<400> SEQUENCE: 66
cgttctcggg gacataaacc ctg                                              23

<210> SEQ ID NO 67
<211> LENGTH: 24
<212> TYPE: DNA
<213> ORGANISM: Artificial Sequence
<220> FEATURE:
<223> OTHER INFORMATION: Primer
```

```
<400> SEQUENCE: 67
cgagccctcg ctatcacaca gtgg                                            24

<210> SEQ ID NO 68
<211> LENGTH: 497
<212> TYPE: DNA
<213> ORGANISM: Rattus norvegicus

<400> SEQUENCE: 68
gtcgtgcctc cgggctgctc atggggctgc gccgctcgcc ctacctgtgg cgccgtgcct      60
tgggtggggc cgctggaccg ctcgtggggc tcccgggaca gatggcccgc agcgctctcc     120
tgcttccttc ccccgggcag gagctgtggg aggtacgaag caggagttca ccggcaggac     180
ttcccgtgca tgcaacccgg agtctgcggg acctggaggg agccggccaa cctgagcagt     240
cgctaagctt tcagtcctgg acttcagcag agcccgctgc tagagccttc ggtgagacgc     300
ttcgtgccca gccatggttc ctgcagcaaa tcatctttgc cgatcctgtc aggctcgacg     360
accgtctcaa gaaccgatgg cgcccccgtg cttgacctaa gcaggagcac agcttgtagc     420
tccagtcagg tctcgttgtc tggtcaataa aatcactctg attcccaaaa aaaaaaaaaa     480
aaaaaaaaaa aaaaaaa                                                   497

<210> SEQ ID NO 69
<211> LENGTH: 21
<212> TYPE: DNA
<213> ORGANISM: Artificial Sequence
<220> FEATURE:
<223> OTHER INFORMATION: Primer

<400> SEQUENCE: 69
ggggcggggc cattgagaag c                                               21

<210> SEQ ID NO 70
<211> LENGTH: 21
<212> TYPE: DNA
<213> ORGANISM: Artificial Sequence
<220> FEATURE:
<223> OTHER INFORMATION: Primer

<400> SEQUENCE: 70
tgaccagaca acgagacctg a                                               21

<210> SEQ ID NO 71
<211> LENGTH: 684
<212> TYPE: DNA
<213> ORGANISM: Rattus norvegicus

<400> SEQUENCE: 71
tgtagtcgca ccaactgact agtctcttcc atcctccgga gctccgacgt tctcggggac      60
ataaaccctg ttcttgtcct aacccgccaa ggggccatgg acttgagcgc gctggcgtcg     120
agcagagaag tacggggccc tgggcccggg gctccggtga accggcccct gctaccgcta     180
ctgctgcttc tgctcttgct acctctgccc gccagcgcct ggtacaagca cgtggcgagc     240
cctcgctatc acacagtggg tcgtgcctcc gggctgctca tggggctgcg ccgctcgccc     300
tacctgtggc gccgtgcctt gggtggggcc gctggaccgc tcgtggggct cccggacag     360 atggcccgca gcgctctcct gcttccttcc cccgggcagg agctgtggga ggtacgaagc     420
aggagttcac cggcaggact tcccgtgcat gcaacccgga gtctgcggga cctggaggga     480
```

```
gccggccaac ctgagcagtc gctaagcttt cagtcctgga cttcagcaga gcccgctgct    540
agagccttcg gtgagacgct tcgtgcccag ccatggttcc tgcagcaaat catctttgcc    600
gatcctgtca ggctcgacga ccgtctcaag aaccgatggc gcccccgtgc ttgacctaag    660
caggagcaca gcttgtagct ccag                                           684
```

<210> SEQ ID NO 72
<211> LENGTH: 185
<212> TYPE: PRT
<213> ORGANISM: Rattus norvegicus

<400> SEQUENCE: 72

```
Met Asp Leu Ser Ala Leu Ala Ser Ser Arg Glu Val Arg Gly Pro Gly
1               5                   10                  15

Pro Gly Ala Pro Val Asn Arg Pro Leu Pro Leu Leu Leu Leu Leu
            20                  25                  30

Leu Leu Leu Pro Leu Pro Ala Ser Ala Trp Tyr Lys His Val Ala Ser
        35                  40                  45

Pro Arg Tyr His Thr Val Gly Arg Ala Ser Gly Leu Leu Met Gly Leu
    50                  55                  60

Arg Arg Ser Pro Tyr Leu Trp Arg Arg Ala Leu Gly Ala Ala Gly
65                  70                  75                  80

Pro Leu Val Gly Leu Pro Gly Gln Met Ala Arg Ser Ala Leu Leu Leu
                85                  90                  95

Pro Ser Pro Gly Gln Glu Leu Trp Glu Val Arg Ser Arg Ser Ser Pro
            100                 105                 110

Ala Gly Leu Pro Val His Ala Thr Arg Ser Leu Arg Asp Leu Glu Gly
        115                 120                 125

Ala Gly Gln Pro Glu Gln Ser Leu Ser Phe Gln Ser Trp Thr Ser Ala
    130                 135                 140

Glu Pro Ala Ala Arg Ala Phe Gly Glu Thr Leu Arg Ala Gln Pro Trp
145                 150                 155                 160

Phe Leu Gln Gln Ile Ile Phe Ala Asp Pro Val Arg Leu Asp Asp Arg
                165                 170                 175

Leu Lys Asn Arg Trp Arg Pro Arg Ala
            180                 185
```

<210> SEQ ID NO 73
<211> LENGTH: 23
<212> TYPE: PRT
<213> ORGANISM: Rattus norvegicus

<400> SEQUENCE: 73

```
Trp Tyr Lys His Val Ala Ser Pro Arg Tyr His Thr Val Gly Arg Ala
1               5                   10                  15

Ser Gly Leu Leu Met Gly Leu
            20
```

<210> SEQ ID NO 74
<211> LENGTH: 30
<212> TYPE: PRT
<213> ORGANISM: Rattus norvegicus

<400> SEQUENCE: 74

```
Trp Tyr Lys His Val Ala Ser Pro Arg Tyr His Thr Val Gly Arg Ala
1               5                   10                  15

Ser Gly Leu Leu Met Gly Leu Arg Arg Ser Pro Tyr Leu Trp
            20                  25                  30
```

<210> SEQ ID NO 75
<211> LENGTH: 69
<212> TYPE: DNA
<213> ORGANISM: Rattus norvegicus

<400> SEQUENCE: 75

```
tggtacaagc acgtggcgag ccctcgctat cacacagtgg gtcgtgcctc cgggctgctc    60
atggggctg                                                            69
```

<210> SEQ ID NO 76
<211> LENGTH: 90
<212> TYPE: DNA
<213> ORGANISM: Rattus norvegicus

<400> SEQUENCE: 76

```
tggtacaagc acgtggcgag ccctcgctat cacacagtgg gtcgtgcctc cgggctgctc    60
atggggctgc gccgctcgcc ctacctgtgg                                     90
```

<210> SEQ ID NO 77
<211> LENGTH: 23
<212> TYPE: DNA
<213> ORGANISM: Artificial Sequence
<220> FEATURE:
<223> OTHER INFORMATION: Probe

<400> SEQUENCE: 77

```
ttcatcctca acctggccat cgc                                            23
```

<210> SEQ ID NO 78
<211> LENGTH: 24
<212> TYPE: DNA
<213> ORGANISM: Artificial Sequence
<220> FEATURE:
<223> OTHER INFORMATION: Primer

<400> SEQUENCE: 78

```
acccagttct tgtcctaacc ctcc                                           24
```

<210> SEQ ID NO 79
<211> LENGTH: 24
<212> TYPE: DNA
<213> ORGANISM: Artificial Sequence
<220> FEATURE:
<223> OTHER INFORMATION: Primer

<400> SEQUENCE: 79

```
cctgcttcgt acctcccaca gctc                                           24
```

<210> SEQ ID NO 80
<211> LENGTH: 311
<212> TYPE: DNA
<213> ORGANISM: Mus musculus

<400> SEQUENCE: 80

```
aagggggcaat tgacgtgagc gcgctggcgt ctaacagaga agtacggggc cctgggcccg    60
ggactcccag gaaccggccc ctgctgcccc tgctgctgct tctgctcttg ctaccgctgc   120
ccgccagcgc ctggtataag cacgtggcga gtccccgcta tcacacagtg ggtcgtgcct   180
ccgggctgct catggggctg cgccgctcgc cctaccagtg gcgccgtgcc ctgggcgggg   240
ctgctggacc cctctcccgg ctcccaggac cggtcgcccg cggcgctctc ctgcttcctt   300
```

-continued

| cctcagggca g | 311 |

```
<210> SEQ ID NO 81
<211> LENGTH: 24
<212> TYPE: DNA
<213> ORGANISM: Artificial Sequence
<220> FEATURE:
<223> OTHER INFORMATION: Primer

<400> SEQUENCE: 81
```

| catgagcagc ccggaggcac gacc | 24 |

```
<210> SEQ ID NO 82
<211> LENGTH: 24
<212> TYPE: DNA
<213> ORGANISM: Artificial Sequence
<220> FEATURE:
<223> OTHER INFORMATION: Primer

<400> SEQUENCE: 82
```

| gtgatagcgg ggactcgcca cgtg | 24 |

```
<210> SEQ ID NO 83
<211> LENGTH: 237
<212> TYPE: DNA
<213> ORGANISM: Mus musculus

<400> SEQUENCE: 83
```

| aaaggctgta gtcgcaccaa ctgactggtc tccatcctct ggagctccga cgtgctcgtt | 60 |
| ctcggagaca taaacccagt tcttgtccta accctccaag gggcaattga cgtgagcgcg | 120 |
| ctggcgtcta acagagaagt acggggccct gggcccggga ctcccaggaa ccggcccctg | 180 |
| ctgcccctgc tgctgcttct gctcttgcta ccgctgcccg ccagcgcctg gtataag | 237 |

```
<210> SEQ ID NO 84
<211> LENGTH: 24
<212> TYPE: DNA
<213> ORGANISM: Artificial Sequence
<220> FEATURE:
<223> OTHER INFORMATION: Primer

<400> SEQUENCE: 84
```

| acccagttct tgtcctaacc ctcc | 24 |

```
<210> SEQ ID NO 85
<211> LENGTH: 24
<212> TYPE: DNA
<213> ORGANISM: Artificial Sequence
<220> FEATURE:
<223> OTHER INFORMATION: Primer

<400> SEQUENCE: 85
```

| gggcaattga cgtgagcgcg ctgg | 24 |

```
<210> SEQ ID NO 86
<211> LENGTH: 598
<212> TYPE: DNA
<213> ORGANISM: Mus musculus

<400> SEQUENCE: 86
```

| cgtctaacag agaagtacgg ggccctgggc ccgggactcc caggaaccgg cccctgctgc | 60 |
| ccctgctgct gcttctgctc ttgctaccgc tgcccgccag cgcctggtat aagcacgtgg | 120 |
| cgagtccccg ctatcacaca gtgggtcgtg cctccgggct gctcatgggg ctgcgccgct | 180 |

```
cgccctacca gtggcgccgt gccctgggcg gggctgctgg acccctctcc cggctcccag     240
gaccggtcgc ccgcggcgct ctcctgcttc cttcctcagg gcaggagctg tgggaggtac     300
gaagcaggag ctcacctgca gggcttcccg tccatgcacc ctggagtccg cgggacctgg     360
agggagtccg ccaaccggag cagtcgctaa gccttcactc ctggatctca gaggagcccg     420
ctgctagagc cttcggagag acgcttcgtg cccagccatg gttcctgcag caagtcatct     480
ttgccgatcc tgtcaggccc aagaaccgat ggcgccccca tgcttgacct aggcaggagc     540
acagcttgaa gctccagtca ggcctcgtgt ttctggtcaa taaaaccaac ctgattcc       598
```

<210> SEQ ID NO 87
<211> LENGTH: 21
<212> TYPE: DNA
<213> ORGANISM: Artificial Sequence
<220> FEATURE:
<223> OTHER INFORMATION: Primer

<400> SEQUENCE: 87

```
aaaggctgta gtcgcaccaa c                                                21
```

<210> SEQ ID NO 88
<211> LENGTH: 21
<212> TYPE: DNA
<213> ORGANISM: Artificial Sequence
<220> FEATURE:
<223> OTHER INFORMATION: Primer

<400> SEQUENCE: 88

```
accagaaaca cgaggcctga c                                                21
```

<210> SEQ ID NO 89
<211> LENGTH: 659
<212> TYPE: DNA
<213> ORGANISM: Mus musculus

<400> SEQUENCE: 89

```
tgactggtct ccatcctctg gagctccgac gtgctcgttc tcggagacat aaacccagtt      60
cttgtcctaa ccctccaagg ggcaattgac gtgagcgcgc tggcgtctaa cagagaagta     120
cggggccctg ggcccgggac tcccaggaac cggcccctgc tgcccctgct gctgcttctg     180
ctcttgctac cgctgcccgc cagcgcctgg tataagcacg tggcgagtcc ccgctatcac     240
acagtgggtc gtgcctccgg gctgctcatg gggctgcgcc gctcgcccta ccagtggcgc     300
cgtgccctgg gcgggctgc tggacccctc tcccggctcc caggaccggt cgcccgcggc     360
gctctcctgc ttccttcctc agggcaggag ctgtgggagg tacgaagcag gagctcacct     420
gcagggcttc ccgtccatgc accctggagt ccgcgggacc tggagggagt ccgccaaccg     480
gagcagtcgc taagccttca ctcctggatc tcagaggagc ccgctgctag agccttcgga     540
gagacgcttc gtgcccagcc atggttcctg cagcaagtca tctttgccga tcctgtcagg     600
cccaagaacc gatggcgccc ccatgcttga cctaggcagg agcacagctt gaagctcca      659
```

<210> SEQ ID NO 90
<211> LENGTH: 176
<212> TYPE: PRT
<213> ORGANISM: Mus musculus

<400> SEQUENCE: 90

```
Leu Ala Ser Asn Arg Glu Val Arg Gly Pro Gly Pro Gly Thr Pro Arg
1               5                   10                  15
```

```
Asn Arg Pro Leu Leu Pro Leu Leu Leu Leu Leu Leu Pro Leu
            20                  25                  30

Pro Ala Ser Ala Trp Tyr Lys His Val Ala Ser Pro Arg Tyr His Thr
            35                  40                  45

Val Gly Arg Ala Ser Gly Leu Leu Met Gly Leu Arg Arg Ser Pro Tyr
50                  55                  60

Gln Trp Arg Arg Ala Leu Gly Gly Ala Ala Gly Pro Leu Ser Arg Leu
65                  70                  75                  80

Pro Gly Pro Val Ala Arg Gly Ala Leu Leu Leu Pro Ser Ser Gly Gln
                85                  90                  95

Glu Leu Trp Glu Val Arg Ser Arg Ser Ser Pro Ala Gly Leu Pro Val
            100                 105                 110

His Ala Pro Trp Ser Pro Arg Asp Leu Glu Gly Val Arg Gln Pro Glu
            115                 120                 125

Gln Ser Leu Ser Leu His Ser Trp Ile Ser Glu Pro Ala Ala Arg
        130                 135                 140

Ala Phe Gly Glu Thr Leu Arg Ala Gln Pro Trp Phe Leu Gln Gln Val
145                 150                 155                 160

Ile Phe Ala Asp Pro Val Arg Pro Lys Asn Arg Trp Arg Pro His Ala
                165                 170                 175
```

<210> SEQ ID NO 91
<211> LENGTH: 23
<212> TYPE: PRT
<213> ORGANISM: Mus musculus

<400> SEQUENCE: 91

```
Trp Tyr Lys His Val Ala Ser Pro Arg Tyr His Thr Val Gly Arg Ala
1               5                   10                  15

Ser Gly Leu Leu Met Gly Leu
            20
```

<210> SEQ ID NO 92
<211> LENGTH: 30
<212> TYPE: PRT
<213> ORGANISM: Mus musculus

<400> SEQUENCE: 92

```
Trp Tyr Lys His Val Ala Ser Pro Arg Tyr His Thr Val Gly Arg Ala
1               5                   10                  15

Ser Gly Leu Leu Met Gly Leu Arg Arg Ser Pro Tyr Gln Trp
            20                  25                  30
```

<210> SEQ ID NO 93
<211> LENGTH: 69
<212> TYPE: DNA
<213> ORGANISM: Mus musculus

<400> SEQUENCE: 93
tggtataagc acgtggcgag tccccgctat cacacagtgg gtcgtgcctc cgggctgctc        60
atggggctg                                                                69

<210> SEQ ID NO 94
<211> LENGTH: 90
<212> TYPE: DNA
<213> ORGANISM: Mus musculus

<400> SEQUENCE: 94

-continued

```
tggtataagc acgtggcgag tccccgctat cacacagtgg gtcgtgcctc cgggctgctc    60
atggggctgc gccgctcgcc ctaccagtgg                                     90
```

<210> SEQ ID NO 95
<211> LENGTH: 23
<212> TYPE: PRT
<213> ORGANISM: Artificial Sequence
<220> FEATURE:
<221> NAME/KEY: Human GPR8 ligand (1-23) oxidant
<222> LOCATION: 21
<223> OTHER INFORMATION: Xaa is Met(O)

<400> SEQUENCE: 95

Trp Tyr Lys His Val Ala Ser Pro Arg Tyr His Thr Val Gly Arg Ala
1               5                   10                  15

Ala Gly Leu Leu Xaa Gly Leu
            20

<210> SEQ ID NO 96
<211> LENGTH: 22
<212> TYPE: PRT
<213> ORGANISM: Homo sapiens

<400> SEQUENCE: 96

Trp Tyr Lys His Val Ala Ser Pro Arg Tyr His Thr Val Gly Arg Ala
1               5                   10                  15

Ala Gly Leu Leu Met Gly
            20

<210> SEQ ID NO 97
<211> LENGTH: 21
<212> TYPE: PRT
<213> ORGANISM: Homo sapiens

<400> SEQUENCE: 97

Trp Tyr Lys His Val Ala Ser Pro Arg Tyr His Thr Val Gly Arg Ala
1               5                   10                  15

Ala Gly Leu Leu Met
            20

<210> SEQ ID NO 98
<211> LENGTH: 20
<212> TYPE: PRT
<213> ORGANISM: Homo sapiens

<400> SEQUENCE: 98

Trp Tyr Lys His Val Ala Ser Pro Arg Tyr His Thr Val Gly Arg Ala
1               5                   10                  15

Ala Gly Leu Leu
            20

<210> SEQ ID NO 99
<211> LENGTH: 19
<212> TYPE: PRT
<213> ORGANISM: Homo sapiens

<400> SEQUENCE: 99

Trp Tyr Lys His Val Ala Ser Pro Arg Tyr His Thr Val Gly Arg Ala
1               5                   10                  15

Ala Gly Leu

<210> SEQ ID NO 100

-continued

```
<211> LENGTH: 18
<212> TYPE: PRT
<213> ORGANISM: Homo sapiens

<400> SEQUENCE: 100

Trp Tyr Lys His Val Ala Ser Pro Arg Tyr His Thr Val Gly Arg Ala
1               5                   10                  15

Ala Gly

<210> SEQ ID NO 101
<211> LENGTH: 17
<212> TYPE: PRT
<213> ORGANISM: Homo sapiens

<400> SEQUENCE: 101

Trp Tyr Lys His Val Ala Ser Pro Arg Tyr His Thr Val Gly Arg Ala
1               5                   10                  15

Ala

<210> SEQ ID NO 102
<211> LENGTH: 16
<212> TYPE: PRT
<213> ORGANISM: Homo sapiens

<400> SEQUENCE: 102

Trp Tyr Lys His Val Ala Ser Pro Arg Tyr His Thr Val Gly Arg Ala
1               5                   10                  15

<210> SEQ ID NO 103
<211> LENGTH: 23
<212> TYPE: PRT
<213> ORGANISM: Artificial Sequence
<220> FEATURE:
<221> NAME/KEY: Porcine GPR8 ligand (1-23) oxidant
<222> LOCATION: 21
<223> OTHER INFORMATION: Xaa is Met(O)

<400> SEQUENCE: 103

Trp Tyr Lys His Thr Ala Ser Pro Arg Tyr His Thr Val Gly Arg Ala
1               5                   10                  15

Ala Gly Leu Leu Xaa Gly Leu
            20

<210> SEQ ID NO 104
<211> LENGTH: 23
<212> TYPE: PRT
<213> ORGANISM: Artificial Sequence
<220> FEATURE:
<221> NAME/KEY: Rat/mouse GPR8 ligand (1-23) oxidant
<222> LOCATION: 21
<223> OTHER INFORMATION: Xaa is Met(O)

<400> SEQUENCE: 104

Trp Tyr Lys His Val Ala Ser Pro Arg Tyr His Thr Val Gly Arg Ala
1               5                   10                  15

Ser Gly Leu Leu Xaa Gly Leu
            20

<210> SEQ ID NO 105
<211> LENGTH: 23
<212> TYPE: PRT
<213> ORGANISM: Artificial Sequence
<220> FEATURE:
<221> NAME/KEY: Fmoc-added human GPR8L (1-23)
<222> LOCATION: 1
```

```
<223> OTHER INFORMATION: Xaa is Fmoc-Trp

<400> SEQUENCE: 105

Xaa Tyr Lys His Val Ala Ser Pro Arg Tyr His Thr Val Gly Arg Ala
1               5                   10                  15

Ala Gly Leu Leu Met Gly Leu
            20

<210> SEQ ID NO 106
<211> LENGTH: 23
<212> TYPE: PRT
<213> ORGANISM: Artificial Sequence
<220> FEATURE:
<221> NAME/KEY: [Na-Acetyl-Trp1]-human GPR8 ligand (1-23)
<222> LOCATION: 1
<223> OTHER INFORMATION: Xaa is Ac-Trp

<400> SEQUENCE: 106

Xaa Tyr Lys His Val Ala Ser Pro Arg Tyr His Thr Val Gly Arg Ala
1               5                   10                  15

Ala Gly Leu Leu Met Gly Leu
            20

<210> SEQ ID NO 107
<211> LENGTH: 22
<212> TYPE: PRT
<213> ORGANISM: Homo sapiens

<400> SEQUENCE: 107

Tyr Lys His Val Ala Ser Pro Arg Tyr His Thr Val Gly Arg Ala Ala
1               5                   10                  15

Gly Leu Leu Met Gly Leu
            20

<210> SEQ ID NO 108
<211> LENGTH: 20
<212> TYPE: PRT
<213> ORGANISM: Homo sapiens

<400> SEQUENCE: 108

His Val Ala Ser Pro Arg Tyr His Thr Val Gly Arg Ala Ala Gly Leu
1               5                   10                  15

Leu Met Gly Leu
            20

<210> SEQ ID NO 109
<211> LENGTH: 15
<212> TYPE: PRT
<213> ORGANISM: Homo sapiens

<400> SEQUENCE: 109

Arg Tyr His Thr Val Gly Arg Ala Ala Gly Leu Leu Met Gly Leu
1               5                   10                  15

<210> SEQ ID NO 110
<211> LENGTH: 9
<212> TYPE: PRT
<213> ORGANISM: Homo sapiens

<400> SEQUENCE: 110

Arg Ala Ala Gly Leu Leu Met Gly Leu
1               5
```

<210> SEQ ID NO 111
<211> LENGTH: 22
<212> TYPE: PRT
<213> ORGANISM: Artificial Sequence
<220> FEATURE:
<221> NAME/KEY: [N-Acetyl-Tyr2]-human GPR8 ligand (2-23)
<222> LOCATION: 1
<223> OTHER INFORMATION: Xaa is Ac-Tyr

<400> SEQUENCE: 111

Xaa Lys His Val Ala Ser Pro Arg Tyr His Thr Val Gly Arg Ala Ala
1               5                   10                  15

Gly Leu Leu Met Gly Leu
            20

<210> SEQ ID NO 112
<211> LENGTH: 23
<212> TYPE: PRT
<213> ORGANISM: Artificial Sequence
<220> FEATURE:
<221> NAME/KEY: [D-Trp1]-human GPR8 ligand (1-23)
<222> LOCATION: 1
<223> OTHER INFORMATION: Xaa is D-Trp

<400> SEQUENCE: 112

Xaa Tyr Lys His Val Ala Ser Pro Arg Tyr His Thr Val Gly Arg Ala
1               5                   10                  15

Ala Gly Leu Leu Met Gly Leu
            20

<210> SEQ ID NO 113
<211> LENGTH: 22
<212> TYPE: PRT
<213> ORGANISM: Artificial Sequence
<220> FEATURE:
<221> NAME/KEY: [N-3-Indolepropanoyl-Tyr2]-human GPR8 ligand (2-23)
<222> LOCATION: 1
<223> OTHER INFORMATION: Xaa is 3-Indolepropanoyl-Tyr

<400> SEQUENCE: 113

Xaa Lys His Val Ala Ser Pro Arg Tyr His Thr Val Gly Arg Ala Ala
1               5                   10                  15

Gly Leu Leu Met Gly Leu
            20

<210> SEQ ID NO 114
<211> LENGTH: 66
<212> TYPE: DNA
<213> ORGANISM: Homo sapiens

<400> SEQUENCE: 114
tggtacaagc acgtggcgag tccccgctac cacacggtgg gccgcgccgc tggcctgctc      60
atgggg                                                                66

<210> SEQ ID NO 115
<211> LENGTH: 63
<212> TYPE: DNA
<213> ORGANISM: Homo sapiens

<400> SEQUENCE: 115
tggtacaagc acgtggcgag tccccgctac cacacggtgg gccgcgccgc tggcctgctc      60
atg                                                                   63

<210> SEQ ID NO 116

```
<211> LENGTH: 60
<212> TYPE: DNA
<213> ORGANISM: Homo sapiens

<400> SEQUENCE: 116
tggtacaagc acgtggcgag tccccgctac cacacggtgg gccgcgccgc tggcctgctc      60

<210> SEQ ID NO 117
<211> LENGTH: 57
<212> TYPE: DNA
<213> ORGANISM: Homo sapiens

<400> SEQUENCE: 117
tggtacaagc acgtggcgag tccccgctac cacacggtgg gccgcgccgc tggcctg         57

<210> SEQ ID NO 118
<211> LENGTH: 54
<212> TYPE: DNA
<213> ORGANISM: Homo sapiens

<400> SEQUENCE: 118
tggtacaagc acgtggcgag tccccgctac cacacggtgg gccgcgccgc tggc            54

<210> SEQ ID NO 119
<211> LENGTH: 51
<212> TYPE: DNA
<213> ORGANISM: Homo sapiens

<400> SEQUENCE: 119
tggtacaagc acgtggcgag tccccgctac cacacggtgg gccgcgccgc t               51

<210> SEQ ID NO 120
<211> LENGTH: 48
<212> TYPE: DNA
<213> ORGANISM: Homo sapiens

<400> SEQUENCE: 120
tggtacaagc acgtggcgag tccccgctac cacacggtgg gccgcgcc                   48

<210> SEQ ID NO 121
<211> LENGTH: 66
<212> TYPE: DNA
<213> ORGANISM: Homo sapiens

<400> SEQUENCE: 121
tacaagcacg tggcgagtcc ccgctaccac acggtgggcc gcgccgctgg cctgctcatg      60
gggctg                                                                66

<210> SEQ ID NO 122
<211> LENGTH: 60
<212> TYPE: DNA
<213> ORGANISM: Homo sapiens

<400> SEQUENCE: 122
cacgtggcga gtccccgcta ccacacggtg ggccgcgccg ctggcctgct catggggctg      60

<210> SEQ ID NO 123
<211> LENGTH: 45
<212> TYPE: DNA
<213> ORGANISM: Homo sapiens

<400> SEQUENCE: 123
cgctaccaca cggtgggccg cgccgctggc ctgctcatgg ggctg                      45
```

<210> SEQ ID NO 124
<211> LENGTH: 27
<212> TYPE: DNA
<213> ORGANISM: Homo sapiens

<400> SEQUENCE: 124
cgcgccgctg gcctgctcat ggggctg                               27

<210> SEQ ID NO 125
<211> LENGTH: 51
<212> TYPE: DNA
<213> ORGANISM: Sus scrofa

<400> SEQUENCE: 125
tggtacaagc acacggcgag tccccgctac cacacggtgg gccgcgccgc g    51

<210> SEQ ID NO 126
<211> LENGTH: 329
<212> TYPE: PRT
<213> ORGANISM: Rattus norvegicus

<400> SEQUENCE: 126

Met His Asn Leu Ser Leu Phe Glu Pro Gly Arg Gly Asn Val Ser Cys
            5                   10                  15

Gly Gly Pro Phe Leu Gly Cys Pro Asn Glu Ser Asn Pro Ala Pro Leu
        20                  25                  30

Pro Leu Pro Gln Pro Leu Ala Val Ala Val Pro Val Val Tyr Gly Val
    35                  40                  45

Ile Cys Ala Val Gly Leu Ala Gly Asn Ser Ala Val Leu Tyr Val Leu
50                  55                  60

Leu Arg Thr Pro Arg Met Lys Thr Val Thr Asn Val Phe Ile Leu Asn
65                  70                  75                  80

Leu Ala Ile Ala Asp Glu Leu Phe Thr Leu Val Leu Pro Ile Asn Ile
                85                  90                  95

Ala Asp Phe Leu Leu Arg Arg Trp Pro Phe Gly Glu Val Met Cys Lys
            100                 105                 110

Leu Ile Val Ala Val Asp Gln Tyr Asn Thr Phe Ser Ser Leu Tyr Phe
        115                 120                 125

Leu Ala Val Met Ser Ala Asp Arg Tyr Leu Val Val Leu Ala Thr Ala
    130                 135                 140

Glu Ser Arg Arg Val Ser Gly Arg Thr Tyr Gly Ala Ala Arg Ala Val
145                 150                 155                 160

Ser Leu Ala Val Trp Ala Leu Val Thr Leu Val Val Leu Pro Phe Ala
                165                 170                 175

Val Phe Ala Arg Leu Asp Glu Glu Gln Gly Arg Arg Gln Cys Val Leu
            180                 185                 190

Val Phe Pro Gln Pro Glu Ala Phe Trp Trp Arg Ala Ser Arg Leu Tyr
        195                 200                 205

Thr Leu Val Leu Gly Phe Ala Ile Pro Val Ser Thr Ile Cys Ala Leu
    210                 215                 220

Tyr Ile Thr Leu Leu Cys Arg Leu Arg Ala Ile Gln Leu Asp Ser His
225                 230                 235                 240

Ala Lys Ala Leu Asp Arg Ala Lys Lys Arg Val Thr Leu Leu Val Val
                245                 250                 255

Ala Ile Leu Ala Val Cys Leu Leu Cys Trp Thr Pro Tyr His Leu Ser
            260                 265                 270

```
Thr Ile Val Ala Leu Thr Thr Asp Leu Pro Gln Thr Pro Leu Val Ile
        275                 280                 285

Gly Ile Ser Tyr Phe Ile Thr Ser Leu Ser Tyr Ala Asn Ser Cys Leu
        290                 295                 300

Asn Pro Phe Leu Tyr Ala Phe Leu Asp Asp Ser Phe Arg Arg Ser Leu
305                 310                 315                 320

Arg Gln Leu Val Ser Cys Arg Thr Ala
                325

<210> SEQ ID NO 127
<211> LENGTH: 987
<212> TYPE: DNA
<213> ORGANISM: Rattus norvegicus

<400> SEQUENCE: 127
atgcacaact tgtcgctctt cgagcctggc aggggcaatg tgtcttgcgg cggcccattt      60
ttgggctgtc ctaacgagtc gaacccagcg cctctgccac tgccgcagcc tctggcggta     120
gcagtgcctg tggtctacgg ggtgatctgc gcggtgggac tggcgggcaa ctccgcggtg     180
ctgtacgtac tgctgcgcac gccgcgcatg aagactgtta ccaacgtgtt cattctcaac     240
ctggctatcg cggacgagct cttcaccctc gtgctgccca tcaacatcgc ggacttcctg     300
ctgaggcgct ggcccttcgg ggaagtcatg tgcaagctca tcgtggctgt cgaccagtac     360
aacactttct ctagcctcta cttcctcgcc gtcatgagcg cagaccgcta cctggttgtc     420
ctggccacag ccgagtcgcg ccgggtgtcc ggcgcactt atggtgcagc gcgggctgtc     480
agtctggcgg tgtgggcgct ggtgacattg gtcgtgctgc cttttgcggt attcgcccgg     540
ctggacgaag agcagggtcg cgtcagtgc gtgctggtct cccgcagcc tgaggccttc     600 tggtggcgcg ccagccgtct gtacactcta gtgttgggct cgccatccc ggtgtccacc     660 atctgcgccc tctatatcac cctgttgtgc cgactgcgtg ctatccagct agacagccac     720
gccaaggccc tggaccgtgc caagaagcgc gtgaccttgt tggtggtggc gattctggct     780
gtgtgcctcc tctgctggac accgtaccac ctgagcacca tagtggcgct caccaccgac     840
ctcccgcaaa caccgttggt catcggcatc tcttacttca tcaccagtct gagctatgcc     900
aacagctgcc tcaacccttt cctctatgcc ttcctggacg acagcttccg caggagcctg     960
cggcagctgg tgtcatgccg cacagcc                                         987

<210> SEQ ID NO 128
<211> LENGTH: 28
<212> TYPE: DNA
<213> ORGANISM: Artificial Sequence
<220> FEATURE:
<223> OTHER INFORMATION: Primer

<400> SEQUENCE: 128
actgatatgc acaacttgtc gctcttcg                                         28

<210> SEQ ID NO 129
<211> LENGTH: 28
<212> TYPE: DNA
<213> ORGANISM: Artificial Sequence
<220> FEATURE:
<223> OTHER INFORMATION: Primer

<400> SEQUENCE: 129
actagttcag gctgtgcggc atgacacc                                         28
```

```
<210> SEQ ID NO 130
<211> LENGTH: 19
<212> TYPE: DNA
<213> ORGANISM: Artificial Sequence
<220> FEATURE:
<223> OTHER INFORMATION: Primer

<400> SEQUENCE: 130
gttggtggtg gcgattctg                                                  19

<210> SEQ ID NO 131
<211> LENGTH: 19
<212> TYPE: DNA
<213> ORGANISM: Artificial Sequence
<220> FEATURE:
<223> OTHER INFORMATION: Primer

<400> SEQUENCE: 131
tggtgagcgc cactatggt                                                  19

<210> SEQ ID NO 132
<211> LENGTH: 24
<212> TYPE: DNA
<213> ORGANISM: Artificial Sequence
<220> FEATURE:
<223> OTHER INFORMATION: Primer

<400> SEQUENCE: 132
gtccgcgatg ttgatgggca gcac                                            24

<210> SEQ ID NO 133
<211> LENGTH: 24
<212> TYPE: DNA
<213> ORGANISM: Artificial Sequence
<220> FEATURE:
<223> OTHER INFORMATION: Primer

<400> SEQUENCE: 133
gaagagctca tcggcgatag ccag                                            24

<210> SEQ ID NO 134
<211> LENGTH: 440
<212> TYPE: DNA
<213> ORGANISM: Mus musculus

<400> SEQUENCE: 134
taagcagtgg taacaacgca gagtacgcgg gggcgcataa gcagtggtaa caacgcagag      60
tcacgcgggg agtgcctggg tgcagatccc tgtaaacgtg ggcgcataaa cctcgagttt     120
cgcggggctg ctgagtggaa tcctggtggt cgcctgctct ccagccctct ccaagatgca     180
taacttaacg ctttcgagt ctggagggga caacgtgtct tgcggcggct catctttggg      240
ctgtcccaac gggtccagcc tggctcctct gccgctgccg cagccactgg cggtagcagt     300
gcctgtcgtc tacggggtaa tttgcgccgt gggactggct ggcaactctg cggtgctgta     360
cgtactgctg cgcacgccgc gcatgaagac tgtcaccaac gtgttcatcc tcaacctggc     420
tatcgccgat gagctcttca                                                 440

<210> SEQ ID NO 135
<211> LENGTH: 24
<212> TYPE: DNA
<213> ORGANISM: Artificial Sequence
<220> FEATURE:
<223> OTHER INFORMATION: Primer
```

<400> SEQUENCE: 135
tttcgcgggg ctgctgagtg gaat                                              24

<210> SEQ ID NO 136
<211> LENGTH: 24
<212> TYPE: DNA
<213> ORGANISM: Artificial Sequence
<220> FEATURE:
<223> OTHER INFORMATION: Primer

<400> SEQUENCE: 136
agtgctgcct gcggtggaaa gagg                                              24

<210> SEQ ID NO 137
<211> LENGTH: 1083
<212> TYPE: DNA
<213> ORGANISM: Mus musculus

<400> SEQUENCE: 137
tttcgcgggg ctgctgagtg gaatcctggt ggtcgcctgc tctccagccc tctccaagat        60
gcataactta acgcttttcg agtctggagg ggacaacgtg tcttgcggcg gctcatcttt       120
gggctgtccc aacgggtcca gcctggctcc tctgccgctg ccgcagccac tggcggtagc       180
agtgcctgtc gtctacgggg taatttgcgc cgtgggactg ctggcaact ctgcggtgct        240
gtacgtactg ctgcgcacgc cgcgcatgaa gactgtcacc aacgtgttca tcctcaacct       300
ggctatcgcc gatgagctct tcaccctcgt gctgcccatc aacatcgcgg acttcctgct       360
gaggcgctgg cccttcgggg aggtcatgtg caagctcatt gtagccgtcg accagtacaa       420
cactttctct agcctctact tcctcgccgt catgagcgcc gaccgatacc tggtggttct       480
ggccacagca gagtcgcgcc gggtgtccgg gcgcacttac ggtgcagcgc gtgctgtcag       540
tctggcggtg tgggcgctgg tgacgctggt cgtgctgccc tttgcggtat tcgctcggct       600
ggacgaggag cagggtcggc gccagtgcgt gctggtcttc ccgcagcccg aggccttctg       660
gtggcgtgcc agccgtctct acacactagt attgggcttt gccatcccgg tgaccaccat       720
ctgtgctctc tataccactc tgctctgccg actgcgtgct atccagctag atagccacgc       780
caaggccctg gatcgtgcca agaagcgcgt gaccttgttg gtggcggcga ttctggctgt       840
gtgcctcctc tgctggacgc cttatcacct gagtaccata gtggccctca ccaccgacct       900
cccgcaaacg ccgctggtca tcggcatctc ttacttcatc accagcctga gctatgctaa       960
cagctgcctc aaccctttcc tctatgcctt cctggacgac agcttccgca gaagcctccg      1020
gcaattggtg tcatgccgtt cagcctgatg cccttccac ctctttccac cgcaggcagc       1080
act                                                                   1083

<210> SEQ ID NO 138
<211> LENGTH: 329
<212> TYPE: PRT
<213> ORGANISM: Mus musculus

<400> SEQUENCE: 138

Met His Asn Leu Thr Leu Phe Glu Ser Gly Gly Asp Asn Val Ser Cys
              5                  10                  15

Gly Gly Ser Ser Leu Gly Cys Pro Asn Gly Ser Ser Leu Ala Pro Leu
         20                  25                  30

Pro Leu Pro Gln Pro Leu Ala Val Ala Val Pro Val Val Tyr Gly Val
     35                  40                  45

```
Ile Cys Ala Val Gly Leu Ala Gly Asn Ser Ala Val Leu Tyr Val Leu
 50                  55                  60

Leu Arg Thr Pro Arg Met Lys Thr Val Thr Asn Val Phe Ile Leu Asn
 65                  70                  75                  80

Leu Ala Ile Ala Asp Glu Leu Phe Thr Leu Val Pro Ile Asn Ile
                 85                  90                  95

Ala Asp Phe Leu Leu Arg Arg Trp Pro Phe Gly Glu Val Met Cys Lys
                100                 105                 110

Leu Ile Val Ala Val Asp Gln Tyr Asn Thr Phe Ser Ser Leu Tyr Phe
                115                 120                 125

Leu Ala Val Met Ser Ala Asp Arg Tyr Leu Val Val Leu Ala Thr Ala
            130                 135                 140

Glu Ser Arg Arg Val Ser Gly Arg Thr Tyr Gly Ala Ala Arg Ala Val
145                 150                 155                 160

Ser Leu Ala Val Trp Ala Leu Val Thr Leu Val Val Leu Pro Phe Ala
                165                 170                 175

Val Phe Ala Arg Leu Asp Glu Glu Gln Gly Arg Arg Gln Cys Val Leu
                180                 185                 190

Val Phe Pro Gln Pro Glu Ala Phe Trp Trp Arg Ala Ser Arg Leu Tyr
            195                 200                 205

Thr Leu Val Leu Gly Phe Ala Ile Pro Val Thr Thr Ile Cys Ala Leu
        210                 215                 220

Tyr Thr Thr Leu Leu Cys Arg Leu Arg Ala Ile Gln Leu Asp Ser His
225                 230                 235                 240

Ala Lys Ala Leu Asp Arg Ala Lys Lys Arg Val Thr Leu Leu Val Ala
                245                 250                 255

Ala Ile Leu Ala Val Cys Leu Leu Cys Trp Thr Pro Tyr His Leu Ser
                260                 265                 270

Thr Ile Val Ala Leu Thr Thr Asp Leu Pro Gln Thr Pro Leu Val Ile
            275                 280                 285

Gly Ile Ser Tyr Phe Ile Thr Ser Leu Ser Tyr Ala Asn Ser Cys Leu
        290                 295                 300

Asn Pro Phe Leu Tyr Ala Phe Leu Asp Asp Ser Phe Arg Arg Ser Leu
305                 310                 315                 320

Arg Gln Leu Val Ser Cys Arg Ser Ala
                325

<210> SEQ ID NO 139
<211> LENGTH: 987
<212> TYPE: DNA
<213> ORGANISM: Mus musculus

<400> SEQUENCE: 139
atgcataact taacgctttt cgagtctgga ggggacaacg tgtcttgcgg cggctcatct      60
ttgggctgtc ccaacgggtc cagcctggct cctctgccgc tgccgcagcc actggcggta     120
gcagtgcctg tcgtctacgg ggtaatttgc gccgtgggac tggctggcaa ctctgcggtg     180
ctgtacgtac tgctgcgcac gccgcgcatg aagactgtca ccaacgtgtt catcctcaac     240
ctggctatcg ccgatgagct cttcacgctc gtgctgccca tcaacatcgc ggacttcctg     300
ctgaggcgct ggcccttcgg ggaggtcatg tgcaagctca ttgtagccgt cgaccagtac     360
aacactttct ctagcctcta cttcctcgcc gtcatgagcg ccgaccgata cctggtggtt     420
ctggccacag cagagtcgcg ccgggtgtcc gggcgcactt acggtgcagc gcgtgctgtc     480
```

```
agtctggcgg tgtgggcgct ggtgacgctg gtcgtgctgc cctttgcggt attcgctcgg    540
ctggacgagg agcagggtcg gcgccagtgc gtgctggtct ccccgcagcc cgaggccttc    600
tggtggcgtg ccagccgtct ctacacacta gtattgggct ttgccatccc ggtgaccacc    660
atctgtgctc tctataccac tctgctctgc cgactgcgtg ctatccagct agatagccac    720
gccaaggccc tggatcgtgc caagaagcgc gtgaccttgt tggtggcggc gattctggct    780
gtgtgcctcc tctgctggac gccttatcac ctgagtacca tagtggccct caccaccgac    840
ctcccgcaaa cgccgctggt catcggcatc tcttacttca tcaccagcct gagctatgct    900
aacagctgcc tcaacccttt cctctatgcc ttcctggacg acagcttccg cagaagcctc    960
cggcaattgg tgtcatgccg ttcagcc                                        987
```

<210> SEQ ID NO 140
<211> LENGTH: 27
<212> TYPE: DNA
<213> ORGANISM: Artificial Sequence
<220> FEATURE:
<223> OTHER INFORMATION: Probe

<400> SEQUENCE: 140

```
tcctctgctg gacaccgtac cacctga                                         27
```

<210> SEQ ID NO 141
<211> LENGTH: 32
<212> TYPE: DNA
<213> ORGANISM: Artificial Sequence
<220> FEATURE:
<223> OTHER INFORMATION: Primer

<400> SEQUENCE: 141

```
atcgatatgg acaacgcctc gttctcggag cc                                   32
```

<210> SEQ ID NO 142
<211> LENGTH: 32
<212> TYPE: DNA
<213> ORGANISM: Artificial Sequence
<220> FEATURE:
<223> OTHER INFORMATION: Primer

<400> SEQUENCE: 142

```
actagtgtca ggctgccgcg cggcaagtta tc                                   32
```

<210> SEQ ID NO 143
<211> LENGTH: 1000
<212> TYPE: DNA
<213> ORGANISM: Homo sapiens

<400> SEQUENCE: 143

```
atcgatatgg acaacgcctc gttctcggag ccctggcccg ccaacgcatc gggcccggac     60
ccggcgctga gctgctccaa cgcgtcgact ctggcgccgc tgccggcgcc gctggcggtg    120
gctgtaccag ttgtctacgc ggtgatctgc gccgtgggtc tggcgggcaa ctccgccgtg    180
ctgtacgtgt gctgcgggc gccccgcatg aagaccgtca ccaacctgtt catcctcaac    240
ctggccatcg ccgacgagct cttcacgctg gtgctgccca tcaacatcgc cgacttcctg    300
ctgcggcagt ggcccttcgg ggagctcatg tgcaagctca tcgtggctat cgaccagtac    360
aacaccttct ccagcctcta cttcctcacc gtcatgagcg ccgaccgcta cctggtggtg    420
ttggccactg cggagtcgcg ccgggtggcc ggccgcacct acagcgccgc gcgcgcggtg    480
agcctggccg tgtgggggat cgtcacactc gtcgtgctgc ccttcgcagt cttcgcccgg    540
```

-continued

```
ctagacgacg agcagggccg gcgccagtgc gtgctagtct ttccgcagcc cgaggccttc    600
tggtggcgcg cgagccgcct ctacacgctc gtgctgggct tcgccatccc cgtgtccacc    660
atctgtgtcc tctataccac cctgctgtgc cggctgcatg ccatgcggct ggacagccac    720
gccaaggccc tggagcgcgc caagaagcgg gtgaccttcc tggtggtggc aatcctggcg    780
gtgtgcctcc tctgctggac gccctaccac ctgagcaccg tggtggcgct caccaccgac    840
ctcccgcaga cgccgctggt catcgctatc tcctacttca tcaccagcct gagctacgcc    900
aacagctgcc tcaacccctt cctctacgcc ttcctggacg ccagcttccg caggaacctc    960
cgccagctga taacttgccg cgcggcagcc tgacactagt                         1000
```

<210> SEQ ID NO 144
<211> LENGTH: 328
<212> TYPE: PRT
<213> ORGANISM: Homo sapiens

<400> SEQUENCE: 144

```
Met Asp Asn Ala Ser Phe Ser Glu Pro Trp Pro Ala Asn Ala Ser Gly
 1               5                  10                  15
Pro Asp Pro Ala Leu Ser Cys Ser Asn Ala Ser Thr Leu Ala Pro Leu
            20                  25                  30
Pro Ala Pro Leu Ala Val Ala Val Pro Val Val Tyr Ala Val Ile Cys
        35                  40                  45
Ala Val Gly Leu Ala Gly Asn Ser Ala Val Leu Tyr Val Leu Leu Arg
    50                  55                  60
Ala Pro Arg Met Lys Thr Val Thr Asn Leu Phe Ile Leu Asn Leu Ala
65                  70                  75                  80
Ile Ala Asp Glu Leu Phe Thr Leu Val Leu Pro Ile Asn Ile Ala Asp
                85                  90                  95
Phe Leu Leu Arg Gln Trp Pro Phe Gly Glu Leu Met Cys Lys Leu Ile
            100                 105                 110
Val Ala Ile Asp Gln Tyr Asn Thr Phe Ser Ser Leu Tyr Phe Leu Thr
        115                 120                 125
Val Met Ser Ala Asp Arg Tyr Leu Val Val Leu Ala Thr Ala Glu Ser
    130                 135                 140
Arg Arg Val Ala Gly Arg Thr Tyr Ser Ala Ala Arg Ala Val Ser Leu
145                 150                 155                 160
Ala Val Trp Gly Ile Val Thr Leu Val Val Leu Pro Phe Ala Val Phe
                165                 170                 175
Ala Arg Leu Asp Asp Glu Gln Gly Arg Arg Gln Cys Val Leu Val Phe
            180                 185                 190
Pro Gln Pro Glu Ala Phe Trp Trp Arg Ala Ser Arg Leu Tyr Thr Leu
        195                 200                 205
Val Leu Gly Phe Ala Ile Pro Val Ser Thr Ile Cys Val Leu Tyr Thr
    210                 215                 220
Thr Leu Leu Cys Arg Leu His Ala Met Arg Leu Asp Ser His Ala Lys
225                 230                 235                 240
Ala Leu Glu Arg Ala Lys Lys Arg Val Thr Phe Leu Val Val Ala Ile
                245                 250                 255
Leu Ala Val Cys Leu Leu Cys Trp Thr Pro Tyr His Leu Ser Thr Val
            260                 265                 270
Val Ala Leu Thr Thr Asp Leu Pro Gln Thr Pro Leu Val Ile Ala Ile
        275                 280                 285
```

```
Ser Tyr Phe Ile Thr Ser Leu Ser Tyr Ala Asn Ser Cys Leu Asn Pro
    290                 295                 300

Phe Leu Tyr Ala Phe Leu Asp Ala Ser Phe Arg Arg Asn Leu Arg Gln
305                 310                 315                 320

Leu Ile Thr Cys Arg Ala Ala Ala
                325
```

<210> SEQ ID NO 145
<211> LENGTH: 32
<212> TYPE: DNA
<213> ORGANISM: Artificial Sequence
<220> FEATURE:
<223> OTHER INFORMATION: Primer

<400> SEQUENCE: 145
atcgatatgg acaacgcctc gttctcggag cc                32

<210> SEQ ID NO 146
<211> LENGTH: 21
<212> TYPE: DNA
<213> ORGANISM: Artificial Sequence
<220> FEATURE:
<223> OTHER INFORMATION: Primer

<400> SEQUENCE: 146
tagaggctgg agaaggtgtt g                           21

<210> SEQ ID NO 147
<211> LENGTH: 21
<212> TYPE: DNA
<213> ORGANISM: Artificial Sequence
<220> FEATURE:
<223> OTHER INFORMATION: Primer

<400> SEQUENCE: 147
catgaagacc gtcaccaacc t                           21

<210> SEQ ID NO 148
<211> LENGTH: 19
<212> TYPE: DNA
<213> ORGANISM: Artificial Sequence
<220> FEATURE:
<223> OTHER INFORMATION: Primer

<400> SEQUENCE: 148
ccagcgtgaa gagctcgtc                              19

<210> SEQ ID NO 149
<211> LENGTH: 20
<212> TYPE: PRT
<213> ORGANISM: Artificial Sequence
<220> FEATURE:
<223> OTHER INFORMATION: [Phe2] human GPR8 ligand (1-20)

<400> SEQUENCE: 149

```
Trp Phe Lys His Val Ala Ser Pro Arg Tyr His Thr Val Gly Arg Ala
1               5                   10                  15

Ala Gly Leu Leu
            20
```

<210> SEQ ID NO 150
<211> LENGTH: 60
<212> TYPE: DNA
<213> ORGANISM: Artificial Sequence
<220> FEATURE:

```
<223> OTHER INFORMATION: Sequence encoding [Phe2] human GPR8 ligand
      (1-20)

<400> SEQUENCE: 150
tggttcaagc acgtggcgag tccccgctac cacacggtgg gccgcgccgc tggcctgctc      60
```